(12) United States Patent
Smith et al.

(10) Patent No.: US 8,377,448 B2
(45) Date of Patent: Feb. 19, 2013

(54) CD47 RELATED COMPOSITIONS AND METHODS FOR TREATING IMMUNOLOGICAL DISEASES AND DISORDERS

(75) Inventors: Craig A. Smith, Seattle, WA (US); Steven Wiley, Seattle, WA (US); Ajamete Kaykas, Seattle, WA (US); Peter Probst, Seattle, WA (US)

(73) Assignee: The Board of Trustees of the Leland Standford Junior University, Palo Alto, CA (US)

( * ) Notice: Subject to any disclaimer, the term of this patent is extended or adjusted under 35 U.S.C. 154(b) by 0 days.

(21) Appl. No.: 12/687,334

(22) Filed: Jan. 14, 2010

(65) Prior Publication Data

US 2010/0239579 A1  Sep. 23, 2010

Related U.S. Application Data

(63) Continuation-in-part of application No. 11/804,992, filed on May 15, 2007, now abandoned.

(60) Provisional application No. 61/144,695, filed on Jan. 14, 2009, provisional application No. 61/174,939, filed on May 1, 2009, provisional application No. 60/800,643, filed on May 15, 2006.

(51) Int. Cl.
    *A61K 39/00* (2006.01)
(52) U.S. Cl. ............ 424/185.1; 424/192.1; 530/300; 530/810
(58) Field of Classification Search ................. None
    See application file for complete search history.

(56) References Cited

U.S. PATENT DOCUMENTS

| | | | |
|---|---|---|---|
| 4,289,872 A | 9/1981 | Denkewalter et al. |
| 4,331,647 A | 5/1982 | Goldenberg |
| 4,376,110 A | 3/1983 | David et al. |
| 4,411,993 A | 10/1983 | Gills |
| 4,464,456 A | 8/1984 | Fujikawa et al. |
| 4,486,530 A | 12/1984 | David et al. |
| 4,543,439 A | 9/1985 | Frackelton, Jr. et al. |
| 4,902,614 A | 2/1990 | Wakabayashi et al. |
| 4,952,496 A | 8/1990 | Studier et al. |
| 5,011,912 A | 4/1991 | Hopp et al. |
| 5,091,513 A | 2/1992 | Huston et al. |
| 5,100,788 A | 3/1992 | Lofdahl et al. |
| 5,132,405 A | 7/1992 | Huston et al. |
| 5,168,049 A | 12/1992 | Meade et al. |
| 5,223,409 A | 6/1993 | Ladner |
| 5,272,254 A | 12/1993 | Meade et al. |
| 5,338,665 A | 8/1994 | Schatz et al. |
| 5,428,130 A | 6/1995 | Capon et al. |
| 5,432,018 A | 7/1995 | Dower et al. |
| 5,476,786 A | 12/1995 | Huston |
| 5,482,856 A | 1/1996 | Fell, Jr. et al. |
| 5,489,528 A | 2/1996 | Kopetzki et al. |
| 5,498,530 A | 3/1996 | Schatz et al. |
| 5,567,588 A | 10/1996 | Gold et al. |
| 5,608,035 A | 3/1997 | Yanofsky et al. |
| 5,627,052 A | 5/1997 | Schrader |
| 5,672,691 A | 9/1997 | Kopetzki et al. |
| 5,698,426 A | 12/1997 | Huse |
| 5,733,731 A | 3/1998 | Schatz et al. |
| 5,751,629 A | 5/1998 | Nova et al. |
| 5,770,577 A | 6/1998 | Kinstler et al. |
| 5,773,569 A | 6/1998 | Wrighton et al. |
| 5,786,331 A | 7/1998 | Barrett et al. |
| 5,789,172 A | 8/1998 | Still et al. |
| 5,792,456 A | 8/1998 | Yelton et al. |
| 5,798,035 A | 8/1998 | Kirk et al. |
| 5,843,725 A | 12/1998 | Sledziewski et al. |
| 5,869,451 A | 2/1999 | Dower et al. |
| 5,877,397 A | 3/1999 | Lonberg et al. |
| 5,880,096 A | 3/1999 | Barrett et al. |
| 5,910,573 A | 6/1999 | Pluckthun et al. |
| 5,922,545 A | 7/1999 | Mattheakis et al. |
| 5,932,946 A | 8/1999 | Miyasaka et al. |
| 6,018,026 A | 1/2000 | Sledziewski et al. |
| 6,291,646 B1 | 9/2001 | Sledziewski et al. |
| 6,300,099 B1 | 10/2001 | Sledziewski et al. |
| 6,323,323 B1 | 11/2001 | Sledziewski et al. |
| 6,395,713 B1 | 5/2002 | Beigelman et al. |
| 6,447,796 B1 | 9/2002 | Vook et al. |
| 6,660,843 B1 | 12/2003 | Feige et al. |
| 6,699,843 B2 | 3/2004 | Pietras et al. |
| 6,703,015 B1 | 3/2004 | Solomon et al. |
| 6,867,289 B1 | 3/2005 | Gorenstein et al. |
| 7,189,830 B2 | 3/2007 | Gillies et al. |
| 7,465,447 B2 | 12/2008 | Gillies et al. |
| 2001/0007666 A1 | 7/2001 | Hofman et al. |
| 2001/0053539 A1 | 12/2001 | Lauffer et al. |

(Continued)

FOREIGN PATENT DOCUMENTS

EP  0318554 A1  12/1988
EP  0511747 A1  11/1992

(Continued)

OTHER PUBLICATIONS

Barazi et al., Regulation of Integrin Function by CD47 Ligands, JBC 277(45):42859-42866 (2002).

(Continued)

*Primary Examiner* — Maher Haddad
(74) *Attorney, Agent, or Firm* — Bozicevic, Field & Francis LLP; Pamela J. Sherwood

(57) ABSTRACT

Provide herein are fusion polypeptides that comprise a CD47 extracellular domain or a variant thereof that is fused to a Fc polypeptide. The fusion polypeptides are useful for treating an immunological disease or disorder in a subject according to the methods described herein. The fusion polypeptides are capable of suppressing immunoresponsiveness of an immune cell, inhibiting production of proinflammatory cytokines, including inhibiting immune complex-induced production of cytokines.

6 Claims, 30 Drawing Sheets

U.S. PATENT DOCUMENTS

| | | |
|---|---|---|
| 2002/0130430 A1 | 9/2002 | Castor |
| 2003/0064480 A1 | 4/2003 | Lauffer et al. |
| 2003/0077829 A1 | 4/2003 | MacLachlan |
| 2003/0118592 A1 | 6/2003 | Ledbetter et al. |
| 2003/0133939 A1 | 7/2003 | Ledbetter et al. |
| 2004/0001853 A1 | 1/2004 | George et al. |
| 2004/0044188 A1 | 3/2004 | Feige et al. |
| 2004/0053845 A1 | 3/2004 | Feige et al. |
| 2004/0057953 A1 | 3/2004 | Feige et al. |
| 2004/0071712 A1 | 4/2004 | Feige et al. |
| 2004/0077022 A1 | 4/2004 | Feige et al. |
| 2004/0082039 A1 | 4/2004 | Gillies et al. |
| 2004/0087778 A1 | 5/2004 | Feige et al. |
| 2004/0147731 A1 | 7/2004 | Parkos |
| 2005/0175614 A1 | 8/2005 | Ledbetter et al. |
| 2005/0249723 A1 | 11/2005 | Lazar |
| 2006/0135749 A1 | 6/2006 | Matozaki et al. |
| 2007/0134234 A1 | 6/2007 | Smith et al. |
| 2007/0142274 A1* | 6/2007 | Berge ........................ 514/12 |
| 2007/0264654 A1 | 11/2007 | Wiley et al. |
| 2008/0131431 A1 | 6/2008 | Smith |

FOREIGN PATENT DOCUMENTS

| | | |
|---|---|---|
| EP | 0578515 A2 | 1/1994 |
| EP | 0774464 A2 | 5/1997 |
| EP | 1637598 A1 | 3/2006 |
| WO | WO89-01476 A1 | 2/1989 |
| WO | WO89-03422 A1 | 4/1989 |
| WO | WO90-09195 A1 | 8/1990 |
| WO | WO91-09967 A1 | 7/1991 |
| WO | WO91-11465 A1 | 8/1991 |
| WO | WO92-02551 A1 | 2/1992 |
| WO | WO92-16221 A1 | 10/1992 |
| WO | WO92-22583 A2 | 12/1992 |
| WO | WO93-06231 A1 | 4/1993 |
| WO | WO93-21259 A1 | 10/1993 |
| WO | WO93-24631 A1 | 12/1993 |
| WO | WO94/02595 A1 | 2/1994 |
| WO | WO96/40987 A1 | 12/1996 |
| WO | WO97/27873 A1 | 9/1997 |
| WO | WO98/15833 A1 | 4/1998 |
| WO | WO99/40940 A1 | 8/1999 |
| WO | WO00/53722 A2 | 9/2000 |
| WO | WO00/53722 A3 | 9/2000 |
| WO | WO03/046185 A1 | 6/2003 |
| WO | WO03/047518 A2 | 6/2003 |
| WO | WO03/047518 A3 | 6/2003 |
| WO | WO2004/108923 A1 | 12/2004 |

OTHER PUBLICATIONS

Yu et al., Engagement of CD47 Inhibits the Contact Hypersensitivity Response Via the Suppression of Motility and B7 Expression by Langerhans Cells,: J. Investigational Dermatology 126:797-807 (2006).

PCT/US10/20945 Search Report and Written Opinion dated Oct. 28, 2010.

Adams, "Improving the tumor specificity and retention of antibody-based molecules," In Vivo 12:11-21 (1998).

Aggarwal, et al., "Interleukin-23 Promotes a Distinct CD4 T Cell Activation State Characterized by the Production of Interleukin-17," J. Biol. Chem 17:278:1910-1914 (2003).

Akhtar, et al., "Cellular uptake and intracellular fate of antisense oligonucleotides," Trends Cell Bio 2:139-144 (1992).

Alcami, et al., "Poxvirusescapturing Cytokines and Chemoki," Semin Virol. 8:419-427 (1998).

Alfonso, et al., "Genome of Deerpox," J. Virol. 79:966-977 (2005).

Alting-Mees, et al., "Monoclonal Antibody Expression Libraries: A Rapid Alternative to Hybridomas," Strategies in Molecular Biology 3:1-9 (1990).

Altschul, "Amino acid substitution matrices from an information theoretic perspective," J. Mo. Biol. 219:555-565 (1991).

Andris-Widhopf, et al., "Methods for the generation of chicken monoclonal antibody fragments by phage display," J. Immunol. Methods 242:159-231 (2000).

Armant, et al., "CD47 Ligation Selectively Downregulates Human Interleukin 12 Production," J. Exp. Med. 190:1175-1181 (1999).

Attwood, T.K., "Genomics. The Babel of bioinformatics," Science 290(5491):471-473 (2000).

Avice, et al., "CD47 Ligation Selectively Inhibits the Development of Human Naive T Cells into Th1 Effectors," J. Immunol. 165:4624 (2000).

Babcook, et al., "A novel strategy for generating monoclonal antibodies from single, isolated lymphocytes producing antibodies of defined specificities," Proc. Natl. Acad Sci. USA 93:7843-7848 (1996).

Babu, et al., "Transgenic mouse models for cardiac dysfunction by a specific gene manipulation," Methods Mol. Med. 112:365-377 (2005).

Baines, et al., Purification of Immunoglobulin G (IgG), in Methods in Molecular Biology, 10:9-104 (the Humana Press, Inc. (1992).

Bajorath, et al., "Model building of antibody combining sites," Ther. Immuol 2:95-103 (1995).

Barbas, et al., "In vitro evolution of a neutralizing human antibody to human immunodeficiency virus type 1 to enhance affinity and broaden strain cross-reactivity," Proc. Natl. Acad Sci. USA 91:3809-3813 (1994).

Becker, et al., "Cutting Edge: IL-23 Cross-Regulates IL-12 Production in T Cell-Dependent Experimental Colitis," J. Immunol 177:2760-2764 (2006).

Bird, et al., "Single-chain antigen-binding proteins," Science 242:423-426 (1988).

Blystone, et al., "Integrin beta 3 Cytoplasmic Tail is Necessary and Sufficient for Regulation of Alpha 5 Beta 1 Phagocytosis by Alpha v Beta 3 and Integrin-Associated Protein," J Cell Biol. 130:745-754 (1995).

Boerner, et al., "Production of antigen-specific human monoclonal antibodies from in vitro-primed human splenocytes ," J. Immunol. 147:86-95 (1991).

Boruchov, et al., "Activating and inhibitory IgG Fc receptors on human DCs mediate opposing functions," J. Clin. Invest. 115:2914-2923 (2005).

Boyman, et al., "Spontaneous Development of Psoriasis in a New Animal Model Shows an Essential Role for Resident T Cells and Tumor Necrosis Factor," J. Exp. Med 199:731-736 (2004).

Brand, et al., "Generation and Characterization of Monoclonal Antibodies to Oleanolic Acid," Planta Med. 70:986-992 (2004).

Brondum, et al., "Functional Abnormalities in Isolated Arteries From Goto-Kakizaki and Steptozotocin-Treated Diabetic Rat Models," Horm. Metab. Res. 37 Suppl 1:56-60 (2005).

Brown, et al., "Integrin-Associated Protein: a 50-kD Plasma Membrane Antigen Physically and Functionally Associated with Integrins," J. Cell Biol. 111:2785-2794 (1990).

Bruggemann, et al., "Production of human antibody repertoires in transgenic mice," Curr. Opin. Biotchnol. 8:455-458 (1997).

Bucher, et al., "Phosphoglycerate Kinase from Brewer's Yeast," Methods in Enzymology 1:415-422 (1967).

Bugert and Darai, "Poxvirus homologues of cellular genes," Virus Genes 21:111-133 (2000).

Burton, et al., "Human antibody effector function," Adv. Immunol. 51:1-84 (1992).

Burton, et al., "Human antibodies from combinatorial libraries," Adv. Immunol. 57:191-280 (1994).

Cameron, et al., "The Complete DNA Sequence of Myxoma Virus," Virology 264-298-318 (1999).

Cameron, et al., "Myxoma Virus M128L is Expressed as a cell Surface CD47-Like Virulence Factor that Contributes to the Downregulation of Macrophage Activation in Vivo," Virology 337:55-67 (2005).

Canfield, et al., "The binding affinity of human IgG for its high affinity Fc receptor is determined by multiple amino acids in the CH2 domain and is modulated by the hinge region," J. Exp. Med 173:1483 (1991).

Carlsson, et al., "Protein thiolation and reversible protein-protein conjugation. N-Succinimidyl 3-(2-pyridyldithio)propionate, a new heterobifunctional reagent," Biochem J. 173:723-737 (1978).

Carrell, et al., "A Novel Procedure for the Synthesis of Libraries Containing Small Organic Molecules," Angew. Chem. Int. Ed. Engl. 33:2059-2061 (1994).

Carrell, et al., "A Solution-Phase Screening Procedure for the Isolation of Active Compounds from a Library of Molecules," Angew. Chem. Int. Ed. Engl. 33: 2061-2064 (1994).

Cascio, "Novel strategies for immortalization of human hepatocytes," Artif. Organs 25:529-538 (2001).

Chappel, et al., "Identification of the Fc gamma receptor class I binding site in human IgG through the use of recombinant IgG1/IgG2 hybrid and point-mutated antibodies," Proc. Natl. Acad. Sci. USA 88:9036-9040 (1991).

Cho, et al., "An unnatural biopolymer," Science 261:1303-1305 (1993).

Chothia, et al., "Brain drain in flood" Nature 342:377-383 (1989).

Cohen, "Naked DNA Points Way to Vaccines," Science 259:1691-1692 (1993).

Coligan, Current Protocols in Immunology 2.7.1-2.7.12;2.9.1-2.9.3 (John Wiley & Sons 1991).

Coligan, Current Protocols in Immunology 1:2.5.1-2.6.7 (John Wiley & Sons 1991).

Coloma, et al., "Design and production of novel tetravalent bispecific antibodies," Nat Biotechnol 15:159-163 (1997).

Cooper, et al., "Transendothelial Migration of Neutrophils Involves Integrin-Associated Protein (CD47)," Proc. Natl. Acad. Sci USA 92:3978-3982 (1995).

Courtenay-Luck, "Genetic Manipulation of Monoclonal Antibodies," in Monoclonal Antibodies: Production, Engineering and Clinical Application, Ritter, et al., (eds.) p. 166 (Cambridge University Press 1995).

Cull, et al., "Screening for receptor ligands using large libraries of peptides linked to the C terminus of the lac repressor," Proc. Natl. Acad. Sci. USA 89:1865-1869 (1992).

Cwirla, et al., "Peptides on phage: a vast library of peptides for identifying ligands," Proc. Natl. Acad. Sci. USA 87:6378-6382 (1990).

Cwirla, et al., "Peptide Agonist of the Thrombopoientin Receptor as Potent as the Natural Cytokine" Science 276:1696-1699 (1997).

Das, et al., "Producing Bispecific and Bifunctional Antibodies," Methods Mol. Med 109:329-346 (2005).

Davies, et al., "Antibody-Antigen Complexes," Ann. Rev. Biochem. 59:439-473 (1990).

Demeure, et al., "CD47 Engagement Inhibits Cytokine Production and Maturation of Human Dendritic Cells," J. Immunol 164:2193-2199 (2000).

Devlin, et al., "Random Peptide Libraries: A Source of Specific Protein Binding Molecules," Science 249:404-406 (1990).

Dewitt, et al., "Diversomers: an approach to nonpeptide, nonoligomeric chemical diversity," Proc. Natl. Acad. Sci U.S.A. 90:6909-6913 (1993).

Drake, et al., "Genetic contributions to lupus-like disease in (NZB x NZW)F1 mice," Immunol. Rev. 144:51-74 (1995).

Drakeman, et al., "Bispecific antibodies for the treatment of tumours and infectious diseases," Expert Opin. Investig. Drugs 6:1169-1178 (1997).

Duerr, et al., "A Genome-Wide Association Study identifies IL23R as an Inflammatory Bowel Disease Gene," Science 314:1461-1463 (2006).

Duncan, et al., "Localization of the binding site for the human high-affinity Fc receptor on IgG" Nature 332:563-564 (1988).

Eghtedarzadeh-Kondri, et al., "Site-Specific Mutagenesis of Immunoglobulin Domains by Multiple-Fragment Homologous Recombination," Biotechniques 23:830-834 (1997).

Erb, et al., "Recursive deconvolution of combinatorial chemical libraries," Proc Natl Acad Sci USA 91:11422-11426 (1994).

Felici, "Selection of antibody ligands from a large library of oligopeptides expressed on a multivalent exposition vector," J. Mol. Biol. 222:301-310 (1991).

Fisch, et al., "A strategy of exon shuffling for making large peptide repertoires displayed on filamentous bacteriophage," Proc. Natl. Acad. Sci USA 93:7761-7766 (1996).

Fodor, "Multiplexed biochemical assays with biological chips," Nature 364:555-556 (1993).

Fukunaga, et al., Src Homology 2 Domain-Containing Protein Tyrosine Phosphatase Substrate 1 Regulates the Migration of Langerhans Cells from the Epidermis to Draining Lymph Nodes, J. Immunol. 172:4091-4099 (2004).

Furth, "Conditional control of gene expression in the mammary Gland," J. Mamm. Gland Biol. Neoplas. 2:373-383 (1997).

Gallop, et al., "Applications of Combinatorial Technologies to Drug Discovery. 1. Background and Peptide Combinatorial Libraries," J. Med. Chem. 37:1233-1251 (1994).

Gately, et al., "The Interleukin-12/Interleukin-12-Receptor System: Role in Normal and Pathologic Immune Responses," Annu. Rev. Immunol. 16:495-521.

Glaser, et al., "Antibody Engineering by Condon-Based Mutagenesis in a Filamentous Phage Vector System," J. Immunol 149:3903-3913 (1992).

Glasky, et al., "Stability of Specific Immunoglobulin Secretion by EBV-Transformed Lymphoblastoid Cells and Human-Murine Heterohybridomas," Hybridoma 8:377-389 (1989).

Goebel, et al., "The Complete DNA Sequence of Vaccinia Virus," Virology 179:247-266 (1990).

Gonzalez, et al., "New Class of Polymers for the Delivery of Macromolecular Terapeutics," Bioconjug. Chem 10:1068-1074 (1999).

Gossen, et al., "Tight control of gene expression in mammalian cells by tetracycline-responsive promoters," Proc Natl. Acad. Sci. USA 89:5547-5551 (1992).

Gossen, et al., "Transcriptional activation by tetracyclines in mammalian cells," Science 268:1766-1769 (1995).

Green, et al., "Production of Polyclonal Antisera," in Immunochemical Protocols (Manson, ed.), p. 1-5 (Humana Press 1992).

Green, et al., "Antigen-specific human monoclonal antibodies from mice engineered with human Ig heavy and light chain YACs," Nature Genet 7:1:13-21 (1994).

Green & Reed "Mitochondria and Apoptosis," Science 281:1309-1312 (1998).

Guzman, et al., "Regulation, modulation, and high-level expression by vectors containing arabinose $P_{BAD}$ promoter," J. Bateriology 177:4121-4130 (1995).

Harris, J. Milton. and Chess, Robert B., "Effect of Pegylation on Pharmaceuticals," Nature 2:214-221 (2003).

Hayden, et al., "Antibody engineering," Curr Opin Immunol 9:201-212 (1997).

Henikoff and Henikoff "Amino acid substitution matrices from protein blocks," Proc. Natl. Acad. Sci. USA 89:10915-10919 (1992).

Hermann, et al., "The Vitronectin Receptor and its Associated CD47 Molecule Mediates Proinflammatory Cytokine Synthesis in Human Monocytes by Interaction with Soluble CD23," J. Cell Biol. 144:767-775 (1999).

Hilkens, et al., "Human Dendritic Cells Require Exogenous Interleukin-12-Inducing Factors to Direct the Development of Naive T-Helper Cells Toward the Th1 Phenotype," Blood 90:1920 (1997).

Hiltunen, "Search for New and Improved Radiolabeling Methods for Monoclonal Antibodies. A Review of Different Methods," Acta Oncol. 32:831-839 (1993).

Hirsh, et al., "The araC promoter: transcription, mapping and interaction with the araBAD promoter," Cell 11:545-550 (1977).

Hofland and Huang, "Formulation and Delivery of Nucleic Acids," Handb. Exp. Pharmacol. 137:165-192 (1999).

Hollenbaugh, et al., "Cleavable CD40Ig fusion proteins and the binding to sgp39," J. Immunol. Methods 188:1-7 (1995).

Holliger, et al., "Diabodies: Small Bispecific Antibody Fragments," Cancer Immunol. Immunother. 45:128-130 (1997).

Hoogenboom, et al., "By-passing immunisation Human antibodies from synthetic repertoires of germline $V_H$ gene segments rearranged in vitro," J. Molec Biol 227:381-388 (1992).

Hopp, et al., "A short polypeptide marker sequence useful for recombinant protein identification and purification," Bio/Technology 6:1204 (1988).

Houghten,"The Use of Synthetic Peptide Combinatorial Libraries for the Identification of Bioactive Peptides." Biotechniques 13:412-421 (1992).

Hulett, et al., "Molecular basis of Fc receptor function," Adv. Immunol 57:1-127 (1994).

Huse, et al., "Generation of a large combinatorial library of the immunoglobulin repertoire in phage lambda," Science 246:1275-1281 (1989).

Huston, et al., "Protein engineering of antibody binding sites: recovery of specific activity in an anti-digoxin single-chain Fv analogue produced in *Escherichia coli*," Proc. Natl Acad. Sci USA 85:5879-5883 (1988).

Hutchins et al., "Improved biodistribution, tumor targeting, and reduced immunogenicity in mice with a y4 variant of Campath-IH," PNAS USA 92:11980-11984 (1995).

Jakobovits, et al., "Production of Antigen-Specific Human Antibodies from Mice Engineered with Human Heavy and Light Chain YACs" Ann. N. Y. Acad. Sci. 764:525-535 (1995).

Jefferis, et al., "IgG-Fc-mediated effector functions: molecular definition of interaction sites for effector ligands and the role of glycosylation," Immunol. Rev. 163:59-76 (1998).

Jia, "Protein Phosphatases: Structures and Implications," Biochem. Cell Biol. 75:17-26 (1997).

Jiang, et al., "Integrin-Associated Protein Is a Ligand for the P84 Neural Adhesion Molecule," J. Biol. Chem. 274:559-562 (1999).

Jones, et al., "Replacing the complementarity-determining regions in a human antibody with those from a mouse," Nature 321:522-525 1986.

Jones, T. D., et al., "The Development of a Modified Human IFN-ALPHA2B Linked to the FC Portion of Human IGG1 as a Novel Potential Therapeutic for the Treatment of Hepatitis C Virus Infection," J. of Interferon and Cytokine Rsch. 24:9:560-572 (2004).

Kakimoto, "Collagen-induced arthritis—characteristics of the animal model and implications for the treatment of autoimmune disease," Chin. Med. Sci. J. 6:78-83 (1991).

Kalinski, P., et al., "IL-4 Is a Mediator of IL-12p70 Induction by Human Th2 Cells: Reversal of Polarized Th2 Phenotype by Dendritic Cells," Am Assoc of Immunology 165: 1877-1881 (2000).

Kang, et al., "Linkage of recognition and replication functions by assembling combinatorial antibody Fab libraries along phage surfaces," Proc. Natl. Acad. Sci. USA 88:4363-4366 (1991).

Kim J-K, et al., "Localization of the Site of the Murine IGG1 Molecule that is Involved in Binding to the Murine Intestinal FC Receptor," European Jrnl of Immunology 24:10:2429-2434 (1994).

Kiriazis, et al., "Genetically engineered models with alterations in cardiac membrane calcium-handling proteins," Annu. Rev. Physiol. 62:321-351 (2000).

Koelemij, et al., "Bispecific antibodies in cancer therapy, from the laboratory to the clinic," J. Immunother. 22:514-524 (1999).

Kohler and Milstein, "Continuous cultures of fused cells secreting antibody of predefined specificity," Nature 256:495-497 (1976).

Kohler and Milstein "Derivation of specific antibody-producing tissue culture and tumor lines by cell fusion," Eur. J. Immunol. 6:511-519 (1976).

Kramer, et al., "The Gapped Duplex DNA Approach to Oligonucleotide-Directed Mutation Construction," Nucleic Acids Res. 12:9441-9456 (1984).

Kunkel, "Rapid and Efficient Site-Secific Mutagenesis Without Phenotypic Selection," Proc. Natl. Acad. Sci USA 82:488-492 (1985).

Kunkel, et al., "Rapid and Efficient Site-Specific Mutagenesis Without Phenotypic Selection," Methods Enzymol. 154:367-382 (1987).

Lam, "A new type of synthetic peptide library for identifying ligand-binding activity," Nature 354:82-84 (1991).

Lamy, et al., "CD47 and the 19 kDa Interacting Protein-3 (BNIP3) in T Cell Apoptosis," J. Biol. Chem 278:26:23915-23921 (2003).

Lam-Tse, et al., "Animal models of endocrine/organspecific autoimmune diseases: do they really help us to understand human autoimmunity?" Springer Semin. Immunopathol. 24:297-321 (2002).

Lankford, et al., "A unique role for IL-23 in promoting cellular immunity" J. Leukoc. Biol. 73:49-56 (2003).

Larrick, et al., Methods: A Companion to Methods in Enzymology 2:106 (1991).

Latour, S., et al., "Bidirectional Negative Regulation of Human T and Dendritic Cells by CD47 and its Cognate Receptor Signal-Regulation of IL-12 Responsiveness and Inhibition of Dendritic Cell Activation," J. of Immunology 167:5:2547-2554 (2001).

Lee, et al., "Modified Liposome Formulations for Cytosolic Delivery of Macromolecules," ACS Symp. Ser. 752:184-192 (2000).

Lindberg, et al., "Molecular Cloning of Integrin-Associated Protein: an Immunoglobulin Family Member with Multiple Membrane-Spanning Domains Implicated in Alpha v Beta 3-Dependent Ligand Binding," J. Cell Biol. 123:485-496 (1993).

Lindberg, et al., "Integrin-Associated Protein Immunoglobulin Domain is Necessary for Efficient Vitronectin Bead Binding," J. Cell Biol. 134:1313-1322 (1996).

Liu, et al., Signal Regulatory Protein (SIRPα), a Cellular Ligand for CD47, Regulates Neutrophil Transmigration, J. Biol. Chem 277:12:10028-10036 (2002).

Lonberg, et al., "Antigen-specific human antibodies from mice comprising four distinct genetic modifications," Nature 368:856 (1994).

Losman, et al., "Baboon anti-idiotype antibodies mimic a carcinoembrynic antigen epitope", Int. J. Cancer 46:310-314 (1990).

Lu, et al., "Homeostatic Regulation of the Immune System by Receptor Tyrosine Kinases of the Tyro 3 Family," Science 293:306-311 (2001).

Lund, et al., ""Multiple binding sites on the CH2 domain of IgG for mouse Fc gamma R11," Molecular Immunology," Mol. Immunol 29:53-59 (1992).

Lund, et al. "Human Fc gamma RI and Fc gamma RII interact with distinct but overlapping sites on human IgG," J. Immunol 147:2657-2662 (1991).

Luo, et al., "Expression of a fusion protein of scFv—biotin mimetic peptide for immunoassay," J. Bioteclmol 65:225 (1998).

Lutz, et al., "An advanced culture method for generating large quantities of highly pure dendritic cells from mouse bone marrow," J. Immunol Methods 223:77-92 (1999).

Manna, et al., "CD47 Mediates Killing of Breast Tumor Cells via Gi-Dependent Inhibition of Protein Kinase A," Cancer Res. 64:1026-1036 (2004).

Mannon, et al., "Anti-Interleukin-12 Antibody for Active Crohn's Disease," N. Engl. J. Med 351:2069 (2004).

Marvin, et al., "Recombinant approaches to IgG-like bispecific antibodies," Acta Pharmacol Sin 26:649-658 (2005).

Mateo, V., et al., "CD47 Ligation Induces Caspase-Independent Cell Death in Chronic Lymphocytic Leukemia," Nature 5:11:1277-1284 (1999).

Maurer, et al., "Lipid-Based Systems for the Intracellular Delivery of Genetic Drugs," Mol. Membr. Biol. 16:129-140 (1999).

McFadden and Barry "How Poxviruses Oppose Apoptosis," Virology 8:429-442 (1998).

McLafferty, et al., "M13 bacteriophage displaying disulfide-constrained microproteins," Gene 128:29-36 (1993).

Messmer, et al., "Specific blocking to improve biopanning in biological samples such as serum and hybridoma supernatants," Biotechniques 30:798-802 (2001).

Miller, et al., "Improved Retroviral Vectors for Gene Transfer and Expression." Biotechniques 7:980-990 (1989).

Miller, "Retrovirus Packaging Cells," Human Gene Therapy, 1:5-14 (1990).

Morrison, et al., "Chimeric human antibody molecules: mouse antigen-binding domains with human constant region domains," Proc Natl Acad Sci USA 81:6851-6855 (1984).

Motegi, et al., "Role of the CD47A-SHPS-1 system in regulation of cell migration," EMBO J. 22:2634-2344 (2003).

Mountain, et al., "Engineering antibodies for therapy," Biotechnol Genet Eng Rev 10:1-142 (1992).

Myers, et al., "Collagen-induced arthritis, an animal model of Autoimmunity," Life Sci. 61:1861-1878 (1997).

Nicholas, et al., "GeneDoc: Analysis and Visualization of Genetic Variation," EMBNEW News 4:14 (1997).

Nielsen, et al., "Identification of Prokaryotic and Eukaryotic Signal Peptides and Prediction of Their Cleavage Sites," Protein Engineering 10:1-6 (1997).

Nielsen, et al., In J. Glasgow et al., eds., Proc. Sixth Int. Conf. on Intelligent Systems for Molecular Biology 122-130 (AAAI Press 1998).

Nisonoff, et al., "Separation of univalent fragments from the bivalent rabbit antibody molecule by reduction of disulfide bonds," Arch. Biochem. Biophys. 90:230-244 (1960).

Okazawa, et al., "Negative Regulation of Phagocytosis in Macrophages by the CD47-SHPS-1 System," J. Immunol. 174:2004-2011 (2005).
Oldenborg, et al., "CD47-Signal Regulatory Protein α(SIRPα) Regulates Fcγ and Complement Receptor—mediated Phagocytosis" J. Exp. Med. 193:855-862 (2001).
Oppmann, et al., "Novel p19 Protein Engages IL-12p40 to Form a Cytokine, IL-23, with Biological Activities Similar as Well as Distinct from IL-12," Immunity 13:5:715-725 (2000).
Oshima, et al., "SHPS-1, a Multifunctional Transmembrane Glycoprotein," FEBS Lett. 519:1-8 (2002).
Padlan, et al., "Identification of specificity-determining residues in antibodies," FASEB 9:133-139 (1995).
Parkos, et al., "CD47 Mediates Post-Adhesive Events Required for Neutrophil Migration Across Polarized Intestinal Epithelia," J. Cell Biol. 132:437-450 (1996).
Pasqualini, et al., "Hybridoma-free generation of monoclonal antibodies," Proc. Natl. Acad. Sci. USA 101:257-259 (2004).
PCT/US91/04666 Search Report Dated Oct. 31, 1991.
PCT/US91/08694 Search Report Dated Mar. 10, 1992.
PCT/US94/08542 Search Report Dated Jan. 25, 1995.
PCT/US07/012234 Search Report Dated Feb. 8, 2008.
Peterson, "Advances in Monoclonal Antibody Technology: Genetic Engineering of Mice, Cells, and Immunoglobulins," ILAR J. 46:314-319 (2005).
Piwnica-Worms, "Expression of Proteins in Insect Cells Using Baculoviral Vectors," Section II, Chapter 16 in Short Protocols in Molecultar Biology, $2^{nd}$ Ed., Ausubel, et al., eds., (John Wiley & Sons 1992) pp. 16-32 to 16-48.
Pluckthun, et al., "Expression of functional antibody Fv and Fab fragments in *Escherichia coli*," Methods Enzymol 178:497-515 (1989).
Popkov, et al., "Rabbit Immune Repertoires as Sources for Therapeutic Monoclonal Antibodies: The Impact of Kappa Allotype-correlated Variation in Cysteine Content on Antibody Libraries Selected by Phage Display," J. Mol. Biol. 325:325-335 (2003).
Porter, et al., "The hydrolysis of rabbit g-globulin and antibodies with Crystalline Papain," Biochem. J. 73:119-127 (1959).
Probst, et al., "A Leishmania protein that modulates interleukin (IL)-12, IL-10 and tumor necrosis factor-alpha production and expression of B7-1 in human monocyte-derived antigen-presenting cells," Eur. J. Immunol. 27:2634-2642 (1997).
Rader, et al., "A phage display approach for rapid antibody humanization: Designed combinatorial V gene libraries," Proc Natl. Acad. Sci USA 95:8910-8915 (1998).
Rader, et al., "The Rabbit Antibody Repertoire as a Novel Source for the Generation of Therapeutic Human Antibodies," J. Biol. Chem 275:13668-13676 (2000).
Reinhold, et al., "In Vivo Expression of Alternatively Spliced Forms of Integrin-Associated Protein (CD47)," J. Cell Sci. 108:3419-3425 (1995).
Riechmann, et al., "Reshaping human antibodies for therapy," Nature 332:323-327 (1988).
Rosok, et al., "A Combinatorial Library Strategy for the Rapid Humanization of Anticarcinoma BR96 Fab ," J. Biol. Chem. 271:22611-22618 (1996).
Routledge, E. G. et al., "The Effect of Aglycosylaion on the Immunogenicity of a Humanized Therapeutic CD3 Monoclonal Antibody," 60:8:847-853 (1995).
Sanger, et al., "DNA sequencing with chain-terminating inhibitors," Proc. Natl. Acad. Sci. USA 74:5463-5467 (1977).
Sarmay, et al., Mapping and comparison of the interaction sites on the Fc region of IgG responsible for triggering antibody dependent cellular cytotoxicity (ADCC) through different types of human Fcγ receptor Mo. Immunol. 29:633-639 (1992).
Sastry, et al., "Cloning of the immunological repertoire in *Escherichia coli* for generation of monoclonal catalytic antibodies: construction of a heavy chain variable region-specific cDNA library," Proc. Natl. Acad. Sci USA 86:5728-5732 (1989).
Sauer, "Inducible Gene Targeting in Mice Using the Cre/lox System," Methods 14:381-392 (1998).
Scatchard, et al., "The Attraction of Proteins for Small Molecules and Icons," Ann. N.Y. Acad. Sci USA 51:660-672 (1949).
Schlebusch, et al., "Production of a single chain fragment (scFv) of the murine anti-idiotypic antibody ACA125 as phage-displayed and soluble antibody by recombinant phage antibody technique," Hybridoma 16:47-52 (1997).
Scott, et al., "Searching for peptide ligands with an epitope library," Science 249:386-390 (1990).
Seet, et al., "Poxviruses and Immune Evasion," Annu. Rev. Immunol 21:377-423 (2003).
Seiffert, et al., "Human Signal-Regulatory Protein Is Expressed on Normal, But Not on Subsets of Leukemic Myeloid Cells and Mediates Cellular Adhesion Involving Its Counterreceptor CD47," Blood 94 3633-3643 (1999).
Seiffert, et al., "Signal-regulatory protein α(SIRPα) but not SIRPβ is involved in T-cell activation, binds to CD47 with high affinity, and is expressed on immature $CD34^+CD38^-$ hematopoietic cells," Blood 97:2741-2749 (2001).
Selbo, et al., "Photochemical Internalisation Increase the Cytotoxic Effect of the Immunotoxin MOC31-Gelonin," Int. J. Cancer 87:853-859 (2000).
Selbo, et al., "Photochemical internalisation: a novel drug delivery system," Tumour Biol. 23:103-112 (2002).
Sensel, et al., "Amino acid differences in the N-terminus of CH2 influence the relative abilities of IgG2 and IgG3 to activate complement.," Mol. Immunol 34:1019-1029 (1997).
Shin, et al., "Production and properties of chimeric antibody molecules," Methods Enzyol. 178:459-476 (1989).
Siemers, et al., "Construction, Expression, and Activities of L49-sFv-β-Lactamase, a Single-Chain Antibody Fusion Protein for Anticancer Prodrug Activation," Bioconjug. Chem 8:510-519 (1997).
Skolnick et al., "From genes to protein structure and function: novel applications of computational approaches in the genomic era," Trends Biotechnol. 18(1):34-39 (2000).
Smith, et al., "Libraries of Peptides and Proteins Displayed of Filimentous Phage," Meth Enzymol 217:228-257 (1993).
Smith, et al., "Nucleotide sequence of the L-arabinose regulatory 189 region of *Escherichia coli* K12," J. Biol. Chem. 253:6931-6933 (1978).
Takasaki, et al., "Structure-based design and characterization of exocyclin peptidomimetics that inhibit TNFβ binding to its receptor," Nature Biotech 15:1266-1270 (1997).
Takeshi, O., et al., "Resistance of B16 Melanoma Cells to CD47-Induced Negative Regulation of Motility as a Result of Aberrant N-Glycosylation of SHPS-1," J. of Bio. Chem. 279:14:13711-13720 (2004).
Taneja, et al., "Lessons from animal models for human autoimmune diseases," Nat. Immunol 2:781-784 (2001).
Taylor, et al., "Human immunoglobulin transgenes undergo rearrangement, somatic mutation and class switching in mice that lack endogenous IgM," Int. Immun. 6:579-591 (1994).
Thommesen, et al., "Lysine 322 in the human IgG3 C(H)2 domain is crucial for antibody dependent complement activation," 86:319-324 (1995).
Thompson, et al., "CLUSTAL W: Improving the Sensitivity of Progressive Multiple Sequence Alignment Through Sequence Weighting, Position-Specific Gap Penalties and Weight Matrix Choice," Nucleic Acids Res. 22:4673-4680 (1994).
Ulmer, et al., "Heterologus protection against influenza by injection of DNA encoding viral protein," Science 259:1745-1749 (1993).
Vernon-Wilson, et al., "CD47 is a Ligand for Rat Macrophage Membrane Signal Regulatory Protein SIRP (OX41) and Human SIRPalpha 1," Eur. J. Immunol. 30:2130-2137 (2000).
Vlijmen, et al., "Diet-Induced Hyperlipoproteinemia and Atherosclerosis in Apolipoprotein E3 Leiden Transgenic Mice," J. Clin. Invest. 93:1403-1410 (1994).
Wakeland, et al., "Genetic Dissection of Systemic Lupus Erythematosus," Curr. Opin. Immunol 11:701-707(1999).
Wallace, et al., "Regulation of Inflammatory Responses by Oncostatin M ," J. Immunol 162:5547-5555 (1999).
Walls, et al., "Vectors for the expression of PCR-amplified immunoglobulin variable domains with human constant regions," Nucleic Acids Res. 21:2921-2929 (1993).

Wang, et al., "The Thrombospondin Receptor CD47 (IAP) Modulates and Associates with α2β1 Integrin in Vascular Smooth Muscle Cells," Mol. Bio. Cell 9:865-874 (1998).

Wang, et al., "Integrin-associated Protein Stimulates α2β1-dependent Chemotaxis via Gi-mediated Inhibition of Adenylate Cyclase and Extracellular-regulated Kinases," J. Cell Biol 147:389-400 (1999).

Ward, et al., "Genetic Manipulation and Expression of Antibodies," in Monoclonal Antibodies: Principles and Applications, Birch, et al., (eds.), p. 137 (Wiley-Liss, Inc. 1995).

Wen, et al., "In vivo evidence for the contribution of human histocompatibility leucocyte antigen (HLA)-DQ molecules to the development of diabetes," J. Exp. Med. 191:97-104 (2000).

Wiekowski, et al., "Ubiquitous Transgenic Expression of the IL-23 Subunit p19 Induces Multiorgan Inflammation, Runting, Infertility, and Premature Death," J. Immunol. 166:7563-7570 (2001).

Williams, et al., "Expression of foreign proteins in *E. coli* using plasmid vectors and purification of specific polyclonal antibodies," In: DNA Cloning 2: Expression Systems. Glover, et al. (eds.) p. 15-58 (Oxford University Press 1995).

Wines, et al., "The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A," J. Immunol 164:5313-5318 (2000).

Winter, et al., "Making Antibodies by Phage Display Technology," Annu. Rev. Immunol 12:433-455 (1994).

Wolff, et al., "Monoclonal Antibody Homodimers: Enhanced Antitumor Activity in Nude Mice Cancer Res,". 53:2560-2565 (1993).

Wright, et al., "Effect of glycosylation on antibody function: implications for genetic engineering," Trends Biotechnol 15:26-32 (1997).

Wu, et al., "Information Superhighway and Computer Databases of Nucleic Acids and Proteins," in Methods in Gene Biotechnology, 123-151 (CRC Press, Inc. 1997).

Zenz, et al., "Psoriasis-like skin disease and arthritis caused by inducible epidermal deletion of Jun proteins," Nature 437:369-375 (2005).

Zukermann, et al., "Discovery of Nanomolar Ligands for 7-Transmembrane G-Protein-Coupled Receptors from a Diverse N-(Substituted)glycine Peptoid Library," J. Med. Chem. 37:2678-2685 (1994).

U.S. Appl. No. 11/804,992 Office Action mailed Dec. 30, 2009.

U.S. Appl. No. 11/804,992 Office Action mailed Apr. 29, 2009.

* cited by examiner

Key:

*Signal Peptide Sequence*
Ig Domain Cysteine Loop
Intracellular
Extracellular
*Trans-Membrane*

```
           *  . :**      *       :::..**::*:* ****::*** : *       . *::**:
         --MLRVRILLIYLCT---FVVITSTKTIEYTACNDTIIIPCTIDN------PTKYIRWKL       Viral CD47
         MWPLVAALLLGSACCGSAQLLFNKTKSVEFTFCNDTVVIPCFVTNMEAQNTTEVYVKWKF       Human CD47

..::* *:: :  :.     ... .:***:.    * ..*.** :. .* :.  *.****  .
         DNHNILTYNKTSKTIILSKWHTSAKLHS--LSDNDVSLIIKYKDILP--GTYTCEDNTGI       Viral CD47
         KGRDIYTFDGALNKSTVPTDFSSAKIEVSQLLKGDASLKMDKSDAVSHTGNYTCEVTELT       Human CD47

:.     ::*   * ..**. :...*:.**. ::::*:: ::. ..::.    :   *
         KS---TVKLVQRHTNWFNDHHTMLMFIFTGITLFLLFLEIAYTSISVVFS---TNLGILQ       Viral CD47
         REGETIIELKYRVVSWFSPNENILIVIFPIFAILLFWGQFGIKTLKYRSGGMDEKTIALL       Human CD47

* *  :*::*  ;  **:**  *. ::*:: ** ::. .: :**: : :    *:. *
         VFGCIIAMIELCGAFLFYPSMFTLRHIIGLLMMTLPSIFLIITKVFSFWLLCKLSCAVHL      Viral CD47
         VAGLVITVIVIVGAILFVPGEYSLKNATGLGLIVTSTGILILLHYYVFSTAIGLTSFVIA      Human CD47

*:   *:  .***;*;**.*..:   *:   .*.**;***.  : ::: :.*::: ..*.*:
         IIYYQLAGYILTVLGLGLSLKECV--DGTLLLSGLGTIMVSEHFSLLFLVCFPSTQRDYY      Viral CD47
         ILVIQVIAYILAVVGLSLCIAACIPMHGPLLISGLSILALAQLLGLVYMKFVASNQKTIQ      Human CD47

--------------------                                              Viral CD47
         PPRKAVEEPLNAFKESKGMMNDE                                           Human CD47
```

MWPLVAALLLGSACCGSAQLLFNKTKSVEFTFCNDTVVIPCFVTNMEAQNTTEVYV
KWKFKGRDIYTFDGALNKSTVPTDFSSAKIEVSQLLKGDASLKMDKSDAVSHTGNYT
CEVTELTREGETIIELKYRVVSWFSPNENKTHTCPPCPAPELLGGPSVFLFPPKPKDT
LMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRWQQGNVFSC
SVMHEALHNHYTQKSLSLSPGK

Legend (color-coded):

- Leader
- N-terminal cysteine, purported to form disulfide bond with same cys in another CD47-Fc monomer, to stabilize dimeric structure.
- EC huCD47 Domain (Underlined is Ig disulfide loop, with intramolecular disulfide-linked cysteines in black bold)
- huIgG1 Fc(cys-asp deleted at N-terminus). No foreign residues anywhere.
- Cysteines involved in Fc disulfide bridges in bold plum
- Putative N-linked glycosylation sequences in bold green, carbohydrates would be located on asparagine (N)

CD47 RELATED COMPOSITIONS AND METHODS FOR TREATING IMMUNOLOGICAL DISEASES AND DISORDERS

CROSS REFERENCES TO RELATED APPLICATIONS

This application claims priority to U.S. Provisional Patent Application No. 61/144,695, filed Jan. 14, 2009, the contents of which are incorporated by reference. This application also claims priority to U.S. Provisional Patent Application No. 61/174,939, filed May 1, 2009. This application is also a continuation-in-part of U.S. patent application Ser. No. 11/804,992, filed May 15, 2007, abandoned, and this application claims priority to U.S. Provisional Patent Application No. 60/800,643, filed May 15, 2006, the contents of all of which are incorporated herein by reference.

BACKGROUND

1. Field

Provided herein are CD47 fusion polypeptides and related compositions that may be useful for treating immunological diseases and disorders, including autoimmune diseases and disorders. The fusion polypeptides described herein alter immunoresponsiveness of the immune cell, such as by inhibiting production of cytokines by the immune cell.

2. Description of the Related Art

Viruses, such as members of poxvirus families, have the capability to evolve and/or the capability to acquire genes from the host that modulate an immune response of the host to the virus and/or that facilitate viral replication (Bugert and Darai, *Virus Genes* 21:111 (2000); Alcami et al., *Semin. Virol.* 8:419 (1998); McFadden and Barry, *Semin. Virol.* 8:429 (1998)). A cellular component in the host that is a ligand for a viral virulence factor may, therefore, be an important immunomodulatory target. Poxviruses form a group of double-stranded DNA viruses that replicate in the cytoplasm of a cell and that have adapted to replicate in numerous different hosts. Poxviruses, including variola virus, the causative agent of smallpox, and vaccinia virus, a prototype poxvirus widely used as a smallpox vaccine, have large genomes of nearly 190 kilobases, which could potentially encode more than 200 proteins (see, e.g., Goebel et al., *Virology* 179:247 (1990)).

Identification of poxvirus virulence factors that are capable of suppressing the host's immune system is useful for identifying cellular polypeptides that are effectors or modulators of an immune response and that can be modulated in a manner that is beneficial for treating immunological disorders, such as, for example, inflammatory diseases and autoimmune diseases, including multiple sclerosis, rheumatoid arthritis, and systemic lupus erythematosus (SLE).

Immunological diseases and disorders afflict more than twenty million people in the United States. Many immunological diseases are debilitating and chronic and thus affect a patient's productivity, well-being, as well as general health. A need exists to identify and develop compositions that can be used for treatment and prophylaxis of such immunological diseases and disorders.

BRIEF DESCRIPTION OF THE DRAWINGS

FIG. 1 presents a schematic of human CD47 expressed on a cell surface and a viral CD47-like polypeptide expressed on a cell surface.

FIG. 2 presents an alignment of human CD47 (SEQ ID NO:9) (GenBank Accession No. NP_001768.1) with vCD47 (SEQ ID NO:3) from Variola minor virus. The asterisk (*) indicates amino acid identity between the sequences and ":" indicates amino acid similarity. The cysteine residues that form an intramolecular disulfide bond are indicated in boldface type. The key indicates that the amino acids of the signal peptide of each polypeptide are italicized; the Ig domain cysteine loop is indicated by a single underline; the intracellular portions of the transmembrane portion (shaded in gray) and the intracytoplasmic tail are indicated by double underlining; and the extracellular portion of the transmembrane portion of the CD47 and viral CD47-like polypeptides are indicated by bold underlining.

FIGS. 3A and 3B show that a human CD47 extracellular domain-Fc fusion polypeptide (CD47-hFc) inhibits *Staphylococcus aureus* Cowan strain (SAC)-induced TNF-alpha (TNF-α) (FIG. 3A) and IL-12p70 (FIG. 3B) production in human dendritic cells. Eight day-old human monocyte-derived DC ($2\times10^4$ cells/96-well) from three donors were treated with the indicated concentrations of hCD47-Fc and human IgG (IgG) in the presence of IFN-γ. Then, the dendritic cells were stimulated with 0.01% SAC. TNF-α and IL12p70 concentrations were determined in supernatants removed from the cells after 18 h.

FIG. 4 illustrates the concentration of TNF-α in supernatants from DCs stimulated with HuS-SAC (human sera-SAC). Eight day-old human monocyte-derived DC ($2\times10^4$ cells/96-well) were treated with the indicated concentrations of hCD47-Fc and hFc-Stub in the presence of IFN-γ. Then, DC were stimulated with 0.01% PBS-SAC or 0.01% HuS-SAC. TNF-α was determined in supernatants removed from the cultures after 18 h.

FIG. 5 illustrates the concentration of IL-23 in supernatants from DCs stimulated with HuS-SAC (human sera-SAC). Eight day-old human monocyte-derived DC ($2\times10^4$ cells/96-well) were treated with the indicated concentrations of hCD47-Fc and hFc-Stub (lacking the CD47 moiety) in the presence of IFN-γ. Then, DC were stimulated with 0.01% FBS (fetal bovine sera)-SAC or 0.01% HuS-SAC. IL-23 was determined in supernatants removed from the cultures after 18 h.

FIG. 6 illustrates that a human CD47 extracellular domain-Fc polypeptide fusion polypeptide (hCD47-Fc) inhibited IgG-mediated TNF-α production in human dendritic cells. Human dendritic cells were combined with hCD47-Fc or hFc-Stub in 96-well plates that had previously been coated with anti-human Fc donkey IgG (right side: immobilized hCD47-Fc) or human dendritic cells were combined with hCD47-Fc or hFc-Stub in the absence of donkey IgG (left side: soluble hCD47-Fc). The dendritic cells were stimulated with 0.1 ng/ml FSL-1 and the presence of TNF-α in the cell supernatants was determined.

FIG. 7 shows human CD47 extracellular domain-Hac polypeptide (non-immunoglobulin) fusion polypeptide (hCD47-Hac) inhibited IgG-mediated TNF-α production in human dendritic cells. Human dendritic cells were combined with hCD47-Hac or a control construct (gluc-Hac: Gaussia luciferase-Hac) in 96-well plates that had previously been coated with mouse IgG (right side: 50 μg/ml mouse IgG) or human dendritic cells were combined with hCD47-Hac or gluc-Hac in the absence of mouse IgG (left side: no mouse IgG). The dendritic cells were stimulated with 0.1 ng/ml FSL-1 and the presence of TNF-α in the cell supernatants was determined.

FIG. 8 presents the effect of a murine CD47 extracellular domain-murine Fc polypeptide fusion protein on cytokine production of stimulated murine dendritic cells. After activating 9 day-old bone marrow-derived DC (2×10⁴/well) with IFN-γ (1000 U/ml) overnight, cells were treated for 1 h with the indicated concentrations of mCD47-Fc and mIgG2a. Then, DC were stimulated with 0.01% IgG2a-SAC. The level of TNF-α and IL-12 was determined in supernatants removed from the cells after 18 h.

FIG. 9 presents the effect of mCD47-Fc in a murine model of collagen antibody induced arthritis (CAIA). PBS, mIgG (500 µg), or mCD47-mFc (500 µg) was administered intravenously to male DBA/1J mice on days 0, 2, 4, 6, and 8. 4 mg of ArthitoMAB™ antibody cocktail was administered intravenously on Day 0. Mice were boosted intraperitoneally with 50 µg of LPS on days 6 and 13.

FIG. 12 shows mature amino acid sequence of hCD47-Fc highlighting important features.

Figure 24:
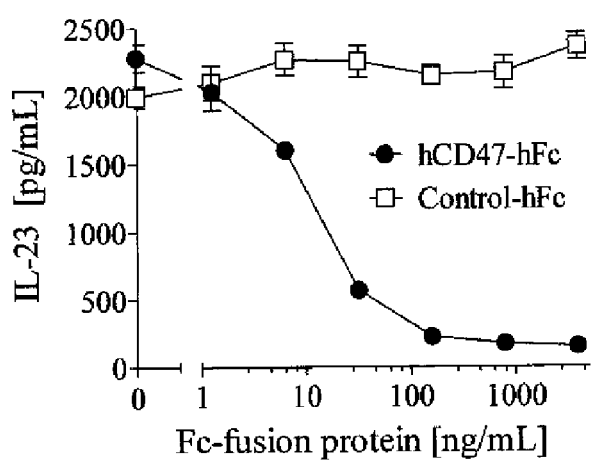

FIG. 24 shows hCD47-inhibits *Staphylococcus aureus*-induced IL-23 production in human dendritic cells. DCs were treated for 2 h with the indicated concentrations of hCD47-hFc (closed circles) and control-Fc (open squares) in the presence of IFN-γ (1000 U/ml). Then, DCs were stimulated with 0.01% SAC. Data shown are the mean (±SEM, n=6). p<0.0001 two way ANOVA.

Figure 25:
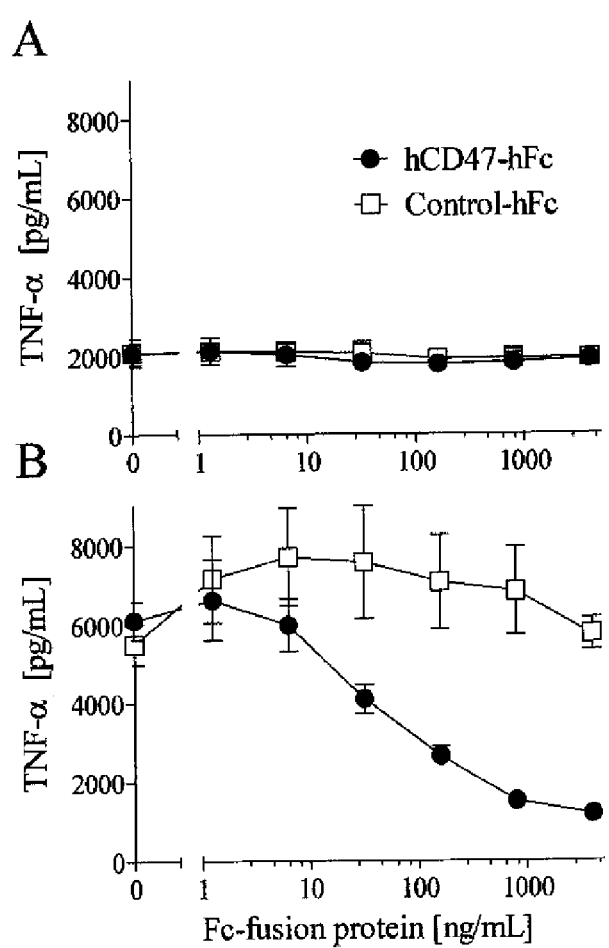

FIG. 25 illustrates that immobilized hCD47-hFc inhibits IgG induced TNF-α production in human DC. (A) After incubating hCD47-hFc and control-Fc at the indicated concentrations for 2 h in 96-well plates coated with 2.5 µg donkey anti human Fc, plates were flicked DCs were added in the presence of IFN-γ (1000 U/ml). (B) Alternatively, DCs were seeded into wells containing soluble hCD47-hFc and control-Fc, respectively without adding plate bound IgG. After 2 h incubation, DCs were stimulated with 100 ng/mL FSL-1. (A, B). hCD47-hFc, close circles; control-Fc, open squares. Data shown are the mean (±SEM, n=6). (A) p<0.0001 two way ANOVA.

Figure 26:
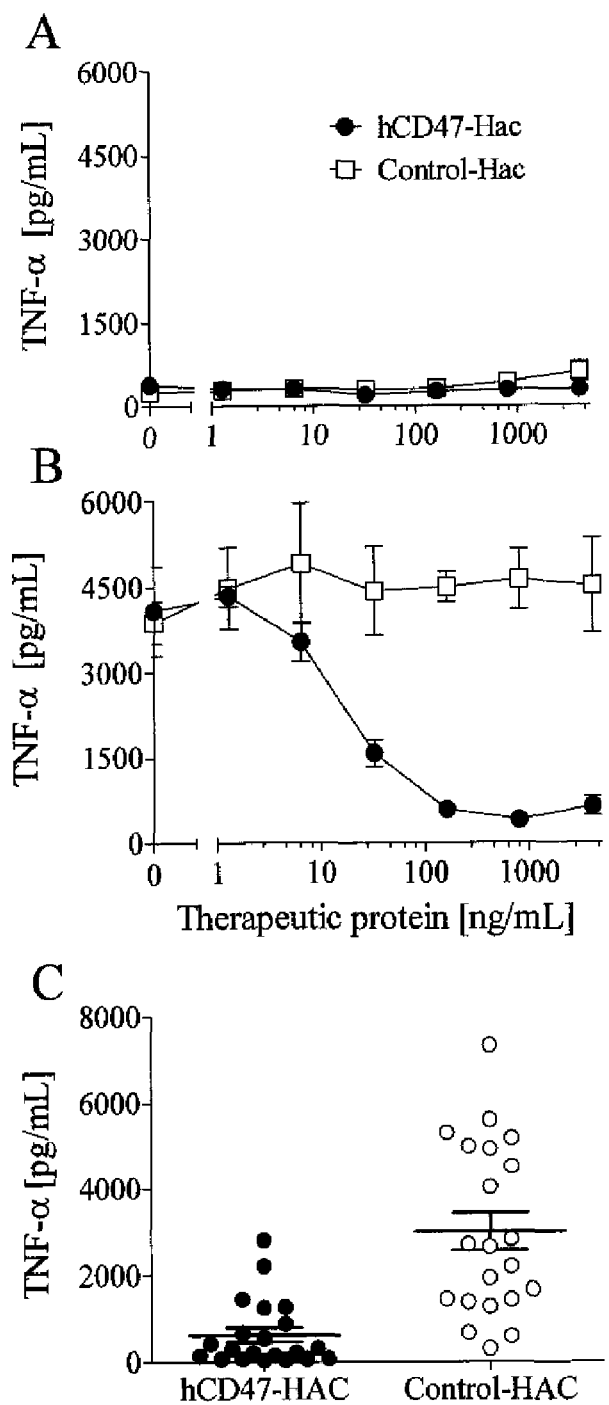

FIG. 26 shows CD47-HAC inhibits IgG mediated activation of human DCs. After incubating hCD47-HAC (closed circles) and control-HAC (open squares) at the indicated concentrations for 2 h in 96-well plates coated with 2.5 µg of transferrin (A) or human IgG (B) DCs were added in the presence of IFN-γ (1000 U/ml). After 2 h incubation, DCs were stimulated with 0.1 ng/mL FSL-1. (A, B). Data shown are the mean (±SEM, n=6). (A) p<0.0001 two way ANOVA. (C) Inhibition of IgG induced TNF-α production in DC from healthy study subjects by hCD47-HAC. After incubating 800 ng/mL hCD47-HAC and control-HAC for 1 h in 96-well plates coated with human IgG DCs were added in the presence of IFN-γ (1000 U/ml). After 2 h incubation, DCs were stimulated with 0.1 ng/mL FSL-1. Data shown were obtained for DCs from 21 healthy study subjects. Shown is the individual TNF-α production and the mean (±SEM) for each group. p<0.0001 two-tailed paired t-test.

Figure 27:
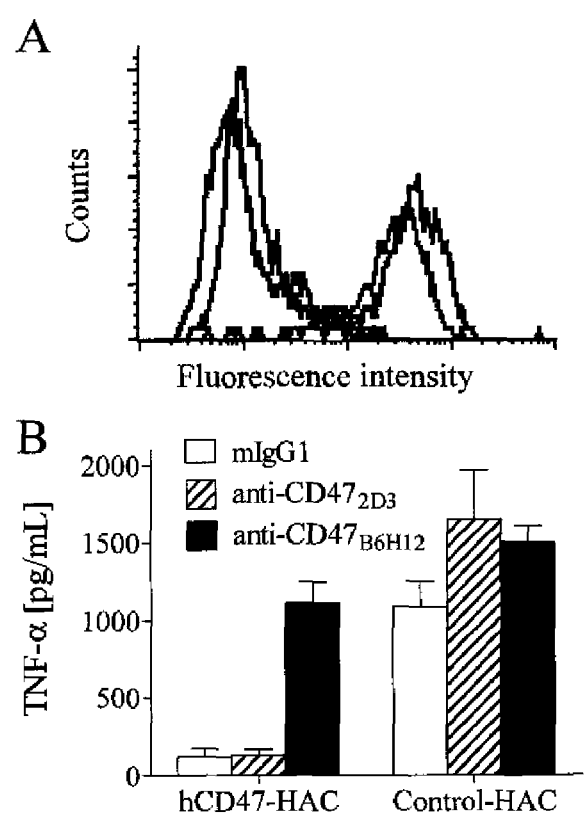

FIG. 27 shows CD47-fusion protein mediated inhibition of IgG-induced TNF-α production is dependent on CD47/SIRPα interaction. (A) HEK293T cells transfected with full-length human SIRPα were stained with different hCD47-HAC (2 µg/mL) preparations. Before staining hCD47-HAC (800 ng/mL) was incubated with either 10 µg/mL anti-human CD47 mAb B6H12 (red line), anti human CD47 mAb 2D3 (green line) or with murine isotype control (blue line) for 1 h. Similar treatment with control-HAC was used as control for staining (black line). Following the primary stain, cells were washed and stained with PE-conjugated streptavidin. Samples were subsequently analyzed by flow cytometry.

(B) CD47-HAC and control HAC (800 ng/mL) were treated with either 10 µg/mL anti-human CD47 mAb B6H12 (black bars), anti human CD47 mAb 2D3 (hatched bars) or with murine isotype (open bars) for 2 h. Then, after incubating the respective hCD47-HAC and control-HAC samples for 2 h in 96-well plates coated with human IgG human DCs were added in the presence of IFN-γ (1000 U/ml). After 2 h incubation, DCs were stimulated with 0.1 ng/mL FSL-1. Data shown is the mean (n=6) and SEM. B6H12 treatment had a significant effect on CD47-HAC activity (p<0.001 Tukey's multiple comparison test)

Figure 28:
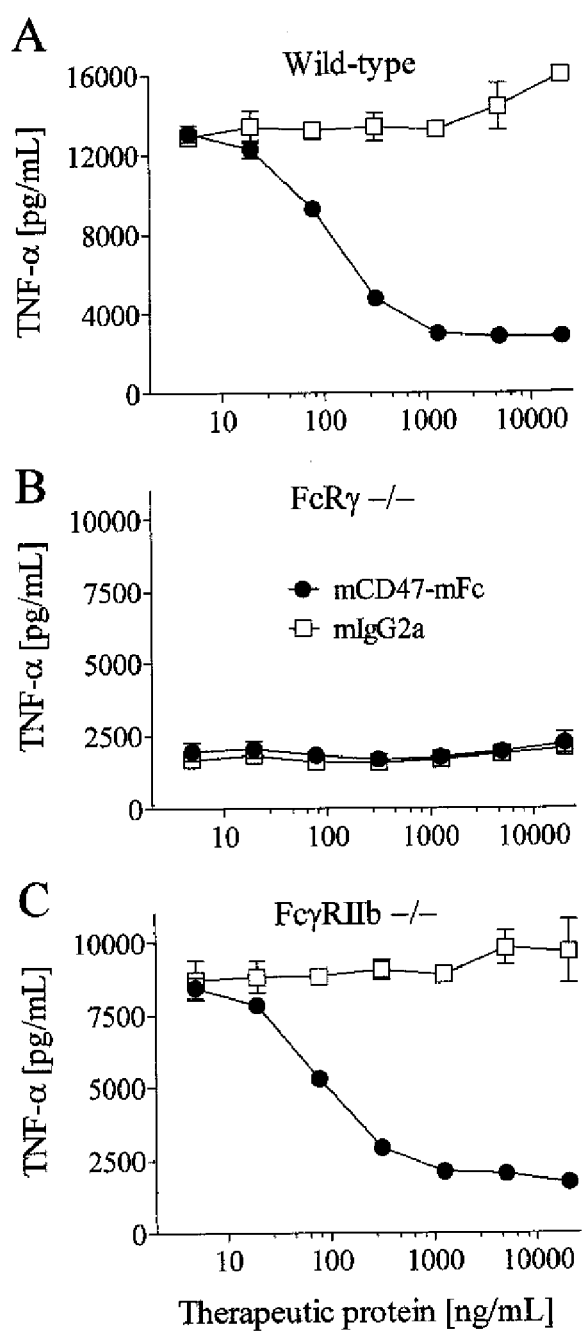

FIG. 28 illustrates mCD47-mFc inhibits FcγR mediated activation of murine DC. Bone marrow-derived IFN-γ-activated DCs, were treated for 1 h with the indicated concentrations of mCD47-mFc (close circles) and mIgG2a (open squares). Then, DCs were stimulated with 0.01% SAC-mIgG2a. DCs were generated from bone marrow of BALB/c wildtype (A), BALB/c FcRγ−/− (B) and BALB/c FcγRIIb−/− mice (C) by IL-4 and GMCSF treatment. SAC-mIgG2a was generated by incubating SAC particles for 1 h with murine IgG2a. (A-C) Data shown are the mean (±SEM, n=6). (A, C) p<0.0001 two way ANOVA.

Figure 29:
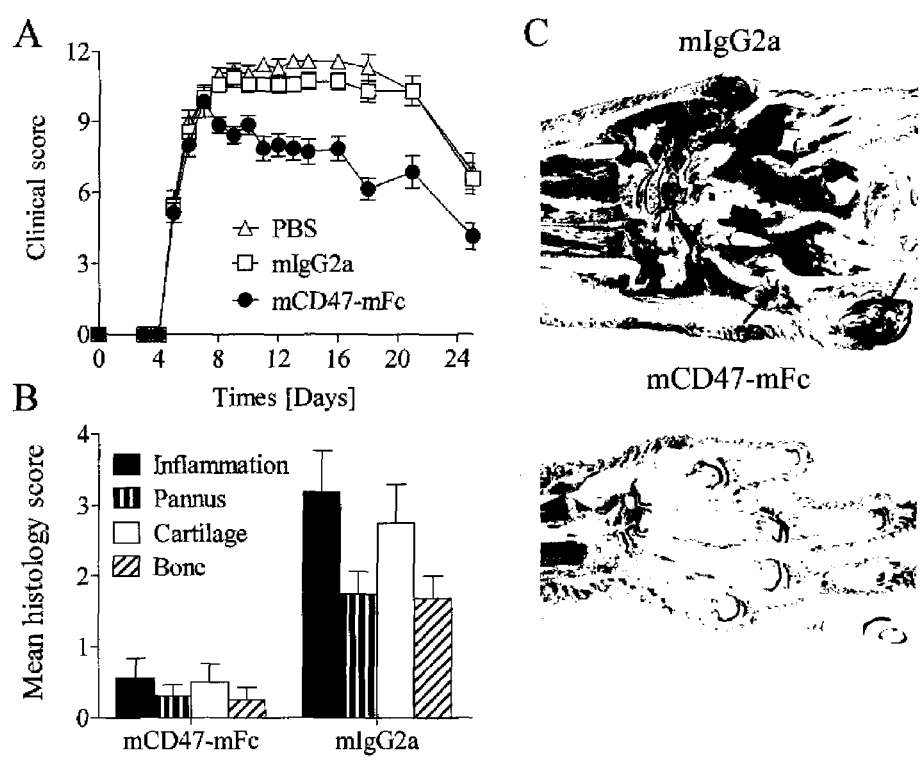

FIG. 29 shows mCD47-mFc ameliorates clinical and histological signs of disease in CAIA (A) Arthritis was induced in DBA/1 mice (n=7 per treatment group) by injection of 2 mg of anti CII Ab cocktail i.v. at day 0 and injection of 50 µg LPS on day 3. Mice were dosed on days 0, 3, 5, 7 and day 10 with mCD47-mFc (500 µg per dose, close circles), mIgG2a (500 µg per dose, open squares) or PBS (open triangles). Clinical scores of 0 to 3 were assigned over 24 days as described in material and methods. Error bars represent SEM. p<0.001 mCD47-mFc compared to IgG2a control as determined by a repeated measure 2-way ANOVA. (B) Mice (n=4 per treatment group) were treated as described above. On day 11 paws were collected for histological examination. Inflammation (black bar), pannus formation (lined bar), cartilage damage (open bar) and bone resorption (hatched bar) was scored by a scale from 0 to 5. Data shown are the mean histology score of 4 mice. Error bars represent SEM. p<0.01 inflammation, pannus; and bone resorption; p<0.05 cartilage. (C) Representative micrographs of histological findings. (Top) Right fore paw of mouse treated with mIgG2a shows severe inflammation (score of 5) and marked cartilage damage (4) with moderate pannus (3) and bone resorption (3). All joints are affected. Arrows show representative affected joints. W identifies wrist. (Bottom) Left fore paw of mouse treated with mCD47-mFc shows no inflammation, cartilage damage, pannus or bone resorption.

DETAILED DESCRIPTION

Described herein are fusion polypeptides that comprise a CD47 extracellular domain polypeptide, or a variant thereof, fused to an immunoglobulin Fc polypeptide, including a human IgG1 Fc polypeptide. The CD47-Fc polypeptide fusion polypeptides described herein are capable of altering the immunoresponsiveness of an immune cell. The CD47-Fc polypeptide fusion proteins described herein, may modulate or alter the immune response of a host, and may particularly inhibit, suppress, or decrease the extent of, an immune response exhibited in an immunological disease or disorder, for example, an inflammatory or autoimmune disease or disorder. In certain embodiments, the CD47-Fc polypeptide fusion proteins inhibit cytokine and/or chemokine production by immune cells, which reduces the inflammatory response of the immune cells.

The CD47-Fc polypeptide fusion proteins described herein may be capable of interacting with a CD47 ligand that is present on the cell surface of an immune cell, and thereby stimulating or inducing the CD47 ligand to deliver a signal to the immune cell, resulting in activation of one or more biological functions of the cell. Such CD47 ligands include but are not limited to SIRP-α, SIRP-beta-2, thrombospondin-1, $\alpha_v\beta_3$ integrin, and $\alpha_2\beta_1$ integrin, which are described in greater detail herein.

In particular embodiments, the fusion polypeptides are capable of inhibiting Fc-mediated activation of an immune cell, and thus may inhibit cytokine and/or chemokine production of immune cells, particularly immune cells that express a CD47 ligand on the cell surface. An Fc-mediated activity includes immune complex-induced immunoresponsiveness of an immune cell. As described herein, the presence of an immune complex (i.e., an antigen-antibody complex) interacting with the immune cell activates the immune cell and induces cytokine production by the immune cell, which can be inhibited by the CD47-Fc fusion polypeptides described herein. Immune complexes can damage tissue by triggering Fc-receptor mediated inflammation, a process implicated in several human immunological diseases, for example, systemic lupus erythematosus, rheumatoid arthritis, and Sjoergen's syndrome. Thus, the fusion polypeptides described herein may be useful for altering immunoresponsiveness of an immune cell and thereby may be useful for treating or preventing an immunological disease or disorder, cardiovascular disease or disorder, metabolic disease or disorder, or a proliferative disease or disorder.

The extracellular CD47 domain moiety of the fusion polypeptide includes a CD47 extracellular domain variant. An exemplary variant comprises the extracellular domain of human CD47 that is truncated or that comprises at least one substitution, insertion, or deletion of an amino acid in the extracellular domain. In other certain embodiments, two fusion polypeptides form a dimer. The two fusion polypeptides dimerize, at least in part, via one or more interchain disulfide bonds between the Fc polypeptide moieties of each of two fusion polypeptides. As described in greater detail herein a fusion polypeptide may also dimerize via the CD47 moieties of each of the two fusion polypeptides, via the formation of an interchain disulfide bond between cysteine residues of the CD47 moieties.

As described herein, a CD47-Fc polypeptide fusion polypeptide may be useful for treating or preventing, inhibiting, slowing the progression of, or reducing the symptoms associated with, an immunological disease or disorder, a cardiovascular disease or disorder, a metabolic disease or disorder, or a proliferative disease or disorder. An immunological disorder includes an inflammatory disease or disorder and an autoimmune disease or disorder. While inflammation or an inflammatory response is a host's normal and protective response to an injury, inflammation can cause undesired damage. For example, atherosclerosis is, at least in part, a pathological response to arterial injury and the consequent inflammatory cascade. A cardiovascular disease or disorder that may be treated, which may include a disease or disorder that is also considered an immunological disease/disorder, includes for example, atherosclerosis, endocarditis, hypertension, or peripheral ischemic disease. A metabolic disease or disorder includes diabetes, obesity, and diseases and disorders associated with abnormal or altered mitochondrial function.

An immunological disease or disorder may be an autoimmune disease or an inflammatory disease. In certain embodiments, the immunological disease or disorder is multiple sclerosis, rheumatoid arthritis, a spondyloarthropathy, systemic lupus erythematosus, graft versus host disease, an antibody-mediated inflammatory or autoimmune disease or disorder, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, or inflammatory autoimmune myositis. A spondyloarthropathy includes, for example, ankylosing spondylitis, reactive arthritis, enteropathic arthritis associated with inflammatory bowel disease, psoriatic arthritis, isolated acute anterior uveitis, undifferentiated spondyloarthropathy, Behcet's syndrome, and juvenile idiopathic arthritis. The fusion polypeptides described herein may also be useful for treating a cardiovascular disease or disorder, such as atherosclerosis, endocarditis, hypertension, or peripheral ischemic disease. In other certain embodiments, the fusion polypeptides described herein may be used for treating a proliferative disease, such as cancer. A cancer or malignancy includes, but is not limited to, a leukemia (e.g., B-cell chronic lymphocytic leukemia), lymphoma, breast cancer, renal cancer, and ovarian cancer.

Figure 1:
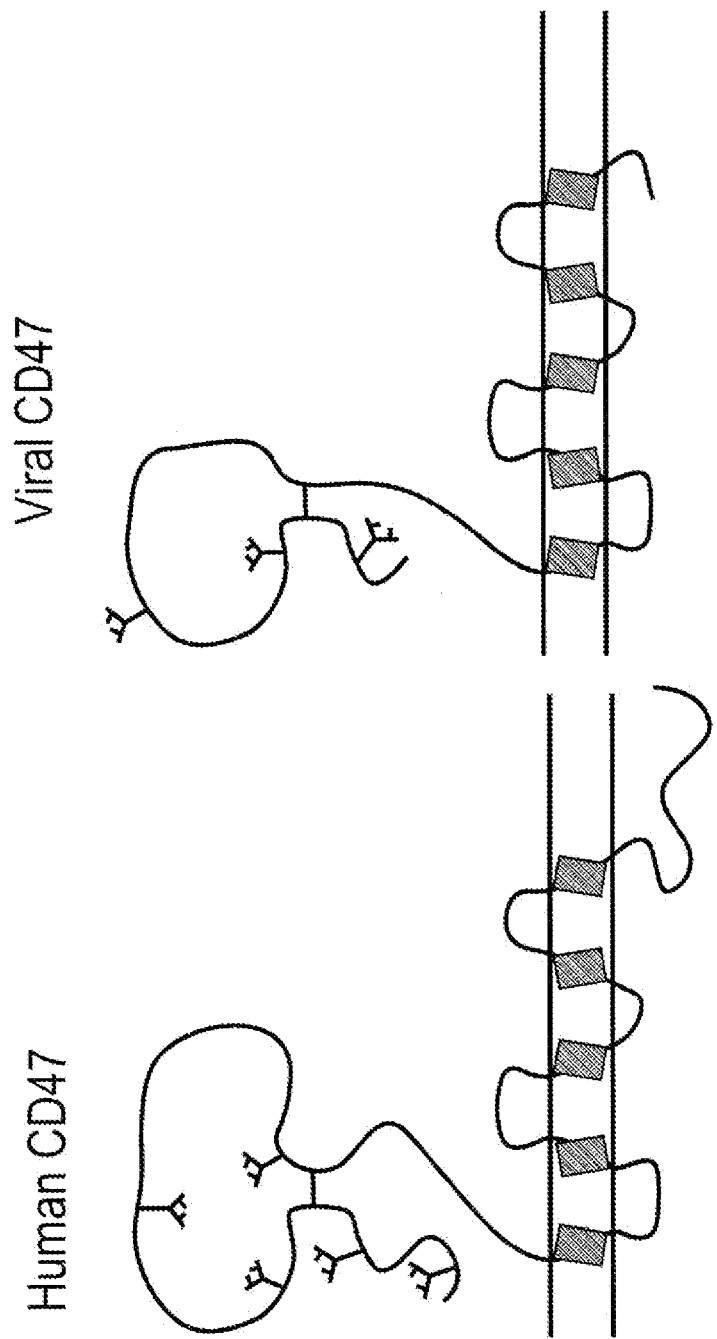

Also described herein are methods for identifying and making CD47 extracellular domain variants that are capable of altering an immune response and the immunoresponsiveness of an immune cell. Such methods include determining interactions among CD47 ligands and a viral virulence factor that is a CD47 ortholog. Viruses have evolved numerous mechanisms to evade detection and elimination by the immune system of an infected host by encoding proteins that are viral homologues of cell cytokines and chemokines and their receptors. For example, the genomes of poxviruses encode a soluble viral tumor necrosis factor (TNF) receptor, which binds to and inhibits the inflammation-inducing cytokine, TNF. Other cellular polypeptides targeted by viral polypeptides or that are homologues of viral polypeptides include interleukin 1, various chemokines, CD30, and CD47. Genes that encode a CD47-like polypeptide have been identified in certain poxvirus family members including orthopoxvirus, capripoxvirus, leporipoxvirus, suipoxvirus, and yatapoxvirus (see, e.g., Cameron et al., *Virology* 264:298-318 (1999); Cameron et al., *Virology* 337:55-67 (2005); Alfonso et al., *J. Virol.* 79:966-977 (2005); Seet et al., *Annu. Rev. Immunol.* 21:377-423 (2003)). This CD47-like polypeptide virulence factor is referred to herein as viral CD47 (vCD47). In certain embodiments, as described in greater detail herein, the fusion polypeptides comprising CD47 extracellular domain, or a variant thereof, alter an immune response by interacting with at least one CD47 ligand in the same manner as viral CD47 interacts with the CD47 ligand.

CD47

CD47 (also known in the art as integrin-associated protein (IAP)) is a mammalian cell surface receptor glycoprotein of approximately 50 kiloDaltons (kD). Structurally, CD47 has an extracellular Ig-like domain, five transmembrane portions, and a short cytoplasmic domain (see FIG. 1 and FIG. 2). CD47 is associated with $\beta_3$ and $\beta_1$ integrins, primarily $\alpha_v\beta_3$ integrin, which is the vitronectin receptor, and with $\alpha_2\beta_1$, which is a collagen and laminin receptor. CD47 is involved with several cellular processes including, for example, neutrophil phagocytosis, T cell activation, T and B cell apoptosis, platelet activation, stroma-supported erythropoiesis, immune cell (e.g., neutrophils) transmigration, and cell adhesion (see, e.g., Latour et al., *J. Immunol.* 167:2547-54 (2001); Fukunaga et al., *J. Immunol.* 172:4091-99 (2004); Parkos et al., *J. Cell Biol.* 132:437-50 (1996); Liu et al., *J. Biol. Chem.* 277:10028-36 (2002); Lamy et al., *J. Biol. Chem.* 278:23915-21 (2003); Cooper et al., *Proc. Natl. Acad. Sci. USA* 92:3978-82 (1995); Motegi et al., *EMBO J.* 22:2634-44 (2003); Manna et al., *Cancer Res.* 64:1026-36 (2004); PCT International Publication No. WO 99/40940; PCT International Publication No. WO 97/27873).

Human CD47 may be present on the surface of a cell as one of four major isoforms (Reinhold et al., *J. Cell Sci.* 108:3419-25 (1995)). Exemplary CD47 nucleotide sequences and the amino acid sequences of the encoded CD47 polypeptides are provided in publicly available databases (see, e.g., GenBank Accession No. NP_001768.1 (SEQ ID NO:9), isoform 1 (see also GenBank Accession No. NM_001777.3 (SEQ ID NO:14)); GenBank Accession No. NP_942088.1 (SEQ ID NO:15), isoform 2 (see also GenBank Accession No. NM_198793.2 (SEQ ID NO:16)); GenBank Accession No. NP_001020250.1 (SEQ ID NO:17), isoform 3 (see also GenBank Accession No. NM_001025079.1 (SEQ ID NO:13)); see also, e.g., GenBank Accession Nos. BT006907.1; BC012884.1; BC010016.2; BC037306.1; BC045593.1; BC053959.1; and BC042889.1). The isoforms are splice variants mapping in the intracytoplasmic domain (see, e.g., Lindberg et al., *J. Cell Biol.* 123:485-96 (1993). Nucleotide sequences that encode CD47 of other mammals, including murine and rat CD47, and CD47 polypeptide sequences of other mammals are also known in the art and readily available to persons skilled in the art in sequence databases (e.g., GenBank, Swissprot, and the like).

Each of the exemplary CD47 sequences provided herein may comprise a nucleotide sequence that encodes a signal peptide. By way of example, the signal peptide of certain human CD47 isoforms is reported to be eighteen amino acids (see, e.g., SEQ ID NO:11). Signal peptides are not exposed on the cell surface of a secreted or transmembrane protein because either the signal peptide is cleaved during translocation of the protein or the signal peptide remains anchored in the outer cell membrane (such a peptide is also called a signal anchor) (see, e.g., Nielsen et al., *Protein Engineering* 10:1-6 (1997); Nielsen et al., in J. Glasgow et al., eds., *Proc. Sixth Int. Conf. on Intelligent Systems for Molecular Biology,* 122-30 (AAAI Press 1998)). The signal peptide sequence of CD47 is believed to be cleaved from the precursor CD47 polypeptide in vivo. Cleavage of a signal peptide, whether the signal peptide is a specific CD47 signal peptide or a heterologous signal peptide, may be imprecise such that the N-terminal amino acid residue may vary.

CD47 is expressed by cells in many different tissues. CD47 is expressed on most, if not all, hematopoietic cells, including thymocytes, T and B cells, monocytes, platelets, and erythrocytes. CD47 is also expressed on epithelia cells, endothelial cells, fibroblasts, sperm, certain tumor cell lines, mesenchymal cells, and certain neuronal cells.

CD47 Fusion Polypeptides
CD47 Extracellular Domain and Variants Thereof

In one embodiment, a CD47 fusion polypeptide comprises a CD47 extracellular domain variant fused to a moiety capable of multimer formation (e.g., dimer formation), including for example, an Fc polypeptide. Described herein are CD47 fusion polypeptides that comprise the extracellular domain of CD47, or a variant thereof, fused to an Fc polypeptide (and variants thereof), as described herein, and that may be used for altering the immunoresponsiveness of an immune cell and for treating immunological diseases and disorders. Alternatively, a fusion polypeptide comprising the extracellular domain of CD47 may be fused to another moiety that is capable of multimer formation. In other particular embodiments, the extracellular domain of CD47 may be fused to a heterologous moiety, wherein that moiety is incapable of multimer formation with another CD47 fusion polypeptide comprising the same moiety. In yet another embodiment, a CD47 fusion polypeptide comprising the extracellular domain of CD47 fused to a first heterologous polypeptide such as a first Fc polypeptide, may be combined with a second CD47 fusion polypeptide comprising the extracellular domain of CD47 fused to a second heterologous polypeptide, such as a second Fc polypeptide, such that the two different fusion polypeptides form heterodimers or heteromultimers.

An Fc polypeptide, or portion thereof (such as at least one immunoglobulin constant region domain, for example, the CH2 domain or CH3 domain) when fused to a peptide or polypeptide of interest acts, at least in part, as a vehicle or carrier moiety that prevents degradation and/or increases half-life, reduces toxicity, reduces immunogenicity, and/or increases biological activity of the peptide such as by forming dimers or other multimers (see, e.g., U.S. Pat. Nos. 6,018,026; 6,291,646; 6,323,323; 6,300,099; 5,843,725). (See also, e.g., U.S. Pat. No. 5,428,130; U.S. Pat. No. 6,660,843; U.S. Patent Application Publication Nos. 2003/064480; 2001/053539; 2004/087778; 2004/077022; 2004/071712; 2004/057953/ 2004/053845/2004/044188; 2004/001853; 2004/082039). Alternative moieties to an immunoglobulin constant region, such as an Fc polypeptide, that may be linked or fused to a CD47 extracellular domain and that contribute to retention of the capability of the CD47 moiety to alter the immunoresponsiveness of an immune cell include, for example, a linear polymer (e.g., polyethylene glycol, polylysine, dextran, etc.; see, for example, U.S. Pat. No. 4,289,872; International Patent Application Publication No. WO 93/21259); a lipid; a cholesterol group (such as a steroid); a carbohydrate or oligosaccharide. In addition, also contemplated and described herein, a CD47 moiety from one species may be fused to an Fc polypeptide (or other heterologous polypeptide moiety) derived from a different species.

In other certain particular embodiments, for example, when more rapid clearance or increased half life of a CD47 extracellular domain (or dimer or other multimer thereof) may be desirable, the CD47 extracellular domain as a monomer or as a dimer or other multimeric form may be used. Thus in these embodiments, the CD47 extracellular domain is not fused to a heterologous moiety.

Isoforms of CD47 have been identified, and the amino acid sequences of several different isoforms have been deduced. The isoforms of CD47 differ from each other primarily in the amino acid sequence of the intracellular portion of CD47. The amino acid sequences of the extracellular portion (also herein called the extracellular domain) of different CD47 isoforms, such as the exemplary isoforms described herein, are highly similar, and in certain exemplary CD47 polypeptides, the amino acid sequences of the extracellular domains of different CD47 isoforms are identical.

In one embodiment, an exemplary fusion polypeptide comprises the extracellular domain of human CD47 fused to a human IgG1 Fc polypeptide. Typically, in the immunoglobulin art, an Fc polypeptide comprises the hinge region that is between the CH1 and CH2 domains. The hinge region comprises cysteine residues that form interchain disulfide bonds between two immunoglobulin chains (one cysteine residue of a heavy chain forms a disulfide bond with a cysteine residue in the light chain and the remaining cysteine residues in the hinge contribute to disulfide bond formation between two heavy chains). In human IgG1 immunoglobulins, the hinge portion of the constant region has three cysteine residues. In certain embodiments, the Fc polypeptides described herein comprise a substitution or a deletion of a cysteine residue in the hinge region. In a particular embodiment, the substituted or deleted cysteine residue is the cysteine residue most proximal to the amino terminus of the hinge region of the Fc portion of a wildtype human IgG1 immunoglobulin. The Fc polypeptide may further comprise a substitution or deletion of an aspartate residue immediately adjacent to the cysteine residue most proximal to the amino terminus of the hinge region of the Fc portion of a wildtype human IgG1 immunoglobulin. The amino acid sequences of the hinge region from IgG1 immunoglobulins, and other human immunoglobulins as well as from other species, are readily available in public databases and also are described in Kabat et al. (in *Sequences of Proteins of Immunological Interest,* 4th ed (U.S. Dept. of Health and Human Services, U.S. Government Printing Office, 1991); also available by license via the Internet).

An exemplary amino acid sequence of such a fusion polypeptide is provided in SEQ ID NO:2. In certain embodiments, the fusion polypeptide is a variant of the amino sequence set forth in SEQ ID NO:2 and comprises an amino acid sequence at least 65%-75%, 75%-80%, 80-85%, 85%-90%, or 95%-99% identical (or to any percent identity not specifically enumerated between 70% to 100%) to the amino acid sequence set forth in SEQ ID NO:2. A CD47-Fc polypeptide fusion protein variant may comprise one or more substitutions, deletions, or insertions of an amino acid in the CD47 moiety of the protein and/or one or more substitutions, deletions, or insertions of an amino acid in the Fc polypeptide moiety. Exemplary variants are described in further detail herein. The CD47-Fc polypeptide and variants thereof retain the capability to alter (i.e., increase or decrease in a statistically significant or biologically significant manner) the immunoresponsiveness of an immune cell.

In other embodiments, the CD47 fusion proteins described herein include fusion proteins that have been modified. By way of example, one or more amino acids of either the CD47 moiety or the heterologous moiety, such as the Fc polypeptide in a CD47-Fc fusion polypeptide, may be pegylated or may be glycosylated. Pegylation is the process by which polyethylene glycol (PEG) chains are attached to a polypeptide. In certain instances, pegylation increases the circulating half-life and reducing clearance of a polypeptide. Methods for pegylating proteins and peptides are understood in the art (see, e.g., Harris et al., *Nature Reviews* (*Drug Discovery*) 2:214-21 (2003); U.S. Pat. No. 5,770,577; International Patent Application Publication WO 92/16221).

Altering immunoresponsiveness of the immune cell includes any one or more of altering immune cell migration; inhibiting production of at least one cytokine, including but not limited to, TNF-α, IL-12, IL-23, IFN-γ, GM-CSF, and IL-6; inhibiting production of a chemokine, including but not limited to MIP-1α; inhibiting maturation of an immune cell such as a dendritic cell; impairing development of a naïve T cell into a Th1 effector cell; and suppressing a proinflammatory response by the immune cell. In another embodiment, the fusion polypeptide alters immunoresponsiveness of an immune cell by interacting with (i.e., binding to) a cell surface receptor that is a CD47 ligand. Altering immunoresponsiveness of a cell by the CD47 fusion polypeptides described herein may also include inhibiting (likely competitively inhibiting) binding of at least one CD47 ligand to a cellular CD47 polypeptide (that is, a CD47 full-length polypeptide that is expressed by a cell and that is present on the cell surface of the cell) and thus inhibiting at least one biological function attributable to cellular CD47 activation or stimulation, and/or inhibiting at least one biological function attributable to the CD47 ligand and thus inhibiting at least one biological function attributable to the CD47 ligand activation or stimulation; For example, the CD47-Fc fusion polypeptide may interact with SIRP-α that is present on an immune cell such as a dendritic cell, a monocyte, a macrophage, a granulocyte, or a bone marrow derived stem cell, thereby stimulating or inducing SIRP-α to signal the immune cell. The fusion polypeptides described herein may interfere with or inhibit an Fc-mediated or immune complex induced activity, such as cytokine or chemokine production, by an immune cell, including an immune cell that expresses SIRP-α.

The fusion polypeptides described herein may alter immunoresponsiveness of an immune cell, such as an immune cell that expresses a CD47 ligand. In a certain specific embodiment, the CD47-Fc fusion polypeptides described herein interact with an immune cell, for example, a dendritic cell, that expresses a CD47 ligand, such as SIRPα, which interaction may result in inhibiting production of at least one cytokine such as TNF-α, IL-12, IL-6, and IL-23. The CD47-Fc fusion polypeptides may activate an immune cell, such as an immune cell that has SIRPα present on the cell surface, by interacting with the immune cell and with SIRPα. Such activation or stimulation of the immune cell may comprise inhibiting an Fc-mediated biological effect (or activity), including cytokine and/or chemokine production by the immune cell. In other embodiments, activation or stimulation of the immune cell may comprise inhibiting an immune-complex induced effect, such as inhibiting immune complex-induced cytokine and/or chemokine production. Thus, cytokine production may be inhibited by interfering with or inhibiting the interaction between an immune complex and the immune cell, which can reduce or inhibit production of one or more cytokines by the immune cell. The CD47-Fc polypeptide, and variants thereof, also may retain the capability to bind at least one CD47 ligand, for example, SIRP-α, SIRP-beta-2, thrombospondin-1, $α_vβ_3$ integrin, and $α_2β_1$ integrin.

A person skilled in the art will readily appreciate that CD47-Fc polypeptide fusion proteins can be made using the extracellular domain of the CD47 polypeptide from a species and fused to an Fc polypeptide from an immunoglobulin from the same or different species. By way of example, the extracellular domain of a murine CD47 is fused to a murine IgG Fc polypeptide, such as an Fc polypeptide derived from an IgG2a or IgG2b immunoglobulin. As described in further detail herein, a CD47 extracellular domain may be fused to other moieties, including other polypeptides.

In certain embodiments, a CD47 fusion polypeptide comprises the extracellular domain of CD47, including the signal peptide (SEQ ID NO:18), such that the extracellular portion of CD47 is typically 142 amino acids in length, and has the amino acid sequence set forth in SEQ ID NO:11. The fusion polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to alter the immunoresponsiveness of an immune cell and/or to bind at least one CD47 ligand.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the CD47 fusion polypeptides are secreted; accordingly, a polynucleotide encoding a CD47 fusion polypeptide may include a nucleotide sequence encoding a signal peptide that is associated with a polypeptide that is normally secreted from a cell.

In other embodiments, the CD47 fusion polypeptide comprises an extracellular domain of CD47 that lacks the signal peptide. In an exemplary embodiment, the CD47 extracellular domain lacking the signal peptide has the amino acid sequence set forth in SEQ ID NO:1 (124 amino acids). As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a CD47 fusion polypeptide comprises a CD47 extracellular domain variant. Such a CD47 fusion polypeptide retains the capability to bind specifically to at least one CD47 ligand, which includes SIRP-α, SIRP-beta 2, thrombospondin-1, $\alpha_v\beta_3$ integrin, and $\alpha_2\beta_1$ integrin, for example. The CD47 extracellular domain variant may have an amino acid sequence that is at least 65%-75%, 75%-80%, 80-85%, 85%-90%, or 95%-99% identical (which includes any percent identity between any one of the described ranges) to SEQ ID NO:1.

In certain particular embodiments, the CD47 extracellular domain variants described herein retain all cysteine residues. For example, cysteine residues that correspond to the cysteine residues at position 15, at position 23, and position 96 of SEQ ID NO:1 are retained. The cysteine residues at position 23 and position 96 correspond to the cysteine residues in the full-length CD47 molecule that typically form an intramolecular (or intrachain) disulfide bond. When the extracellular domain of CD47 comprises the signal peptide, the cysteine residues retained are located at positions 33, 41, and 114 of SEQ ID NO:11, and the cysteine residues at positions 41 and 114 typically form an intramolecular disulfide bond. Without wishing to be bound by any particular theory, the cysteine residue nearest the amino terminal end of the extracellular CD47 domain, that is, the cysteine residue at position 15 of SEQ ID NO:1 and at position 33 of SEQ ID NO:11 may form an interchain disulfide bond such that the CD47 moieties of two CD47-Fc polypeptide fusion proteins form a CD47 dimer, thus forming a fusion polypeptide dimer.

Without wishing to be bound by theory, the intramolecular disulfide bond appears to contribute to the conformation of the immunoglobulin-like domain structure of CD47 expressed on a cell surface and to the retention of the immunoglobulin-like structure of the CD47 fusion polypeptides described herein. Persons skilled in the art will appreciate that the cysteine residues that typically form an intramolecular disulfide bond in CD47 may be located at positions that differ from the numbered positions of the cysteine residues in SEQ ID NO:1 or SEQ ID NO:11 and that determining the location of corresponding cysteine residues in another amino acid sequence that form an intramolecular disulfide bond in a CD47 polypeptide is well within the routine practice of the skilled artisan using alignment programs and molecular modeling programs described herein and used in the art. Similarly, determining the corresponding amino acids of CD47 molecules compared to particular amino acids provided in the exemplary amino acid sequences described herein can be readily determined using alignment tools described herein and routinely used by persons skilled in the art.

In another embodiment, the CD47 extracellular domain variant comprises a substitution or a deletion of the cysteine residue that is most proximal to the amino terminal end of the CD47 extracellular domain. This cysteine residue is located at a position corresponding to the cysteine residue at position 15 of SEQ ID NO:1 and is located at position 33 of SEQ ID NO:11. In a particular embodiment, the cysteine residue may be substituted with any amino acid, for example the cysteine residue may be substituted with a serine residue. In another particular embodiment, the cysteine residue may be substituted with one, two, or three, or four amino acids. For example, the cysteine residue most proximal to the amino terminal end of CD47 (i.e., the cysteine at position 15 of SEQ ID NO:1 or position 33 of SEQ ID NO:11) may be substituted with a tripeptide that is a potential glycosylation site, for example, a tripeptide that has the sequence Asn-X-Ser wherein X may be any amino acid except cysteine. Substitution or deletion of the cysteine residues most proximal to the amino terminus of the CD47 extracellular domain moiety eliminates the ability of a CD47 extracellular domain moiety of one fusion polypeptide to form a dimer with another CD47 extracellular domain moiety via formation of a disulfide bond between the cysteine residues of the CD47 extracellular domain moieties of two CD47 fusion polypeptides.

The percent identity of the amino acid sequence of a CD47 extracellular domain variant to the amino acid sequence set forth in either SEQ ID NO:1 or SEQ ID NO:11, or the percent identify between a fusion polypeptide comprising the amino acid sequence set forth in SEQ ID NO:2 and another fusion polypeptide, can be readily determined by persons skilled in the art by sequence comparison. As used herein, two amino acid sequences have 100% amino acid sequence identity if the amino acid residues of the two amino acid sequences are the same when aligned for maximal correspondence. Sequence comparisons of polypeptides and polynucleotides (for example, the polynucleotides that encode the polypeptides described herein) can be performed using any method such as those that use computer algorithms well known to persons having ordinary skill in the art. Such algorithms include Align or the BLAST algorithm (see, e.g., Altschul, *J. Mol. Biol.* 219:555-565, 1991; Henikoff and Henikoff, *Proc. Natl. Acad. Sci. USA* 89:10915-10919, 1992), which are available at the NCBI website (see [online] Internet at ncbi.nlm.nih.gov/cgi-bin/BLAST). Default parameters may be used. In addition, standard software programs are available, such as those included in the LASERGENE bioinformatics computing suite (DNASTAR, Inc., Madison, Wis.); CLUSTALW program (Thompson et al., *Nucleic Acids Res.* 22:4673-80 (1991)); and "GeneDoc" (Nicholas et al., *EMBNEW News* 4:14 (1991)). Other methods for comparing two amino acid sequences by determining optimal alignment are practiced by persons having skill in the art (see, for example, Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," *in Methods in Gene Biotechnology*, pages 123-151 (CRC Press, Inc. 1997); and Bishop (ed.), *Guide to Human Genome Computing,* 2nd Ed. (Academic Press, Inc. 1998)).

A CD47 extracellular domain variant may differ from a wildtype CD47 amino acid sequence (such as the amino acid sequence set forth in SEQ ID NO:1 or SEQ ID NO:11) due to an insertion, deletion, addition, and/or substitution of at least one amino acid and may differ due to the insertion, deletion, addition, and/or substitution of at least two, three, four, five, six, seven, eight, nine, or ten amino acids or may differ by any number of amino acids between 10 and 45 amino acids. A CD47 extracellular domain variant includes, for example, a naturally occurring polymorphism (i.e., allelic variant) or a recombinantly manipulated or engineered CD47 extracellular domain variant.

A CD47 extracellular domain variant that differs from the amino acid sequence set forth in SEQ ID NO:1 includes a variant with at least one deletion from either the amino terminal end or carboxy terminal end or from both the amino terminal end and the carboxy terminal end of the CD47 extracellular domain. Such a CD47 extracellular domain variant may also be referred to herein as a truncated CD47 extracellular domain. The truncation may include a deletion of at least 1, 2, 3, 4, 5, 6, 7, 8, 9, 10, 12, or 15-20 amino acids from the amino terminal end or carboxy terminal end of the CD47 extracellular domain or may include a deletion of between 1-20 amino acids from each terminal end. A truncated CD47 extracellular domain may retain the cysteine residues that correspond to residues at positions 23 and 96 of SEQ ID NO:1 (or at positions 41 and 114 of SEQ ID NO:11) so that the intramolecular disulfide bond is formed in the truncated CD47 extracellular domain variant.

A CD47 fusion polypeptide comprising a CD47 extracellular domain variant that retains the capability to bind specifically to at least one CD47 ligand means that the capability of the variant to bind the CD47 ligand is statistically and/or biologically similar to the capability of the wild type CD47 extracellular domain to bind the CD47 ligand. For example, when the binding affinity and/or other kinetic parameters (e.g., Vmax, $k_{on}$, $k_{off}$) of the variant polypeptide and the wildtype (or non-variant) polypeptide are compared, the binding affinity and/or other kinetic parameters are substantially similar (i.e., within experimental error and variation) between the variant and the wild type polypeptides. Alternatively, or in addition to, a CD47 fusion polypeptide comprising a CD47 extracellular domain variant that retains the capability to bind specifically to at least one CD47 ligand has the capability to effect a biological activity or function that occurs when wild-type CD47 extracellular domain binds the CD47 ligand. Exemplary biological activities are described in detail herein.

Assays for assessing whether a CD47 extracellular domain variant folds into a conformation comparable to the non-variant polypeptide or fragment include, for example, the ability of the protein to react with mono- or polyclonal antibodies that are specific for native or unfolded epitopes, the retention of ligand-binding functions, and the sensitivity or resistance of the mutant protein to digestion with proteases (see Sambrook et al., supra). CD47 extracellular domain variants as described herein can be identified, characterized, and/or made according to these methods described herein or other methods known in the art, which are routinely practiced by persons skilled in the art.

A CD47 fusion polypeptide that comprises a CD47 extracellular domain variant that retains the capability to bind to at least one CD47 ligand and/or the capability to alter (i.e., increase or decrease in a statistically significant or biologically significant manner) immunoresponsiveness of an immune cell include variants that contain conservative amino acid substitutions. A variety of criteria known to persons skilled in the art indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine) In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

In certain embodiments, a fusion polypeptide comprising a CD47 extracellular domain, or a variant thereof, is recombinantly expressed. For instance, a CD47 extracellular domain, or variant thereof, fused in frame with an Fc polypeptide, as described in detail herein, may be recombinantly expressed. A recombinant expression construct may be prepared for the expression of a fusion polypeptide according to standard techniques and methods practiced by a skilled person in the molecular biology art. In order to obtain efficient transcription and translation, the polynucleotide sequence in each construct should include at least one appropriate expression control sequence (also called a regulatory sequence), such as and leader sequence and particularly a promoter operatively linked to the nucleotide sequence encoding the CD47 extracellular domain, or variant thereof. Alternatively, the at least one expression control sequence, such as a promoter, may be operatively linked to a nucleotide sequence encoding the signal peptide sequence located at the amino terminal end of the CD47 extracellular domain.

Particular methods for producing polypeptides recombinantly are generally well known and routinely used. For example, molecular biology procedures are described by Sambrook et al. (*Molecular Cloning, A Laboratory Manual*, 2nd ed., Cold Spring Harbor Laboratory, New York, 1989; see also Sambrook et al., 3rd ed., Cold Spring Harbor Laboratory, New York, (2001)). DNA sequencing can be performed as described in Sanger et al. (*Proc. Natl. Acad. Sci. USA* 74:5463 (1977)) and the Amersham International plc sequencing handbook and including improvements thereto. Recombinant expression of the fusion polypeptides is described in greater detail herein.

Exemplary nucleotide sequences that encode CD47 from which the nucleotide sequence encoding the CD47 extracellular domain portion of a CD47 fusion polypeptide can be readily obtained are provided herein and are readily available from public databases (see, e.g., GenBank Accession Nos. NM_001777.3 (SEQ ID NO:19); NM_198793.2 (SEQ ID NO:16); NM_001025079.1; BT006907.1; BC012884.1;

BC010016.2; BC037306.1; BC045593.1; BC053959.1; and BC042889.1). The nucleotide sequence of a CD47 extracellular domain variant can be determined and/or identified by comparing the nucleotide sequence of a polynucleotide encoding the variant with a polynucleotide described herein or known in the art that encodes a CD47 polypeptide using any one of the alignment algorithms described herein and used in the art. The percent identity between two polynucleotides may thus be readily determined. Polynucleotides have 100% nucleotide sequence identity if the nucleotide residues of the two sequences are the same when aligned for maximal correspondence. In particular embodiments, the nucleotide sequence of a CD47 extracellular domain variant-encoding polynucleotide is at least 70%, 75%, 80%, 85%, 90%, 95%, or 98% identical to one or more of the polynucleotide sequences that encode a CD47 extracellular domain, which are described herein. Polynucleotide variants also include polynucleotides that differ in nucleotide sequence identity due to the degeneracy of the genetic code and encode a CD47 extracellular domain having an amino acid sequence disclosed herein or known in the art. A polynucleotide that encodes a CD47 fusion polypeptide as described herein also includes a polynucleotide that is complementary to such a polynucleotide. Certain polynucleotides that encode a CD47 extracellular domain, variant, or fragment thereof may also be used as probes, primers, short interfering RNA (siRNA), or antisense oligonucleotides. Polynucleotides may be single-stranded DNA or RNA (coding or antisense) or double-stranded RNA (e.g., genomic or synthetic) or DNA (e.g., cDNA or synthetic).

Polynucleotide variants may be identified by alignment procedures described herein and also may be identified by hybridization methods. Hybridization of two polynucleotides may be performed using methods that incorporate the use of suitable moderately stringent conditions, for example, pre-washing in a solution of 5×SSC, 0.5% SDS, 1.0 mM EDTA (pH 8.0); hybridizing at 50° C.-70° C., 5×SSC for 1-16 hours; followed by washing once or twice at 22-65° C. minutes with one or more each of 2×, 0.5×, and 0.2×SSC containing 0.05-0.1% SDS. For additional stringency, conditions may include a wash in 0.1×SSC and 0.1% SDS at 50-60° C. for 15 minutes. As understood by persons having ordinary skill in the art, variations in stringency of hybridization conditions may be achieved by altering the time, temperature, and/or concentration of the solutions used for pre-hybridization, hybridization, and wash steps. Suitable conditions may also depend in part on the particular nucleotide sequences of the probe used (i.e., for example, the guanine plus cytosine (G/C) versus adenine plus thymidine (A/T) content). Accordingly, a person skilled in the art will appreciate that suitably stringent conditions can be readily selected without undue experimentation when a desired selectivity of the probe is identified.

CD47 extracellular domain variants may be readily prepared by genetic engineering and recombinant molecular biology methods and techniques. Analysis of the primary and secondary amino acid sequence of a CD47 polypeptide and of the CD47 extracellular domain and computer modeling of same to analyze the tertiary structure of the polypeptide may aid in identifying specific amino acid residues that can be substituted, added, or deleted without altering the structure and as a consequence, potentially the function, of the CD47 polypeptide. Modification of a polynucleotide, such as DNA, encoding a CD47 extracellular domain variant may be performed by a variety of methods, including site-specific or site-directed mutagenesis of the DNA, which methods include DNA amplification using primers to introduce and amplify alterations in the DNA template, such as PCR splicing by overlap extension (SOE). Mutations may be introduced at a particular location by synthesizing oligonucleotides containing a mutant sequence, flanked by restriction sites enabling ligation to fragments of the native sequence. Following ligation, the resulting reconstructed sequence encodes a variant (or derivative) having the desired amino acid insertion, substitution, or deletion.

Site directed mutagenesis of a polynucleotide such that it encodes a CD47 extracellular domain variant may be performed according to any one of numerous methods described herein and practiced in the art (Kramer et al., *Nucleic Acids Res.* 12:9441 (1984); Kunkel *Proc. Natl. Acad. Sci. USA* 82:488-92 (1985); Kunkel et al., *Methods Enzymol.* 154:367-82 (1987)). Random mutagenesis methods to identify residues that, when mutated (e.g., substituted or deleted), alter binding of the CD47 extracellular domain to a ligand, or that alter binding of the CD47 extracellular domain variant to a CD47-specific antibody, can also be performed according to procedures that are routinely practiced by a person skilled in the art (e.g., alanine scanning mutagenesis; error prone polymerase chain reaction mutagenesis; and oligonucleotide-directed mutagenesis (see, e.g., Sambrook et al. *Molecular Cloning: A Laboratory Manual,* 3rd ed., Cold Spring Harbor Laboratory Press, NY (2001)). In certain embodiments, a CD47 extracellular domain variant retains the capability to bind to at least one CD47 ligand (e.g., SIRP-α, SIRP-beta-2, thrombospondin-1, $\alpha_v\beta_3$ integrin, and $\alpha_2\beta_1$ integrin). In certain other embodiments, a CD47 fusion polypeptide comprising a CD47 extracellular domain variant retains the capability to bind to at least two, three, four, or five CD47 ligands. Further, as described herein, the CD47 extracellular domain variant and the fusion polypeptide comprising the variant retain at least one biological function, which are described herein, of the wild type CD47 moiety.

Site directed mutagenesis techniques may also be used to make a CD47 fusion polypeptide comprising a CD47 extracellular domain variant that exhibits an alteration (i.e., statistically or biologically significant increase or decrease) in the capability of the variant to bind specifically to a CD47 ligand when compared with the wildtype CD47 polypeptide. Such a CD47 extracellular domain variant may, for example, have at least one substitution, deletion, or addition of an amino acid such that the variant retains the capability to bind at least one CD47 ligand and exhibits a decreased (i.e., reduced, diminished) capability to bind specifically to at least one second CD47 ligand when compared with CD47 without the mutation. In other certain embodiments, the CD47 extracellular domain variant retains the capability to bind to at least two, three, or four, CD47 ligands and exhibits a reduced or decreased capability to bind to at least one CD47 ligand.

CD47 Ligands

CD47 ligands include various polypeptides, such as signal regulatory proteins (SIRPs, such as SIRP-α, SIRP-beta-2); thrombospondin-1 and fragments and portions thereof such as the carboxy terminal portion of thrombospondin-1; and certain integrins, particularly $\beta_3$ and $\beta_1$ integrins, for example, $\alpha_v\beta_3$ integrin and $\alpha_2\beta_1$ integrin. CD47 ligands also include antibodies that specifically bind to CD47, particularly antibodies that bind to the extracellular domain of CD47.

As used herein, a CD47 fusion polypeptide is said to be "specific for" or to "specifically bind" a CD47 ligand if the CD47 extracellular domain moiety reacts at a detectable level with the ligand, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. The ability of the CD47 fusion polypeptide to bind to a CD47 ligand may also be expressed as a dissociation constant $K_D$, and a CD47 fusion polypeptide specifically binds to a CD47 ligand if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M.

Affinities of CD47, including the affinities of the extracellular domain of CD47, and the CD47 fusion polypeptides described herein, and its cognate ligands can be readily determined using conventional techniques, for example, those described by Scatchard et al. (*Ann. N.Y. Acad. Sci. USA* 51:660 (1949)) and by surface plasmon resonance (SPR; BIAcore™, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the surface plasmon resonance signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-65 (1993)).

Binding of a fusion polypeptide (which also includes fusion polypeptide dimers) comprising a CD47 extracellular domain, or variant thereof, as described herein, to a CD47 ligand may prevent interaction between any one or more of the aforementioned CD47 ligands with CD47 expressed on the surface of a cell. Without wishing to be bound by theory, interaction between the fusion polypeptide and the CD47 ligand may alter a biological function of cell surface-expressed CD47 by preventing or inhibiting the cell surface CD47 from interacting with the CD47 ligand. In addition to, or alternatively, interaction between the fusion polypeptide and the CD47 ligand may initiate or stimulate a biological function of the CD47 ligand. For example, the CD47 fusion polypeptides described herein may alter the interaction, likely inhibit (i.e., prevent, diminish, reduce, decrease) binding of CD47 to $\beta_3$ and $\beta_1$ integrins, such as $\alpha_v\beta_3$ integrin and $\alpha IIb\beta_3$, and $\alpha_2\beta_1$ integrin, respectively, which have been described as CD47 ligands (see, e.g., Lindberg et al., *J. Cell Biol.* 123:485-96 (1993); Lindberg et al., *J. Cell Biol.* 134:1313-22 (1996); Wang et al., *Mol. Biol. Cell* 9:865-74 (1998); Wang et al., *J. Cell Biol.* 147:389-400 (1999); Brown et al., *J. Cell Biol.* 111:2785-94 (1990)). The integrin $\alpha_v\beta_3$ is a cell receptor that is expressed by many cell types and that binds to a variety of different polypeptides via the RGD (arginine-glycine-aspartic acid) sequence (Brown et al., *J. Cell Biol.* 111:2785-94 (1990); Blystone et al., *J. Cell Biol.* 130:745-54 (1995)).

In another embodiment, a fusion polypeptide comprising a CD47 extracellular domain, or variant thereof, as described herein, may bind to one or more members of a family of transmembrane glycoproteins referred to as SIRPs (signal regulatory proteins) such as SIRPα and SIRP-beta-2. Interaction between the fusion polypeptide and a SIRP polypeptide may stimulate at least one biological function of a SIRP. For instance, the fusion polypeptides may alter the interaction between CD47 expressed on the surface of a cell and SIRPα (signal regulatory protein-α), which is also referred to in the art as SHPS-1 (Src homology 2 domain-containing protein tyrosine phosphatase-1 (SHP) substrate-1). SIRPs including SIRPα are expressed in hematopoietic cells including monocytes, granulocytes, dendritic cells, and $CD34^+CD38^-CD133^+$ bone marrow stem cells, and has been reported to be expressed on smooth muscle cells (see, e.g., Latour et al., *J. Immunol.* 167:2547-54 (2001); Liu et al., *J. Biol. Chem.* 277: 10028-36 (2002); Seiffert et al., *Blood* 94:3633-43 (1999); Seiffert et al., *Blood* 97:2741-49 (2001); Jiang et al. *J. Biol. Chem.* 274:559-62 (1999); Vernon-Wilson et al., *Eur. J. Immunol.* 30:2130-37 (2000); Oshima et al., *FEBS Lett.* 519: 1-8 (2002)). SIRPα is believed to be an important immune inhibitor receptor on macrophages, and its interaction with CD47 prevents autologous phagocytosis (see, e.g., Oldenborg et al., *J. Exp. Med.* 193:855-62 (2001); Okazawa et al., *J. Immunol.* 174:2004-11 (2005)).

Interaction between a cell that expresses CD47 and a cell that expresses SIRPα can regulate cell migration, such as polymorphonuclear (PMN) cell transmigration and migration of Langerhans cells (see, e.g., Liu et al., supra; Motegi et al., *EMBO J.* 22:2634-44 (2003); Fukunaga et al., *J. Immunol.* 172:4091-99 (2004); Parkos et al., *J. Cell Biol.* 132:437-50 (1996)). A CD47-Fc fusion polypeptide described herein may inhibit migration of a cell that expresses SIRPα on the cell surface (i.e., the migrating cell) by inhibiting (i.e., preventing, blocking, or interfering with) the interaction between the migrating cell and a cell that has cellular CD47 present on the cell surface (such as an epithelial or endothelial cell).

Binding of a fusion polypeptide comprising a CD47 extracellular domain, or variant thereof, to SIRPα may alter the immunoresponsiveness of immune cells by inhibiting, decreasing, reducing, or preventing migration of immune cells and thus may inhibit, suppress, or decrease an inflammatory response in a host. SIRP polypeptides, such as SIRPα, are believed to act as negative regulatory cell receptors, such that, for example, stimulation of SIRP may inhibit Fc-mediated activation that may otherwise result in cytokine and/or chemokine production by an immune cell. Without wishing to be bound by theory, interaction between the CD47-Fc fusion polypeptides described herein and a SIRP polypeptide expressed by an immune cell induces a negative signal via SIRP signaling that may result in inhibition or decrease in an inflammatory response, such as production of cytokines, such as IL-6, IL-12, IL-23, TNF-α.

In another embodiment, binding of a fusion polypeptide comprising a CD47 extracellular domain, or variant thereof, to a CD47 ligand, may alter expression and/or secretion of cytokines, such as IL-12, IL-23, TNF-α, IFN-γ, IL-6, GM-CSF, and IL-10. Binding of a fusion polypeptide described herein to a CD47 ligand, such as SIRPα, may suppress release of cytokines such as IL-12, IL-23, TNF-α, IL-6, and IL-10. See, e.g., Latour et al., supra; Hermann et al., *J. Cell Biol.* 144:767-75 (1999); Armant et al., *J. Exp. Med.* 190:1175-81 (1999); Demeure et al., *J. Immunol.* 164:2193-99 (2000).

In another embodiment, a fusion polypeptide comprising a CD47 extracellular domain, or variant thereof, as described herein, may bind to thrombospondin-1, and in a particular embodiment may bind to the carboxy terminal portion of thrombospondin-1, also called Tp-47 in the art (see, e.g., Latour et al., supra). Thrombospondin-1 is an extracellular matrix protein that is released by platelets upon activation and is also produced by macrophages and monocytes. Binding of thrombospondin to cell-surface CD47 negatively regulates IL-12 production by antigen presenting cells (APC) and inhibits development of naïve T cells into Th1 effector cells (see, e.g., Armant et al., *J. Exp. Med.* 190:1175 (1999); Demeure et al., *J. Immunol.* 164:2193 (2000); Avice et al., *J. Immunol.* 165:4624 (2000)). The cytokine IL-12 can act as an inflammatory mediator, and uncontrolled IL-12 production and responsiveness are associated with certain immunological diseases, such as autoimmune diseases. Binding of the fusion polypeptides described herein to thrombospondin-1 may alter immunoresponsiveness of an immune cell by down regulating or facilitating decreased expression of IL-12.

Interaction between thrombospondin-1 and CD47 expressed on the cell surface also may induce apoptosis of activated T cells, which may be mediated by BNIP3 (Bcl-2 homology 3 (BH3)-only protein 19 kDa interacting protein-3) (Lamy et al., *J. Biol. Chem.* 278 (23915-21 (2003)). A fusion polypeptide comprising a CD47 extracellular domain, or variant thereof, as described herein, may inhibit binding of thrombospondin-1 to CD47 expressed by T cells, thereby altering apoptosis in lymphocytes. Accordingly, the fusion polypeptides described herein may be used for treating proliferative diseases, such as cancer.

The term IL-12 refers to the cytokine IL-12 produced by immune cells, including dendritic cells, and includes IL-12 related monomers and dimers that are described in the art. A bioactive form of IL-12 is a heterodimer called IL12p70 that is comprised of independently regulated subunits called p40 (IL12p40) and p35 (IL12p35) having an approximate molecular weight of 40 kilodaltons and 35 kilodaltons, respectively. IL12p40 may also exists as a dimer (IL12 $(p40)_2$). See, for example, Gately et al., *Annu. Rev. Immunol.* 16:495 (1998); Hildens et al., *Blood* 90:1920 (1997); Kalinski et al., *J. Immunol.* 165:1877-81 (2000). IL-23 also comprises the p40 subunit of IL12 and is produced, for example, by dendritic cells and may act on memory T cells (see, e.g., Oppmann et al., *Immunity* 13:715-25 (2000); Wiekowski et al., *J. Immunol.* 166:7563-7570 (2001); Aggarwal, et al., *J. Biol. Chem.* 17:278:1910-14 (2003), Epub 2002 Nov. 3). The effect of IL-23 production and inflammatory diseases has recently led to the observation that expression of a receptor for IL-23 is associated with inflammatory diseases such as Crohn's disease and ulcerative colitis (see, e.g., Duerr et al., *Science* 314:1461-63 (2006); see also, e.g., Mannon et al., *N. Engl. J. Med.* 351:2069 (2004); Becker et al., *J. Immunol.* 177:2760-64 (2006); Lankford et al., *J. Leukoc. Biol.* 73:49-56 (2003)).

The CD47-Fc polypeptide fusion proteins described herein may also affect the capability of an immune complex to induce production of cytokines by an immune cell; thus the fusion proteins described herein may inhibit induction by an immune complex of cytokine production in an immune cell (i.e., inhibit immune complex-induced cytokine production by an immune cell). An immune cell includes but is not limited to an immune cell that expresses a CD47 ligand, for example, that expresses SIRPα. As described herein, such immune cells include, for example, a dendritic cell, a monocyte, macrophage, granulocyte, and a bone-derived stem cell. Thus, in certain specific embodiments, the CD47-Fc polypeptide fusion proteins described herein are capable of altering the immunoresponsiveness of a dendritic cell. Interaction of a CD47-Fc polypeptide fusion protein with an immune cell, for example, a dendritic cell, or with a ligand or other cell that interacts with the immune cell, such as the dendritic cell, alters (generally inhibits) the production of cytokines, including but not limited to IL-6, IL-12, IL-23, and TNF-α, by the dendritic cell. In other certain embodiments, the CD47-Fc polypeptide fusion proteins described herein alter, and in certain particular embodiments, inhibit or decrease, the capability of an immune complex to induce production of cytokines by an immune cell. In particular embodiments, the CD47-Fc fusion polypeptides described herein inhibit immune complex-induced cytokine production by an immune cell, such as a dendritic cell. Thus, and as discussed herein, the CD47-Fc polypeptide fusion proteins may be used for treatment of immunological diseases or disorders, such as autoimmune diseases (by way of example, arthritis). In addition, a CD47-Fc polypeptide fusion protein may inhibit or prevent maturation of a dendritic cell. The CD47 Fc fusion polypeptides described herein may also interact with SIRPα present on the cell surface of a neuronal, and consequently affect signaling of a neuronal cell function.

Viral CD47 Polypeptides and Extracellular Domain Fragments Thereof

In another embodiment, the CD47 extracellular domain is a viral CD47-like polypeptide, for example, a poxvirus CD47-like polypeptide such as a variola minor poxvirus CD47-like polypeptide (see, e.g., SEQ ID NOS: 3 and 4). By encoding proteins that are viral homologues of cell cytokines and chemokines and their receptors, members of the poxvirus family have evolved numerous mechanisms to evade detection and elimination by an infected host's immune system. One viral virulence factor includes a polypeptide that shares structural homology with CD47. The viral CD47 polypeptides (also called viral CD47-like polypeptides or vCD47) have amino acid sequences that share 30% or less primary sequence homology; however, comparison of structural features of viral CD47 to immunomodulatory polypeptides indicates that the viral CD47 polypeptides have an N-terminal signal sequence, five to six transmembrane domains, and a short intracellular (i.e., cytoplasmic) tail, similar to CD47 (see, e.g., Cameron et al., *Virology* 264:298-318 (1999); Cameron et al., Virology 337:55-67 (2005); Alfonso et al., J. Virol. 79:966-77 (2005); Seet et al., *Annu. Rev. Immunol.* 21:377-423 (2003)).

Viral genomic sequences that encode viral CD47-like polypeptides have been identified in several poxviruses, including myxoma and orthopoxviruses as well as chordopoxvirus, a capripoxvirus, a leporipoxvirus, a suipoxvirus, a yatapoxvirus, and a deerpox virus. Exemplary amino acid sequences of viral CD47-like polypeptides include the A44L polypeptide encoded by the genome of Variola minor virus (GenBank Accession No. CAB54747.1 (SEQ ID NO:3)); Vaccinia virus-Western Reserve (GenBank Accession No. AAO89441.1); Vaccinia virus (Acambis 3000 modified virus Ankara) (GenBank Accession No. AAT10547.1); Vaccinia virus (GenBank Accession No. YP_233044.1); and the M128L polypeptide encoded by the genome of the Lausanne strain of Myxoma virus (GenBank Accession Nos. NP_051842.1 and AAF15016.1). By way of example, an alignment of the amino acid sequences of the A44L polypeptide and a human CD47 isoform (see FIG. 2) indicates that the primary sequences of the two polypeptides are approximately 25% identical and approximately 60% similar.

In certain embodiments, a fusion polypeptide is provided herein that comprises a viral CD47 (vCD47) extracellular domain fused to a fused to a moiety capable of multimer formation (e.g., dimer formation), including for example, an Fc polypeptide and variants thereof. In one embodiment, the viral CD47 extracellular domain moiety is derived from the A44L amino acid sequence and comprises 105 amino acids (SEQ ID NO:4), which lacks the 20-amino acid signal peptide sequence (amino acids at positions 1-20 of SEQ ID NO:3) (see also FIG. 2). In certain other embodiments, a fusion polypeptide comprises a viral CD47 extracellular domain derived from another poxvirus CD47-like polypeptide described herein or known in the art. Persons skilled in the art can readily determine the portion of a viral CD47-like polypeptide that comprises the signal peptide, extracellular domain, transmembrane domains, and intracellular domains using alignment methods and other methods, such as von Heijne transmembrane plots described herein and used in the art In other embodiments, a vCD47 fusion polypeptide comprises a vCD47 extracellular domain variant. Such a vCD47 fusion polypeptide retains the ability to bind specifically to at least one CD47 ligand. Such ligands are described herein and include SIRP-α, SIRP-beta 2, thrombospondin-1, $\alpha_v\beta_3$ integrin, and $\alpha_2\beta_1$ integrin, for example. The vCD47 fusion polypeptide that comprises a vCD47 variant also retains the capability to competitively inhibit binding of CD47 to at least one CD47 ligand. The vCD47 extracellular domain variant may have an amino acid sequence that is at least 65%-75%, 75%-80%, 80-85%, 85%-90%, or 95%-99% identical (which includes any percent identity between any one of the described ranges) to the amino acid sequence of the corresponding wildtype poxvirus CD47-like polypeptide, such as a Variola minor vCD47 extracellular domain as set forth in SEQ ID NO:4. Such vCD47 extracellular domain variants may retain cysteine residues that form the intramolecular disulfide bond, which confers an immunoglobulin domain-like structure. By way of example, the cysteine residues in the Variola minor vCD47 (A44L) amino acid sequence that typically form an intramolecular disulfide bond are located at positions that correspond to the cysteine residues at position 16 and position 79 of SEQ ID NO:4. Persons skilled in the art will appreciate that the cysteine residues that typically form an intramolecular disulfide bond in one vCD47 may be located at positions that differ from the numbered positions of the cysteine residues in SEQ ID NO:4 and that determining the location of corresponding cysteine residues in another amino acid sequence that form an intramolecular disulfide bond in a vCD47 polypeptide is well within the routine practice of the skilled artisan using alignment programs and molecular modeling programs described herein and used in the art.

The percent identity of a vCD47 extracellular domain variant compared with the wildtype vCD47 amino acid sequence can be readily determined by persons skilled in the art by sequence comparison. As used herein, two amino acid sequences have 100% amino acid sequence identity if the amino acid residues of the two amino acid sequences are the same when aligned for maximal correspondence. Sequence comparisons of polypeptides and polynucleotides can be performed using any method including using computer algorithms well known to persons having ordinary skill in the art, and include algorithms described herein for alignment of CD47 polypeptides and the polynucleotides that encode the CD47 polypeptides.

A vCD47 extracellular domain variant may differ from a wildtype vCD47 amino acid sequence (e.g., the amino acid sequence set forth in SEQ ID NO:4) due to an insertion, deletion, addition, and/or substitution of at least one amino acid and may differ due to the insertion, deletion, addition, and/or substitution of at least two, three, four, five, six, seven, eight, nine, or ten amino acids or may differ by any number of amino acids between 10 and 45 amino acids. A vCD47 extracellular domain variant includes, for example, a naturally occurring polymorphism that occurs due to a mutation introduced into the viral genome during infection and/or replication in a host or a recombinantly manipulated or engineered vCD47 extracellular domain variant.

A vCD47 extracellular domain variant that differs from the amino acid sequence set forth in SEQ ID NO:4, for example, includes a variant with at least one deletion from either the amino terminal end or carboxy terminal end or from both the amino terminal end and the carboxy terminal end of the vCD47 extracellular domain. Such a vCD47 extracellular domain variant may also be referred to herein as a truncated vCD47 extracellular domain. The truncation may include a deletion of at least 1, 2, 3, 4, 5, 6, 7, 8, 9, 10, 12, or more amino acids from the amino terminal end or carboxy terminal end of the CD47 extracellular domain or may include a deletion of between 1-20 amino acids from each terminal end. In particular embodiments, a truncated vCD47 extracellular domain variant retains the cysteine residues that form the intramolecular disulfide bond.

A vCD47 fusion polypeptide that comprises a vCD47 extracellular domain variant that retains the capability to bind to at least one CD47 ligand and/or the capability to competitively inhibit binding of CD47 to a CD47 ligand includes variants that contain conservative amino acid substitutions. A variety of criteria known to persons skilled in the art indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

In certain embodiments, a fusion polypeptide comprising a vCD47 extracellular domain, or a variant thereof, is recombinantly expressed. For instance, a vCD47 extracellular domain, or variant thereof, is fused in frame with a Fc polypeptide, or variant thereof, as described in detail herein. A recombinant expression construct may be prepared for the expression of a vCD47 fusion polypeptide according to standard techniques and methods practiced by a skilled person in the molecular biology art. In order to obtain efficient transcription and translation, the polynucleotide sequence in each construct should include appropriate regulatory sequences, particularly a promoter and leader sequence operatively linked to a nucleotide sequence encoding the vCD47 extracellular domain, or variant thereof, or the promoter may be operatively linked to the nucleotide sequence encoding the signal peptide sequence located at the amino terminal end of the vCD47 extracellular domain. Particular methods for producing polypeptides recombinantly are generally well known and routinely used. For example, molecular biology procedures are described by Sambrook et al. (*Molecular Cloning, A Laboratory Manual,* 2nd ed., Cold Spring Harbor Laboratory, New York, 1989; see also Sambrook et al., 3rd ed., Cold Spring Harbor Laboratory, New York, (2001)). DNA sequencing can be performed as described in Sanger et al. (*Proc. Natl. Acad. Sci. USA* 74:5463 (1977)) and the Amersham International plc sequencing handbook and including improvements thereto.

Exemplary nucleotide sequences that encode the vCD47 extracellular domain portion of a vCD47 fusion polypeptide are provided herein and are readily available from public databases that provide the genomic sequences of various poxviruses, including, for example, Myxoma virus (GenBank Accession No. AF170726.2); Variola minor virus (GenBank Accession No. Y16780.1); Yaba monkey tumor virus (GenBank Accession Nos. NC_005179.1; AY386371.1); Yaba-like disease virus (GenBank Accession Nos. AJ293568.1; NC_002642.1); mule deerpox virus (NC_006966.1).

The nucleotide sequence of a vCD47 extracellular domain variant can be determined and/or identified by comparing the nucleotide sequence of a polynucleotide encoding the variant with a polynucleotide described herein or known in the art that encodes a vCD47 polypeptide using any one of the alignment algorithms described herein and used in the art. The percent identity between two polynucleotides may thus be readily determined. Polynucleotides have 100% nucleotide sequence identity if the nucleotide residues of the two sequences are the same when aligned for maximal correspondence. In particular embodiments, the nucleotide sequence of a vCD47 extracellular domain variant-encoding polynucleotide is at least 70%, 75%, 80%, 85%, 90%, 95%, or 98% identical to one or more of the polynucleotide sequences that encode a wild type vCD47 extracellular domain, which are described herein. Polynucleotide variants also include polynucleotides that differ in nucleotide sequence identity due to the degeneracy of the genetic code but encode a vCD47 extracellular domain having an amino acid sequence disclosed herein or known in the art. A polynucleotide that encodes a vCD47 fusion polypeptide as described herein also includes a polynucleotide that is complementary to such a polynucleotide. Certain polynucleotides that encode a vCD47 extracellular domain, variant, or fragment thereof may also be used as probes and primers. Polynucleotides may be single-stranded DNA or RNA (coding or antisense) or double-stranded RNA (e.g., genomic or synthetic) or DNA (e.g., cDNA or synthetic). Polynucleotide variants may be identified by alignment procedures described herein and also may be identified by hybridization methods as described herein for identifying and characterizing polynucleotide variants that encode CD47.

vCD47 extracellular domain variants may be readily prepared by genetic engineering and recombinant molecular biology methods and techniques. Analysis of the primary and secondary amino acid sequence of a vCD47 polypeptide and of the vCD47 extracellular domain and computer modeling of same to analyze the tertiary structure of the polypeptide may aid in identifying specific amino acid residues that can be substituted, added, or deleted without altering the structure and as a consequence, potentially the function, of the vCD47 polypeptide. Modification of DNA encoding a vCD47 extracellular domain variant may be performed by a variety of methods, including site-specific or site-directed mutagenesis of the DNA, which methods include DNA amplification using primers to introduce and amplify alterations in the DNA template, such as PCR splicing by overlap extension (SOE). Mutations may be introduced at a particular location by synthesizing oligonucleotides containing a mutant sequence, flanked by restriction sites enabling ligation to fragments of the native sequence. Following ligation, the resulting reconstructed sequence encodes a variant (or derivative) having the desired amino acid insertion, substitution, or deletion.

Site directed mutagenesis of a polynucleotide to encode a vCD47 extracellular domain variant may be performed according to any one of numerous methods described herein and practiced in the art (Kramer et al., *Nucleic Acids Res.* 12:9441 (1984); Kunkel *Proc. Natl. Acad. Sci. USA* 82:488-92 (1985); Kunkel et al., *Methods Enzymol.* 154:367-82 (1987)). Random mutagenesis methods to identify residues that, when mutated (e.g., substituted or deleted), alter the binding affinity of the vCD47 extracellular domain to a CD47 ligand or that alter the capability the vCD47 extracellular domain variant to competitively inhibit binding of CD47 to a CD47 ligand can also be performed according to procedures that are routinely practiced by a person skilled in the art (e.g., alanine scanning mutagenesis; error prone polymerase chain reaction mutagenesis; and oligonucleotide-directed mutagenesis (see, e.g., Sambrook et al. *Molecular Cloning: A Laboratory Manual,* 3rd ed., Cold Spring Harbor Laboratory Press, NY (2001)). In certain embodiments, a vCD47 extracellular domain variant retains the capability to bind to at least one CD47 ligand (e.g., SIRP-α, SIRP-beta-2, thrombospondin-1, $α_vβ_3$ integrin, and $α_2β_1$ integrin). In certain other embodiments, a vCD47 fusion polypeptide comprising a vCD47 extracellular domain variant that retains the capability to bind to at least two, three, four, or five, CD47 ligands.

Site directed mutagenesis techniques may also be used to make a fusion polypeptide comprising a vCD47 extracellular domain variant that exhibits an alteration (i.e., statistically or biologically significant increase or decrease) in the capability of the variant to bind specifically to a CD47 ligand when compared with the wildtype vCD47 polypeptide. Such a vCD47 extracellular domain variant may, for example, have at least one substitution, deletion, or addition of an amino acid such that the variant retains the capability to bind at least one CD47 ligand and exhibits a decreased (i.e., reduced, diminished) capability to bind specifically to at least one second CD47 ligand when compared with vCD47 without the mutation. In other certain embodiments, the vCD47 extracellular domain variant retains the capability to bind to at least two, three, or four, CD47 ligands and exhibits a reduced or decreased capability to bind to at least one CD47 ligand.

In another embodiment, a fusion polypeptide comprises a vCD47 extracellular domain variant fused to a Fc polypeptide (or variant thereof), wherein the vCD47 extracellular domain variant comprises an amino acid sequence at least 65%-75%, 75%-80%, 80-85%, 85%-90%, or 95%-99% identical to SEQ ID NO:4 and retains the capability to bind at least one CD47 ligand (e.g., SIRP-α, SIRP-beta-2, thrombospondin-1, $α_vβ_3$ integrin, and $α_2β_1$ integrin). In another particular embodiment, the vCD47 extracellular domain variant comprises a substitution or a deletion of the cysteine residue that is most proximal to the amino terminal end of the vCD47 extracellular domain. In certain embodiments, this cysteine residue is located at a position corresponding to the cysteine residue at position 8 of SEQ ID NO:4. In a particular embodiment, the cysteine residue may be substituted with any amino acid, for example the cysteine residue may be substituted with a serine residue. In another particular embodiment, the cysteine residue may be substituted with one, two, or three, or four amino acids. For example, the cysteine residue most proximal to the amino terminal end of CD47, which corresponds to the cysteine at position 8 of SEQ ID NO:4, may be substituted with a tripeptide that is a potential glycosylation site, for example, a tripeptide that has the sequence Asn-X-Ser wherein X may be any amino acid except cysteine. If desired, substitution or deletion of a cysteine residue that corresponds to the cysteine at position 8 of SEQ ID NO:4 abrogates the possibility that a vCD47 extracellular domain moiety of one fusion polypeptide will form a dimer with another vCD47 extracellular domain moiety via formation of a disulfide bond between the cysteine residues that are located most proximal to the amino terminal end of the vCD47 extracellular domain amino acid sequence.

A fusion polypeptide comprising a vCD47 extracellular domain, or a variant thereof, may be used in competition binding assays to identify a binding site of CD47 that interacts with a CD47 ligand. The fusion polypeptide comprising a vCD47 extracellular domain, or a variant thereof, may be also used to alter (i.e., increase or decrease in a statistically significant or biologically significant manner) immunoresponsiveness of an immune cell. Such a fusion polypeptide may therefore also be used to alter the immune response of a subject and thereby may be useful for treating an immunological disease or disorder.

In one embodiment, a fusion polypeptide comprising vCD47 extracellular domain or a variant thereof as described herein may be used for treating a patient who presents an acute immune response. For example, a fusion polypeptide comprising vCD47 extracellular domain or a variant thereof may suppress an immune response associated with a disease or condition such as acute respiratory distress syndrome (ARDS). ARDS, which may develop in adults and in children, often follows a direct pulmonary or systemic insult (for example, sepsis, pneumonia, aspiration) that injures the alveolar-capillary unit. Several cytokines are associated with development of the syndrome, including, for example, tumor necrosis factor-alpha (TNF-α), interleukin-beta (IL-β), IL-10, and soluble intercellular adhesion molecule 1 (sICAM-1). The increased or decreased level of these factors and cytokines in a biological sample may be readily determined by methods and assays described herein and practiced routinely in the art to monitor the acute state and to monitor the effect of treatment.

To reduce or minimize the possibility or the extent of an immune response that is specific for vCD47, or fragment thereof, the fusion polypeptide may be administered in a limited number of doses, may be produced or derived in a manner that alters glycosylation of vCD47, and/or may be administered under conditions that reduce or minimize antigenicity of vCD47. For example, a fusion polypeptide comprising vCD47 extracellular domain or a variant thereof may be administered prior to, concurrently with, or subsequent to the administration in the host of a second composition that suppresses an immune response, particularly a response that is specific for vCD47.

Use of Fusion Polypeptides Comprising a CD47 Extracellular Domain, or Variant Thereof, for Altering Immunoresponsiveness of an Immune Cell In one embodiment, any one of the fusion polypeptides comprising a CD47 extracellular domain, or variant thereof, or any one of the fusion polypeptides comprising a vCD47 extracellular domain as described herein may be used to alter (enhance or suppress in a statistically significant or biologically significant manner) the immunoresponsiveness of an immune cell. Any one of the fusion polypeptides described herein may alter or affect the immunoresponsiveness of an immune cell by effecting a biological function or action, including any one or more (or at least one of) the following: inhibiting maturation of dendritic cells; impairing development of naïve T cells into Th1 effector cells; suppressing cytokine release by dendritic cells; altering cell migration; inhibiting production of at least one cytokine, for example, at least one of TNF-α, IL-12, IL-23, IFN-γ, GM-CSF, and IL-6; inhibiting immune complex-induced production of at least one cytokine by an immune cell, such, for example, a dendritic cell; inhibiting activation of an immune cell that expresses a CCD47 ligand, for example SIRP-alpha, inhibiting production of a chemokine by an immune cell; inhibiting Fc-mediated cytokine production; and suppressing a proinflammatory response.

An immune cell is any cell of the immune system, including a lymphocyte and a non-lymphoid cell such as accessory cell. Lymphocytes are cells that specifically recognize and respond to foreign antigens, and accessory cells are those that are not specific for certain antigens but are involved in the cognitive and activation phases of immune responses. For example, mononuclear phagocytes (macrophages), other leukocytes (e.g., granulocytes, including neutrophils, eosinophils, basophils), and dendritic cells function as accessory cells in the induction of an immune response. Immune cells include cells that express a CD47 ligand. For example, an immune cell includes a cell that expresses SIRP-α, which includes a monocyte, macrophage, dendritic cell, granulocyte, and a $CD34^{+}CD38^{-}CD133^{+}$ bone marrow stem/progenitor cell (see, g., Seiffert et al., *Blood* 94:3633 (1999); Seiffert et al., *Blood* 97:2741 (2001)). The activation of lymphocytes by a foreign antigen leads to induction or elicitation of numerous effector mechanisms that function to eliminate the antigen. Accessory cells such as mononuclear phagocytes that effect or are involved with the effector mechanisms are also called effector cells.

Major classes of lymphocytes include B lymphocytes (B cells), T lymphocytes (T cells), and natural killer (NK) cells, which are large granular lymphocytes. B cells are capable of producing antibodies. T lymphocytes are further subdivided into helper T cells (CD4+) and cytolytic or cytotoxic T cells (CD8+). Helper cells secrete cytokines that promote proliferation and differentiation of the T cells and other cells, including B cells and macrophages, and recruit and activate inflammatory leukocytes. Another subgroup of T cells, called regulatory T cells or suppressor T cells actively suppress activation of the immune system and prevent pathological self-reactivity, that is, autoimmune disease.

In general, an immune response includes (1) a humoral response, in which antibodies specific for antigens are produced by differentiated B lymphocytes known as plasma cells, and (2) a cell mediated response, in which various types of T lymphocytes act to eliminate antigens by a number of mechanisms. For example, helper T cells that are capable of recognizing specific antigens may respond by releasing soluble mediators such as cytokines to recruit additional cells of the immune system to participate in an immune response. Also, cytotoxic T cells that are also capable of specific antigen recognition may respond by binding to and destroying or damaging an antigen-bearing cell or particle.

An immune response in a host or subject may be determined by any number of well-known immunological methods described herein and with which those having ordinary skill in the art will be readily familiar. Such assays include, but need not be limited to, in vivo or in vitro determination of soluble antibodies, soluble mediators such as cytokines (e.g., IFN-γ, IL-2, IL-4, IL-10, IL-12, IL-6, IL-23, TNF-α, and TGF-β), lymphokines, chemokines, hormones, growth factors, and the like, as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cell maturation, such as maturation of dendritic cells in response to a stimulus; alteration in relationship between a Th1 response and a Th2 response; cellular differentiation by cells of the immune system, including altered surface antigen expression profiles or the onset of apoptosis (programmed cell death). Procedures for performing these and similar assays are may be found, for example, in Lefkovits (*Immunology Methods Manual: The Comprehensive Sourcebook of Techniques,* 1998). See also *Current Protocols in Immunology*; Weir, *Handbook of Experimental Immunology*, Blackwell Scientific, Boston, Mass. (1986); Mishell and Shigii (eds.) *Selected Methods in Cellular Immunology*, Freeman Publishing, San Francisco, Calif. (1979); Green and Reed, *Science* 281:1309 (1998) and references cited therein).

Levels of cytokines may be determined according to methods described herein and practiced in the art, including ELISA, ELISPOT, and flow cytometry (to measure intracellular cytokines). Immune cell proliferation and clonal expansion resulting from an antigen-specific elicitation or stimulation of an immune response may be determined by isolating lymphocytes, such as spleen cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of a fusion polypeptide described herein on the balance between a Th1 immune response and a Th2 immune response may be examined, for example, by determining levels of Th1 cytokines, such as IFN-γ, IL-12, IL-2, and TNF-β, and Type 2 cytokines, such as IL-4, IL-5, IL-9, IL-10, and IL-13.

Methods and techniques for determining the effect of a fusion polypeptide comprising a CD47 extracellular domain, or variant thereof, (or viral CD47 extracellular domain or variant thereof) may also be found in Armant et al., *J. Exp. Med.* 190:1175 (1999); Demeure et al., *J. Immunol.* 164:2193 (2000); Avice et al., *J. Immunol.* 165:4624 (2000); Lamy et al., *J. Biol. Chem.* 278 (23915-21 (2003); Hermann et al., *J. Cell Biol.* 144:767-75 (1999); Liu et al., *J. Biol. Chem.* 277: 10028-36 (2002); Seiffert et al., *Blood* 94:3633-43 (1999); Seiffert et al., *Blood* 97:2741-49 (2001); Motegi et al., *EMBO J.* 22:2634-44 (2003); Fukunaga et al., *J. Immunol.* 172:4091-99 (2004); Parkos et al., *J. Cell Biol.* 132:437-50 (1996); and International Application Publication Nos. WO 99/40940 and WO 97/27873.

In certain embodiments, a fusion polypeptide described herein that comprises a CD47 extracellular domain or variant thereof exhibits the capability to competitively inhibit binding of at least one CD47 ligand to CD47 expressed by a cell and located at the cell surface. The CD47 ligand may be at least one of SIRP-α, SIRP-beta-2, thrombospondin-1, $α_vβ_3$ integrin, and $α_2β_1$ integrin. In certain other embodiments, such a fusion polypeptide also has the capability to competitively inhibit binding of viral CD47 polypeptide to at least one CD47 ligand. The viral CD47 polypeptide includes an isolated full-length viral CD47 polypeptide, a viral CD47 extracellular domain, or viral CD47 expressed on the surface of a cell. In certain embodiments, the fusion polypeptide competitively inhibits binding of an at least one CD47 ligand to cell surface-expressed CD47 and competitively inhibits binding of the same ligand to viral CD47. In other embodiments, the at least one, two, three, four, or five, or more CD47 ligands that are competitively inhibited from binding to a cell-surface expressed CD47 in the presence of a fusion polypeptide comprising CD47 extracellular domain or variant thereof may not be the same one, two, three, four, or five, or more CD47 ligands that are competitively inhibited from binding to viral CD47. The viral CD47 polypeptide includes an isolated full-length viral CD47 polypeptide, a viral CD47 extracellular domain, or viral CD47 expressed on the surface of a cell. Examples of viral CD47 polypeptides are described herein and can be readily identified in the relevant art by a skilled artisan. Any of a number of assays described herein and practiced in the art for determining the level of binding between a fusion polypeptide comprising a CD47 extracellular domain or variant thereof and a CD47 ligand can be modified to a format for determining the capability of the fusion polypeptide to bind to the ligand in the presence of a viral CD47 polypeptide. Such modifications are routinely performed by persons skilled in the art.

Fc Polypeptide Moiety of the Fusion Polypeptides

In one embodiment, a fusion polypeptide comprising a CD47 extracellular domain, or a variant thereof, is fused to an Fc polypeptide. An Fc polypeptide, which includes a mutein Fc polypeptide (that is, an Fc polypeptide into which a substitution, deletion, or insertion of at least one amino acid has been introduced, also called a Fc polypeptide variant), is derived from the constant region portion of an immunoglobulin. An Fc polypeptide comprises the heavy chain CH2 domain, the CH3 domain, and a portion of, or the entire, hinge region that is located between the heavy chain CH1 domain and CH2. Historically, the Fc fragment was derived by papain digestion of an immunoglobulin and included the hinge region of the immunoglobulin. Fc regions are monomeric polypeptides that may be linked into dimeric or multimeric forms by covalent (e.g., particularly disulfide bonds) and non-covalent association. The number of cysteine residues in the hinge portion of an Fc polypeptide varies depending on the immunoglobulin class (e.g., IgG, IgA, IgE) or subclass (e.g., human IgG1, IgG2, IgG3, IgG4, IgA1, IgA2), and thus the number of intermolecular disulfide bonds that form between the hinge portions of monomeric subunits of Fc polypeptides varies.

In one embodiment, the Fc polypeptide is of human origin and may be from any of the immunoglobulin classes, such IgG or IgA, and from any subclass such as human IgG1, IgG2, IgG3, and IgG4. In a certain embodiment, the Fc polypeptide is derived from a human IgG1 immunoglobulin. In another embodiment, the CD47 extracellular domain-Fc fusion polypeptide comprises an Fc polypeptide from a non-human animal, for example, but not limited to, a mouse, rat, rabbit, camel, shark, non-human primate, or hamster. The amino acid sequence of an Fc polypeptide derived from an immunoglobulin of the same host species to which an CD47 extracellular domain-Fc fusion polypeptide may be administered is likely to be non-immunogenic, or less immunogenic, than an Fc polypeptide from a non-syngeneic host. In certain other embodiments, a particular property attributed to an Fc polypeptide of a non-syngeneic species (for example, a Fc polypeptide from a non-human species fused to a human CD47 extracellular domain for administration to a human subject) may be desirable. Such an Fc polypeptide may be altered, such as by introducing amino acid substitutions or in some manner altering the glycosylation pattern, to reduce the immunogenicity of the Fc polypeptide when introduced into a non-syngeneic host. As described herein, immunoglobulin sequences of a variety of species are available in the art, for example, in Kabat et al. (in *Sequences of Proteins of Immunological Interest,* 4th ed (U.S. Dept. of Health and Human Services, U.S. Government Printing Office, 1991)). A person skilled in the molecular biology art can readily prepare such fusion polypeptides according to methods described herein and practiced routinely in the art.

In one embodiment, a fusion polypeptide comprising a CD47 (e.g., a human CD47) extracellular domain fused to a Fc polypeptide comprises the amino acid sequence set forth in SEQ ID NO:39. In other specific embodiments, the amino acid sequence of the fusion polypeptide comprises an amino acid sequence that is at least 65%-75%, 75%-80%, 80%-85%, 85%-90%, or 95%-99% identical (which includes any percent identity between any one of the described ranges) to SEQ ID NO:39. As discussed herein, the CD47 extracellular domain moiety of the fusion polypeptide may contain at least one amino acid substitution, deletion, or insertion compared with a wildtype CD47 sequence. In addition, or instead, the Fc polypeptide moiety may comprises at least one amino acid substitution, deletion, or insertion compared with a wildtype Fc amino acid sequence. Furthermore, as described in Kabat et al., the Fc polypeptides of all immunoglobulins, while conserved, are not necessarily identical. Therefore, natural Fc polypeptides (that is, those identified as being produced in a human or non-human animal) are not necessarily identical, and for example, may be at least 85%, 90%, or 95% identical to the amino acid sequence set forth in any of the sequences disclosed herein and known in the art but which may readily be used for making a fusion polypeptide described herein.

```
SEQ ID NO: 39
corresponds to the following sequence:
QLLFNKTKSVEFTFCNDTVVIPCFVTNMEAQNTTEVYVKWKFKGRDIYTF

DGALNKSTVPTDFSSAKIEVSQLLKGDASLKMDKSDAVSHTGNYTCEVTE

LTREGETIIELKYRVVSWFSPNENKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK
```

In one embodiment, a fusion polypeptide comprises an extracellular domain of CD47 fused to a human IgG1 Fc polypeptide, wherein the Fc polypeptide comprises a deletion of a cysteine residue in the hinge region, wherein the deleted cysteine residue is the cysteine residue most proximal to the amino terminus of the hinge region of the Fc portion of a wildtype human IgG1 immunoglobulin. The Fc polypeptide further comprises a deletion of an aspartate residue immediately adjacent to the cysteine residue most proximal to the amino terminus of the hinge region of the Fc portion of said wildtype human IgG1 immunoglobulin, wherein the fusion polypeptide alters the immunoresponsiveness of an immune cell. The fusion polypeptide further comprises an amino acid sequence at least 95% identical to the amino acid sequence set forth in SEQ ID NO:5 provided that said SEQ ID NO:5 is modified by deleting a serine residue at position 21 of Said SEQ ID NO: 51; and said SEQ ID NO:5 is further modified to retain Leu-Leu-Gly-Gly-Pro-Ser residues located at positions 1-6 of SEQ ID NO:21.

In another embodiment a fusion polypeptide comprises an extracellular domain of CD47 fused to a human IgG1 Fc polypeptide, wherein the fusion polypeptide comprises an amino acid sequence at least 95% identical to the amino acid sequence set forth in SEQ ID NO:1 and an amino acid sequence at least 95% identical to the amino acid sequence set forth in SEQ ID NO:6 provided that said SEQ ID NO:6 is modified by deleting a cysteine residue in the hinge region, wherein the deleted cysteine residue is the cysteine residue most proximal to the amino terminus of the hinge region of the Fc portion of a wildtype human IgG1 immunoglobulin, and said SEQ ID NO:6 is further modified by deleting an aspartate residue immediately adjacent to the cysteine residue most proximal to the amino terminus of the hinge region of the Fc portion of said wildtype human IgG1 immunoglobulin, wherein the fusion polypeptide alters the immunoresponsiveness of an immune cell.

In another embodiment, a fusion polypeptide comprises an extracellular domain of CD47 fused to a human IgG1 Fc polypeptide, wherein the fusion polypeptide alters the immunoresponsiveness of an immune cell; wherein the fusion polypeptide comprises an amino acid sequence at least 95% identical to the amino acid sequence set forth in SEQ ID NO:1 and an amino acid sequence at least 95% identical to the amino acid sequence set forth in SEQ ID NO:7 with the proviso that said SEQ ID NO:7 is modified to retain Leu-Leu-Gly-Gly-Pro-Ser residues located at positions 1-6 of SEQ ID NO:21.

In one embodiment, a fusion polypeptide comprising a CD47 (e.g., a human CD47) extracellular domain fused to a Fc polypeptide comprises the amino acid sequence set forth in SEQ ID NO:2. In other specific embodiments, the amino acid sequence of the fusion polypeptide comprises an amino acid sequence that is at least 65%-75%, 75%-80%, 80-85%, 85%-90%, or 95%-99% identical (which includes any percent identity between any one of the described ranges) to SEQ ID NO:2. As discussed herein, the CD47 extracellular domain moiety of the fusion polypeptide may contain at least one amino acid substitution, deletion, or insertion compared with a wildtype CD47 sequence. In addition, or instead, the Fc polypeptide moiety may comprises at least one amino acid substitution, deletion, or insertion compared with a wildtype Fc amino acid sequence. Furthermore, as described in Kabat et al., the Fc polypeptides of all immunoglobulins, while conserved, are not necessarily identical. Therefore, natural Fc polypeptides (that is, those identified as being produced in a human or non-human animal) are not necessarily identical, and for example, may be at least 85%, 90%, or 95% identical to the amino acid sequence set forth in any of the sequences disclosed herein and known in the art but which may readily be used for making a fusion polypeptide described herein.

In certain embodiments, the Fc polypeptide is a mutein Fc polypeptide (also called an Fc polypeptide variant herein), which has a substitution, deletion, or addition of at least 1, 2, 3, 4, 5, 6, 7, 8, 9, 10, or 10-15, 16-25 amino acids. In one embodiment, the mutein Fc polypeptide has at least 1, 2, 3, or more amino acid substitutions, deletions, or additions in the hinge region of the Fc polypeptide. In another embodiment, the mutein Fc polypeptide has at least 1, 2, 3, 4, 5, 6, 7, 8, 9, 10 or more amino acid substitutions, deletions, or additions in the CH2 domain and/or in the CH3 domain of the Fc polypeptide. A mutein Fc polypeptide also includes fragments of an Fc polypeptide, such as an Fc polypeptide that is truncated at the C-terminal end (that is at least 1, 2, 3, 4, 5, 10, 15, 20, or more amino acids have been removed or deleted).

In certain embodiments, the Fc polypeptides described herein contain multiple cysteine residues, such as at least some or all of the cysteine residues in the hinge region, to permit interchain disulfide bonds to form between the Fc polypeptide portions of two separate fusion proteins, such that two CD47 extracellular domain (or variant thereof)/Fc polypeptides fusion proteins form dimers through interaction between the Fc portions of the fusion polypeptide. In other embodiments, the Fc polypeptide comprises substitutions or deletions of cysteine residues in the hinge region such that an Fc polypeptide fusion protein is monomeric and fails to form a dimer (see, e.g., U.S. Patent Application Publication No. 2005/0175614).

An Fc polypeptide may be fused to a CD47 extracellular domain via covalent attachment such as by conjugation procedures practiced in the art for covalently linking two separate amino acid-containing moieties, for example, using maleimide or carbidiimide coupling chemistry (see also, e.g., Carlsson et al., *Biochem. J.* 173:723-37 (1978)). The site of conjugation can be at either the amino terminus or the carboxy terminus or in the middle of the sequence. The point of conjugation may be a sulfhydryl (SH) group or an amino group ($NH_2$).

An Fc polypeptide, and any one or more constant region domains, and fusion proteins comprising at least one immunoglobulin constant region domain may also be readily prepared according to recombinant molecular biology techniques with which a skilled artisan is quite familiar. One means to minimize immunogenicity of a CD47-Fc fusion polypeptide is to fuse the CD47 moiety to an Fc polypeptide using the nucleotide sequence and the encoded amino acid sequence derived from the animal species for whose use the Fc fusion polypeptide is intended. In one embodiment, the Fc polypeptide is of human origin and may be from any one of the human immunoglobulin classes, including, for example, human IgG1 and IgG2.

An Fc polypeptide that is a mutein Fc polypeptide may also be referred to as a Fc polypeptide variant. One such Fc polypeptide variant has one or more cysteine residues (such as one or more cysteine residues in the hinge region that forms an interchain disulfide bond) substituted with another amino acid, such as serine, to reduce the number of interchain disulfide bonds that can form between the two heavy chain constant region polypeptides. For example, the cysteine residue most proximal to the amino terminal end of the hinge region, which forms a disulfide bond with a light chain constant region to form a whole immunoglobulin molecule, may be substituted, for example, with a serine residue. Alternatively, any one or more cysteine residues, including the cysteine residue most proximal to the amino terminus of the hinge region, may be deleted from the hinge region of the Fc polypeptide.

In one embodiment, a mutein Fc polypeptide comprises a mutation of at least one cysteine residue in the hinge region of an Fc polypeptide. For certain immunoglobulin Fc portions, the cysteine residue in the mutein Fc that is substituted or deleted is the cysteine residue that is most proximal to the amino terminus of the hinge region of an Fc polypeptide (e.g., for example, the cysteine residue most proximal to the amino terminus of the hinge region of the Fc portion of a wildtype human IgG1 immunoglobulin). By way of illustration, the hinge of a human IgG1 Fc polypeptide has three cysteine residues (see, e.g., positions 1, 7, and 10 of SEQ ID NO:6). In certain embodiments, the cysteine residue that is most proximal to the amino terminal end of the human IgG1 Fc polypeptide, which corresponds to a cysteine residue at position 1 of SEQ ID NO:6, is deleted. Alternatively, the cysteine residue at this position is substituted with another amino acid that is incapable of forming a disulfide bond, for example, a serine residue.

In another embodiment, a mutein Fc polypeptide that comprises a deletion or substitution of the cysteine residue most proximal to the amino terminus of the hinge region of an Fc polypeptide further comprises a deletion or substitution of the adjacent amino acid that is toward the carboxy terminus (i.e., the adjacent C-terminal amino acid). In a certain embodiment, the cysteine residue most proximal to the amino terminus of the hinge portion and the adjacent C-terminal residue are both deleted from the hinge region of a mutein Fc polypeptide. In a specific embodiment, the mutein Fc polypeptide comprises a deletion of a cysteine residue that corresponds to the cysteine at position 1 of SEQ ID NO:6 and a deletion of an aspartic acid that corresponds to the aspartic acid at position 2 of SEQ ID NO:6. Fc polypeptides that comprise deletion of these cysteine and aspartic acid residues in the hinge region may be efficiently expressed in a host cell, and in certain instances, may be more efficiently expressed in a cell than an Fc polypeptide that retains the wildtype cysteine and aspartate residues.

In other embodiments, the Fc polypeptide may comprise at least one (i.e., one or more) substitutions, deletions, or insertions that increase or enhance the capability of the Fc polypeptide to alter the immunoresponsiveness of an immune cell. In particular embodiments, a substitution, deletion, or insertion of an amino acid is introduced into an Fc polypeptide to enhance or increase the capability of a CD47 extracellular domain-Fc polypeptide fusion protein to suppress the immunoresponsiveness of an immune cell, and thus, in certain embodiments, to enhance the capability of the fusion protein to treat an immune disease or disorder.

In a certain embodiment, the Fc polypeptide is mutated to decrease the capability of the Fc polypeptide moiety of the fusion protein to bind to an Fc receptor that is expressed by an immune cell. Without wishing to be bound by theory, to decrease or abrogate the capability of the Fc polypeptide to bind to an Fc receptor of an immune cell, may decrease, minimize, or abrogate a signal that activates immunoresponsiveness of the immune cell in a manner that is undesired.

In one certain embodiment, Fc polypeptide may be an aglycosylated Fc polypeptide. Any one or more of an N-glycosylation site or an O-glycosylation site present in the Fc polypeptide may be removed by introducing one or more substitutions or deletions of an amino acid residue that may be glycosylated. For example, the asparagine residue of an N-linked glycosylation site (i.e., Asn-X-Ser/Thr, wherein X is any amino acid except Pro or Asp) may be substituted with another amino acid. The asparagine residue at position 219 of SEQ ID NO:2 corresponds to the asparagine residue at position 297 of a human IgG1 Fc polypeptide that is described in the art as being glycosylated (see Asn at position 78 of SEQ ID NO:6, an exemplary wildtype human IgG1 Fc polypeptide sequence). Thus an exemplary CD47 extracellular-Fc fusion polypeptide comprises the amino acid sequence set forth in SEQ ID NO:28. In another embodiment, the lysine residue at the N-terminus of the hinge region (see lysine at position 3 of SEQ ID NO 6) may be deleted (see, e.g., SEQ ID NO:29, which has a deletion of the lysine residue located at position 144 in SEQ ID NO:2). In certain other embodiments, the Fc polypeptide comprises a substitution of the asparagine residue that corresponds to position 219 of SEQ ID NO:2 and deletion (or substitution) of the lysine residue at position 144 of SEQ ID NO:2.

The capability of a CD47 extracellular domain-Fc polypeptide fusion protein to alter, preferably suppress, the immunoresponsiveness of an immune cell may be increased or enhanced by incorporation of a linker polypeptide between the CD47 moiety and the Fc polypeptide moiety. Without wishing to be bound by any particular theory, a linker polypeptide may increase the flexibility, or remove constraint, of the CD47 extracellular domain moiety (which includes a CD47 extracellular domain dimer) to adopt an effective or more effective conformation to interact with an immune cell and affect the cell's immunoresponsiveness, or to interact with a molecule that, in turn, interacts with an immune cell to affect the immunoresponsiveness of the immune cell.

A CD47 extracellular domain (or variant or fragment thereof) fused in frame with an Fc polypeptide or Fc polypeptide variant (e.g., a mutein Fc polypeptide) may comprise a polypeptide linker or spacer sequence between the CD47 extracellular domain polypeptide and Fc polypeptide. The linker (or spacer) may be a single amino acid (such as for example a glycine residue) or may be two, three, four, five, six, seven, eight, nine, or ten amino acids, or may be any number of amino acids between 5 and 100 amino acids, between 5 and 50, 5 and 30, or 5 and 20 amino acids. A polypeptide linker may also include a short peptide linker that may comprise at least two amino acids that are encoded by a nucleotide sequence that is a restriction enzyme recognition site. Examples of such restriction enzyme recognition sites include, for example, BamHI, ClaI, EcoRI, HindIII, KpnI, NcoI, NheI, PmlI, PstI, SalI, and XhoI.

Thus, polypeptide linkers may separate the CD47 extracellular domain moiety from the Fc polypeptide moiety by a distance sufficient to aid or ensure that each polypeptide moiety properly folds into the secondary and tertiary structures necessary for the desired biological activity. By way of example, the linker should permit the extracellular domain of CD47 to assume the proper spatial orientation to form a binding site for a CD47 ligand. Suitable polypeptide linkers may adopt a flexible extended conformation that does not exhibit a propensity for developing an ordered secondary structure that could interact or interfere with the functional protein domains, and that also would have a minimal hydrophobic or charged character, which could promote an undesirable interaction with the functional CD47 domain. Typical surface amino acids in flexible protein regions include glycine (Gly), asparagine (Asn) and serine (Ser). Virtually any permutation of amino acid sequences containing Gly, Asn, and Ser would be expected to satisfy the above criteria for a peptide linker sequence. Other near-neutral amino acids, such as threonine (Thr) and alanine (Ala), may also be used in the linker sequence. Suitable polypeptide linkers (or spacer peptides) may comprise from 5 to 100 amino acids and in certain embodiments, comprise from 5 to 20 amino acids in length. Examples of such linkers include, but are not limited to ($Gly_4$ Ser (SEQ ID NO:30))$_n$, wherein n=1-12 or n=1-8, or n=1-4; $Gly_4$ $SerGly_5$ Ser (SEQ ID NO:31), and ($Gly_4$ $SerGly_5$ Ser) (SEQ ID NO:31)$_m$ wherein m=2-4. See also SEQ ID NOS:32 and 33 comprising a human CD47 extracellular domain fused to an Fc polypeptide ($Gly_4$ Ser) linker wherein n=1 and 2, respectively.

As described herein, in certain embodiments, a mutein Fc polypeptide that is fused with a CD47 extracellular domain, or a variant thereof, comprises a substitution or a deletion of the cysteine residue that is most proximal to the amino terminus of the hinge region of an Fc polypeptide and a deletion of the adjacent aspartic acid residue (toward the C-terminal end of the Fc polypeptide). In other embodiments, the fusion polypeptide may further comprise at least one, two, or three or more amino acid substitutions in the CH2 domain of the Fc polypeptide that reduce the capability of the mutein Fc polypeptide to bind to an IgFc receptor. In specific embodiments, the at least one, two, or three amino acids substitutions in the CH2 domain are substitutions of an amino acid(s) located at a position that corresponds to EU numbered position 234, 235, and/or 237.

In another embodiment, a mutein Fc polypeptide is an Fc polypeptide variant that has at least one, two, three, four, five, six, seven, or more amino acids involved in an effector function substituted or deleted such that the Fc polypeptide has a reduced level of an effector function. The Fc portion of the immunoglobulin mediates certain effector functions of an immunoglobulin. Three general categories of effector functions associated with the Fc region include (1) activation of the classical complement cascade, (2) interaction with effector cells, and (3) compartmentalization of immunoglobulins.

Such a mutein Fc polypeptide may also comprise the mutations in the hinge region described herein and/or may comprise one or more mutations that alter the glycosylation pattern of the Fc polypeptide.

Amino acids in the Fc region may be substituted to reduce or abrogate binding of the Fc polypeptide to a component of the complement cascade (see, e.g., Duncan et al., *Nature* 332:563-64 (1988); Morgan et al., *Immunology* 86:319-24 (1995)); or to reduce or abrogate the ability of the Fc polypeptide to bind to an IgG Fc receptor expressed by an immune cell (Wines et al., *J. Immunol.* 164:5313-18 (2000); Chappel et al., *Proc. Natl. Acad. Sci. USA* 88:9036 (1991); Canfield et al., *J. Exp. Med.* 173:1483 (1991); Duncan et al., supra); or to alter antibody-dependent cellular cytotoxicity. Such an Fc polypeptide variant that differs from the wildtype Fc polypeptide is also called herein a mutein Fc polypeptide.

In one embodiment, a CD47 extracellular domain or variant thereof is fused in frame with an Fc polypeptide that comprises at least one substitution of a residue that in the wildtype Fc region polypeptide contributes to binding of an Fc polypeptide or immunoglobulin to one or more IgG Fc receptors expressed on certain immune cells. Such a mutein Fc polypeptide comprises at least one substitution of an amino acid residue in the CH2 domain of the mutein Fc polypeptide, such that the capability of the fusion polypeptide to bind to an IgG Fc receptor, such as an IgG Fc receptor present on the surface of an immune cell, is reduced.

By way of background, on human leukocytes three distinct types of Fc IgG-receptors are expressed that are distinguishable by structural and functional properties, as well as by antigenic structures, which differences are detected by CD specific monoclonal antibodies. The IgG Fc receptors are designated FcγRI (CD64), FcγRII (CD32), and FcγRIII (CD16) and are differentially expressed on overlapping subsets of leukocytes.

FcγRI (CD64), a high-affinity receptor expressed on monocytes, macrophages, neutrophils, myeloid precursors, and dendritic cells, comprises isoforms 1a and 1b. FcγRII (CD32), comprised of isoforms IIa, IIb1, IIb2, IIb3, and IIc, is a low-affinity receptor that is the most widely distributed human FcγR type; it is expressed on most types of blood leukocytes, as well as on Langerhans cells, dendritic cells, and platelets. FcγRIII (CD16) has two isoforms, both of which are capable of binding to human IgG1 and IgG3. The FcγRIIIa isoform has an intermediate affinity for IgG and is expressed on macrophages, monocytes, natural killer (NK) cells, and subsets of T cells. FcγRIIIb is a low-affinity receptor for IgG and is selectively expressed on neutrophils.

Residues in the amino terminal portion of the CH2 domain that contribute to IgG Fc receptor binding include residues at positions between Leu234-Ser239 (Leu-Leu-Gly-Gly-Pro-Ser (SEQ ID NO:21) (EU numbering system, Kabat et al., supra) (see, e.g., Morgan et al., *Immunology* 86:319-24 (1995), and references cited therein). The position of these amino acids in an IgG immunoglobulin is designated using the EU numbering system, which is a widely used nomenclature in the antibody art when referring to residues of the Fc portion of an IgG immunoglobulin that bind to an IgG Fc receptor. The residues Leu234-Ser239 correspond to positions 15-20 of the amino acid sequence of a human IgG1 Fc polypeptide (SEQ ID NO:6). Substitution of the amino acid at one or more of these six positions (i.e., one, two, three, four, five, or all six) in the CH2 domain results in a reduction of the capability of the Fc polypeptide to bind to one or more of the IgG Fc receptors (or isoforms thereof) (see, e.g., Burton et al., *Adv. Immunol.* 51:1 (1992); Hulett et al., *Adv. Immunol.* 57:1 (1994); Jefferis et al., *Immunol. Rev.* 163:59 (1998); Lund et al., *J. Immunol.* 147:2657 (1991); Sarmay et al., *Mol. Immunol.* 29:633 (1992); Lund et al., *Mol. Immunol.* 29:53 (1992); Morgan et al., supra). In addition to substitution of one or more amino acids at EU positions 234-239, one, two, or three or more amino acids adjacent to this region (either to the carboxy terminal side of position 239 or to the amino terminal side of position 234) may also be substituted.

By way of example, substitution of the leucine residue at position 235 (which corresponds to position 16 of SEQ ID NO:6) with a glutamic acid residue or an alanine residue abolishes or reduces, respectively, the affinity of an immunoglobulin (such as human IgG3) for FcγRI (Lund et al., 1991, supra; Canfield et al., supra; Morgan et al., supra). As another example, replacement of the leucine residues at positions 234 and 235 (which correspond to positions 15 and 16 of SEQ ID NO:6), for example, with alanine residues, abrogates binding of an immunoglobulin to FcγRIIa (see, e.g., Wines et al., supra). Alternatively, leucine at position 234 (which corresponds to position 15 of SEQ ID NO:6), leucine at position 235 (which corresponds to position 16 of SEQ ID NO:6), and glycine at position 237 (which corresponds to position 18 of SEQ ID NO:6), each may be substituted with a different amino acid, such as leucine at position 234 may be substituted with an alanine residue (L234A), leucine at 235 may be substituted with an alanine residue (L235A) or with a glutamic acid residue (L235E), and the glycine residue at position 237 may be substituted with another amino acid, for example an alanine residue (G237A).

In one embodiment, a mutein Fc polypeptide that is fused in frame to a CD47 extracellular domain (or variant thereof) comprises one, two, three, four, five, or six mutations at positions 15-20 of SEQ ID NO:6 that correspond to positions 234-239 of a human IgG1 CH2 domain (EU numbering system) as described herein. An exemplary mutein Fc polypeptide has the amino acid sequence set forth in SEQ ID NO:7 in which substitutions corresponding to (L234A), (L235E), and (G237A) may be found at positions 13, 14, and 16 of SEQ ID NO:7.

In a specific embodiment, a mutein Fc polypeptide comprises the amino acid sequence set forth in SEQ ID NO:7, which differs from the wildtype Fc polypeptide (SEQ ID NO:6) wherein the cysteine residue at position 1 of SEQ ID NO:6 is deleted and the aspartic acid at position 2 of SEQ ID NO:6 is deleted and the leucine reside at position 15 of SEQ ID NO:6 is substituted with an alanine residue, the leucine residue at position 16 is substituted with a glutamic acid residue, and the glycine residue at position 18 is substituted with an alanine residue. Thus, an exemplary mutein Fc polypeptide comprises an amino acid sequence at its amino terminal portion of KTHTCPPCPAPEAEGAPS (SEQ ID NO:22) (see SEQ ID NO:7, an exemplary Fc mutein sequence). Thus, an exemplary Fc mutein polypeptide comprises deletion of a cysteine residue most proximal to the amino terminus of the hinge, a deletion of the aspartate residue adjacent to this cysteine, and substitutions of amino acids at positions that correspond to EU234, EU235, and EU237.

Other Fc variants encompass similar amino acid sequences of known Fc polypeptide sequences that have only minor changes, for example by way of illustration and not limitation, covalent chemical modifications, insertions, deletions and/or substitutions, which may further include conservative substitutions. Amino acid sequences that are similar to one another may share substantial regions of sequence homology. Similarly, nucleotide sequences that encode the Fc variants may encompass substantially similar nucleotide sequences and have only minor changes, for example by way of illustration and not limitation, covalent chemical modifications, insertions, deletions, and/or substitutions, which may further include silent mutations owing to degeneracy of the genetic code. Nucleotide sequences that are similar to one another may share substantial regions of sequence homology.

The nucleotide sequences that encode Fc polypeptides from various classes and isotypes of immunoglobulins from various species are known and available in GenBank databases and in Kabat (Kabat et al., in *Sequences of Proteins of Immunological Interest*, 4th ed., (U.S. Dept. of Health and Human Services, U.S. Government Printing Office, 1991), see also updates to the online Kabat database available by license). Any of these polynucleotide sequences (or any degenerate polynucleotide sequence that encodes the Fc polypeptide of interest) may be used for preparing a recombinant construct according to molecular biology methods routinely practiced by persons skilled in the art. To minimize the immunogenicity of the Fc polypeptide in the host or subject to which a fusion polypeptide comprising a CD47 extracellular domain (or variant thereof) may be administered, the sequence of the Fc polypeptide is typically chosen from immunoglobulins of the same species, that is, for example, a human Fc polypeptide sequence is fused to a human CD47 extracellular domain, or variant thereof, that will be administered to a human subject or host.

In other embodiments, the fusion polypeptide comprises a viral CD47 extracellular domain, or variant thereof, as described herein, fused to any one of the mutein Fc polypeptides described above.

Production of a Fusion Polypeptide Comprising a CD47 Extracellular Domain Fused to a Mutein Fc Polypeptide Any one of the fusion polypeptides described herein that comprise a CD47 extracellular domain, or variant thereof, fused in frame to an Fc polypeptide, or variant thereof, or that comprise a viral CD47 extracellular domain, or variant thereof, fused in frame to a Fc polypeptide, or variant thereof, may be produced, made, or manufactured according to methods described herein and routinely practiced in the art. In certain embodiments, the fusion polypeptides are recombinant fusion polypeptides. A recombinant expression construct may be prepared for the expression of a fusion polypeptide according to standard techniques and methods practiced by a skilled person in the molecular biology art. In order to obtain efficient transcription and translation, the polynucleotide sequence in each construct includes appropriate regulatory sequences, particularly a promoter and leader sequence operatively linked to the nucleotide sequence encoding a CD47 extracellular domain, or variant thereof, or may be operatively linked to a nucleotide sequence encoding a signal peptide sequence located at the amino terminal end of the CD47 extracellular domain. The polynucleotide encoding the CD47 extracellular domain further may further comprise a nucleotide sequence that encodes a Fc polypeptide, including a mutein Fc polypeptide, that is expressed in frame with the CD47 extracellular domain, or variant thereof. In addition, as described herein, the polynucleotide may also encode, in frame, a polypeptide linker (or spacer peptide or polypeptide) between the CD47 moiety and the Fc polypeptide moiety.

Numerous vectors are available from commercial vendors for cloning and preparing recombinant expression constructs. Methods and techniques for producing polypeptides recombinantly are generally well known and routinely used. For example, molecular biology procedures are described by Sambrook et al. (*Molecular Cloning, A Laboratory Manual*, 2nd ed., Cold Spring Harbor Laboratory, New York, 1989; see also Sambrook et al., 3rd ed., Cold Spring Harbor Laboratory, New York, (2001)). As described herein, in certain embodiments, the fusion polypeptide further comprises a linker or spacer polypeptide sequence (a polypeptide sequence as described herein is intended to include a peptide sequence) between the CD47 extracellular domain, or variant thereof, and the Fc polypeptide. Persons skilled in the art can readily prepare polynucleotide sequences that encode a linker (or spacer), which linker may be a single amino acid (such as for example a glycine residue) or may be two, three, four, five, six, seven, eight, nine, or ten amino acids, or may be any number of amino acids between 5 and 100 amino acids, and in certain embodiments between 5 and 20 amino acids, which are described in greater detail herein. A polypeptide linker may also include a short peptide such as a peptide linker that is at least two amino acids that are encoded by a nucleotide sequence that is a restriction enzyme recognition site. Examples of such restriction enzyme recognition sites include, for example, BamHI, ClaI, EcoRI, HindIII, KpnI, NcoI, NheI, PmlI, PstI, SalI, and XhoI.

A recombinant expression construct may be prepared for the expression of a fusion polypeptide according to standard techniques and methods practiced by a skilled person in the molecular biology art. In order to obtain efficient transcription and translation, the polynucleotide sequence in each construct should include appropriate regulatory sequences, particularly a promoter and leader sequence operatively linked to the nucleotide sequence encoding the CD47 extracellular domain, or variant thereof, or may be operatively linked to a nucleotide sequence encoding the signal peptide sequence located at the amino terminal end of the CD47 extracellular domain. Particular methods for producing polypeptides recombinantly are generally well known and routinely used. For example, molecular biology procedures are described by Sambrook et al. (*Molecular Cloning, A Laboratory Manual,* 2nd ed., Cold Spring Harbor Laboratory, New York, 1989; see also Sambrook et al., 3rd ed., Cold Spring Harbor Laboratory, New York, (2001)).

A recombinant construct prepared according to methods routinely practiced in the art may be introduced into a host cell via any one of several transformation, transfection, or transduction methods. Suitable host cells include prokaryotes, insect cells, yeast, and higher eukaryotic cells (including mammalian cells). In certain other embodiments, the fusion polypeptide may be expressed in a eukaryotic host cell, including yeast (e.g., *Saccharomyces cerevisiae, Schizosaccharomyces pombe,* and *Pichia pastoris*); an animal cell (including mammalian cells) or plant cells. Examples of suitable animal cells include, for example, COS, CHO, or HEK293 cells. Examples of plant cells include tobacco, corn, soybean, and rice cells. By using methods known to those having ordinary skill in the art and based on the present disclosure, a nucleic acid vector may be designed for expressing foreign sequences in a particular host system, and then polynucleotide sequences encoding the fusion polypeptide may be inserted. The regulatory elements will vary according to the particular host. See, for example, products and methods provided by commercial vendors, for example, Invitrogen (Carlsbad, Calif.); Stratagene (San Diego, Calif.); and BioCarta Inc. (San Diego, Calif.).

Methods for manufacturing the CD47 Fc fusion polypeptides are also provided herein. Methods as described above may be adapted for larger scale manufacturing of the CD47 Fc polypeptide fusion proteins. Manufacturing the polypeptides may comprise growing host cells that express such polypeptides in bioreactors, which reactors may also include matrices to which the host cells may attach, which, without wishing to be bound by theory permits cell cultures at high density.

Antibodies that Specifically Bind to CD47 and Antibodies that Specifically Bind to a CD47 Ligand Also provided herein are antibodies, and antigen-binding fragments thereof, that specifically bind to the extracellular domain of CD47. The anti-CD47 antibodies described herein competitively inhibit binding of a CD47 ligand to CD47 and competitively inhibit binding of a CD47 ligand to viral CD47 (i.e., a viral CD-47 like polypeptide). A CD47 ligand includes, for example, SIRP-α, SIRP-beta-2, thrombospondin-1, $α_vβ_3$ integrin, and $α_2β_1$ integrin. Without wishing to be bound by theory, an antibody, or antigen-binding fragment thereof, that competitively inhibits binding of viral CD47 to a CD47 ligand may manifest a similar immunosuppressive effect that occurs when viral CD47 is expressed by a cell that is infected with the poxvirus containing the genome that encodes the viral CD47. Thus, in other embodiments, antibodies, and antigen-binding fragments thereof, are provided herein that bind specifically to a CD47 ligand and that inhibit binding of a viral CD47 to bind to the CD47 ligand. An antibody that is specific for a CD47 ligand is understood to mean that the antibody binds specifically to one CD47 ligand, that is, an antibody is provided that specifically binds to the CD47 ligand SIRP-α. A different antibody, and antigen-binding fragment thereof, specifically binds to a second CD47 ligand such as thrombospondin-1. That is when an antibody, or antigen-binding fragment thereof, is referred to herein as an antibody that binds to a CD47 ligand, this means that the antibody has a single specificity and does not bind to multiple CD47 ligands.

Such an antibody, or antigen-binding fragment thereof, may modulate or alter the immune response of a host, and may particularly inhibit, suppress, or decrease the extent of, an immune response exhibited in an immunological disease or disorder, for example, an inflammatory or autoimmune disease or disorder. In certain embodiments, an anti-CD47 antibody, or antigen-binding fragment thereof, or an anti-CD47 ligand antibody, or antigen-binding fragment thereof, alters the ability of an accessory cell to release cytokines and/or to mature. An antibody that specifically binds to CD47 or an antibody that specifically binds to a CD47 ligand may have the capability to alter (enhance or suppress in a statistically significant or biologically significant manner) the immunoresponsiveness of an immune cell. Such an antibody or antigen binding fragment thereof may alter or affect the immunoresponsiveness of an immune cell by effecting a biological function or action, including any one or more (or at least one of) the following: inhibit maturation of dendritic cells; impair development of naïve T cells into Th1 effector cells; suppress cytokine release by dendritic cells; alter cell migration; inhibit production of at least one cytokine, for example, at least one of TNF-α, IL-12, IL-23, IFN-γ, GM-CSF, and IL-6; inhibit maturation of a dendritic cell; impair development of a naïve T cell into a Th1 effector cell; suppress cytokine secretion by a dendritic cell; inhibit production of a chemokine, for example MIP-1α; and suppress a proinflammatory response. An anti-CD47 ligand antibody that specifically binds to its cognate CD47 ligand may also inhibit an activity of function attributable to that CD47 ligand.

A viral CD47 may be any one of the poxvirus CD47-like polypeptides described herein or known in the art. Viral genomic sequences that encode viral CD47-like polypeptides have been identified in several poxviruses, including myxoma and orthopoxviruses as well as chordopoxvirus, a capripoxvirus, a leporipoxvirus, a suipoxvirus, a yatapoxvirus, and a deerpox virus. Exemplary amino acid sequences of poxvirus CD47-like polypeptides include the A44L polypeptide encoded by the genome of Variola minor virus (GenBank Accession No. CAB54747.1 (SEQ ID NO:3)); Vaccinia virus-Western Reserve (GenBank Accession No. AA089441.1); Vaccinia virus (modified virus Ankara) (GenBank Accession No. AAT10547.1); and Myxoma M128L polypeptide (GenBank Accession Nos. NP_051842.1 and AAF15016.1).

The antibodies and antigen-binding fragment described herein that specifically bind to CD47 or that specifically bind to a CD47 ligand may be useful for altering immunoresponsiveness of an immune cell and thereby may be useful for treating or preventing an immunological disease or disorder, cardiovascular disease or disorder, metabolic disease or disorder, or a proliferative disease or disorder. An immunological disease or disorder may be an autoimmune disease or an inflammatory disease. In certain embodiments, the immunological disease or disorder is multiple sclerosis, rheumatoid arthritis, a spondyloarthropathy, systemic lupus erythematosus, an antibody-mediated inflammatory or autoimmune disease or disorder, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, or inflammatory autoimmune myositis. A spondyloarthropathy includes, for example, ankylosing spondylitis, reactive arthritis, enteropathic arthritis associated with inflammatory bowel disease, psoriatic arthritis, isolated acute anterior uveitis, undifferentiated spondyloarthropathy, Behcet's syndrome, and juvenile idiopathic arthritis. The fusion polypeptides described herein may also be useful for treating a cardiovascular disease or disorder, such as atherosclerosis, endocarditis, hypertension, or peripheral ischemic disease.

As described herein, the anti-CD47 antibodies or anti-CD47 ligand antibodies may be useful for treating or preventing, inhibiting, slowing the progression of, or reducing the symptoms associated with, an immunological disease or disorder, a cardiovascular disease or disorder, a metabolic disease or disorder, or a proliferative disease or disorder. An immunological disorder includes an inflammatory disease or disorder and an autoimmune disease or disorder. While inflammation or an inflammatory response is a host's normal and protective response to an injury, inflammation can cause undesired damage. For example, atherosclerosis is, at least in part, a pathological response to arterial injury and the consequent inflammatory cascade. A cardiovascular disease or disorder that may be treated, which may include a disease and disorder that is also considered an immunological disease/disorder, includes for example, atherosclerosis, endocarditis, hypertension, or peripheral ischemic disease. A metabolic disease or disorder includes diabetes, obesity, and diseases and disorders associated with abnormal or altered mitochondrial function.

Any one or more of the fusion polypeptides comprising a CD47 extracellular domain or variant thereof as described herein may also be used in methods for screening samples containing antibodies, for example, samples of purified antibodies, antisera, or cell culture supernatants, or any other biological sample that may contain one or more antibodies specific for one or more of the fusion polypeptides. One or more of the fusion polypeptides comprising a CD47 extracellular domain or variant thereof may also be used in methods for identifying and selecting from a biological sample one or more B cells that are producing an antibody that specifically binds to the extracellular domain of CD47 (e.g., plaque forming assays and the like). The B cells may then be used as source of the specific antibody-encoding polynucleotide that can be cloned and/or modified by recombinant molecular biology techniques known in the art and described herein.

As used herein, an antibody is said to be "immunospecific," "specific for" or to "specifically bind" a CD47 extracellular domain (or variant thereof) if it reacts at a detectable level with the CD47 extracellular domain (or variant thereof), preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and an anti-CD47 extracellular domain (or variant thereof) antibody, for example, specifically binds to CD47 if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M.

Affinities of binding partners or antibodies can be readily determined using conventional techniques, for example, those described by Scatchard et al. (*Ann. N.Y. Acad. Sci. USA* 51:660 (1949)) and by surface plasmon resonance (SPR; BIAcore™, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the surface plasmon resonance signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-2565 (1993)).

Binding properties of an antibody to CD47 (particularly, the CD47 extracellular domain) or of an antibody that binds to a CD47 ligand may generally be determined and assessed using immunodetection methods including, for example, an enzyme-linked immunosorbent assay (ELISA), immunoprecipitation, immunoblotting, countercurrent immunoelectrophoresis, radioimmunoassays, dot blot assays, inhibition or competition assays, and the like, which may be readily performed by those having ordinary skill in the art (see, e.g., U.S. Pat. Nos. 4,376,110 and 4,486,530; Harlow et al., *Antibodies: A Laboratory Manual*, Cold Spring Harbor Laboratory (1988)). Immunoassay methods may include controls and procedures to determine whether antibodies bind specifically to CD47 and do not recognize or cross-react with unrelated polypeptides. Similarly, immunoassay methods may include controls and procedures to determine that an antibody that bind specifically to a CD47 ligand does not recognize or cross-react with unrelated polypeptides. In addition, an immunoassay performed for detection of anti-CD47 antibodies that are produced in response to immunization of a host with CD47, or a CD47 extracellular domain, conjugated to a particular carrier polypeptide may incorporate the use of the extracellular domain that is conjugated to a different carrier polypeptide than that used for immunization to reduce or eliminate detection of antibodies that bind specifically to the immunizing carrier polypeptide. Alternatively, CD47 or a CD47 extracellular domain that is not conjugated to a carrier molecule may be used in an immunoassay for detecting immunospecific antibodies.

Antibodies may generally be prepared by any of a variety of techniques known to persons having ordinary skill in the art. See, e.g., Harlow et al., *Antibodies: A Laboratory Manual*, Cold Spring Harbor Laboratory (1988); Peterson,

*ILAR J.* 46:314-19 (2005)). Isolated CD47, the extracellular domain of CD47, peptides or fragments thereof, or a cell expressing CD47 may be used as an immunogen for immunizing an animal for production of either polyclonal antibodies or monoclonal antibodies.

An immunogen may comprise a portion of the extracellular region, which may be used to generate and/or identify antibodies or antigen-binding fragments thereof that are capable of altering (increasing or decreasing in a statistically significant or biological significant manner, preferably decreasing) the immunoresponsiveness of an immune cell. Exemplary peptide immunogens may comprise 6, 7, 8, 9, 10, 11, 12, 20-25, 21-50, 26-30, 31-40, 41-50, 51-60, 61-70, or 71-75 consecutive amino acids of a CD47 extracellular domain. Similarly, peptide immunogens may be prepared from the extracellular domains of a CD47 ligand.

Peptides and fragments of the extracellular domain of CD47 that are useful as immunogens include portions of the extracellular domain that have a binding site to which a CD47 ligand binds. One method for determining the amino acid sequence of a CD47 ligand binding site, or a portion of the ligand binding site, includes peptide mapping techniques. For example, peptides may be randomly generated by proteolytic digestion of the extracellular domain of CD47 using any one or more of various proteases, the peptides separated and/or isolated (e.g., by gel electrophoresis, column chromatography), followed by determination of which peptide(s) a CD47 ligand binds to, and then sequencing the peptides. The CD47 extracellular domain peptides may also be generated using recombinant methods described herein and practiced in the art. Peptides randomly generated by recombinant methods may also be used to prepare peptide combinatorial libraries or phage libraries as described herein and in the art. Alternatively, the amino acid sequences of portions of the extracellular domain of CD47 that interact with a CD47 ligand may be determined by computer modeling of CD47, or of a portion thereof, for example, the extracellular portion, and/or by x-ray crystallography (which may include preparation and analysis of crystals of the CD47 extracellular domain only or of the extracellular domain CD47-CD47 ligand complex). Conversely, peptides and fragments of the extracellular domain of a CD47 ligand that are useful as immunogens include portions of the extracellular domain that have a binding site to which CD47 and/or to which vCD47 binds and may be identified as described above for the CD47 peptides.

Immunogenic peptides of a CD47 extracellular domain (or immunogenic peptides of a CD47 ligand extracellular domain) may also be determined by computer analysis of the amino acid sequence of the domain to determine a hydrophilicity plot. Portions of the extracellular domain that are accessible to an antibody are most likely portions of the protein that are in contact with the aqueous environment and are hydrophilic. Regions of hydrophilicity can be determined using computer programs available to persons skilled in the art and which assign a "hydrophilic index" to each amino acid in a protein and then plot a profile.

Preparation of an immunogen, particularly polypeptide fragments or peptides, for injection into animals may include covalent coupling of the CD47 extracellular domain (or variant thereof) or peptide, (or the CD47 ligand extracellular domain or peptide thereof) to another immunogenic protein, for example, a carrier protein such as keyhole limpet hemocyanin (KLH) or bovine serum albumin (BSA) or the like. A polypeptide or peptide immunogen may include one or more additional amino acids at either the N-terminal or C-terminal end that facilitate the conjugation procedure (e.g., the addition of a cysteine to facilitate conjugation of a peptide to KLH). Other amino acid residues within a polypeptide or peptide may be substituted to prevent conjugation at that particular amino acid position to a carrier polypeptide (e.g., substituting a serine residue for cysteine at internal positions of a polypeptide/peptide) or may be substituted to facilitate solubility or to increase immunogenicity.

An antibody that specifically binds to CD47 and an antibody that specifically binds to a CD47 ligand may belong to any immunoglobulin class, for example IgG, IgE, IgM, IgD, or IgA. It may be obtained from or derived from an animal, for example, fowl (e.g., chicken) and mammals, which include but are not limited to a mouse, rat, hamster, rabbit, or other rodent, a cow, horse, sheep, goat, camel, human, or other primate. The antibody may be an internalising antibody. In one such technique, an animal is immunized, for example, with an extracellular domain or fragment thereof as described herein as an antigen to generate polyclonal antisera. Suitable animals include, for example, rabbits, sheep, goats, pigs, cattle, and may also include smaller mammalian species, such as mice, rats, and hamsters, or other species.

Polyclonal antibodies that bind specifically to an antigen, such as CD47 or a CD47 ligand, can be prepared using methods described herein and practiced by persons skilled in the art (see, for example, Green et al., "Production of Polyclonal Antisera," in *Immunochemical Protocols* (Manson, ed.), pages 1-5 (Humana Press 1992); Harlow et al., *Antibodies: A Laboratory Manual*, Cold Spring Harbor Laboratory (1988); Williams et al., "Expression of foreign proteins in *E. coli* using plasmid vectors and purification of specific polyclonal antibodies," in *DNA Cloning* 2: *Expression Systems, 2nd Edition*, Glover et al. (eds.), page 15 (Oxford University Press 1995)). Although polyclonal antibodies are typically raised in animals such as rats, mice, rabbits, goats, cattle, or sheep, an antibody may also be obtained from a subhuman primate. General techniques for raising diagnostically and therapeutically useful antibodies in baboons may be found, for example, in International Patent Application Publication No. WO 91/11465 (1991) and in Losman et al., *Int. J. Cancer* 46:310, 1990.

In addition, the antigen (CD47, the CD47 extracellular domain polypeptide, fragment or peptide thereof, or a cell expressing CD47; a CD47 ligand, extracellular domain of the ligand or a cell expressing the ligand) used as an immunogen may be emulsified in an adjuvant. See, e.g., Harlow et al., *Antibodies: A Laboratory Manual*, Cold Spring Harbor Laboratory (1988). Adjuvants typically used for immunization of non-human animals include but are not limited to Freund's complete adjuvant, Freund's incomplete adjuvant, montanide ISA, Ribi Adjuvant System (RAS) (Corixa Corporation, Seattle, Wash.), and nitrocellulose-adsorbed antigen. The immunogen may be injected into the animal via any number of different routes, including intraperitoneally, intravenously, intramuscularly, intradermally, intraocularly, or subcutaneously. In general, after the first injection, animals receive one or more booster immunizations according to a preferred schedule that may vary according to, inter alia, the antigen, the adjuvant (if any) and/or the particular animal species. The immune response may be monitored by periodically bleeding the animal, separating the sera from the collected blood, and analyzing the sera in an immunoassay, such as an ELISA or Ouchterlony diffusion assay, or the like, to determine the specific antibody titer. Once an adequate antibody titer is established, the animals may be bled periodically to accumulate the polyclonal antisera. Polyclonal antibodies that bind specifically to the antigen may then be purified from such antisera, for example, by affinity chromatography using protein A or protein G immobilized on a suitable solid support (see, e.g., Coligan, supra, p. 2.7.1-2.7.12; 2.9.1-2.9.3; Baines et al., Purification of Immunoglobulin G (IgG), in *Methods in Molecular Biology*, 10:9-104 (The Humana Press, Inc. (1992)). Alternatively, affinity chromatography may be performed wherein the antigen, or a fragment thereof, or an antibody specific for an Ig constant region of the particular immunized animal species is immobilized on a suitable solid support.

Monoclonal antibodies that specifically bind to CD47 and particularly, to the CD47 extracellular domain, or monoclonal antibodies specific for a CD47 ligand, and hybridomas, which are examples of immortal eukaryotic cell lines, that produce monoclonal antibodies having the desired binding specificity, may also be prepared, for example, using the technique of Kohler and Milstein (*Nature*, 256:495-97 (1976), *Eur. J. Immunol.* 6:511-19 (1975)) and improvements thereto (see, e.g., Coligan et al. (eds.), *Current Protocols in Immunology*, 1:2.5.1-2.6.7 (John Wiley & Sons 1991); U.S. Pat. Nos. 4,902,614, 4,543,439, and 4,411,993; *Monoclonal Antibodies, Hybridomas: A New Dimension in Biological Analyses*, Plenum Press, Kennett et al. (eds.) (1980); and *Antibodies: A Laboratory Manual*, Harlow and Lane (eds.), Cold Spring Harbor Laboratory Press (1988); see also, e.g., Brand et al., *Planta Med.* 70:986-92 (2004); Pasqualini et al., *Proc. Natl. Acad. Sci. USA* 101:257-59 (2004)). An animal, for example, a rat, hamster, or more commonly, a mouse, is immunized with an immunogen prepared as described above. The presence of specific antibody production may be monitored after the initial injection (injections may be administered by any one of several routes as described herein for generation of polyclonal antibodies) and/or after a booster injection by obtaining a serum sample and detecting the presence of an antibody that binds to the antigen using any one of several immunodetection methods known in the art and described herein.

From animals producing specific antibodies, lymphoid cells (most commonly cells from the spleen or lymph node) are removed to obtain B-lymphocytes, which are lymphoid cells that are antibody-forming cells. The lymphoid cells, typically spleen cells, may be immortalized by fusion with a drug-sensitized myeloma (e.g., plasmacytoma) cell fusion partner, preferably one that is syngeneic with the immunized animal and that optionally has other desirable properties (e.g., inability to express endogenous Ig gene products, e.g., P3X63-Ag 8.653 (ATCC No. CRL 1580); NS0; SP20)). The lymphoid cells and the myeloma cells may be combined for a few minutes with a membrane fusion-promoting agent, such as polyethylene glycol or a nonionic detergent, and then plated at low density on a selective medium that supports the growth of hybridoma cells, but not unfused myeloma cells. A preferred selection media is HAT (hypoxanthine, aminopterin, thymidine). After a sufficient time, usually about one to two weeks, colonies of cells are observed. Antibodies produced by the cells may be tested for binding activity to the antigen. The hybridomas are cloned (e.g., by limited dilution cloning or by soft agar plaque isolation) and positive clones that produce an antibody specific to the antigen are selected and cultured. Hybridomas producing monoclonal antibodies with high affinity and specificity for the CD47 extracellular domain are preferred. Similarly, hybridomas producing monoclonal antibodies with high affinity and specificity for the CD47 ligand, particularly, the extracellular domain, are preferred.

Monoclonal antibodies may be isolated from the supernatants of hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Contaminants may be removed from the subsequently harvested ascites fluid (usually within 1-3 weeks) by conventional techniques, such as chromatography (e.g., size-exclusion, ion-exchange), gel filtration, precipitation, extraction, or the like (see, e.g., Coligan, supra, p. 2.7.1-2.7.12; 2.9.1-2.9.3; Baines et al., Purification of Immunoglobulin G (IgG), in *Methods in Molecular Biology*, 10:9-104 (The Humana Press, Inc. (1992)). For example, antibodies may be purified by affinity chromatography using an appropriate ligand selected based on particular properties of the monoclonal antibody (e.g., heavy or light chain isotype, binding specificity, etc.). Examples of a suitable ligand, immobilized on a solid support, include Protein A, Protein G, an anti-constant region (light chain or heavy chain) antibody, an anti-idiotype antibody, the CD47 extracellular domain or fragment thereof.

An antibody that specifically binds to CD47 or an antibody that specifically binds to a CD47 ligand may be a human monoclonal antibody. Human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein.

For example, human monoclonal antibodies may be obtained from transgenic mice that have been engineered to produce specific human antibodies in response to antigenic challenge. Methods for obtaining human antibodies from transgenic mice are described, for example, by Green et al., *Nature Genet.* 7:13 (1994); Lonberg et al., *Nature* 368:856 (1994); Taylor et al., *Int. Immun.* 6:579 (1994); U.S. Pat. No. 5,877,397; Bruggemann et al., *Curr. Opin. Biotechnol.* 8:455-58 (1997); Jakobovits et al., *Ann. N.Y. Acad. Sci.* 764:525-35 (1995). In this technique, elements of the human heavy and light chain locus are artificially introduced by genetic engineering into strains of mice derived from embryonic stem cell lines that contain targeted disruptions of the endogenous murine heavy chain and light chain loci. (See also Bruggemann et al., *Curr. Opin. Biotechnol.* 8:455-58 (1997)). For example, human immunoglobulin transgenes may be minigene constructs, or transloci on yeast artificial chromosomes, which undergo B cell-specific DNA rearrangement and hypermutation in the mouse lymphoid tissue. Human monoclonal antibodies may be obtained by immunizing the transgenic mice, which may then produce human antibodies specific for the antigen. Lymphoid cells of the immunized transgenic mice can be used to produce human antibody-secreting hybridomas according to the methods described herein. Polyclonal sera containing human antibodies may also be obtained from the blood of the immunized animals.

Another method for generating human antigen-specific monoclonal antibodies includes immortalizing human peripheral blood cells by EBV transformation. See, e.g., U.S. Pat. No. 4,464,456. Such an immortalized B cell line (or lymphoblastoid cell line) producing a monoclonal antibody that specifically binds to the CD47 extracellular domain can be identified by immunodetection methods as provided herein, for example, an ELISA, and then isolated by standard cloning techniques. The stability of the lymphoblastoid cell line producing an antibody of intereset may be improved by fusing the transformed cell line with a murine myeloma to produce a mouse-human hybrid cell line according to methods known in the art (see, e.g., Glasky et al., *Hybridoma* 8:377-89 (1989)). Still another method to generate human monoclonal antibodies is in vitro immunization, which includes priming human splenic B cells with antigen, followed by fusion of primed B cells with a heterohybrid fusion partner. See, e.g., Boerner et al., *J. Immunol.* 147:86-95 (1991).

In certain embodiments, a B cell that is producing the desired antibody is selected, and the light chain and heavy chain variable regions are cloned from the B cell according to molecular biology techniques known in the art (WO 92/02551; U.S. Pat. No. 5,627,052; Babcook et al., *Proc. Natl. Acad. Sci. USA* 93:7843-48 (1996)) and described herein. B cells from an immunized animal are isolated from the spleen, lymph node, or peripheral blood sample by selecting a cell that is producing an antibody that specifically binds to the antigen, for example, the CD47 extracellular domain or a CD47 ligand. B cells may also be isolated from humans, for example, from a peripheral blood sample. Methods for detecting single B cells that are producing an antibody with the desired specificity are well known in the art, for example, by plaque formation, fluorescence-activated cell sorting, in vitro stimulation followed by detection of specific antibody, and the like. Methods for selection of specific antibody producing B cells include, for example, preparing a single cell suspension of B cells in soft agar that contains the antigen or a fragment thereof. Binding of the specific antibody produced by the B cell to the antigen results in the formation of a complex, which may be visible as an immunoprecipitate. After the B cells producing the specific antibody are selected, the specific antibody genes may be cloned by isolating and amplifying DNA or mRNA according to methods known in the art and described herein.

Chimeric antibodies, including humanized antibodies, may also be generated. A chimeric antibody has at least one constant region domain derived from a first mammalian species and at least one variable region domain derived from a second, distinct mammalian species. See, e.g., Morrison et al., *Proc. Natl. Acad. Sci. USA,* 81:6851-55 (1984). In one embodiment, a chimeric antibody may be constructed by cloning the polynucleotide sequence that encodes at least one variable region domain derived from a non-human monoclonal antibody, such as the variable region derived from a murine, rat, or hamster monoclonal antibody, into a vector containing a nucleic acid sequence that encodes at least one human constant region (see, e.g., Shin et al., *Methods Enzymol.* 178:459-76 (1989); Walls et al., *Nucleic Acids Res.* 21:2921-29 (1993)). By way of example, the polynucleotide sequence encoding the light chain variable region of a murine monoclonal antibody may be inserted into a vector containing a nucleic acid sequence encoding the human kappa light chain constant region sequence. In a separate vector, the polynucleotide sequence encoding the heavy chain variable region of the monoclonal antibody may be cloned in frame with sequences encoding the human IgG1 constant region. The particular human constant region selected may depend upon the effector functions desired for the particular antibody (e.g., complement fixing, binding to a particular Fc receptor, etc.). Another method known in the art for generating chimeric antibodies is homologous recombination (e.g., U.S. Pat. No. 5,482,856). Preferably, the vectors will be transfected into eukaryotic cells for stable expression of the chimeric antibody.

A non-human/human chimeric antibody may be further genetically engineered to create a "humanized" antibody. Such a humanized antibody may comprise a plurality of CDRs derived from an immunoglobulin of a non-human mammalian species, at least one human variable framework region, and at least one human immunoglobulin constant region. Humanization may in certain embodiments provide an antibody that has decreased binding affinity for the CD47 extracellular domain when compared, for example, with either a non-human monoclonal antibody from which a CD47-binding variable region is obtained, or a chimeric antibody having such a V region and at least one human C region, as described above. Humanization of an antibody that specifically binds to a CD47 ligand may be accomplished by similar methods described herein for preparing an anti-CD47 antibody. Useful strategies for designing humanized antibodies may therefore include, for example by way of illustration and not limitation, identification of human variable framework regions that are most homologous to the non-human framework regions of the chimeric antibody. Without wishing to be bound by theory, such a strategy may increase the likelihood that the humanized antibody will retain specific binding affinity for CD47, wherein the humanized antibody has substantially the same affinity as the non-humanized antibody, and in certain other embodiments the humanized antibody may exhibit a greater affinity for CD47 than the non-humanized antibody (see, e.g., Jones et al., *Nature* 321:522-25 (1986); Riechmann et al., *Nature* 332:323-27 (1988)).

Designing a humanized antibody may therefore include determining CDR loop conformations and structural determinants of the non-human variable regions, for example, by computer modeling, and then comparing the CDR loops and determinants to known human CDR loop structures and determinants (see, e.g., Padlan et al., *FASEB* 9:133-39 (1995); Chothia et al., *Nature,* 342:377-83 (1989)). Computer modeling may also be used to compare human structural templates selected by sequence homology with the non-human variable regions (see, e.g., Bajorath et al., *Ther. Immunol.* 2:95-103 (1995); EP-0578515-A3). If humanization of the non-human CDRs results in a decrease in binding affinity, computer modeling may aid in identifying specific amino acid residues that could be changed by site-directed or other mutagenesis techniques to partially, completely, or supraoptimally (i.e., increase to a level greater than that of the non-humanized antibody) restore affinity. Those having ordinary skill in the art are familiar with these techniques and will readily appreciate numerous variations and modifications to such design strategies.

One such method for preparing a humanized antibody is called veneering. Veneering framework (FR) residues refers to the selective replacement of FR residues from, e.g., a rodent heavy or light chain V region, with human FR residues in order to provide a xenogeneic molecule comprising an antigen-binding site that retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface (see, e.g., Davies et al., *Ann. Rev. Biochem.* 59:439-73, (1990)). Thus, antigen binding specificity can be preserved in a humanized antibody when the CDR structures, their interaction with each other, and their interaction with the rest of the V region domains are carefully maintained. By using veneering techniques, exterior (e.g., solvent-accessible) FR residues that are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in *Sequences of Proteins of Immunological Interest*, 4th ed., (U.S. Dept. of Health and Human Services, U.S. Government Printing Office, 1991), updates to the Kabat database, and other accessible U.S. and foreign databases (both nucleic acid and protein). Solvent accessibilities of V region amino acids can be deduced from the known three-dimensional structure for human and murine antibody fragments. Initially, the FR amino acid sequence of the variable domains of an antibody molecule of interest are compared with corresponding FR sequences of human variable domains obtained from the above-identified databases and publications. The most homologous human V regions are then compared residue by residue to corresponding murine amino acids. The residues in the murine FR that differ from the human counterpart are replaced by the residues present in the human moiety using recombinant techniques well known in the art. Residue switching is only carried out with moieties that are at least partially exposed (solvent accessible), and care is exercised in the replacement of amino acid residues that may have a significant effect on the tertiary structure of V region domains, such as proline, glycine, and charged amino acids.

In this manner, the resultant "veneered" antigen-binding sites are designed to retain the rodent CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs that are believed to influence the "canonical" tertiary structures of the CDR loops (see, e.g., Chothia et al., *Nature*, 342:377-383 (1989)). These design criteria are then used to prepare recombinant nucleotide sequences that combine the CDRs of both the heavy and light chain of an antigen-binding site into human-appearing FRs that can be used to transfect mammalian cells for the expression of recombinant human antibodies that exhibit the antigen specificity of the rodent antibody molecule.

For particular uses, antigen-binding fragments of antibodies may be desired. Antibody fragments, F(ab')$_2$, Fab, Fab', Fv, and Fd, can be obtained, for example, by proteolytic hydrolysis of the antibody, for example, pepsin or papain digestion of whole antibodies according to conventional methods. As an illustration, antibody fragments can be produced by enzymatic cleavage of antibodies with pepsin to provide a fragment denoted F(ab')$_2$. This fragment can be further cleaved using a thiol reducing agent to produce an Fab' monovalent fragment. Optionally, the cleavage reaction can be performed using a blocking group for the sulfhydryl groups that result from cleavage of disulfide linkages. As an alternative, an enzymatic cleavage of an antibody using papain produces two monovalent Fab fragments and an Fc fragment (see, e.g., U.S. Pat. No. 4,331,647; Nisonoff et al., *Arch. Biochem. Biophys.* 89:230 (1960); Porter, *Biochem. J.* 73:119 (1959); Edelman et al., in *Methods in Enzymology* 1:422 (Academic Press 1967); Weir, *Handbook of Experimental Immunology*, Blackwell Scientific, Boston (1986)). The antigen binding fragments may be separated from the Fc fragments by affinity chromatography, for example, using immobilized protein A, protein G, an Fc specific antibody, or immobilized CD47 or CD47 extracellular domain polypeptide or a fragment thereof Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein that acts like an antibody in that it binds to a specific antigen to form a complex. For example, antibody fragments include isolated fragments consisting of the light chain variable region, Fv fragments consisting of the variable regions of the heavy and light chains, recombinant single chain polypeptide molecules in which light and heavy variable regions are connected by a peptide linker (scFv proteins), and minimal recognition units consisting of the amino acid residues that mimic the hypervariable region. The antibody of the present invention preferably comprises at least one variable region domain. The variable region domain may be of any size or amino acid composition and will generally comprise at least one hypervariable amino acid sequence responsible for antigen binding and which is adjacent to or in frame with one or more framework sequences. In general terms, the variable (V) region domain may be any suitable arrangement of immunoglobulin heavy ($V_H$) and/or light ($V_L$) chain variable domains. Thus, for example, the V region domain may be monomeric and be a $V_H$ or $V_L$ domain, which is capable of independently binding antigen with acceptable affinity. Alternatively, the V region domain may be dimeric and contain $V_H$-$V_H$, $V_H$-$V_L$, or $V_L$-$V_L$, dimers. Preferably, the V region dimer comprises at least one $V_H$ and at least one $V_L$ chain that are non-covalently associated (hereinafter referred to as $F_v$). If desired, the chains may be covalently coupled either directly, for example via a disulfide bond between the two variable domains, or through a linker, for example a peptide linker, to form a single chain Fv (scF$_v$).

A minimal recognition unit is an antibody fragment comprising a single complementarity-determining region (CDR). Such CDR peptides can be obtained by constructing polynucleotides that encode the CDR of an antibody of interest. The polynucleotides are prepared, for example, by using the polymerase chain reaction to synthesize the variable region using mRNA isolated from or contained within antibody-producing cells as a template according to methods practiced by persons skilled in the art (see, for example, Larrick et al., *Methods: A Companion to Methods in Enzymology* 2:106, (1991); Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)). Alternatively, such CDR peptides and other antibody fragment can be synthesized using an automated peptide synthesizer.

According to certain embodiments, non-human, human, or humanized heavy chain and light chain variable regions of any of the Ig molecules described herein may be constructed as scF$_v$ polypeptide fragments (single chain antibodies). See, e.g., Bird et al., *Science* 242:423-426 (1988); Huston et al., *Proc. Natl. Acad. Sci. USA* 85:5879-83 (1988)). Multi-functional scFv fusion proteins may be generated by linking a polynucleotide sequence encoding an scFv polypeptide in-frame with at least one polynucleotide sequence encoding any of a variety of known effector proteins. These methods are known in the art, and are disclosed, for example, in EP-B1-0318554, U.S. Pat. No. 5,132,405, U.S. Pat. No. 5,091,513, and U.S. Pat. No. 5,476,786. By way of example, effector proteins may include immunoglobulin constant region sequences. See, e.g., Hollenbaugh et al., *J. Immunol. Methods* 188:1-7 (1995). Other examples of effector proteins are enzymes. As a non-limiting example, such an enzyme may provide a biological activity for therapeutic purposes (see, e.g., Siemers et al., *Bioconjug. Chem.* 8:510-19 (1997)), or may provide a detectable activity, such as horseradish peroxidase-catalyzed conversion of any of a number of well-known substrates into a detectable product, for diagnostic uses.

The scFv may, in certain embodiments, be fused to peptide or polypeptide domains that permit detection of specific binding between the fusion protein and antigen. For example, the fusion polypeptide domain may be an affinity tag polypeptide. Binding of the scFv fusion protein to a binding partner (e.g., a CD47 extracellular domain) may therefore be detected using an affinity polypeptide or peptide tag, such as an avidin, streptavidin or a His (e.g., polyhistidine) tag, by any of a variety of techniques with which those skilled in the art will be familiar. Detection techniques may also include, for example, binding of an avidin or streptavidin fusion protein to biotin or to a biotin mimetic sequence (see, e.g., Luo et al., *J. Biotechnol.* 65:225 (1998) and references cited therein), direct covalent modification of a fusion protein with a detectable moiety (e.g., a labeling moiety), non-covalent binding of the fusion protein to a specific labeled reporter molecule, enzymatic modification of a detectable substrate by a fusion protein that includes a portion having enzyme activity, or immobilization (covalent or non-covalent) of the fusion protein on a solid-phase support. An scFv fusion protein comprising a CD47-specific immunoglobulin-derived polypeptide may be fused to another polypeptide such as an effector peptide having desirable affinity properties (see, e.g., U.S. Pat. No. 5,100,788; WO 89/03422; U.S. Pat. No. 5,489,528; U.S. Pat. No. 5,672,691; WO 93/24631; U.S. Pat. No. 5,168, 049; U.S. Pat. No. 5,272,254; EP 511,747). As provided herein, scFv polypeptide sequences may be fused to fusion polypeptide sequences, including effector protein sequences, that may include full-length fusion polypeptides and that may alternatively contain variants or fragments thereof. An scFv fusion protein comprising a CD47 ligand specific immunoglobulin derived polypeptide may be similarly prepared.

Antibodies may also be identified and isolated from human immunoglobulin phage libraries, from rabbit immunoglobulin phage libraries, from mouse immunoglobulin phage libraries, and/or from chicken immunoglobulin phage libraries (see, e.g., Winter et al., *Annu. Rev. Immunol.* 12:433-55 (1994); Burton et al., *Adv. Immunol.* 57:191-280 (1994); U.S. Pat. No. 5,223,409; Huse et al., *Science* 246:1275-81 (1989); Schlebusch et al., *Hybridoma* 16:47-52 (1997) and references cited therein; Rader et al., *J. Biol. Chem.* 275:13668-76 (2000); Popkov et al., *J. Mol. Biol.* 325:325-35 (2003); Andris-Widhopf et al., *J. Immunol. Methods* 242:159-31 (2000)). Antibodies isolated from non-human species or non-human immunoglobulin libraries may be genetically engineered according to methods described herein and known in the art to "humanize" the antibody or fragment thereof. Immunoglobulin variable region gene combinatorial libraries may be created in phage vectors that can be screened to select Ig fragments (Fab, Fv, scFv, or multimers thereof) that bind specifically to CD47 as described herein (see, e.g., U.S. Pat. No. 5,223,409; Huse et al., *Science* 246:1275-81 (1989); Sastry et al., *Proc. Natl. Acad. Sci. USA* 86:5728-32 (1989); Alting-Mees et al., *Strategies in Molecular Biology* 3:1-9 (1990); Kang et al., *Proc. Natl. Acad. Sci. USA* 88:4363-66 (1991); Hoogenboom et al., *J. Molec. Biol.* 227:381-388 (1992); Schlebusch et al., *Hybridoma* 16:47-52 (1997) and references cited therein; U.S. Pat. No. 6,703,015).

For example, a library containing a plurality of polynucleotide sequences encoding Ig variable region fragments may be inserted into the genome of a filamentous bacteriophage, such as M13 or a variant thereof, in frame with the sequence encoding a phage coat protein such as gene III or gene VIII. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using λImmunoZap™(H) and λImmunoZap™(L) vectors (Stratagene, La Jolla, Calif.). Briefly, mRNA is isolated from a B cell population and used to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high-level expression of monoclonal antibody fragments from *E. coli*.

Phage that display an Ig fragment (e.g., an Ig V-region or Fab) that binds to CD47, and the CD47 extracellular domain in particular, may be selected by mixing the phage library with CD47 or the CD47 extracellular domain or a fragment thereof, or by contacting the phage library with such polypeptide or peptide molecules immobilized on a solid matrix under conditions and for a time sufficient to allow binding. Unbound phage are removed by a wash, and specifically bound phage (i.e., phage that contain an CD47 extracellular domain-specific Ig fragment) are then eluted (see, e.g., Messmer et al., *Biotechniques* 30:798-802 (2001)). Eluted phage may be propagated in an appropriate bacterial host, and generally, successive rounds of binding to CD47 or an CD47 extracellular domain and elution can be repeated to increase the yield of phage expressing the CD47-specific immunoglobulin. Such methods may also be used to identify phage that express a CD47 ligand specific immunoglobulin.

Phage display techniques may also be used to select Ig fragments or single chain antibodies that bind to the CD47 and the CD47 extracellular domain. For examples of suitable vectors having multicloning sites into which candidate nucleic acid molecules (e.g., DNA) encoding such antibody fragments or related peptides may be inserted, see, e.g., McLafferty et al., *Gene* 128:29-36 (1993); Scott et al., *Science* 249:386-90 (1990); Smith et al., *Meth. Enzymol.* 217: 228-57 (1993); Fisch et al., *Proc. Natl. Acad. Sci. USA* 93:7761-66 (1996)). The inserted DNA molecules may comprise randomly generated sequences, or may encode variants of a known peptide or polypeptide domain (such as a CD47 ligand) that specifically binds to CD47. Generally, the nucleic acid insert encodes a peptide of up to 60 amino acids, or may encode a peptide of 3 to 35 amino acids, or may encode a peptide of 6 to 20 amino acids. The peptide encoded by the inserted sequence is displayed on the surface of the bacteriophage. Phage expressing a binding domain for CD47 may be selected on the basis of specific binding to an immobilized CD47 or CD47 extracellular domain or a fragment thereof. Well-known recombinant genetic techniques may be used to construct fusion proteins containing the fragment. For example, a polypeptide may be generated that comprises a tandem array of two or more similar or dissimilar affinity selected CD47 binding peptide domains, in order to maximize binding affinity for CD47 of the resulting product. Such methods may also be used to select Ig fragments or single chain antibodies that bind to a CD47 ligand.

Combinatorial mutagenesis strategies using phage libraries may also be used for humanizing non-human variable regions (see, e.g., Rosok et al., *J. Biol. Chem.* 271:22611-18

(1996); Rader et al., *Proc. Natl. Acad. Sci. USA* 95:8910-15 (1998)). Humanized variable regions that have binding affinity that is minimally reduced or that is comparable to the non-human variable region can be selected, and the nucleotide sequences encoding the humanized variable regions may be determined by standard techniques (see, Sambrook et al., *Molecular Cloning: A Laboratory Manual*, Cold Spring Harbor Press (2001)). The affinity selected Ig-encoding sequence may then be cloned into another suitable vector for expression of the Ig fragment or, optionally, may be cloned into a vector containing Ig constant regions, for expression of whole immunoglobulin chains.

Similarly, portions or fragments, such as Fab and Fv fragments, of CD47-specific antibodies may be constructed using conventional enzymatic digestion or recombinant DNA techniques to incorporate the variable regions of a gene that encodes an antibody specific for CD47 and in particular embodiments, for the CD47 extracellular domain. Within one embodiment, in a hybridoma the variable regions of a gene expressing a monoclonal antibody of interest are amplified using nucleotide primers. These primers may be synthesized by one of ordinary skill in the art, or may be purchased from commercially available sources (see, e.g., Stratagene (La Jolla, Calif.), which sells primers for amplifying mouse and human variable regions. The primers may be used to amplify heavy or light chain variable regions, which may then be inserted into vectors such as ImmunoZAP™ H or ImmunoZAP™ L (Stratagene), respectively. These vectors may then be introduced into *E. coli*, yeast, or mammalian-based systems for expression. Large amounts of a single-chain protein containing a fusion of the $V_H$ and $V_L$ domains may be produced using these methods (see Bird et al., *Science* 242: 423-426 (1988)). In addition, such techniques may be used to humanize a non-human antibody V region without altering the binding specificity of the antibody. Such methods may also be used to make fragments of antibodies that bind to a CD47 ligand.

In certain other embodiments, specific antibodies are multimeric antibody fragments. Useful methodologies are described generally, for example in Hayden et al., *Curr Opin. Immunol.* 9:201-12 (1997) and Coloma et al., *Nat. Biotechnol.* 15:159-63 (1997). For example, multimeric antibody fragments may be created by phage techniques to form miniantibodies (U.S. Pat. No. 5,910,573) or diabodies (Holliger et al., *Cancer Immunol. Immunother.* 45:128-30 (1997)). Multimeric fragments may be generated that are multimers of a specific Fv.

Multimeric antibodies include bispecific and bifunctional antibodies comprising a first Fv specific for an antigen associated with a second Fv having a different antigen specificity (see, e.g., Drakeman et al., *Expert Opin. Investig. Drugs* 6:1169-78 (1997); Koelemij et al., *J. Immunother.* 22:514-24 (1999); Marvin et al., *Acta Pharmacol. Sin.* 26:649-58 (2005); Das et al., *Methods Mol. Med.* 109:329-46 (2005)). For example, in one embodiment, a bispecific antibody comprises an Fv, or other antigen-binding fragment described herein, that specifically binds to the antigen and comprises an Fv, or other antigen-binding fragment, that specifically binds to another cell surface polypeptide, for example, a cell surface antigen that when bound by a specific antibody contributes to, facilitates, or is capable of altering (suppressing or enhancing) immunoresponsiveness of an immune cell.

Introducing amino acid mutations into immunoglobulin molecules may be useful to increase the specificity or affinity of the immunoglobulin for the specific antigen, or to alter an effector function. Immunoglobulins exhibiting higher affinity for the antigen may be generated by site-directed mutagenesis of particular residues. Computer assisted three-dimensional molecular modeling may be used to identify the amino acid residues to be changed in order to improve affinity for the antigen (see, e.g., Mountain et al., *Biotechnol. Genet. Eng. Rev.* 10:1-142 (1992)). Alternatively, combinatorial libraries of CDRs may be generated in M13 phage and screened for immunoglobulin fragments with improved affinity (see, e.g., Glaser et al., *J. Immunol.* 149:3903-13 (1992); Barbas et al., *Proc. Natl. Acad. Sci. USA* 91:3809-13 (1994); U.S. Pat. No. 5,792,456).

In certain embodiments, the antibody may be genetically engineered to have an altered effector function. For example, the antibody may have an altered capability (increased or decreased in a biologically or statistically significant manner) to mediate complement dependent cytotoxicity (CDC) or antibody dependent cellular cytotoxicity (ADCC) or an altered capability for binding to effector cells via Fc receptors present on the effector cells. Effector functions may be altered by site-directed mutagenesis (see, e.g., Duncan et al., *Nature* 332:563-64 (1988); Morgan et al., *Immunology* 86:319-24 (1995); Eghtedarzedeh-Kondri et al., *Biotechniques* 23:830-34 (1997)). For example, mutation of the glycosylation site on the Fc portion of the immunoglobulin may alter the capability of the immunoglobulin to fix complement (see, e.g., Wright et al., *Trends Biotechnol.* 15:26-32 (1997)). Other mutations in the constant region domains may alter the ability of the immunoglobulin to fix complement or to effect ADCC (see, e.g., Duncan et al., *Nature* 332:563-64(1988); Morgan et al., *Immunology* 86:319-24 (1995); Sensel et al., *Mol. Immunol.* 34:1019-29 (1997)). (See also, e.g., U.S. Patent Publication Nos. 2003/0118592; 2003/0133939).

The nucleic acid molecules encoding an antibody or fragment thereof that specifically binds CD47, as described herein, may be propagated and expressed according to any of a variety of well-known procedures for nucleic acid excision, ligation, transformation, and transfection. Thus, in certain embodiments expression of an antibody fragment may be preferred in a prokaryotic host cell, such as *Escherichia coli* (see, e.g., Pluckthun et al., *Methods Enzymol.* 178:497-515 (1989)). In certain other embodiments, expression of the antibody or an antigen-binding fragment thereof may be preferred in a eukaryotic host cell, including yeast (e.g., *Saccharomyces cerevisiae, Schizosaccharomyces pombe*, and *Pichia pastoris*); animal cells (including mammalian cells); or plant cells. Examples of suitable animal cells include, but are not limited to, myeloma, COS, CHO, or hybridoma cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the CD47-binding antibody (or fragment thereof) may be inserted. The regulatory elements will vary according to the particular host. Similarly, nucleic acid molecules encoding an antibody or fragment thereof that specifically binds a CD47 ligand may be propagated and expressed according to any of a variety of well-known procedures for nucleic acid excision, ligation, transformation, and transfection.

One or more replicable expression vectors containing a polynucleotide encoding a variable and/or constant region may be prepared and used to transform an appropriate cell line, for example, a non-producing myeloma cell line, such as a mouse NSO line or a bacteria, such as *E. coli*, in which production of the antibody will occur. In order to obtain efficient transcription and translation, the polynucleotide sequence in each vector should include appropriate regulatory sequences, particularly a promoter and leader sequence operatively linked to the variable domain sequence. Particular methods for producing antibodies in this way are generally well known and routinely used. For example, molecular biology procedures are described by Sambrook et al. (*Molecular Cloning, A Laboratory Manual*, 2nd ed., Cold Spring Harbor Laboratory, New York, 1989; see also Sambrook et al., 3rd ed., Cold Spring Harbor Laboratory, New York, (2001)). DNA sequencing can be performed as described in Sanger et al. (*Proc. Natl. Acad. Sci. USA* 74:5463 (1977)) and the Amersham International plc sequencing handbook and including improvements thereto.

Site directed mutagenesis of an immunoglobulin variable (V region), framework region, and/or constant region may be performed according to any one of numerous methods described herein and practiced in the art (Kramer et al., *Nucleic Acids Res.* 12:9441 (1984); Kunkel *Proc. Natl. Acad. Sci. USA* 82:488-92 (1985); Kunkel et al., *Methods Enzymol.* 154:367-82 (1987)). Random mutagenesis methods to identify residues of the antibody that are either important to binding to the antigen or that, when changed, do not alter binding of the antigen to the antibody can also be performed according to procedures that are routinely practiced by a person skilled in the art (e.g., alanine scanning mutagenesis; error prone polymerase chain reaction mutagenesis; and oligonucleotide-directed mutagenesis (see, e.g., Sambrook et al. *Molecular Cloning: A Laboratory Manual*, 3rd ed., Cold Spring Harbor Laboratory Press, NY (2001))). Additionally, numerous publications describe techniques suitable for the preparation of antibodies by manipulation of DNA, creation of expression vectors, and transformation of appropriate cells (Mountain et al., in *Biotechnology and Genetic Engineering Reviews* (ed. Tombs, M P, 10, Chapter 1, Intercept, Andover, UK (1992)); International Patent Publication No. WO 91/09967).

The antibodies and antigen-binding fragments thereof that specifically bind to CD47, including antibodies that specifically bind to the CD47 extracellular domain, may also be useful as reagents for immunochemical analyses to detect the presence of CD47, or a fragment thereof, in a biological sample. The following methods may also be adapted for detecting the presence of a CD47 ligand. In certain embodiments, an antibody that specifically binds to the CD47 extracellular domain may be used to detect expression of CD47. In certain particular embodiments, one antibody or a panel of antibodies may be exposed to cells that express CD47, and expression of CD47 may be determined by detection using another CD47-specific antibody that binds to a different epitope than the antibody or antibodies initially permitted to interact with the cells.

For such a purpose CD47-binding immunoglobulin (or fragment thereof) as described herein may contain a detectable moiety or label such as an enzyme, cytotoxic agent, or other reporter molecule, including a dye, radionuclide, luminescent group, fluorescent group, or biotin, or the like. The CD47-specific immunoglobulin or fragment thereof may be radiolabeled for diagnostic or therapeutic applications. Techniques for radiolabeling of antibodies are known in the art (see, e.g., Adams, *In Vivo* 12:11-21 (1998); Hiltunen, *Acta Oncol.* 32:831-9 (1993)). The effector or reporter molecules may be attached to the antibody through any available amino acid side-chain, terminal amino acid, or carbohydrate functional group located in the antibody, provided that the attachment or attachment process does not adversely affect the binding properties such that the usefulness of the molecule is abrogated. Particular functional groups include, for example, any free amino, imino, thiol, hydroxyl, carboxyl, or aldehyde group. Attachment of the antibody or antigen-binding fragment thereof and the effector and/or reporter molecule(s) may be achieved via such groups and an appropriate functional group in the effector or reporter molecule. The linkage may be direct or indirect through spacing or bridging groups (see, e.g., International Patent Application Publication Nos. WO 93/06231, WO 92/22583, WO 90/091195, and WO 89/01476; see also, e.g., commercial vendors such as Pierce Biotechnology, Rockford, Ill.).

As provided herein and according to methodologies well known in the art, polyclonal and monoclonal antibodies may be used for the affinity isolation of CD47 and fragments thereof (see, e.g., Hermanson et al., *Immobilized Affinity Ligand Techniques*, Academic Press, Inc. New York, (1992)). Briefly, an antibody (or antigen-binding fragment thereof) may be immobilized on a solid support material, which is then contacted with a sample that contains CD47. The sample interacts with the immobilized antibody under conditions and for a time that are sufficient to permit binding of CD47 to the immobilized antibody; non-binding components (that is, those components unrelated to CD47) of the sample are removed; and then CD47 is released from the immobilized antibody using an appropriate eluting solution.

In certain embodiments, anti-idiotype antibodies that recognize and bind specifically to an antibody (or antigen-binding fragment thereof) that specifically binds to CD47, including an antibody that specifically binds to the CD47 extracellular domain, are provided, and methods for using these anti-idiotype antibodies are also provided. Anti-idiotype antibodies may be generated as polyclonal antibodies or as monoclonal antibodies by the methods described herein, using an anti-CD47 extracellular domain antibody (or antigen-binding fragment thereof) as immunogen. Anti-idiotype antibodies or fragments thereof may also be generated by any of the recombinant genetic engineering methods described above or by phage display selection. Anti-idiotype antibodies may be further engineered to provide a chimeric or humanized anti-idiotype antibody, according to the description provided in detail herein. An anti-idiotype antibody may bind specifically to the antigen-binding site of the anti-CD47 extracellular domain antibody such that binding of the antibody to the CD47 extracellular domain extracellular domain is competitively inhibited. Alternatively, an anti-idiotype antibody as provided herein may not competitively inhibit binding of an anti-CD47 extracellular domain antibody to the CD47 extracellular domain.

In one embodiment, an anti-idiotype antibody may be used to alter the immunoresponsiveness of an immune cell. In certain embodiments, an anti-idiotype antibody may be used to suppress the immunoresponsiveness of an immune cell and to treat an immunological disease or disorder. An anti-idiotype antibody specifically binds to an antibody that specifically binds to the CD47 extracellular domain, and the antigen-binding site of the anti-idiotype antibody mimics the epitope of the CD47 extracellular domain, that is, the anti-idiotype antibody will bind to cognate ligands as well as antibodies that specifically bind to the CD47. Thus, an anti-idiotype antibody may be useful for preventing, blocking, or reducing binding of a cognate ligand that when such ligand binds to CD47, it alters (i.e., increases or decreases in a statistically or biologically significant manner) the immunoresponsiveness of an immune cell.

Anti-idiotype antibodies are also useful for immunoassays to determine the presence of anti-CD47 antibodies in a biological sample. For example, immunoassays, such as an ELISA and other assays described herein that are practiced by persons skilled in the art, may be used to determine the presence of an immune response induced by administering (i.e., immunizing) a host with a fusion polypeptide comprising the extracellular domain of CD47 (or a variant thereof) as described herein.

Methods for Determining the Effects of Extracellular Domain CD47-Fusion Polypeptides and of Other Agents that Specifically Bind to CD47

Binding of a fusion polypeptide comprising the extracellular domain of a CD47 (or variant thereof) fused to a heterologous polypeptide moiety, such as a Fc polypeptide (or variant thereof), alters at least one biological function of CD47 that is expressed by a cell. Also as described herein, the interaction between the fusion polypeptide and a CD47 ligand secreted by a cell or expressed on the cell surface of an immune cell may alter (i.e., suppresses or enhances) the immunoresponsiveness of the cell. Alteration of the immunoresponsiveness of an immune cell may also be effected by a bioactive agent (compound or molecule) in a manner similar to a fusion polypeptide comprising the extracellular domain of CD47. Bioactive agents include, for example, small molecules, nucleic acids (such as aptamers), antibodies and fragments thereof (which are discussed in detail herein), and peptide fusion proteins (such as peptide-Fc fusion proteins). An agent may interact with and bind to the extracellular domain of CD47 at a location or binding site of CD47 that is the same location or proximal to the same location as where a CD47 ligand binds. In addition, the agent described herein that specifically binds to CD47 may inhibit binding of a viral CD47-like polypeptide to the CD47 ligand. Alternatively, alteration of immunoresponsiveness by an agent in a manner similar to the effect of a fusion polypeptide comprising a CD47 extracellular domain, or variant thereof, may result from binding or interaction of the agent with the CD47 ligand at the same location or at a location distal from that at which the fusion polypeptide binds. An agent that specifically binds to a CD47 ligand includes an antibody, or antigen binding fragment thereof, that specifically binds to the CD47 ligand, such as an antibody that specifically binds to SIRPα. Binding studies, including competitive binding assays, and functional assays, which indicate the level of immunoresponsiveness of a cell, may be performed according to methods described herein and practiced in the art to determine and compare the capability and level with which an agent binds to and affects the immunoresponsiveness of an immune cell.

Methods are provided herein for identifying an agent that alters (e.g., suppresses or enhances in a statistically or biologically significant manner) immunoresponsiveness of an immune cell and for characterizing and determining the level of suppression or enhancement of such an agent once identified. Such methods, which are discussed in greater detail herein and are familiar to persons skilled in the art, include but are not limited to, binding assays, such as immunoassays (e.g., ELISA, radioimmunoassay, immunoblot, etc.), competitive binding assays, and surface plasmon resonance. These methods comprise contacting (mixing, combining with, or in some manner permitting interaction among) (1) a candidate agent; (2) a viral CD47-like polypeptide (a number of which are described in detail herein and which may also include the extracellular domain of a viral CD47-like polypeptide, or a fusion polypeptide comprising the extracellular domain of a viral CD47-like polypeptide); and (3) a CD47 ligand (for example, SIRP-α, SIRP-beta 2, thrombospondin-1, $\alpha_v\beta_3$ integrin, and $\alpha_2\beta_1$ integrin), under conditions and for a time sufficient to permit interaction between the CD47 ligand and a viral CD47-like polypeptide. Such exemplary methods and techniques may also be used to characterize the CD47 fusion polypeptides described herein.

Accordingly, the methods described herein, which refer to a candidate agent, also may be used when the candidate agent is any one of the fusion polypeptides described herein.

Conditions for a particular assay include temperature, buffers (including salts, cations, media), and other components that maintain the integrity of the candidate agent (or CD47 fusion polypeptide); viral CD47-like polypeptide; and CD47 ligand, with which a person skilled in the art will be familiar and/or which can be readily determined. The interaction, or level of binding, of the viral CD47-like polypeptide to the CD47 ligand in the presence of the candidate agent may be determined and compared to a level of binding of the viral CD47-like polypeptide to the CD47 ligand in the absence of the candidate agent. A decrease in the level of binding of the viral CD47-like polypeptide to the CD47 ligand in the presence of the candidate agent indicates that the candidate agent inhibits binding of the viral CD47-like polypeptide to the CD47 ligand. The candidate agent is then contacted (mixed, combined with, or in some manner permitted to interaction) with a CD47 ligand and an immune cell that expresses CD47, under conditions and for a time sufficient to permit interaction between a CD47 ligand and CD47. The level of binding between the CD47 ligand and the immune cell in the presence of the candidate agent is compared with the level of binding of the CD47 ligand to the immune cell in the absence of the candidate agent. A decrease in the level of binding of the CD47 ligand to the immune cell expressing CD47 in the presence of the candidate agent indicates that the candidate agent alters the immunoresponsiveness of the immune cell. In a specific embodiment of the method, the candidate agent suppresses immunoresponsiveness of the immune cell.

In another embodiment, a method for identifying an agent that alters (suppresses or enhances) immunoresponsiveness of an immune cell comprises determining the level of immunoresponsiveness of an immune cell that expresses CD47 in the presence of the agent. In certain specific embodiments, an agent is identified that suppresses immunoresponsiveness of an immune cell. Immunoresponsiveness may be determined according to methods practiced in the art such as measuring levels of cytokines, cell maturation (e.g., maturation of dendritic cells), proliferation, and stimulation. Immunoresponsiveness of an immune cell may also be determined by evaluating changes in cell adhesion and cell migration and by examining expression, cellular location, and post-translational modification of cellular proteins, such as determining the tyrosine phosphorylation pattern of cellular proteins, including but not limited to cytoskeletal proteins and other proteins that affect cell adhesion and migration.

Numerous assays and techniques are practiced by persons skilled in the art for determining the interaction between, or binding between, a biological molecule and a cognate ligand. Accordingly, interaction between a CD47 ligand and CD47, including the effect of a bioactive agent on this interaction and/or binding in the presence of the agent, can be readily determined by such assays and techniques as described in detail herein and routinely practiced by persons skilled in the art.

Appropriate conditions for permitting interaction of the reaction components according to this method and other methods described herein include, for example, appropriate concentrations of reagents and components (including a CD47 ligand, the candidate agent, an immune cell that expresses CD47, and/or a viral CD47-like polypeptide, or fragment or extracellular domain thereof (or fusion polypeptide comprising a viral CD47-like extracellular domain), temperature, and buffers with which a skilled person will be familiar. Concentrations of reaction components, buffers, temperature, and time period sufficient to permit interaction of the reaction components can be determined and/or adjusted according to methods described herein and with which persons skilled in the art are familiar. To practice the methods described herein, a person skilled in the art will also readily appreciate and understand which controls are appropriately included when practicing these methods.

Numerous assays and techniques are practiced by persons skilled in the art for determining the interaction between or binding between a biological molecule and a cognate ligand. Accordingly, interaction between a CD47 ligand and a viral CD47-like polypeptide and interaction between an immune cell expressing CD47 and a CD47 ligand, including the effect of a bioactive agent on this interaction and/or binding in the presence of the agent can be readily determined by such assays and techniques, which may include a competitive assay format. Exemplary methods include but are not limited to fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence, immunoassays, (such as enzyme-linked immunosorbant assays (ELISA), radioimmunoassay, immunoblotting, immunohistochemistry, and the like), surface plasmon resonance, cell-based assays such as those that use reporter genes, and functional assays (e.g., assays that measure immune function and immunoresponsiveness). Many of the methods described herein and known to those skilled in the art may be adapted to high throughput screening for analyzing large numbers of bioactive agents such as from libraries of compounds to determine the effect of an agent on the binding, interaction, or biological function of CD47 and a CD47 ligand and the effect of an agent on immunoresponsiveness of an immune cell (see, e.g., *High Throughput Screening: The Discovery of Bioactive Substances*, Devlin, ed., (Marcel Dekker New York, 1997)).

The techniques and assay formats may also include secondary reagents, such as specific antibodies, that are useful for detecting and/or amplifying a signal that indicates formation of a complex, such as between a CD47 ligand and a viral CD47-like polypeptide (or extracellular domain thereof or fusion polypeptide comprising the extracellular domain), or such as between an immune cell expressing CD47 and a CD47 ligand. One or more of the assay components or secondary reagents may be attached to a detectable moiety (or label or reporter molecule) such as an enzyme, cytotoxicity agent, or other reporter molecule, including a dye, radionuclide, luminescent group, fluorescent group, or biotin, or the like. Techniques for radiolabeling of antibodies and other polypeptides are known in the art (see, e.g., Adams, *In Vivo* 12:11-21 (1998); Hiltunen, *Acta Oncol.* 32:831-9 (1993)). The detectable moiety may be attached to a polypeptide (e.g., an antibody), such as through any available amino acid sidechain, terminal amino acid, or carbohydrate functional group located in the polypeptide, provided that the attachment or attachment process does not adversely affect the binding properties such that the usefulness of the molecule is abrogated. Particular functional groups include, for example, any free amino, imino, thiol, hydroxyl, carboxyl, or aldehyde group. Attachment of the polypeptide and the detectable moiety may be achieved via such groups and an appropriate functional group in the detectable moiety. The linkage may be direct or indirect through spacing or bridging groups (see, e.g., International Patent Application Publication Nos. WO 93/06231, WO 92/22583, WO 90/091195, and WO 89/01476; see also, e.g., commercial vendors such as Pierce Biotechnology, Rockford, Ill.).

The immune cell may be present in or isolated from a biological sample as described herein. For example, the immune cell may be obtained from a primary or long-term cell culture or may be present in or isolated from a biological sample obtained from a subject (human or non-human animal).

Methods are also provided and described herein for determining the effect of a CD47 Fc fusion polypeptide (or an agent that acts in a similar manner as a CD47 Fc fusion polypeptide, for example, an anti-CD47 ligand antibody) on Fc-mediated activation of an immune cell, for example, determining the capability of a fusion polypeptide to inhibit cytokine or chemokine production of an immune cell. Methods are also provided for determining the effect of CD47 Fc fusion polypeptide (or an agent) on immune complex induced cytokine production or chemokine production. Exemplary methods are provided in the examples.

A "biological sample" as used herein refers in certain embodiments to a sample containing at least one CD47 ligand or a CD47 polypeptide or variant or fragment (e.g., the extracellular domain) thereof. A biological sample may also contain a viral CD47-like polypeptide or variant or fragment (e.g., the extracellular domain) thereof. A biological sample may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture (e.g., immune cells, virus infected cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

The capability of a fusion polypeptide comprising a CD47 extracellular domain or variant thereof as described herein, and of an agent (e.g., an antibody or antigen-binding fragment thereof that specifically binds to CD47; an aptamer; peptide-IgFc fusion polypeptide; an antibody or antigen-binding fragment thereof that specifically binds to a CD47 ligand) described herein to suppress immunoresponsiveness of an immune cell and thus be useful for treating an immunological disease or disorder, such as an autoimmune disease or inflammatory disease or disorder, cardiovascular disease or disorder, a metabolic disease or disorder, or a proliferative disease or disorder, may be determined and evaluated in any one of a number of animal models described herein and used by persons skilled in the art (see, e.g., reviews by Taneja et al., *Nat. Immunol.* 2:781-84 (2001); Lam-Tse et al., *Springer Semin. Immunopathol.* 24:297-321 (2002)). For example, mice that have three genes, Tyro3, Mer, and Axl that encode receptor tyrosine kinases, knocked out exhibit several symptoms of autoimmune diseases, including rheumatoid arthritis and SLE (Lu et al., *Science* 293:228-29 (2001)). A murine model of spontaneous lupus-like disease has been described using NZB/WF1 hybrid mice (see, e.g., Drake et al., *Immunol. Rev.* 144:51-74 (1995)). An animal model for type I diabetes that permits testing of agents and molecules that affect onset, modulation, and/or protection of the animal from disease uses MHC transgenic (Tg) mice. Mice that express the HLA-DQ8 transgene (HLA-DQ8 is the predominant predisposing gene in human type 1 diabetes) and the HLA-DQ6 transgene (which is diabetes protective) were crossed with RIP (rat insulin promoter). B7-1-Tg mice to provide HLA-DQ8 RIP.B7-1 transgenic mice that develop spontaneous diabetes (see Wakeland et al., *Curr. Opin. Immunol.* 11:701-707 (1999); Wen et al., *J. Exp. Med.* 191:97-104 (2000)). (See also Brondum et al., *Horm. Metab. Res.* 37 Suppl 1:56-60 (2005)).

Animal models that may be used for characterizing the fusion polypeptide described herein and agents that are useful for treating immunological diseases and disorders, such as rheumatoid arthritis include a collagen-induced arthritis model (see, e.g., Kakimoto, *Chin. Med. Sci. J.* 6:78-83 (1991); Myers et al., *Life Sci.* 61:1861-78 (1997)) and an anti-collagen antibody-induced arthritis model (or collagen antibody induced arthritis (CAIA) (see, e.g., Kakimoto, supra; Wallace et al., *J. Immunol.* 162:5547 (1999)). Other applicable animal models for immunological diseases include an experimental autoimmune encephalomyelitis model (also called experimental allergic encephalomyelitis model), an animal model of multiple sclerosis; a psoriasis model that uses AGR129 mice that are deficient in type I and type II interferon receptors and deficient for the recombination activating gene 2 (Zenz et al., Nature 437:369-75 (2005); Boyman et al., *J. Exp. Med.* 199:731-36 (2004); published online Feb. 23, 2004); and a TNBS (2,4,6-trinitrobenzene sulphonic acid) mouse model for inflammatory bowel disease. Numerous animal models for cardiovascular disease are available and include models described in van Vlijmen et al., *J Clin. Invest.* 93:1403-10 (1994); Kiriazis et al., *Annu. Rev. Physiol.* 62:321-51 (2000); Babu et al., *Methods Mol. Med.* 112:365-77 (2005).

Small Molecules

Bioactive agents may also include natural and synthetic molecules, for example, small molecules that bind to CD47, a viral CD47-like polypeptide, or to a CD47 ligand, and/or to a complex between CD47 and a CD47 ligand or between the viral CD47-like polypeptide and a CD47 ligand. Candidate agents for use in a method of screening for and identifying an agent that alters (suppresses or enhances) immunoresponsiveness of an immune cell and/or that inhibits binding of a CD47 ligand to CD47, may be provided as "libraries" or collections of compounds, compositions, or molecules.

Such molecules typically include compounds known in the art as "small molecules" and have molecular weights less than $10^5$ daltons, less than $10^4$ daltons, or less than $10^3$ daltons. For example, members of a library of test compounds can be administered to (combined with, added to) a plurality of samples, each containing at least one CD47 ligand as provided herein, and then the samples are assayed for their capability to enhance or inhibit binding or interaction of a viral CD47-like polypeptide to the ligand and/or to enhance or inhibit binding of the at least one CD47 ligand to CD47 expressed on the cell surface of a cell; and/or the capability of the test compounds to alter immunoresponsiveness of immune cells. Compounds so identified as capable of influencing CD47 function are valuable for therapeutic and/or diagnostic purposes because they permit treatment and/or detection of diseases associated with CD47 activity.

Candidate agents further may be provided as members of a combinatorial library, which preferably includes synthetic agents prepared according to a plurality of predetermined chemical reactions performed in a plurality of reaction vessels. For example, various starting compounds may be prepared according to one or more of solid-phase synthesis, recorded random mix methodologies, and recorded reaction split techniques that permit a given constituent to traceably undergo a plurality of permutations and/or combinations of reaction conditions. The resulting products comprise a library that can be screened followed by iterative selection and synthesis procedures, such as a combinatorial library of synthetic peptides (see, e.g., International Patent Application Nos. PCT/US91/08694 and PCT/US91/04666) or other compositions that may include small molecules (see, e.g., International Patent Application No. PCT/US94/08542, EP Patent No. 0774464, U.S. Pat. No. 5,798,035, U.S. Pat. No. 5,789,172, U.S. Pat. No. 5,751,629, which are hereby incorporated by reference in their entireties). Those having ordinary skill in the art will appreciate that a diverse assortment of such libraries may be prepared according to established procedures and tested according to the present disclosure. Certain combinatorial libraries of small molecules and combinatorial libraries of peptides may also be obtained commercially.

Examples of methods for the synthesis of molecular libraries can be found in the art, for example in DeWitt et al., *Proc. Natl. Acad. Sci. U.S.A.* 90:6909 (1993); Erb et al., *Proc. Natl. Acad. Sci. USA* 91:11422 (1994); Zuckermann et al., *J. Med. Chem.* 37:2678 (1994); Cho et al., *Science* 261:1303 (1993); Carrell et al., *Angew. Chem. Int. Ed. Engl.* 33:2059 (1994); Carell et al., *Angew. Chem. Int. Ed. Engl.* 33:2061 (1994); and in Gallop et al., *J. Med. Chem.* 37:1233 (1994). Libraries of compounds may be presented in solution (e.g., Houghten, *Biotechniques* 13:412-21(1992)); or on beads (Lam, *Nature* 354:82-84 (1991)); chips (Fodor, *Nature* 364:555-56 (1993)); bacteria (Ladner, U.S. Pat. No. 5,223,409); spores (Ladner, supra); plasmids (Cull et al., *Proc. Natl. Acad. Sci. USA* 89:1865-69(1992)); or on phage (Scott and Smith, *Science* 249:386-390 (1990); Devlin, *Science* 249:404-406 (1990); Cwirla et al., *Proc. Natl. Acad. Sci. USA* 87:6378-82 (1990); Felici, *J. Mol. Biol.* 222:301-10 (1991); Ladner, supra).

Peptide-Immunoglobulin Constant Region Fusion Polypeptides

In one embodiment, a bioactive agent that is used for altering the immunoresponsiveness of an immune cell and that may be used for treating an immunological disease or disorder is a peptide-immunoglobulin (Ig) constant region fusion polypeptide, which includes a peptide-IgFc fusion polypeptide. The peptide may be any naturally occurring or recombinantly prepared molecule. A peptide-Ig constant region fusion polypeptide, such as a peptide-IgFc fusion polypeptide (also referred to in the art as a peptibody (see, e.g., U.S. Pat. No. 6,660,843)), comprises a biologically active peptide or polypeptide capable of altering the activity of a protein of interest, such as CD47 expressed by an immune cell or a CD47 ligand. The peptide may be fused in-frame with a portion, at least one constant region domain (e.g., CH1, CH2, CH3, and/or CH4), or the Fc polypeptide (CH2-CH3) of an immunoglobulin. An Fc polypeptide, which includes a mutein Fc polypeptide is described herein in detail, is also referred to herein as the Fc portion or the Fc region.

In one embodiment, the peptide portion of the fusion polypeptide is capable of interacting with or binding to CD47, and effecting the same biological activity as a viral CD47-like polypeptide when it binds to CD47, and/or effecting the same biological activity as a CD47 ligand, thus suppressing (inhibiting, preventing, decreasing, or abrogating) the immunoresponsiveness of an immune cell. Methods are provided herein for identifying a peptide that is capable of altering (e.g., suppressing) immunoresponsiveness of an immune cell (that is, a peptide that acts as viral CD47-like polypeptide mimic). For example, such a peptide may be identified by determining its capability to inhibit or block binding of a CD47 ligand to a cell that expresses CD47. Alternatively, a candidate peptide may be permitted to contact or interact with an immune cell that expresses CD47, and the capability of the candidate peptide to suppress or enhance immunoresponsiveness of the immune cell can be measured according to methods described herein and practiced in the art. Candidate peptides may be provided as members of a combinatorial library, which includes synthetic peptides prepared according to a plurality of predetermined chemical reactions performed in a plurality of reaction vessels. For example, various starting peptides may be prepared according to standard peptide synthesis techniques with which a skilled artisan will be familiar.

Peptides that alter the immunoresponsiveness of an immune cell may be identified and isolated from combinatorial libraries (see, e.g., International Patent Application Nos. PCT/US91/08694 and PCT/US91/04666) and from phage display peptide libraries (see, e.g., Scott et al., *Science* 249: 386 (1990); Devlin et al., *Science* 249:404 (1990); Cwirla et al., *Science* 276: 1696-99 (1997); U.S. Pat. No. 5,223,409; U.S. Pat. No. 5,733,731; U.S. Pat. No. 5,498,530; U.S. Pat. No. 5,432,018; U.S. Pat. No. 5,338,665; 1994; U.S. Pat. No. 5,922,545; International Application Publication Nos. WO 96/40987 and WO 98/15833). In phage display peptide libraries, random peptide sequences are fused to a phage coat protein such that the peptides are displayed on the external surface of a filamentous phage particle. Typically, the displayed peptides are contacted with a ligand or binding molecule of interest to permit interaction between the peptide and the ligand or binding molecule, unbound phage are removed, and the bound phage are eluted and subsequently enriched by successive rounds of affinity purification and repropagation. The peptides with the greatest affinity for the ligand or binding molecule or target molecule of interest (e.g., CD47) may be sequenced to identify key residues, which may identify peptides within one or more structurally related families of peptides. Comparison of sequences of peptides may also indicate which residues in such peptides may be safely substituted or deleted by mutagenesis. These peptides may then be incorporated into additional peptide libraries that can be screened and peptides with optimized affinity can be identified.

Additional methods for identifying peptides that may alter the immunoresponsiveness of an immune cell and thus be useful for treating and/or preventing an immunological disease or disorder include, but are not limited to, (1) structural analysis of protein-protein interaction such as analyzing the crystal structure of the CD47 target (particularly the CD47 extracellular domain) (see, e.g., Jia, *Biochem. Cell Biol.* 75:17-26 (1997)) to identity and to determine the orientation of critical residues of CD47, which will be useful for designing a peptide (see, e.g., Takasaki et al., *Nature Biotech.* 15: 1266-70 (1997)); (2) a peptide library comprising peptides fused to a peptidoglycan-associated lipoprotein and displayed on the outer surface of bacteria such as *E. coli*; (3) generating a library of peptides by disrupting translation of polypeptides to generate RNA-associated peptides; and (4) generating peptides by digesting polypeptides with one or more proteases. (See also, e.g., U.S. Pat. Nos. 6,660,843; 5,773,569; 5,869,451; 5,932,946; 5,608,035; 5,786,331; 5,880,096). A peptide may comprise any number of amino acids between 3 and 75 amino acids, 3 and 60 amino acids, 3 and 50 amino acids, 3 and 40 amino acids, 3 and 30 amino acids, 3 and 20 amino acids, or 3 and 10 amino acids. A peptide that has the capability of alter the immunoresponsiveness of an immune cell (e.g., in certain embodiments, to suppress the immunoresponsiveness of the immune cell and in certain other embodiments, to enhance immunoresponsiveness of the immune cell) may also be further derivatized to add or insert amino acids that are useful for constructing a peptide-Ig constant region fusion protein (such as amino acids that are linking sequences or that are spacer sequences).

A peptide that may be used to construct a peptide-Ig constant region fusion polypeptide (including a peptide-IgFc fusion polypeptide) may be derived from a CD47 ligand (e.g., SIRP-α, SIRP-beta-2, thrombospondin-1, $\alpha_v\beta_3$ integrin, and $\alpha_2\beta_1$). Peptides may be randomly generated by proteolytic digestion of a CD47 ligand using any one or more of various proteases, isolated, and then analyzed for their capability to alter the immunoresponsiveness of an immune cell. CD47 ligand peptides may also be generated using recombinant methods described herein and practiced in the art. Randomly generated peptides may also be used to prepare peptide combinatorial libraries or phage libraries as described herein and in the art. Alternatively, the amino acid sequences of portions of a CD47 ligand that interact with CD47 may be determined by computer modeling of CD47, or of a portion of CD47, for example, the extracellular portion thereof, and/or x-ray crystallography (which may include preparation and analysis of crystals of the CD47 extracellular domain only or of the CD47 extracellular domain complexed with a CD47 ligand).

The IgFc portion of a peptide-IgFc fusion polypeptide may be any of the Fc polypeptides or mutein Fc polypeptides that are described in detail herein for fusing to a CD47 extracellular domain. As described in detail above, an Fc polypeptide of an immunoglobulin comprises the heavy chain CH2 domain and CH3 domain and a portion of or the entire hinge region that is located between CH1 and CH2. Fc regions are monomeric polypeptides that may be linked into dimeric or multimeric forms by covalent (e.g., particularly disulfide bonds) and non-covalent association. The number of intermolecular disulfide bonds between monomeric subunits of Fc polypeptides varies depending on the immunoglobulin class (e.g., IgG, IgA, IgE) or subclass (e.g., human IgG1, IgG2, IgG3, IgG4, IgA1, IgA2). An Fc polypeptide, and any one or more constant region domains, and fusion proteins comprising at least one immunoglobulin (Ig) constant region domain can be readily prepared according to recombinant molecular biology techniques with which a skilled artisan is quite familiar.

The Fc polypeptide is preferably prepared using the nucleotide and the encoded amino acid sequences derived from the animal species for whose use the peptide-IgFc fusion polypeptide is intended. In one embodiment, the Fc polypeptide is of human origin and may be from any of the immunoglobulin classes, such as human IgG1 and IgG2.

An Fc polypeptide as described herein also includes Fc polypeptide variants (also referred to herein as mutein Fc polypeptides). An Fc polypeptide or mutein Fc polypeptide that may be fused to a peptide as described above includes any one of the mutein Fc polypeptides described above. One such Fc polypeptide variant has one or more cysteine residues (such as one or more cysteine residues in the hinge region) substituted with another amino acid, such as serine, or deleted to reduce the number of disulfide bonds that may form between two Fc polypeptide monomers.

Also as described in detail herein, another example of an Fc polypeptide variant is a variant that has one or more amino acids involved in, or associated with, an effector function substituted or deleted such that the Fc polypeptide has a reduced level of an effector function. For example, amino acids in the Fc region may be substituted to reduce or abrogate binding of a component of the complement cascade (see, e.g., Duncan et al., *Nature* 332:563-64 (1988); Morgan et al., *Immunology* 86:319-24 (1995)) or to reduce or abrogate the ability of the Fc polypeptide to bind to an IgG Fc receptor expressed by an immune cell (Wines et al., *J. Immunol.* 164: 5313-18 (2000); Chappel et al., *Proc. Natl. Acad. Sci. USA* 88:9036 (1991); Canfield et al., *J. Exp. Med.* 173:1483 (1991); Duncan et al., supra); or to alter antibody-dependent cellular cytotoxicity.

In certain embodiments, a mutein Fc polypeptide that is fused with a peptide comprises a substitution or a deletion of the cysteine residue that is most proximal to the amino terminus of the hinge region of an Fc polypeptide and a deletion of the adjacent aspartic acid residue (toward the C-terminal end of the Fc polypeptide). The mutein Fc polypeptide may further comprise at least one, two, or three or more amino acid substitutions in the CH2 domain of the Fc polypeptide. In a particular embodiment, at least one of the amino acid substitutions in the CH2 domain reduces the capability of the mutein Fc polypeptide to bind to an IgFc receptor. In specific embodiments, the at least one, two, or three amino acids substitutions in the CH2 domain are substitutions of an amino acid(s) located at a position that corresponds to EU numbered position 234, 235, and/or 237. Exemplary mutein Fc polypeptides are described in detail herein and exemplary amino acid sequences of mutein Fc polypeptides include, but are not limited to, the amino acid sequences set forth in SEQ ID NOSs:7, 8 and 23.

Aptamers

Aptamers are DNA or RNA molecules, generally single-stranded, that have been selected from random pools based on their ability to bind other molecules, including nucleic acids, proteins, lipids, etc. Unlike antisense polynucleotides, short interfering RNA (siRNA), or ribozymes that bind to a polynucleotide that comprises a sequence that encodes a polypeptide of interest and that alter transcription or translation, aptamers can target and bind to polypeptides. Aptamers may be selected from random or unmodified oligonucleotide libraries by their ability to bind to specific targets, in this instance, CD47 (see, e.g., U.S. Pat. No. 6,867,289; U.S. Pat. No. 5,567,588). Aptamers have capacity to form a variety of two- and three-dimensional structures and have sufficient chemical versatility available within their monomers to act as ligands (i.e., to form specific binding pairs) with virtually any chemical compound, whether monomeric or polymeric. Molecules of any size or composition can serve as targets. An iterative process of in vitro selection may be used to enrich the library for species with high affinity to the target. This process involves repetitive cycles of incubation of the library with a desired target, separation of free oligonucleotides from those bound to the target, and amplification of the bound oligonucleotide subset, such as by using the polymerase chain reaction (PCR). From the selected sub-population of sequences that have high affinity for the target, a sub-population may be subcloned and particular aptamers examined in further detail to identify aptamers that alter a biological function of the target (see, e.g., U.S. Pat. No. 6,699,843).

Aptamers may comprise any deoxyribonucleotide or ribonucleotide or modifications of these bases, such as deoxythiophosphate (or phosphorothioate), which have sulfur in place of oxygen as one of the non-bridging ligands bound to the phosphorus. Monothiophosphates αS have one sulfur atom and are thus chiral around the phosphorus center. Dithiophosphates are substituted at both oxygens and are thus achiral. Phosphorothioate nucleotides are commercially available or can be synthesized by several different methods known in the art.

Expression of a Fusion Polypeptide Comprising CD47 Extracellular Domain, a Fusion Polypeptide Comprising a Viral CD47-Like Extracellular Domain, and Polypeptide Agents Any of the fusion polypeptides described herein, including a fusion polypeptide comprising a CD47 extracellular domain, or variant thereof, fused to a mutein Fc polypeptide, a fusion polypeptide comprising a viral CD47-like extracellular domain fused to a mutein Fc polypeptide, and peptide-IgFc fusion polypeptides, may be expressed using vectors and constructs, particularly recombinant expression constructs, that include any polynucleotide encoding such polypeptides. Host cells are genetically engineered with vectors and/or constructs to produce these polypeptides and fusion proteins, or fragments or variants thereof, by recombinant techniques. Each of the polypeptides and fusion polypeptides described herein can be expressed in mammalian cells, yeast, bacteria, insect, or other cells under the control of appropriate promoters. Cell-free translation systems can also be employed to produce such proteins using RNAs derived from DNA constructs. Appropriate cloning and expression vectors for use with prokaryotic and eukaryotic hosts are described, for example, by Sambrook, et al., *Molecular Cloning: A Laboratory Manual*, Third Edition, Cold Spring Harbor, New York, (2001).

Generally, recombinant expression vectors include origins of replication, selectable markers permitting transformation of the host cell, for example, the ampicillin resistance gene of *E. coli* and *S. cerevisiae* TRP1 gene, and a promoter derived from a highly expressed gene to direct transcription of a downstream structural sequence. Promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences.

Optionally, a heterologous sequence can encode a fusion protein that further includes an amino terminal or carboxy terminal identification peptide or polypeptide that imparts desired characteristics, e.g., that stabilizes the produced polypeptide or that simplifies purification of the expressed recombinant product. Such identification peptides include a polyhistidine tag (his tag) or FLAG® epitope tag (DYKDDDDK, SEQ ID NO:24), beta-galactosidase, alkaline phosphatase, GST, or the XPRESS™ epitope tag (DLYDDDDK, SEQ ID NO:25; Invitrogen Life Technologies, Carlsbad, Calif.) and the like (see, e.g., U.S. Pat. No. 5,011,912; Hopp et al., (*Bio/Technology* 6:1204 (1988)). The affinity sequence may be supplied by a vector, such as, for example, a hexa-histidine tag that is provided in pBAD/His (Invitrogen). Alternatively, the affinity sequence may be added either synthetically or engineered into the primers used to recombinantly generate the nucleic acid coding sequence (e.g., using the polymerase chain reaction).

Host cells containing described recombinant expression constructs may be genetically engineered (transduced, transformed, or transfected) with the vectors and/or expression constructs (for example, a cloning vector, a shuttle vector, or an expression construct). The vector or construct may be in the form of a plasmid, a viral particle, a phage, etc. The engineered host cells can be cultured in conventional nutrient media modified as appropriate for activating promoters, selecting transformants, or amplifying particular genes or encoding-nucleotide sequences. Selection and maintenance of culture conditions for particular host cells, such as temperature, pH and the like, will be readily apparent to the ordinarily skilled artisan. Preferably the host cell can be adapted to sustained propagation in culture to yield a cell line according to art-established methodologies. In certain embodiments, the cell line is an immortal cell line, which refers to a cell line that can be repeatedly (at least ten times while remaining viable) passaged in culture following log-phase growth. In other embodiments the host cell used to generate a cell line is a cell that is capable of unregulated growth, such as a cancer cell, or a transformed cell, or a malignant cell.

Useful bacterial expression constructs are constructed by inserting into an expression vector a structural DNA sequence encoding a desired protein together with suitable translation initiation and termination signals in operable reading phase with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice. Any other plasmid or vector may be used as long as they are replicable and viable in the host. Thus, for example, the nucleic acids as provided herein may be included in any one of a variety of expression vector constructs as a recombinant expression construct for expressing a polypeptide. Such vectors and constructs include chromosomal, nonchromosomal, and synthetic DNA sequences, e.g., bacterial plasmids; phage DNA; baculovirus; yeast plasmids; vectors derived from combinations of plasmids and phage DNA; viral DNA, such as vaccinia, adenovirus, fowl pox virus, and pseudorabies. However, any other vector may be used for preparation of a recombinant expression construct as long as it is replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. Numerous standard techniques are described, for example, in Ausubel et al. (*Current Protocols in Molecular Biology* (Greene Publ. Assoc. Inc. & John Wiley & Sons, Inc., 1993)); Sambrook et al. (*Molecular Cloning: A Laboratory Manual*, 3rd Ed., (Cold Spring Harbor Laboratory 2001)); Maniatis et al. (*Molecular Cloning*, (Cold Spring Harbor Laboratory 1982)), and elsewhere.

The DNA sequence encoding a polypeptide in the expression vector is operatively linked to at least one appropriate expression control sequences (e.g., a promoter or a regulated promoter) to direct mRNA synthesis. Representative examples of such expression control sequences include LTR or SV40 promoter, the *E. coli* lac or trp, the phage lambda $P_L$ promoter, and other promoters known to control expression of genes in prokaryotic or eukaryotic cells or their viruses. Promoter regions can be selected from any desired gene using CAT (chloramphenicol transferase) vectors or other vectors with selectable markers. Particular bacterial promoters include lad, lacZ, T3, T5, T7, gpt, lambda $P_R$, $P_L$, and trp. Eukaryotic promoters include CMV immediate early, HSV thymidine kinase, early and late SV40, LTRs from retroviruses, and mouse metallothionein-I. Selection of the appropriate vector and promoter and preparation of certain recombinant expression constructs comprising at least one promoter or regulated promoter operatively linked to a nucleic acid described herein is well within the level of ordinary skill in the art.

Design and selection of inducible, regulated promoters and/or tightly regulated promoters are known in the art and will depend on the particular host cell and expression system. The pBAD Expression System (Invitrogen Life Technologies, Carlsbad, Calif.) is an example of a tightly regulated expression system that uses the *E. coli* arabinose operon ($P_{BAD}$ or $P_{ARA}$) (see Guzman et al., *J. Bacteriology* 177:4121-30 (1995); Smith et al., *J. Biol. Chem.* 253:6931-33 (1978); Hirsh et al., *Cell* 11:545-50 (1977)), which controls the arabinose metabolic pathway. A variety of vectors employing this system are commercially available. Other examples of tightly regulated promoter-driven expression systems include PET Expression Systems (see U.S. Pat. No. 4,952,496) available from Stratagene (La Jolla, Calif.) or tet-regulated expression systems (Gossen et al., *Proc. Natl. Acad. Sci. USA* 89:5547-51 (1992); Gossen et al., *Science* 268:1766-69 (1995)). The pLP-TRE2 Acceptor Vector (BD Biosciences Clontech, Palo Alto, Calif.) is designed for use with CLONTECH's Creator™ Cloning Kits to rapidly generate a tetracycline-regulated expression construct for tightly controlled, inducible expression of a gene of interest using the site-specific Cre-lox recombination system (see, e.g., Sauer, *Methods* 14:381-92 (1998); Furth, *J. Mamm. Gland Biol. Neoplas.* 2:373 (1997)), which may also be employed for host cell immortalization (see, e.g., Cascio, *Art Organs* 25:529 (2001)).

The vector may be a viral vector such as a retroviral vector. For example, retroviruses from which the retroviral plasmid vectors may be derived include, but are not limited to, Moloney Murine Leukemia Virus, spleen necrosis virus, Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus. A viral vector also includes one or more promoters. Suitable promoters that may be employed include, but are not limited to, the retroviral LTR; the SV40 promoter; and the human cytomegalovirus (CMV) promoter described in Miller et al., *Biotechniques* 7:980-990 (1989), or any other promoter (e.g., eukaryotic cellular promoters including, for example, the histone, pol III, and β-actin promoters). Other viral promoters that may be employed include, but are not limited to, adenovirus promoters, thymidine kinase (TK) promoters, and B 19 parvovirus promoters.

The retroviral plasmid vector is employed to transduce packaging cell lines (e.g., PE501, PA317, ψ-2, ψ-AM, PA12, T19-14X, VT-19-17-H2, ψCRE, ψCRIP, GP+E-86, GP+envAm12, DAN; see also, e.g., Miller, *Human Gene Therapy*, 1:5-14 (1990)) to form producer cell lines. The vector may transduce the packaging cells through any means known in the art, such as, for example, electroporation, the use of liposomes, and calcium phosphate precipitation. The producer cell line generates infectious retroviral vector particles that include the nucleic acid sequence(s) encoding the polypeptides or fusion proteins described herein. Such retroviral vector particles then may be employed, to transduce eukaryotic cells, either in vitro or in vivo. Eukaryotic cells that may be transduced include, for example, embryonic stem cells, embryonic carcinoma cells, hematopoietic stem cells, hepatocytes, fibroblasts, myoblasts, keratinocytes, endothelial cells, bronchial epithelial cells, and other culture-adapted cell lines.

As another example, host cells transduced by a recombinant viral construct directing the expression of polypeptides or fusion proteins may produce viral particles containing expressed polypeptides or fusion proteins that are derived from portions of a host cell membrane incorporated by the viral particles during viral budding. The polypeptide-encoding nucleic acid sequences may be cloned into a baculovirus shuttle vector, which is then recombined with a baculovirus to generate a recombinant baculovirus expression construct that is used to infect, for example, Sf9 host cells (see, e.g., *Baculovirus Expression Protocols, Methods in Molecular Biology* Vol. 39, Richardson, Ed. (Human Press 1995); Piwnica-Worms, "Expression of Proteins in Insect Cells Using Baculoviral Vectors," Section II, Chapter 16 in *Short Protocols in Molecular Biology*, $2^{nd}$ Ed., Ausubel et al., eds., (John Wiley & Sons 1992), pages 16-32 to 16-48).

Treatment of Immunological Disorders and Disease

In another embodiment, methods are provided for treating and/or preventing immunological diseases and disorders, particularly an inflammatory disease or disorder, an autoimmune disease or disorder, cardiovascular disease or disorder, a metabolic disease or disorder, or a proliferative disease or disorder as described herein. A subject in need of such treatment may be a human or may be a non-human primate or other animal (i.e., veterinary use) who has developed symptoms of an immunological disease or who is at risk for developing an immunological disease. Examples of non-human primates and other animals include but are not limited to farm animals, pets, and zoo animals (e.g., horses, cows, buffalo, llamas, goats, rabbits, cats, dogs, chimpanzees, orangutans, gorillas, monkeys, elephants, bears, large cats, etc.).

As described herein, a method is provided for altering (e.g., suppressing or enhancing) an immune response in a subject (host or patient) who has or who is at risk for developing an immunological disease or disorder, by administering a composition that comprises a pharmaceutically acceptable carrier (also referred to herein as a pharmaceutically or physiologically suitable carrier or excipient) and any one of the fusion polypeptides described herein that comprise a CD47 extracellular domain, or variant thereof, fused to a Fc polypeptide, or variant thereof (which also includes fusion polypeptide dimers). In certain embodiments, the composition suppresses the immune response by suppressing (i.e., decreasing, reducing, inhibiting, abrogating) immunoresponsiveness of an immune cell. In other embodiments, CD47-Fc polypeptide fusion proteins described herein suppress immunoresponsiveness of an immune cell and inhibit (i.e., decrease, reduce, suppress, abrogate) the production of at least one cytokine and/or at least one chemokine by an immune cell. In other embodiments, the fusion proteins block or inhibit interaction between an immune complex and an immune cell, such as a dendritic cell, and thus inhibits the production of cytokines and/or chemokines by the immune cell, for example, a dendritic cell. The fusion polypeptides described herein may also alter cell migration; inhibit (i.e., decrease, block, reduce, abrogate) production of at least one cytokine, including but not limited to, TNF-α, IL-12, IL-23 IFN-γ, GM-CSF, and IL-6; inhibit maturation of a dendritic cell; impair (i.e., inhibit, prevent, slow, or in some manner deleteriously affect) development of a naïve T cell into a Th1 effector cell; inhibit (i.e., decrease, block, reduce, abrogate) immune complex-induced production of a cytokine (e.g., TNF-α, IL-12, IL-23 IFN-γ, GM-CSF, and IL-6) by an immune cell (e.g., a dendritic cell); inhibit (i.e., decrease, block, reduce, abrogate) Fc-mediated production of a cytokine (e.g., TNF-α, IL-12, IL-23 IFN-γ, GM-CSF, and IL-6) by an immune cell (e.g., a dendritic cell); suppress (i.e., inhibit, decrease, block, reduce, abrogate) cytokine and/or chemokine secretion by an immune cell, including but not limited to a dendritic cell; inhibit activation of an immune cell wherein the immune cell expresses SIRPα on the cell surface; suppress a proinflammatory response in a biologically or clinically significant manner.

In other certain embodiments, the composition comprises an antibody, or antigen-binding fragment thereof, that specifically binds to CD47 and a pharmaceutically acceptable (i.e., suitable) carrier. In another certain embodiment, a composition is provided that comprises an agent that binds to CD47, such as a small molecule, an aptamer, or a peptide Fc fusion polypeptide and a pharmaceutically acceptable (i.e., suitable) carrier.

Also provided is a method for altering (e.g., suppressing or enhancing) an immune response in a subject (host or patient) who has or who is at risk for developing an immunological disease or disorder, by administering any one of the aforementioned compositions. In one embodiment, a method for altering an immune response in a subject comprises administering a composition that comprises a pharmaceutically suitable carrier and any one of the fusion polypeptides described herein that comprise a CD47 extracellular domain, or variant thereof, fused to an Fc polypeptide or variant thereof; a composition that comprises a pharmaceutically suitable carrier and at least one antibody, or antigen-binding fragment thereof, that specifically binds to CD47, as described in detail herein. In another embodiment, a method of altering an immune response in a subject comprises administering a composition comprising an agent that binds to CD47 as described in detail herein, such as a small molecule, an aptamer, or a peptide Fc fusion polypeptide and a pharmaceutically suitable carrier. In a particular embodiment, such a method suppresses an immune response in a subject. In another particular embodiment, such a method enhances an immune response in a subject.

In another embodiment, a method for treating an immunological disease or disorder is provided wherein the method comprises administering to a subject in need thereof a pharmaceutically suitable carrier and an agent that alters a biological activity of at CD47. An agent as described herein (including an antibody, or antigen-binding fragment thereof, for example an antibody that specifically binds to a CD47 ligand, such as SIRPalpha); a small molecule; an aptamer; a peptide-IgFc fusion polypeptide or peptide Ig constant region domain fusion polypeptide; and a fusion polypeptide comprising a CD47 extracellular domain, all of which are described in detail herein) that is useful for treating an immunological disease or disorder is capable of altering (increasing or decreasing in a statistically significant or biological significant manner) at least one biological activity (function) of CD47. Such an agent used for treating an immunological disease or disorder may therefore affect or alter any one or more of the biological activities or functions of CD47, including at least one of the following: altering immunoresponsiveness of an immune cell; altering cell migration; inhibiting production of at least one cytokine selected from TNF-α, IL-12, IL-23 IFN-γ, GM-CSF, and IL-6; inhibiting maturation of a dendritic cell; impairing development of a naïve T cell into a Th1 effector cell; inhibiting immune complex-induced production of a cytokine (e.g., TNF-α, IL-12, IL-23, IFN-γ, GM-CSF, and IL-6) by an immune cell (e.g., a dendritic cell); suppressing cytokine secretion by a dendritic cell; and suppressing a proinflammatory response.

Methods are also provided for treating an immunological disease or disorder in a subject in need thereof, wherein the composition administered to the subject comprises a pharmaceutically suitable carrier and an agent, which agent has the capability to specifically bind to CD47 and to impair (i.e., inhibit, prevent, reduce) binding of a viral CD47-like polypeptide to at least one CD47 ligand (e.g., SIRP-α, SIRP-beta-2, thrombospondin-1, $\alpha_v\beta_3$ integrin, and $\alpha_2\beta_1$ integrin). The agent also includes an antibody, or antigen-binding fragment thereof that specifically binds to a CD47 ligand (e.g., different antibodies that each specifically bind to the respective cognate ligand, such as SIRP-α, SIRP-beta-2, thrombospondin-1, $α_vβ_3$ integrin, and $α_2β_1$ integrin) The capability of the agent to bind to CD47 and to impair binding of the vCD47 to at least one CD47 ligand may be determined by employing assays and techniques described herein using an isolated CD47 polypeptide (or fragment thereof, such as the extracellular domain) or using a cell that expresses CD47 on its surface. The vCD47 polypeptide may be any one of the poxvirus CD47-like polypeptides described herein, for example, variola minor CD47-like polypeptide, which has the amino acid sequence set forth in SEQ ID NO:3. An agent that specifically binds to CD47 and that impairs binding of a viral CD47-like polypeptide to a CD47 ligand may also be used for treating a disease or disorder that is associated with alteration of at least one of cell migration, cell proliferation, and cell differentiation.

The fusion polypeptides, agents, and methods described herein may be used for treating (i.e., curing, preventing, ameliorating the symptoms of, or slowing, inhibiting, or stopping the progression of) an immunological disease or disorder. Such diseases and disorders that are autoimmune or inflammatory disorders include but are not limited to multiple sclerosis, rheumatoid arthritis, an antibody-mediated inflammatory disease or disorder, a spondyloarthropathy, systemic lupus erythematosus, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, or inflammatory autoimmune myositis. A spondyloarthropathy includes, for example, ankylosing spondylitis, reactive arthritis, enteropathic arthritis associated with inflammatory bowel disease, psoriatic arthritis, isolated acute anterior uveitis, undifferentiated spondyloarthropathy, Behcet's syndrome, and juvenile idiopathic arthritis.

An immunological disorder or disease also includes a cardiovascular disease or disorder, a metabolic disease or disorder, or a proliferative disease or disorder. A cardiovascular disease or disorder that may be treated according to the methods and with the fusion polypeptides and agents described herein includes, for example, atherosclerosis, endocarditis, hypertension, or peripheral ischemic disease. Metabolic diseases that also are immunological disorders or diseases include diabetes, Crohn's Disease, and inflammatory bowel disease. An exemplary proliferative disease is cancer. A cancer or malignancy includes, but is not limited to, a leukemia (e.g., B-cell chronic lymphocytic leukemia), lymphoma, breast cancer, renal cancer, and ovarian cancer.

As used herein, a patient (or subject) may be any mammal, including a human, that may have or be afflicted with an immunological disease or disorder, or that may be free of detectable disease. Accordingly, the treatment may be administered to a subject who has an existing disease, or the treatment may be prophylactic, administered to a subject who is at risk for developing the disease or condition.

A composition may be a pharmaceutical composition that is a sterile aqueous or non-aqueous solution, suspension or emulsion, which additionally comprises a physiologically acceptable or suitable carrier. A pharmaceutically acceptable or suitable carrier may include (or refer to) an excipient (i.e., a non-toxic material that does not interfere with the activity of the active ingredient) and/or a diluent. Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remingtons Pharmaceutical Sciences*, Mack Publishing Co. (A. R. Gennaro ed. 1985). In general, the type of excipient is selected based on the mode of administration. Pharmaceutical compositions may be formulated for any appropriate manner of administration, including, for example, topical, oral, nasal, intrathecal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The fusion polypeptides and agents described herein, including antibodies and antigen-binding fragments thereof that specifically bind to CD47, small molecules, aptamers, and peptide-fusion proteins, may be formulated for sustained or slow release. Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

The dose of the composition for treating an immunological disease or disorder may be determined according to parameters understood by a person skilled in the medical art. Accordingly, the appropriate dose may depend upon the patient's (e.g., human) condition, that is, stage of the disease, general health status, as well as age, gender, and weight, and other factors familiar to a person skilled in the medical art.

Pharmaceutical compositions may be administered in a manner appropriate to the disease to be treated (or prevented) as determined by persons skilled in the medical art. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with an immunological disease or disorder.

Optimal doses may generally be determined using experimental models and/or clinical trials. The optimal dose may depend upon the body mass, weight, or blood volume of the patient. In general, the amount of polypeptide, such as a fusion polypeptide as described herein or an antibody or antigen-binding fragment thereof as described herein, present in a dose, or produced in situ by DNA present in a dose, ranges from about 0.01 µg to about 1000 µg per kg of host. The use of the minimum dosage that is sufficient to provide effective therapy is usually preferred. Patients may generally be monitored for therapeutic or prophylactic effectiveness using assays suitable for the condition being treated or prevented, which assays will be familiar to those having ordinary skill in the art. When administered in a liquid form, suitable dose sizes will vary with the size of the patient, but will typically range from about 1 ml to about 500 ml (comprising from about 0.01 µg to about 1000 µg per kg) for a 10-60 kg subject.

For pharmaceutical compositions comprising an agent that is a nucleic acid molecule including an aptamer, the nucleic acid molecule may be present within any of a variety of delivery systems known to those of ordinary skill in the art, including nucleic acid, and bacterial, viral and mammalian expression systems such as, for example, recombinant expression constructs as provided herein. Techniques for incorporating DNA into such expression systems are well known to those of ordinary skill in the art. The DNA may also be "naked," as described, for example, in Ulmer et al., *Science* 259:1745-49, 1993 and reviewed by Cohen, *Science* 259: 1691-1692, 1993. The uptake of naked DNA may be increased by coating the DNA onto biodegradable beads, which are efficiently transported into the cells.

Nucleic acid molecules may be delivered into a cell according to any one of several methods described in the art (see, e.g., Akhtar et al., *Trends Cell Bio.* 2:139 (1992); *Delivery Strategies for Antisense Oligonucleotide Therapeutics*, ed. Akhtar, 1995, Maurer et al., *Mol. Membr. Biol.* 16:129-40 (1999); Hofland and Huang, *Handb. Exp. Pharmacol.* 137: 165-92 (1999); Lee et al., *ACS Symp. Ser.* 752:184-92 (2000); U.S. Pat. No. 6,395,713; International Patent Application Publication No. WO 94/02595); Selbo et al., *Int. J. Cancer* 87:853-59 (2000); Selbo et al., *Tumour Biol.* 23:103-12 (2002); U.S. Patent Application Publication Nos. 2001/ 0007666, and 2003/077829). Such delivery methods known to persons having skill in the art, include, but are not restricted to, encapsulation in liposomes, by iontophoresis, or by incorporation into other vehicles, such as biodegradable polymers; hydrogels; cyclodextrins (see, e.g., Gonzalez et al., *Bioconjug. Chem.* 10:1068-74 (1999); Wang et al., International Application Publication Nos. WO 03/47518 and WO 03/46185); poly(lactic-co-glycolic)acid (PLGA) and PLCA microspheres (also useful for delivery of peptides and polypeptides and other substances) (see, e.g., U.S. Pat. No. 6,447,796; U.S. Patent Application Publication No. 2002/ 130430); biodegradable nanocapsules; and bioadhesive microspheres, or by proteinaceous vectors (International Application Publication No. WO 00/53722). In another embodiment, the nucleic acid molecules for use in altering (suppressing or enhancing) an immune response in an immune cell and for treating an immunological disease or disorder can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives (see also, e.g., U.S. Patent Application Publication No. 2003/ 0077829).

Also provided herein are methods of manufacture for producing an agent that suppresses immunoresponsiveness of an immune cell. The methods comprise identifying an agent that alters immunoresponsiveness of an immune cell. Identifying an agent may be accomplished by any one of the methods described herein, which includes contacting (i) a candidate agent; (ii) a viral CD47-like polypeptide (which are described in detail herein); and (iii) a CD47 ligand (e.g., SIRP-α, SIRP-beta-2, thrombospondin-1, $\alpha_v\beta_3$ integrin, and $\alpha_2\beta_1$ integrin), under conditions and for a time sufficient to permit interaction between the CD47 ligand and the viral CD47-like polypeptide. The method further comprises determining a level of binding of the viral CD47-like polypeptide to the CD47 ligand in the presence of the candidate agent and comparing a level of binding of the viral CD47-like polypeptide to the CD47 ligand in the absence of the candidate agent. A decrease in the level of binding of the viral CD47-like polypeptide to the CD47 ligand in the presence of the candidate agent indicates that the candidate agent inhibits binding of the viral CD47-like polypeptide to the CD47 ligand. The candidate agent is then contacted with (i.e., mixed, combined, or in some manner permitted to interact with) an immune cell that expresses CD47, and a CD47 ligand under conditions and for a time sufficient to permit interaction between a CD47 ligand and CD47. The level of binding of the CD47 ligand to the immune cell in the presence of the candidate agent is determined and compared with a level of binding of the CD47 ligand to the immune cell in the absence of the candidate agent. A decrease in the level of binding of the CD47 ligand to the immune cell in the presence of the candidate agent indicates that the candidate agent alters immunoresponsiveness of the immune cell. Then the agent is produced according to small scale or large scale manufacturing practices known in the art that are useful and practical for producing the particular agent.

The agent may be any agent described herein, such as, for example, a fusion polypeptide comprising a CD47 extracellular domain or variant thereof, an antibody, or antigen-binding fragment thereof that specifically binds to CD47; a small molecule; an aptamer; and a peptide-IgFc fusion polypeptide, or an antibody or antigen binding fragment thereof that binds specifically to a CD47 ligand. In a particular embodiment, the agent is a fusion polypeptide comprising a CD47 extracellular domain or variant thereof or an antibody, or antigen-binding fragment thereof, which may be produced according to methods described herein and that are adapted for large-scale manufacture. For example, production methods include batch cell culture, which is monitored and controlled to maintain appropriate culture conditions. Purification of the fusion polypeptide or antibody, or antigen-binding fragment thereof, may be performed according to methods described herein and known in the art and that comport with laws and guidelines of domestic and foreign regulatory agencies.

Examples

Example 1

Inhibition of *Staphylococcus aureus* Cowan Strain (SAC)-Induced Cytokine Production in Human Dendritic Cells by a Human CD47-Fc Polypeptide As described herein, a cognate ligand of CD47 is the signal-regulator protein alpha (Sirp-α) (see also, e.g., Latour et al., *J. Immunol.* 167:2547-54 (2001)). The capability of a huCD47 extracellular domain-Fc polypeptide construct to inhibit *Staphylococcus aureus* cell (SAC)-induced cytokine production in human monocyte derived dendritic cells is described in this example.

The human CD47 extracellular domain fused to a human IgG Fc polypeptide was prepared using molecular biology methods and techniques and protein expression methods and techniques with which persons skilled in the art are familiar. The amino acid sequence of the human CD47 extracellular domain Fc polypeptide used in these examples is provided in SEQ ID NO:2. The polypeptide sequence of the CD47 extracellular domain is provided in SEQ ID NO:11 (with the signal peptide) and in SEQ ID NO:1 (without the signal peptide). The amino acid sequence of the human IgG Fc polypeptide used in these examples is provided in SEQ ID NO:23.

Human monocyte-derived dendritic cells were prepared as described (Probst et al., *Eur. J. Immunol.* 27:2634-42 (1997)). Peripheral blood mononuclear cells (PBMC) were prepared from heparinized blood of healthy donors by gradient centrifugation in Histopaque-1077 (Sigma-Aldrich, St. Louis, Mo.). For this experiments, PBMCs were obtained from three different donors. Briefly, monocytes were generated by an adherent step by culturing $15 \times 10^6$ PBMC in RPMI (Lonza, Walkersville, Md.) with 2% human serum (HuS) per well of a 6 well plate. After 2 h, adherent cells were washed twice with PBS and then cultured with dendritic cell differentiation medium (Exvivo 15, Lonza), 10 ng/ml human granulocyte-macrophage colony stimulating Factor (GMCSF) (PeproTech®, Rocky Hill, N.J.), 10 ng/ml human IL-4 (PeproTech®, Rocky Hill, N.J.). After one day, non-adherent cells were gently removed and dendritic cells were generated from the remaining cells by culture for an additional 7 days in dendritic cell differentiation medium.

The eight day-old human monocyte-derived dendritic cells ($2 \times 10^4$ cells per well of a 96 well plate) from each of the three donors were treated in the presence of IFN-γ (1000 U/ml) for 1 hour with varying concentrations (five-fold dilutions between 0.006 and 20 µg/ml) of either the human CD47-human Fc polypeptide or a control molecule, in this instance, human IgG. The cells were then stimulated overnight with 0.01% SAC (Pansorbin® Cells, Calbiochem, San Diego Calif.). Supernatants from the stimulated cell cultures were collected 18 h after stimulation with SAC and stored immediately at −20° C.

Figure 3A:
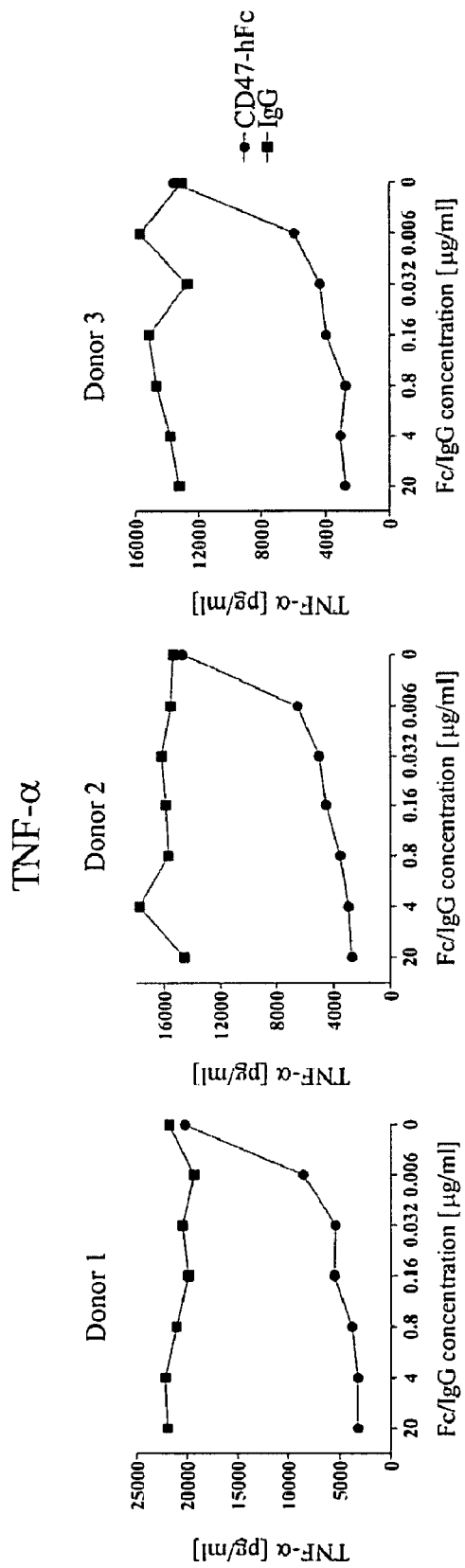
Figure 3B:
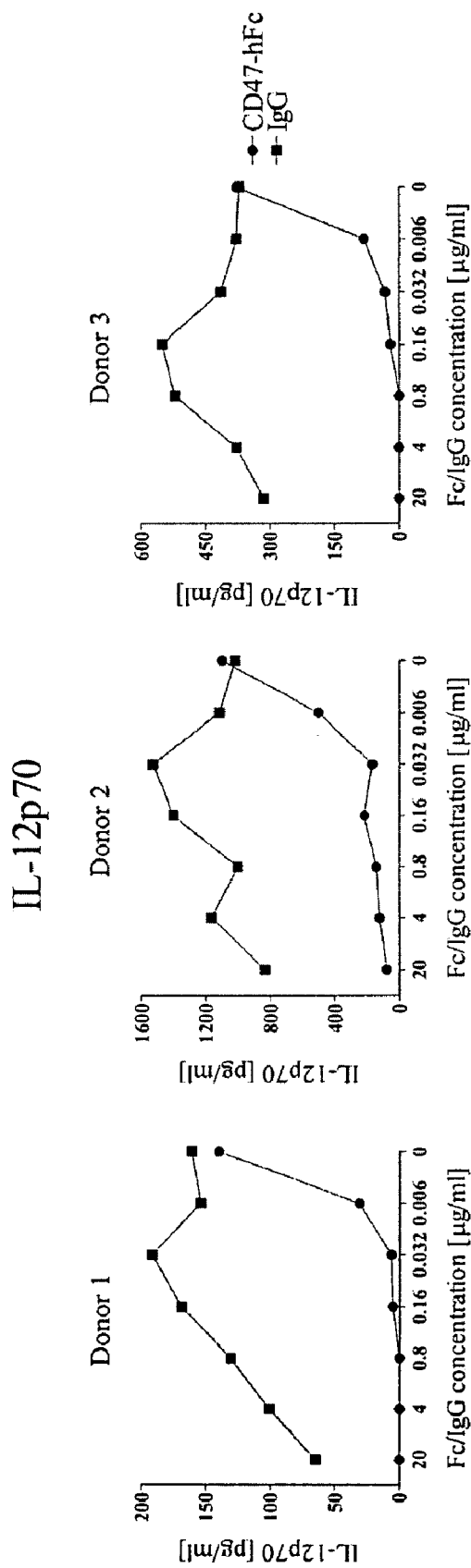

The presence of TNF-α, IL-12p70, IL-6 and MIP-1alpha in each supernatant was determined by ELISA, using commercially prepared kits according to protocols provided by the manufacturer (R&D Systems, Minneapolis, Minn.). The data are presented in FIG. 3. The hCD47-Fc construct reduced the SAC-induced TNF-α and IL-12p70 production in a dose dependent manner with an $IC_{50}$ below 6 ng/ml. Human IgG control did not affect SAC-induced TNF-α production and had limited effects on IL-12 production, thus demonstrating that the CD47 domain of the CD47-Fc fusion polypeptide is inhibiting cytokine secretion of DC in response to SAC.

As shown in Table I, human CD47-Fc reduced the secretion of IL-6 and MIP-1alpha by human dendritic cells in response to PBS-SAC.

TABLE 1

Inhibition of PBS-SAC mediated cytokine production in human monocyte derived dendritic cells by hCD47-Fc

| hCD47-Fc µg/ml | DC Donor 5 | | | | DC Donor 6 | | | |
| --- | --- | --- | --- | --- | --- | --- | --- | --- |
| | TNFα pg/mL | IL-6 pg/mL | MIP-1α pg/mL | IL-12 pg/mL | TNFα pg/mL | IL-6 pg/mL | MIP-1α pg/mL | IL-12 pg/mL |
| 20.0000 | 873 | 961 | 9148 | 41 | 160 | 175 | 1977 | 6 |
| 4.0000 | 958 | 1047 | 10807 | 31 | 198 | 193 | 2381 | 16 |
| 0.8000 | 1199 | 1181 | 10460 | 52 | 320 | 215 | 3323 | 16 |
| 0.1600 | 1379 | 1273 | 13567 | 66 | 576 | 455 | 4742 | 12 |
| 0.0320 | 1413 | 1176 | 13705 | 99 | 722 | 520 | 5155 | 28 |
| 0.0064 | 2627 | 1725 | 15816 | 291 | 1414 | 867 | 6640 | 56 |
| 0.0013 | 4748 | 2338 | 22079 | 594 | 2669 | 1297 | 10420 | 264 |
| 0.0000 | 5375 | 3030 | 21702 | 912 | 2576 | 1119 | 8325 | 173 |
| hFc-Stub µg/ml | TNFa pg/mL | IL-6 pg/mL | MIP-1α pg/mL | IL-12 pg/mL | TNFα pg/mL | IL-6 pg/mL | MIP-1α pg/mL | IL-12 pg/mL |
| 20.0000 | 5920 | 3602 | 24910 | 934 | 2914 | 1179 | 8565.35 | 128 |
| 4.0000 | 6791 | 3597 | 22991 | 758 | 3425 | 1127 | 9150.823 | 105 |
| 0.8000 | 7911 | 3532 | 29238 | 916 | 3448 | 1553 | 10647.34 | 225 |
| 0.1600 | 7715 | 3332 | 32091 | 829 | 4390 | 1689 | 12610.59 | 296 |
| 0.0320 | 6666 | 3334 | 25806 | 850 | 3861 | 1446 | 10859.59 | 280 |
| 0.0064 | 7707 | 2771 | 19491 | 692 | 3846 | 1661 | 11104.85 | 345 |
| 0.00 | 5371 | 2955 | 19281 | 826 | 2569 | 1291 | 8596.011 | 219 |

Incubation of SAC with human serum (HuS-SAC) increased SAC-induced TNF-α and IL-23 production in human DC. Heat-inactivated human serum (prepared from a normal healthy donor pool) (100 µl) was incubated with an equal volume of 12% SAC for one hour, washed with PBS, and then resuspended with PBS to a final concentration of 1.2% SAC. Preparation of PBS-SAC or FBS (fetal bovine serum)-SAC followed the same protocol by adding PBS or FBS, respectively, instead of human serum.

Figure 4:
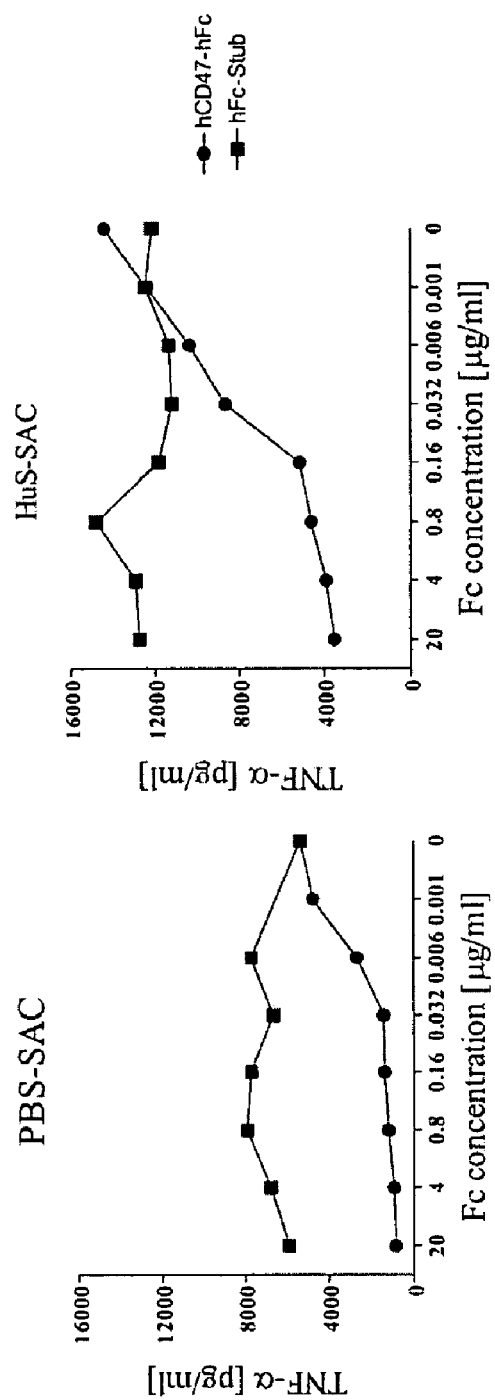
Figure 5:
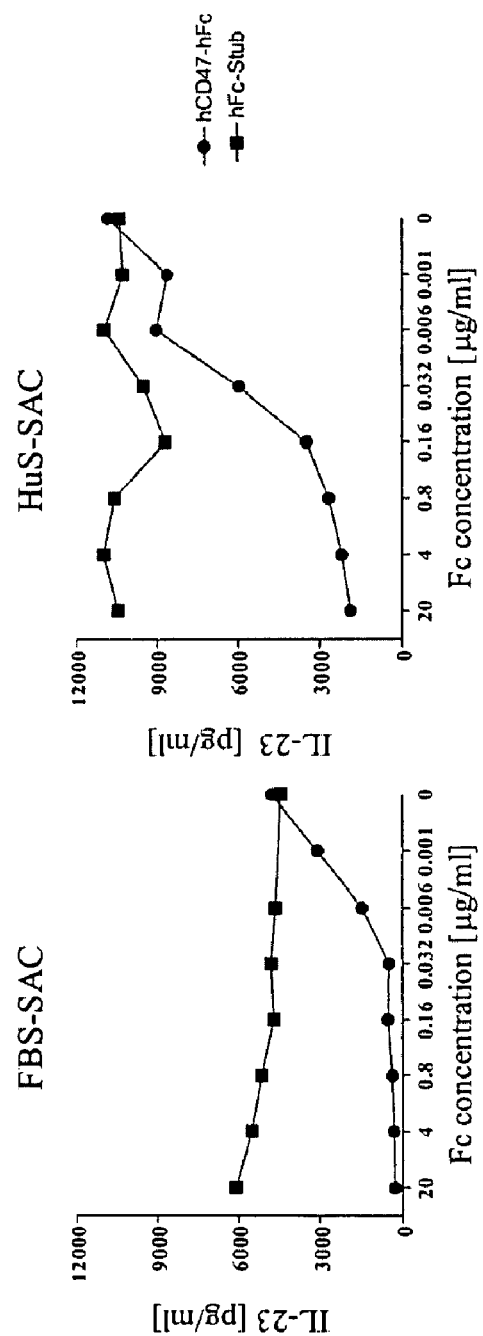

Eight day-old human monocyte-derived DC ($2\times10^4$ cells/96-well) (prepared as described above) were treated for 1 h in the presence of IFN-γ (1000 U/ml) with varying concentrations (five-fold dilutions between 0.001 and 20 µg/ml) of either the human CD47-human Fc polypeptide or a control molecule, in this instance, a human Fc polypeptide that was not fused to a CD47 extracellular domain (hFc-Stub). Then, DC were stimulated with 0.01% HuS-SAC or with 0.01% PBS-SAC (used in experiments that measured TNF-α) or with 0.01% FBS-SAC (used in experiments that measured IL-23). Supernatants were collected from the stimulated cell cultures after 18 h and stored as described above until the concentrations of TNF-α and IL-23 were determined. The presence of TNF-α was determined as described above. The presence of IL-23 in the supernatants was determined using a commercially prepared kit according to the manufacturer's instructions (eBioscience, San Diego Calif.). The results are presented in FIGS. 4 and 5.

Incubation of SAC with human sera increased SAC-induced TNF-α and IL-23 production in human DC. hCD47-Fc inhibited HuS-SAC induced TNF-α and IL-23 production with an $IC_{50}$ below 0.16 µg/ml, whereas the Fc-Stub control had no effect on cytokine secretion. Without wishing to be bound by theory, the human IgG present in the human sera may saturate the protein A binding sites on SAC and trigger an Fc-receptor-mediated enhancement of cytokine secretion.

Example 2

Inhibition of Immune Complex-Induced Cytokine Production in Human Dendritic Cells by a Human CD47-Fc Polypeptide Antigen-antibody complexes (i.e., immune complexes) can damage tissue by triggering Fc-receptor mediated inflammation, a process implicated in a variety of human diseases such as systemic lupus erythematosus, rheumatoid arthritis, and Sjoergen's syndrome. The effect of hCD47-Fc on immune complex (IC)-mediated inflammation was determined using in vitro assays that were developed to mimic IC-mediated cytokine induction in human dendritic cells by modifying previously described methods (see, e.g., Boruchov et al, *J. Clin. Invest.* 115:2914-23 (2005)). Dendritic cells (DC) were activated with IFN-γ and low dose of Toll like receptor (TLR) ligands (for example, FSL-1 or LPS) to resemble DC in inflamed tissue.

96 well plates were coated with 50 µl per well of 50 µg/ml anti-human Fc donkey IgG (Jackson ImmunoResearch Laboratories, West Grove, Pa.) in 0.1 M $NaHCO_3/Na_2CO_3$ buffer overnight. Then plates were washed twice with PBS and then incubated with either CD47-Fc or hFc-Stub at varying concentrations between 0.005 and 20 µg/ml (four-fold dilutions). After 2 h, plates were washed once with PBS before adding dendritic cells to the culture. Eight day-old human monocyte-derived DC ($2\times10^4$/well), prepared as described in Example 1, were added in the presence of IFN-γ (1000 U/ml). Alternatively, in control plates that were not coated with donkey anti-human Fc, DC were seeded into wells containing either soluble hCD47-Fc or hFc-Stub. After two hours, DC were stimulated with 0.1 ng/ml FSL-1 (a TLR-2 ligand) (Invivo-Gen, San Diego Calif.). Supernatants were collected after 18 hours and the concentration of TNF-α in the supernatants as described in Example 1.

Figure 6:
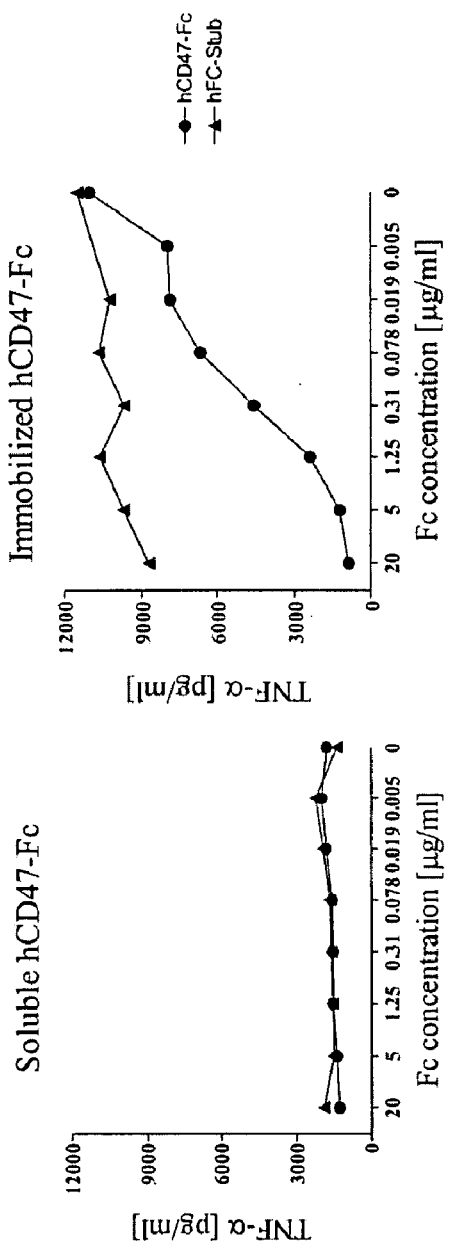

The results are presented in FIG. 6. The presence of donkey IgG (right side of FIG. 6) resulted in an approximately 6-fold increase in TNF-α production by human DC in response to the TLR2 ligand, FSL-1, when compared to DC in the absence of plate-bound IgG (left side of FIG. 6). hCD47-Fc inhibited the IgG-mediated increase in TNF-α production in a dose dependent manner when compared to the Fc-Stub control. hCD47-Fc had no effect on FSL-1-induced cytokine production in the absence of plate-bound IgG, demonstrating that the CD47 moiety of the hCD47-Fc fusion polypeptide inhibited the Fc-receptor mediated activation of DC.

Example 3

Inhibition of IgG-Induced Cytokine Production in Human Dendritic Cells by a Human CD47 Fusion Polypeptide Dimer This Example describes the capability of a human CD47 extracellular domain fusion polypeptide dimer to inhibit IgG-mediated cytokine production in human dendritic cells.

A fusion polypeptide comprising the extracellular domain of human CD47 fused to a non-immunoglobulin moiety. As described herein, a fusion polypeptide dimer may form via the CD47 moieties of a fusion polypeptide, which are capable of forming an interchain disulfide bond. The non-immunoglobulin moiety fused to the CD47 moiety is referred to as a Hac moiety and comprises an hemagglutinin (HA) binding site, C-TAG (protein C-tag derived from the heavy chain of human protein C), and two streptavidin binding sites (2×SBP) (see, e.g., SEQ ID NO:34 sets forth the amino acid sequence of the HAC moiety, wherein the HA epitope is located at the amino terminal end of the Hac moiety fused to a C-TAG, which is fused to 2×SBP; SEQ ID NO:35 sets forth the nucleotide sequence encoding this Hac moiety). As described herein the extracellular domain of human CD47 may comprise the exemplary sequence set forth in SEQ ID NO:11 (with signal peptide sequence) or SEQ ID NO:1 (without the signal peptide sequence). The polypeptide was constructed according to molecular biology methods and protein expression methods routinely practiced by a person skilled in the art.

96 well plates were coated with 50 µl per well of 50 µg/ml mouse IgG (Jackson ImmunoResearch Laboratories, West Grove, Pa.) in 0.1 M $NaHCO_3/Na_2CO_3$ buffer overnight. Then plates were washed twice with PBS and then incubated with either hCD47-Hac or a control construct. The control constructs included a Gaussia luciferase fused to the same Hac moiety (gluc-Hac) or vCCI (also called p35), a soluble viral chemokine inhibitor from cowpox (p35-Hac). The hCd47-Hac and control construct were added to mouse IgG coated plates at varying concentrations between 0.001 and 0.8 µg/ml (five-fold dilutions). After 2 h, plates were washed once with PBS before adding dendritic cells to the culture. Dendritic cells were obtained and prepared from two different donors. Eight day-old human monocyte-derived DC ($2\times10^4$/well), prepared as described in Example 1, were added in the presence of IFN-γ (1000 U/ml). Alternatively, in control plates that were not coated with mouse IgG, DC were seeded into wells containing either hCD47-Hac or the control construct. After two hours, DC were stimulated with 0.1 ng/ml FSL-1 (InvivoGen). Supernatants were collected after 18 hours and the concentration of TNF-α in the supernatants as described in Example 1.

Figure 7:
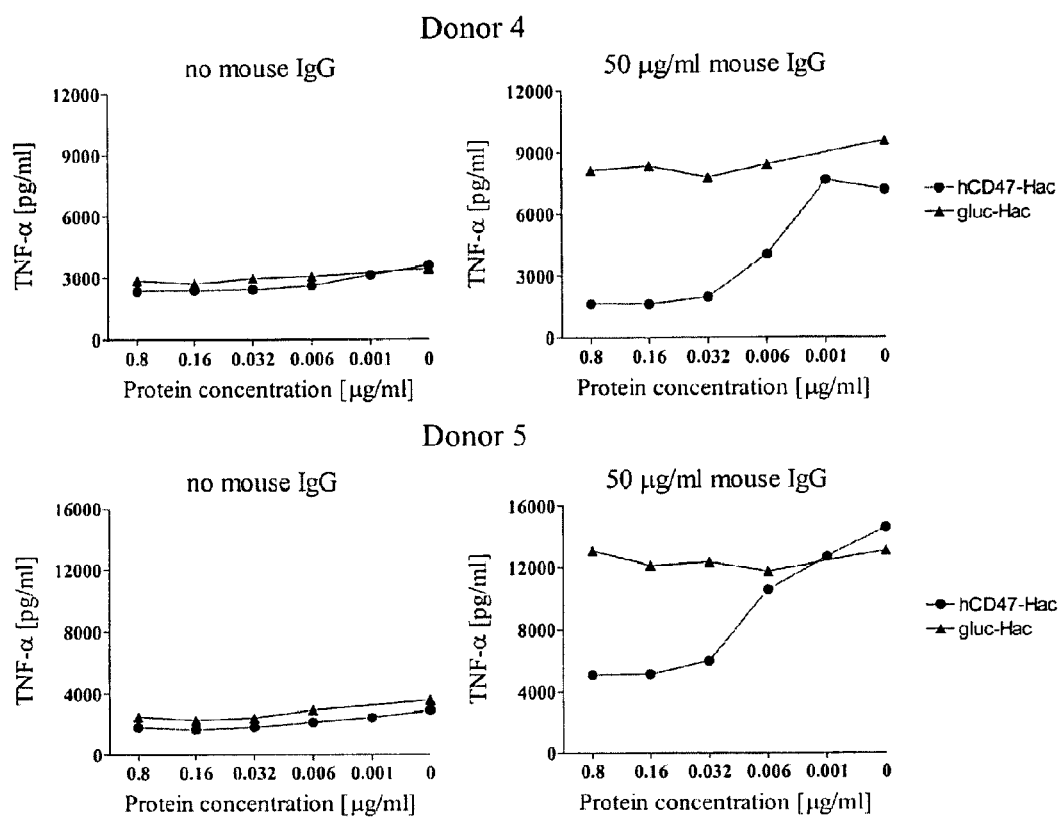

Results are presented in FIG. 7. Like hCD47-Fc, hCD47-Hac had no effect on TNF-α secretion by DC in response to FSL-1 in the absence of mouse IgG, but hCD47-Hac did inhibit immune complex-induced TNF-α production. The control construct gluc-Hac did not affect Fc-receptor-mediated cytokine production, confirming that the CD47 portion of the construct is blocking Fc-receptor mediated activation of DC.

Example 4

Inhibition of Fc-Mediated Cytokine Production in Bone Marrow Derived Murine Dendritic Cells by a Murine CD47-Fc Polypeptide Fusion Protein Prior to performing animal studies in mouse animal models, experiments were performed to demonstrate that a murine CD47 extracellular domain-murine Fc fusion polypeptide interfered with (i.e., inhibited) IgG complex-Fc-receptor-induced inflammation.

A murine CD47-Fc construct containing the extracellular domain of murine CD47 and the Fc portion of murine IgG2a (mCD47-Fc) was expressed and purified. The murine CD47 extracellular domain was derived from the amino acid sequence encoded by the polynucleotide sequence set forth in GenBank Accession No. NM_010581 (which provides the encoded amino acid sequence). Alternatively, the amino acid sequence of a murine CD47 set forth in GenBank Accession No. Q61735 (no version number provided) may be used.

To mimic immune-complex mediated inflammation, bone marrow derived DC (BMDC) and macrophages from BALB/c and C57BL/6 mice were stimulated with SAC-saturated with mIgG2a (IgG2a-SAC). BALB/c and C57BL/6 derived dendritic cells differ in cytokine production in response to SAC and SAC-IgG2a. In addition, investigators report that C57BL/6 mice express higher levels of Fc-receptors than BALB/c mice. Therefore, the effect of the mCD47-Fc construct on immune cells from two different strains of mice was examined.

Murine bone marrow derived DC were prepared according to the protocol of Lutz et al. (*J. Immunol. Methods* 223:77-92 (1999)). Cells were cultured in murine dendritic cell differentiation medium (IMDM (Invitrogen, Carlsbad, Calif.), 10% FBS (Hyclone, Logan, Utah), 50 µM 2-ME, 20 ng/ml murine GM-CSF (PeproTech) and 10 ng/ml murine IL-4 (PeproTech) for 9 days before use in cytokine assays. SAC-saturated with mIgG2a was prepared similarly to SAC saturated with human sera (see Example 1).

Nine day-old BMDC ($2\times10^4$ cells/96-well) were treated overnight in the presence of IFN-γ (1000 U/ml). Then varying concentrations (five-fold dilutions between 0.006 and 20 µg/ml) of either the mCD47-Fc polypeptide or a control molecule, in this instance, murine IgG2a were added to the cells, followed by stimulation with 0.01% IgG2a-SAC. Supernatants were collected from the stimulated cell cultures after 18 h and stored as described above until the concentrations of murine TNF-α and murine IL-12 were determined using ELISA kits according to the manufacturer's instructions.

Figure 8:
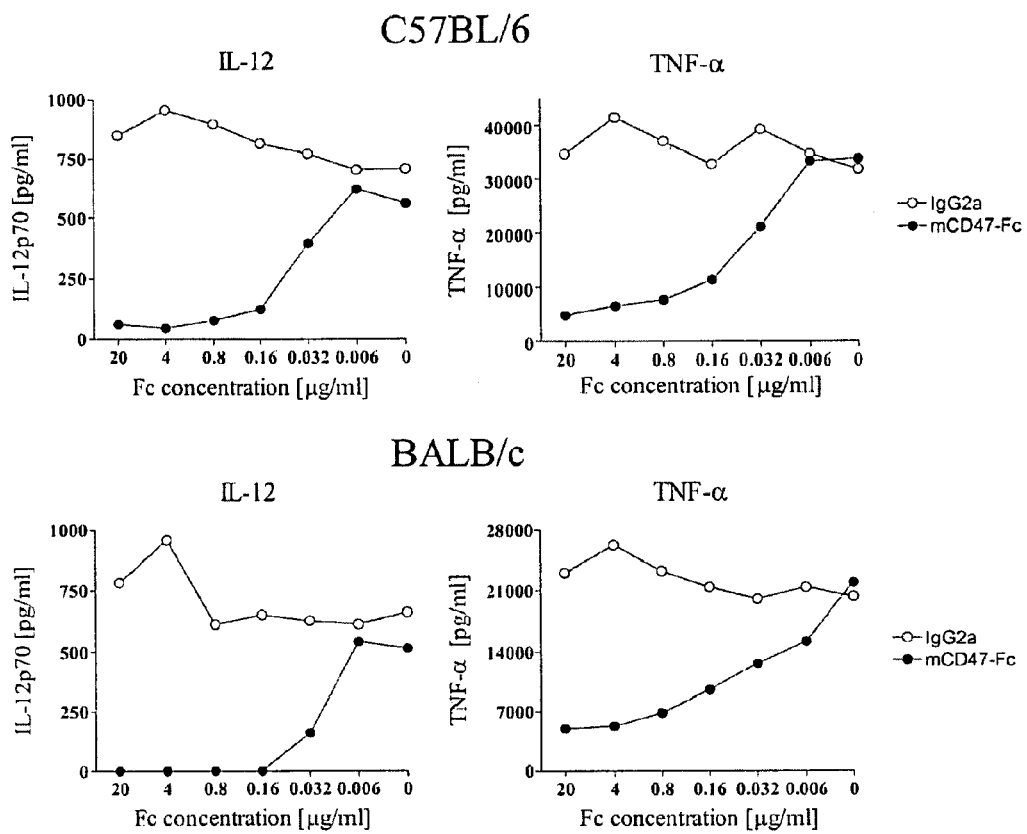

The results are presented in FIG. 8. Murine CD47-Fc inhibited IgG2a-SAC-induced IL-12p70 and TNF-α production in BMDC in a dose dependent manner, whereas the IgG2a control antibody did not reduce IgG2a-SAC-induced cytokine secretion.

Example 5

Effect of Fc-Mediated Cytokine Production in Bone Marrow Derived Murine Dendritic Cells by a Murine CD47-Fc Polypeptide Fusion Protein in Wild Type and FcRγ (−/−) Mice To further demonstrate that mCD47-Fc blocks IgG/Fc-receptor mediated activation of DC, experiments were performed with DC from B57BL/6 FcRγ (−/−) and C57BL/6 wildtype controls. The B57BL/6 FcRγ (−/−) do not express the common γ chain of activating Fc receptors. Thus, DC from FcRγ (−/−) mice do not produce inflammatory cytokines in response to complexed IgG.

BMDC from C57BL/6 FcRγ (−/−) and C57BL/6 wildtype controls were prepared as described in Example 4. Also as described in Example 4, nine day-old BMDC ($2\times10^4$ cells/96-well) were treated overnight in the presence of IFN-γ (1000 U/ml). Then varying concentrations (five-fold dilutions between 0.006 and 20 µg/ml) of either the mCD47-Fc polypeptide or the control molecule, murine IgG2a, were added to the cells, followed by stimulation with 0.01% IgG2a-SAC. Supernatants were collected from the stimulated cell cultures after 18 h and stored as described above until the concentrations of murine TNF-α in the supernatants were determined.

Figure 9:
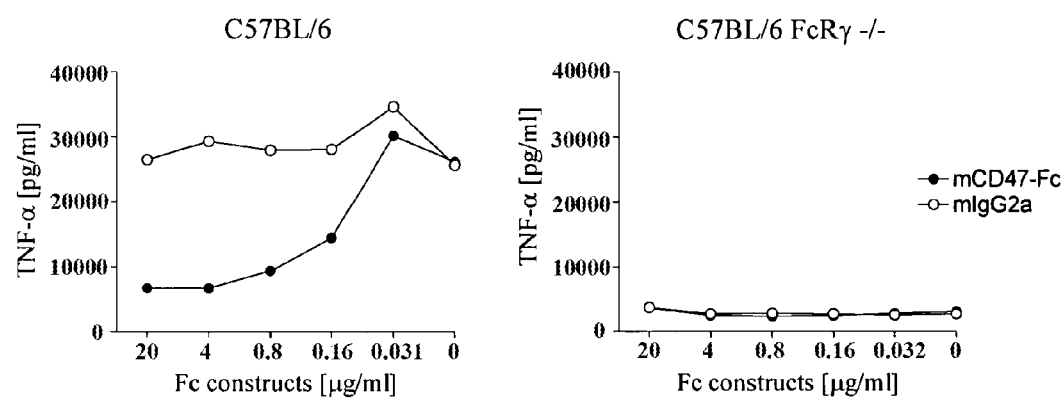
Figure 10:
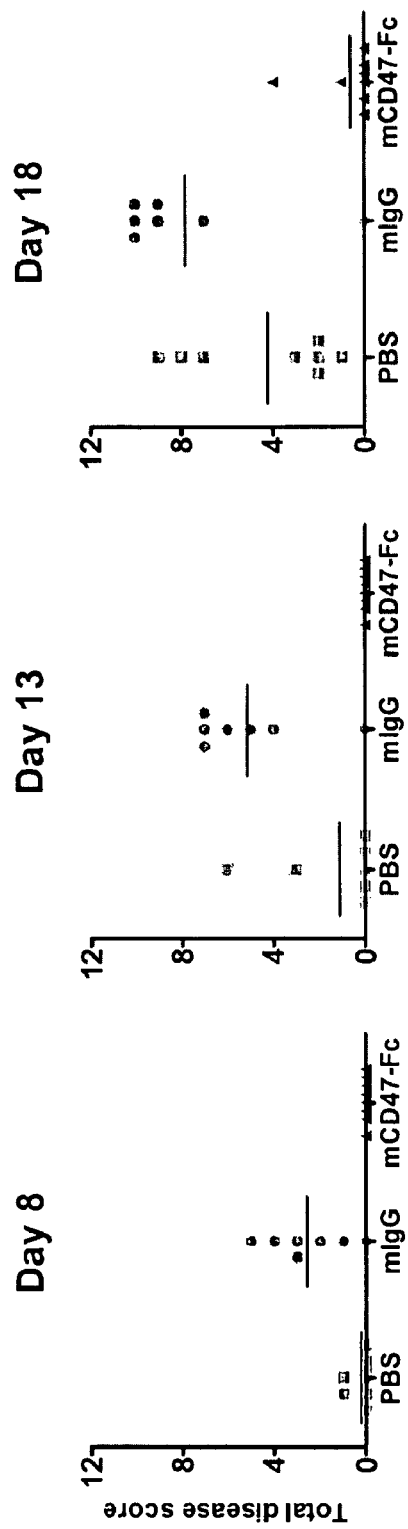
FIG. 10 shows total disease scores for individual mice are shown for days 8, 13, and 18.

The results are presented in FIG. 9. IgG2a-SAC was a very potent stimulator of TNF-α in wildtype DC. Wildtype DC secreted approximately 80 times more TNF-α in response to IgG2a-SAC when compared to DC from FcRγ (−/−) mice. In DC from wildtype mice, mCD47-Fc inhibited IgG2a-SAC-induced cytokine production in a dose dependent manner ($IC_{50}$ below 0.16 µg/ml) when compared to the IgG2a control. Murine CD47-Fc did not affect TNF-α secretion in FcRγ (−/−) mice.

Example 6

Effect of a Murine CD47-Fc Polypeptide Fusion Protein on Development of Collagen Antibody-Induced Arthritis in a Murine Model Because murine CD47-Fc inhibited Fc-receptor mediated cytokine production, mCD47-Fc was evaluated in the FcRγ dependent model of collagen antibody induced arthritis (CAIA) (Wallace et al., *J. Immunol.* 162:5547 (1999)) in DBA/1J mice (The Jackson Laboratory, Bar Harbor, Me.). Animal studies were performed according to Institutional Animal Care and Use Committee (IACUC) approved protocols. CAIA was induced in 8-week old male DBA/1J mice by intravenous injection (Day 0) of 4 mg of ArthritoMAB™ antibody (MD Biosciences Inc., St. Paul, Minn.) followed by intraperitoneal administration of an LPS (*Escherichia coli* 055:B5; Sigma BioSciences, St. Louis, Mo.) boost (50 µg) on Day 6 and again on Day 13. Prophylactic treatment of animals with mCD47-mFc (500 µg) or mIgG (500 µg) (from murine serum; Sigma Biosciences), or PBS began on day 0 (1 hour prior to ArthritoMAB™) and continued every other day until day 8. Clinical assessment of arthritis was determined by observers blinded to the treatment group. Mice paws were examined for disease severity and graded on a scale of 0 to 4 for each paw, according to changes in redness and swelling (0, normal; 1, mild swelling of a single area; 2, moderate swelling involving more than one area; 3, severe arthritis involving the entire paw; 4, severe arthritis resulting in ankylosis and loss of joint movement [deformity]). Each limb was graded, resulting in a maximal clinical severity score of 16 for each animal. The clinical severity score and number of paws affected were monitored daily during the entire study period.

Results are shown in FIG. 9. Prophylactic treatment of mice with mCD47-Fc reduced the incidence rates and total disease scores when compared to mice treated with PBS or murine IgG. On Day 18 post ArthritoMAB™ treatment, only 2 out of 8 mice treated with mCD47-Fc showed signs of disease, whereas all mice in the PBS group and 7 out of 8 mice in the mIgG treatment group showed signs of disease. Furthermore, the severity of inflammation was higher in the control groups with mean total disease scores of 4.2 in the PBS group and 7.9 in the mIgG treatment group compared to 0.6 in the mCD47-Fc treatment group.

Example 7

Biochemical Characterization Human CD47-Fc Polypeptide of SEQ ID NO 39

In this Example, "(hCD47-Fc)" refers to hCD47-Fc of SEQ ID NO:39. This example summarizes the biochemical characterization of hCD47-Fc that has been expressed from CHO cells.

As discussed above CD47, also known as Integrin Associated Protein (IAP), is a ~55 kDa membrane-bound protein. The protein consists of an extracellular IgV domain, 5 membrane-spanning domains, and a short intracellular tail (Immunology 106, 564-576; 2002). It has been proposed to associate with both SIRP-α (signal regulatory protein) and thrombospondin, and is believed to play a role in the signaling events leading to an immunological response. There are four known isoforms of hCD47, relating to differences in the c-terminal, intracytoplasmic portion of the protein (J Cell Sci 108, 3419-3425: 1995). Certain viruses encode a mimic of CD47 (vCD47) that is equivalent to the extracellular domain of the human protein.

Figure 11:
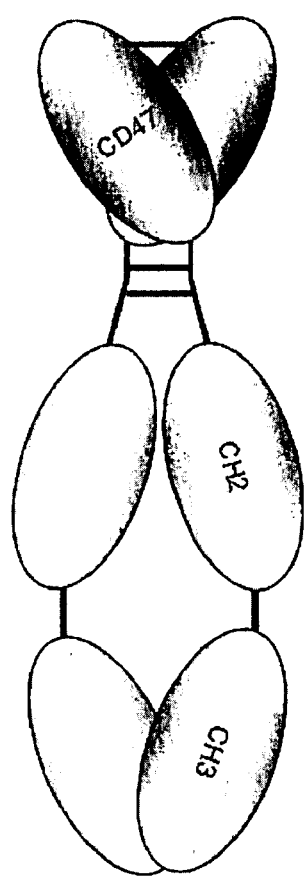
FIG. 11 shows proposed schematic structure of hCD47-Fc. Red lines denote putative disulfide bonds.

The extracellular domain of hCD47 has been expressed as a fusion protein to the native Fc portion of a human IgG1 antibody (FIG. 11). The Fc region of the protein does not contain any mutations/modifications to reduce Fc binding to cellular Fc receptors. The Fc fragment used in hCD47-Fc includes the CH2 and CH3 domains and the two cysteines in the hinge region between CH1 and CH2. These two cysteines form two disulfide bonds that hold the two heavy chains of an antibody together (FIG. 12, highlighted in plum). It is contemplated that these cysteines are used to form disulfide bonds between two monomers of hCD47-Fc. It does not have the cysteine in the Fc region that is involved in heavy/light chain interactions (this cys was deleted from the construct).

There is a cysteine in the N-terminal, extracellular portion of hCD47 that is thought to form a disulfide bond to one of the transmembrane loops in the native protein (FIG. 12, highlighted in grey). Since the transmembrane portion is absent in the hCD47-Fc construct, this cysteine could exist as a free thiol. It is contemplated that this N-terminal cysteine may form a disulfide bond between two monomers of hCD47-Fc. This disulfide, along with the disulfide bonds present in the Fc region of the molecule, may result in hCD47-Fc existing primarily as a dimer in solution. There may also be an intramolecular disulfide bond thought to be present between two cysteines in the IgG loop (FIG. 12, highlighted in black bold).

There are several glycosylation sites present in hCD47-Fc. The Fc portion of the molecule contains a single N-linked glycosylation site. This glycosylation site has been shown to have a role in Fc receptor binding. There are 5 putative N-linked sites present on the CD47 portion of the molecule (predicted using NetNGlyc 1.0 Server, Asn-Xaa-Ser/Thr). Finally, there is a 7th N-linked site that was created at the fusion junction between the CD47 and Fc regions of the protein. This glycosylation site could serve to mask the antigenicity of the fusion.

Figure 13:
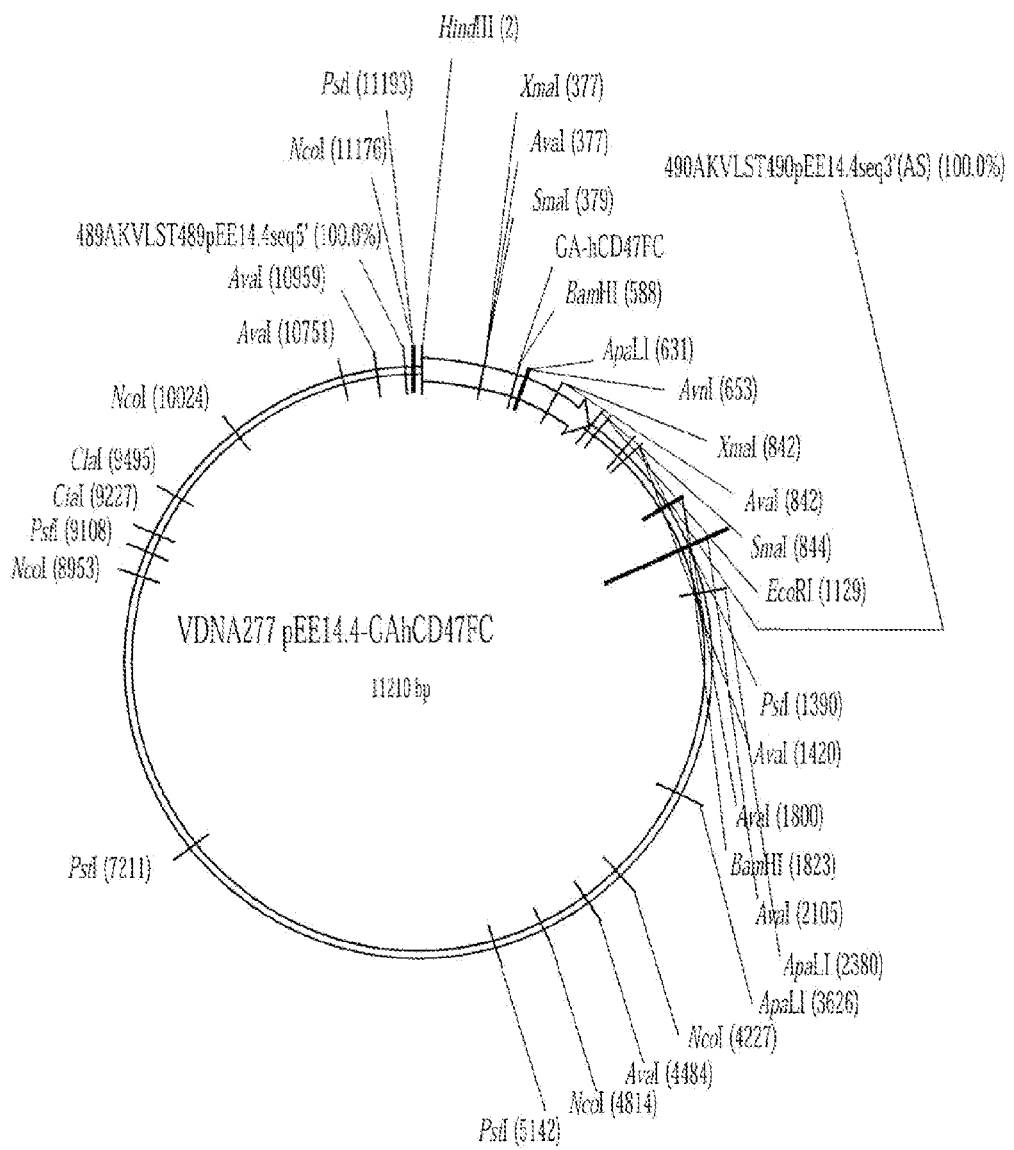
FIG. 13 shows GS vector map for hCD47-Fc of SEQ ID NO:39.

The hCD47-Fc gene was inserted into pEE14.4 vector (FIG. 13). This vector uses the human cytomegalovirus major intermediate early promoter (hCMV-MIE), and contains the SV40 origin of replication. Selection is based on requirement for glutamine synthetase activity to provide glutamine to the Chinese Hamster Ovary (CHO) cells when cultured in glutamine-free media. Methionine sulphoximine is added to the culture media to inhibit the endogenous GS activity in CHO cells. The pEE14.4 vector containing the hCD47-Fc gene was transfected into the suspension-adapted CHOK1SV cell line.

Methods

Multi-Angle Light Scattering (MALS) of hCD47-Fc

A Superdex 10/300 GL column was attached to a GE Healthcare AKTA Purifier 10 chromatography system. The column was equilibrated in PBS (Gibco, pH 7.2, 154 mM NaCl) at a flow rate of 0.25 mL/min. This same flow rate was used for used for sample data collection, unless otherwise noted. The system was plumbed with 0.25 mm PEEK tubing. The column outlet was connected to the UV monitor of the Purifier, and set to 280 nm. A cable connected one of the auxiliary outputs of the Purifier to a Wyatt miniDawn TREOS Multi-Angle Laser Light Scattering detector. This system has a nominal laser wavelength of 658 nm. The outlet of the TREOS was connected to the inlet of a Wyatt Optilab DSP refractometer calibrated at 658 nm. The instruments were initially calibrated at the factory with toluene. Band broadening inter-detector delay, normalization parameters, etc. were determined via injection of 100 μL of Pierce Bovine Serum Albumin (2 mg/mL). The TREOS has three detectors to collect light scattering data. Typically, only data from detector #2 and #3 were used, as they provided the best signal to noise (Detector #1 was excluded). Proteins less than 500 kDa do not exhibit much angular dependence to the light scattering signal, so exclusion of the first detector was not predicted to have any impact on the results of the analysis. Data was collected and analyzed via a laptop running Astra software, version 5.3.2.10. The Protein Conjugate Analysis function in Astra was used to determine the molecular weight of hCD47-Fc, using the three detector method (UV, refractive index, and light-scattering) to account for the peptide and carbohydrate mass of the molecule. Manual injection of a minimum of 100 μg of hCD47-Fc was performed, using a 100 μL loop connected to the injection valve of the AKTA purifier.

Extinction Coefficient of hCD47-Fc

The extinction coefficient for (hCD47-Fc) calculated using an algorithm. The mature amino acid sequence of hCD47-Fc (sequence in FIG. 12, minus leader sequence) was run through the EXPASY ProtParam tool: www.expasy.org/tools/protparam.html. This algorithm is based on the method originally developed by Gill and von Hippel (Anal. Biochem. 182:319-326) which calculates the extinction coefficient based on the number of Tryptophan, Tyrosine and Cystine residues (Phenylalanine does not absorb much at 280 nm, and neither does Cysteine).

The theoretical peptide molecular weight for CD47-Fc is 39,496 kDa. The ProtParam algorithm generates a theoretical extinction coefficient of 52,870 or 52,370 M-1 cm-1, depending on the assumption that either all cysteines are free thiols, or all are involved in disulfide bonds. hCD47-Fc is likely closer to the former (all cysteines involved in disulfide bonds). Therefore, the value of 52,370 M-1 cm-1 was used as the molar extinction coefficient. ProtParam also reports the extinction coefficient in units of Abs 0.1% value (=1 mg/mL). This provides for an easy method for determine protein concentrations of reasonably pure samples, as the absorbance at 280 nm can be divided by this value to produce the mg/mL concentration of hCD47-Fc $(A280\ nm)/(1.339) = mg/mL$      Equation 1

This equation does not account for any mass due to the carbohydrate mass resulting from occupation of glycosylation sites. The glycosylation won't contribute to the absorbance at 280 nm, but does add to the dry mass of the sample.

The extinction coefficient used by the Astra software to analyze MALS data was required to be in units of mL/(g·cm). This was calculated as follows:

$$52{,}370\ M^{-1}\ cm^{-1} = (39{,}496\ L)/(mol \cdot cm) \quad \text{Equation 2}$$

$$(52{,}370\ L)/(mol \cdot cm) \cdot (1\ mol)/(39{,}496\ g) = 1.326\ L/(g \cdot cm) \quad \text{Equation 3}$$

$$1.326\ L/(g \cdot cm) \cdot 1\ mL/0.001\ L = 1326\ mL/(g \cdot cm) \quad \text{Equation 4}$$

As a result of this conversion, the protein extinction coefficient used to analyze MALLS data was 1326 mL/(g·cm). The dn/dc value (change in refractive index as a function of change in concentration) utilized for hCD47-Fc peptide was 0.185. The dn/dc value used to account for the carbohydrate due to glycosylation (modifier dn/dn) was 0.140. These values were recommended by Wyatt as general values to use when the dn/dc is not to be determined experimentally.

Isoelectric Focusing (IEF) of hCD47-Fc

Precast vertical gels from Invitrogen were utilized to run IEF to determine the isoelectric point (pI) of hCD47-Fc. Using the ProtParam utility, the theoretical pI of mature CD47-Fc was determined to be 6.5. CHO cell lines are known to express proteins with N-linked carbohydrates containing sialic acid. Sialic acid was expected to produce more acidic forms of the protein, decreasing the overall pI. Initially, IEF gels with a pH range of 3-10 were utilized. Due to the apparent absence of bands at pH>7, subsequent IEF analysis were performed using pH 3-7 gels. This provided greater resolution between the glycoforms of hCD47-Fc in this range. Serva IEF markers were utilized to determine the pI of hCD47-Fc. 10-15 µL of the pI marker were loaded. 5-10 µg of protein were diluted 1:1 with 2× sample buffer and loaded onto the gel. The appropriate anode and cathode buffers were prepared from concentration stock solutions purchased from Invitrogen. Gels were run in three steps:

1. 100 V for 60 min.
2. 200 V for 60 min.
3. 300 V for 45 min.

After the gel had finished running, it was removed from the plastic cassette, and fixed in a 10% acetic acid/30% ethanol solution for approximately 30 minutes. The fixing solution was removed from the gel via 3-4 washes with Milli-Q water, each wash lasting ~20 minutes. The removal of the fixing solution was required to avoid precipitation of components in the Invitrogen Simply Blue SafeStain (the stain was observed to fall out of solution if the wash step was skipped).

SDS-PAGE of hCD47-Fc

Reduced and non-reduced samples were prepared for LDS-PAGE analysis by diluting sample 1:4 with Invitrogen's 4× NuPAGE LDS sample buffer and 1 µL TCEP solution for reduced gels and 1 µL water for non-reduced gels. Samples were heated in a dry heating block at 95° C. for 4 minutes. For reduced gels, 500 µL of Novex antioxidant was added to the inner chamber of the gel apparatus to ensure reducing conditions throughout the run. 20 µL were loaded into each lane of an Invitrogen 10-well NuPAGE 4-12% Bis-Tris gel. Gels were run under reduced or non-reduced conditions at 200 V for 45 minutes. Gels were stained with Invitrogen's Simply Blue SafeStain for one hour and de-stained in three changes of deionized water for a minimum of three hours at room temperature. Destained gels were placed in a tray containing Invitrogen's gel drying solution, incubated for 3-5 minutes and dried between two cellophane sheets wetted in the same solution using Invitrogen's mini gel drying rack. Images were captured as JPEG files using Adobe Photo Shop™ and a flat bed scanner.

Native-PAGE of hCD47-Fc

Native gels from Invitrogen were used to analyze the MW of hCD47-Fc in native (non-reducing, non-denaturing) conditions. The cathode and anode buffers were prepared from concentrated stock solutions purchased from Invitrogen. NativePAGE MW markers from Invitrogen were utilized. 12 µL of sample (~16 µg of protein) was loaded onto the gel. The gel was run for 90 minutes at 150 V. Since the gel was run in the presence of G-250 dye, it was initially fixed and destained with a 10% acetic acid/30% ethanol solution, then further destained with an 8% acetic acid solution. Images were captured as JPEG files using Adobe Photo Shop™ and a flat bed scanner.

Deglycosylation of hCD47-Fc

Treatment of hCD47-Fc with PNGase F was performed in order to verify whether the heterogeneity observed on the IEF gels was resulting from carbohydrate differences within the several N-linked glycosylation sites. Timing of the deglycosylation or the ratio of PNGase F to hCD47-Fc was not optimized. Rough incubation times were utilized, and the completeness of deglycosylation was assessed via SDS-PAGE.

5 µL of PNGase-F (New England Biolabs) was added to ~200 µg of purified hCD47-Fc in PBS, and allowed to incubate overnight at room temperature. hCD47-Fc was shown to be stable at room temperature (tested out to ~25 days), so there was no risk to the protein by allowing for excessive incubation time. It was determined that while denaturing conditions (using the buffer provided by NEB) accelerated the rate of deglycosylation, native conditions reached the same endpoint when sufficient time was provided (data not shown). This permitted the protein to be evaluated in vitro without having to refold or dialyze away the denaturant. The deglycosylated protein was compared to an untreated control via reduced SDS-PAGE and IEF gel.

Figure 14:
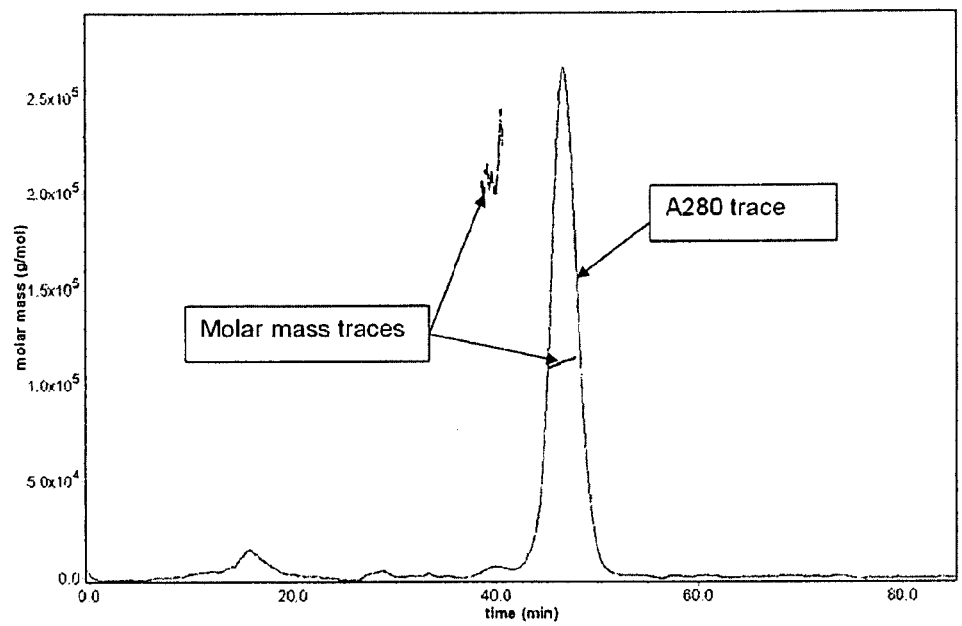
FIG. 14 shows SEC with Multi-Angle Light-scattering trace for hCD47-Fc of SEQ ID NO:39.

Analysis of MALS data collected on hCD47-Fc suggested that the protein exists as a dimer under native conditions (FIG. 14). The MW of hCD47-Fc was determined to be ~110 kDa. There is a smaller peak on the leading edge of the main peak. The molar mass of this leading peak is ~210 kDa, suggesting it may represent a small amount of tetrameric CD47-Fc contaminant in the sample. The protein conjugate analysis provides information about the relative percentage of carbohydrate and peptide in the complex. In the case of hCD47-Fc, the data analysis suggests that the dimer peak contains ~84 kDa of peptide, and ~28 kDa of carbohydrate. This is very close to twice the predicted monomer peptide MW (39.5 kDa), consistent with hCD47-Fc existing as a dimer in solution.

Figure 15:
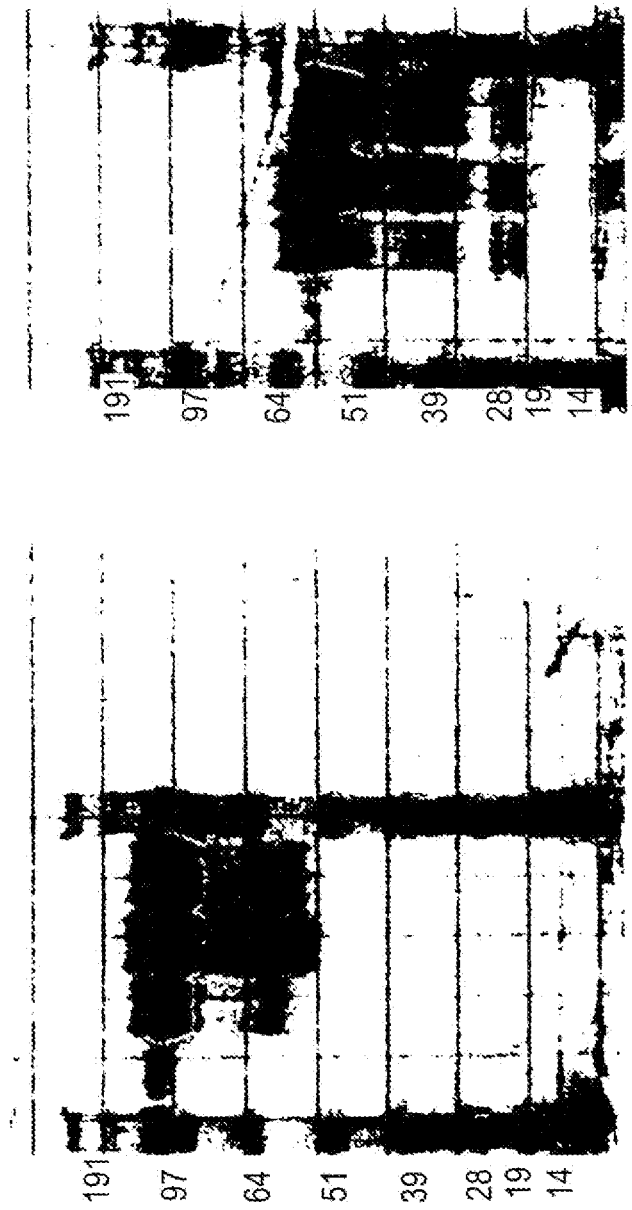
FIG. 15 shows non-reduced (left) and reduced SDS-PAGE gel analysis of hCD47-Fc of SEQ ID NO:39.
Figure 16:
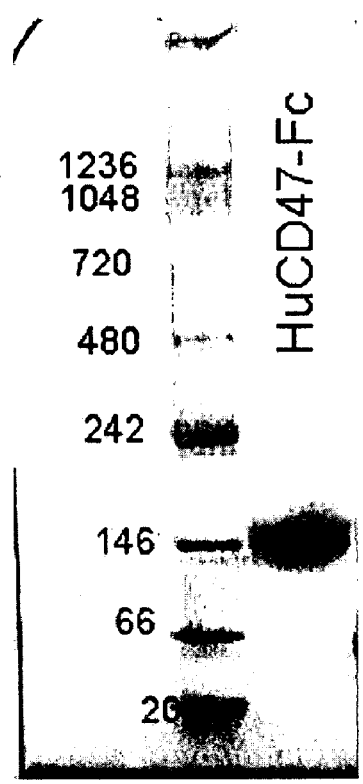
FIG. 16 shows native PAGE on hCD47-Fc of SEQ ID NO:39.

The 110 kDa molecular weight determined via light scattering is consistent with the approximate MW observed on SDS-PAGE. hCD47-Fc runs even with the 97 kDa MW marker (FIG. 15, left panel) under denaturing, non-reduced conditions. Under reducing, denaturing conditions, the protein runs as a monomer (FIG. 15, right panel), in between the 64 and 51 kDa MW markers. When hCD47-Fc is run on a native gel, it appears to run a bit larger than expected, running even with the 146 kDa markers (FIG. 16). However, unlike MALS, which is a shape-independent measure of MW, PAGE gels can be affected by the shape of the protein and result in incorrect assessments of the true MW of the molecule. The fact that the monomer version of hCD47-Fc was only detected under reducing conditions was consistent with the dimer being held together via disulfide bonds. Reduction and alkylation of hCD47-Fc (data not shown) indicates that the dimer will form in the absence of the disulfide linkages, implying that there is a van der Waals attraction between the Fc and/or CD47 pairs in the dimer. Under native conditions, SEC analysis on the reduced and alkylated protein shows that the protein is still a dimer in solution. However, under denaturing conditions on SDS-PAGE, the interaction is disrupted by the denaturant, and only the monomer is detected.

Figure 17:
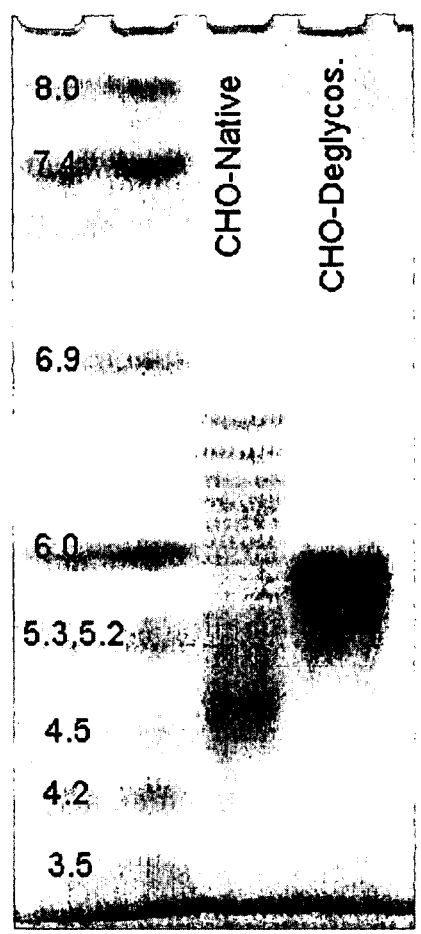
FIG. 17 show pH 3-10 IEF-PAGE on hCD47-Fc of SEQ ID NO:39.
Figure 18:
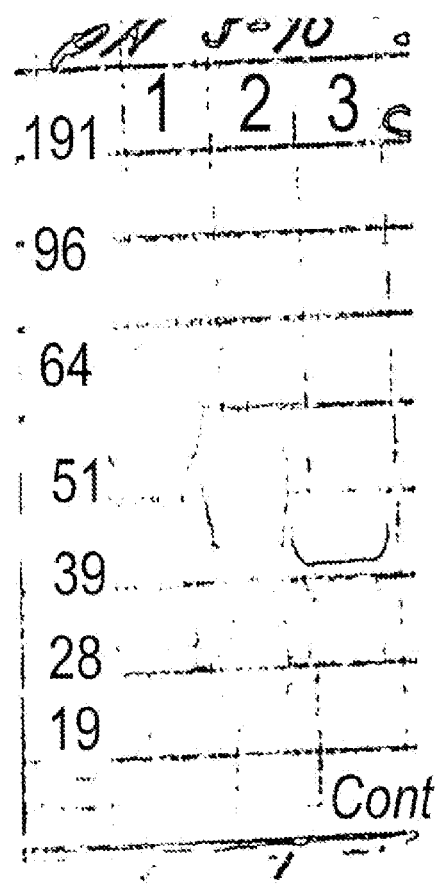
FIG. 18 shows reduced SDS-PAGE gel on native (Lane 1), deglycosylated for 4 hours (Lane 2) and deglycosylated over night at room temperature (Lane 3).

IEF gel analysis of hCD47-Fc shows presence of multiple isoforms (FIG. 17), spanning the pH range between the 4.2 and 6.9 pI markers. The source of this heterogeneity is likely sialylated carbohydrates on the multiple N-linked glycosylation sites in hCD47-Fc. To verify this, hCD47-Fc was treated with PNGase-F, an endoglycosidase that will remove N-linked glycosylation from the protein. Treatment with PNGase-F drastically reduced the heterogeneity of the sample, relative to the untreated control (FIG. 7). The theoretical pI of the hCD47-Fc peptide is 6.5. The deglycosylated version of the protein is running a bit below 6.0. This may suggest that the protein still wasn't fully deglycosylated, despite the simplification of the banding pattern observed on the IEF gel. There may be O-linked sites present in the molecule that would not be affected by the PNGase-F treatment. SDS-PAGE analysis was performed on the native and deglycosylated protein after 4 hours and overnight incubation at room temperature (~16 hours). After four hours, the protein is still being stripped of its sugars, based on the observation that is still running as a broad, fuzzy band. While it is running at a lower molecular weight than the untreated monomer, after 16 hours of treatment additional mass has been removed. The sample treated for the extended period is running closer to the theoretical monomer peptide MW of 39.5 kDa.

Example 8

Signal Regulatory Protein Alpha as a Novel Therapeutic Target for the Treatment of FcΓ Receptor-Mediated Inflammatory Diseases Summary Dendritic cells (DCs) play a key role in the induction of protective immunity against pathogens and tolerance against self. Under inflammatory conditions, over-production of cytokines and presentation of self antigens by DCs may lead to autoimmunity. Signal regulatory protein alpha (SIRPα) is a membrane protein primarily expressed on myeloid and neuronal cells. The interaction between SIRPα and its widely expressed ligand, CD47, plays an important role in regulating myeloid cell function. In the present study we identified a novel inhibitory pathway mediated by SIRPα ligation. CD47 fusion proteins containing the extracellular Ig-V domain of CD47 inhibited the immune complex-mediated activation of human DCs. Inhibition of immune complex-induced TNF-α production was dependent on CD47/SIRPα interactions. In experiments using FcRγ$^{-/-}$ mice we demonstrated that ligation of SIRPα by CD47-Fc blocks the Fc receptor dependent activation of DCs by complexed IgG. Moreover, CD47-Fc ameliorated clinical and histological signs of disease in the collagen antibody induced arthritis model, supporting the novel concept that ligation of SIRPα by CD47-Fc inhibits immune complex-mediated Fc receptor-dependent inflammation. These data indicate that ligation of SIRPα by CD47-Fc may be a novel therapeutic for the treatment of immune complex-mediated inflammatory diseases.

Dendritic cells (DCs) are the professional antigen presenting cells that orchestrate protective immune responses against pathogens and contribute to the induction of tolerance against self [1; 2]. DCs are found throughout the body as immature precursors. After an encounter with environmental or endogenous stimuli DCs mature, migrate to the draining lymph nodes and present antigens to T cells [3]. Maturation can be triggered by Toll like receptor ligands, immune complexes, lymphocytes and cytokines [3]. The ability of DCs to prime T cells, modulate regulatory or effector T cells responses and contribute to the inflammatory response largely depends on the expression of co-stimulatory molecules and on the secretion of immunomodulatory and inflammatory cytokines [3]. It has been postulated that the overproduction of inflammatory cytokines like TNF-α, IL-23 and type I IFNs by DCs plays an important step in the development of autoimmunity and in the maintenance of chronic inflammatory diseases [3; 4]. The activation state of DCs is tightly controlled by immunoregulatory cytokines like IL-10 [5]. In addition to cytokines, cell-cell interactions mediate by a host of cell surface receptors also regulate the functions of myeloid cells including DCs [6].

Signaling regulatory protein alpha (SIRPα) has been shown to be a key regulator of myeloid function [7; 8]. It is expressed mainly on myeloid cells and neuronal cells but also found on endothelial and smooth muscle cells. SIRPα is a type I transmembrane protein with three extracellular Ig-like domains. The cytoplasmic tail contains immunoreceptor tyrosine-based inhibitory motifs (ITIMs). After phosphorylation ITIMs recruit the cytoplasmic SH2 domain containing phosphatases SHP-1 and SHP-2 which mediates the regulatory functions of SIRPα [7-9]. Ligation of SIRPα by CD47 or the lung surfactant proteins A and D inhibits the phagocytic function of macrophages [10; 11] and the release of inflammatory cytokines in response to *Staphylococcus aureus* particles and LPS, respectively [12; 13].

The SIRPα ligand CD47 is a ubiquitously expressed pentaspanning transmembrane protein with a single IgV-like extracellular domain [14]. CD47 is also known as integrin-associated protein as it was first identified through its association with a subset of integrins [15]. While CD47 associates with integrins through the transmembrane region; it binds SIRPα and SIRPγ, an additional SIRP family member expressed on T cells, bind via the extracellular domain of CD47 [7].

Recently, it has been reported that a CD47-Fc fusion protein inhibits cytokine production in human DCs and DC migration by ligating SIRPα [13; 16]. Furthermore, a viral homolog of CD47 in Myxoma virus contributes to the inhibition of macrophage function in Myxoma virus infected rabbits [17] suggesting that this virus may target the SIRPα regulatory pathway to inhibit macrophages. Based on these observations we further characterized the effects of human CD47-fusion proteins on dendritic cells and macrophages and explored the therapeutic potential of a CD47-Fc fusion protein on the regulation of APC function. Our studies have identified a novel inhibitory pathway in which ligation of SIRPα inhibited IgG-mediated Fc receptor-dependent secretion of inflammatory cytokines in dendritic cells and macrophages. We tested the hypothesis that a CD47-Fc therapeutic may ameliorate immune complex-mediated inflammatory diseases. In proof of principle in vivo studies in mice, we demonstrated that murine mCD47-mFc ameliorated the development of collagen antibody-induced arthritis.

Results

CD47-Fusion Proteins

To study the interaction between the extracellular domain of CD47 and SIRPα three human CD47-fusion proteins were generated. Briefly, the human extracellular Ig-V domain of CD47 was fused to either the Fc region of human IgG1

(hCD47-hFc) or alternatively to a 10 kDa tag containing two distinct affinity epitopes (hemagglutinin, C-tag) followed by two streptavidin-binding peptide sequences (hCD47-HAC). mCD47-mFc was generated by fusing the murine extracellular Ig-V domain of CD47 with the Fc region of murine IgG2a. The Fc and HAC tags were used to facilitate the purification of the protein to homogeneity. All CD47-fusion proteins were purified as dimers.

hCD47-hFc Inhibits *Staphylococcus aureus* Induced IL-23 Production

Since IL-23 is an important cytokine in inflammation [18] we determined the effect of hCD47-hFc on SAC-induced IL-23 production in DCs. As shown in (FIG. 24) hCD47-hFc significantly inhibited the SAC-induced IL-23 secretion in a dose dependent manner ($IC_{50}$, 11 ng/mL), thus expanding the reported list of inflammatory cytokines inhibited by CD47-Fc. Furthermore, hCD47-hFc reduced the secretion of the inflammatory cytokines/chemokine IL-6, IL-12, TNF-α and MIP-1α (data not shown). The control-Fc protein did not affect SAC induced cytokine production demonstrating that the CD47 domain of hCD47-hFc was responsible for the inhibitory function activity of the molecule in this assay (FIG. 24).

hCD47-Fusion Proteins Inhibit IgG-Mediated Activation of DC

It has been shown that components of the *Staphylococcus* cell wall stimulate DCs via Toll like receptor 2 (TLR2) [19]. Furthermore, since SAC particles contain protein A the inhibitory effect of hCD47-hFc on SAC induced cytokine production may be dependent on the binding of hCD47-hFc to protein A via the Fc region. Examined herein is the preposition of whether immobilization of hCD47-hFc is required to inhibit TLR2 mediated activation of human DCs. To test this hypothesis DCs were stimulated with the synthetic TLR2 ligand FSL-1. In addition, hCD47-hFc was immobilized by affinity binding of hCD47-hFc to anti-human Fc coated plates. hCD47-hFc did not inhibit FSL-1 induced TNF-α production in human DCs when hCD47-hFc was not immobilized with anti-Fc (FIG. 25A). In contrast, immobilized hCD47-hFc significantly inhibited the FSL-1 mediated TNF-α production of DCs in a dose dependent manner (FIG. 25B, IC50 78 ng/mL, p<0.0001 two-way ANOVA when compared to the control-Fc fusion. Notably, plate-bound anti-Fc IgG increased TNF-α production by human DCs in response to the FSL-1 ~3-4 fold when compared to cultures without plate-bound IgG. Without wishing to be bound by any particular theory, these data imply that the immobilized IgG induced an Fc receptor mediated signal that enhanced the TNF-α secretion by DCs in response to FSL-1. Thus, since hCD47-hFc inhibited the TNF-α production of DC in response to IgG and FSL-1, hCD47-hF may interfere with the Fc-receptor mediated activation of DCs.

Since immune-complexes can damage tissue by triggering Fc-receptor mediated inflammation [20], we evaluated the activity of CD47-fusion proteins on immune-complex-mediated activation of DCs. Briefly, following a protocol by Banki et al. [21; 22] human IgG (hIgG) was immobilized to mimic Fc-receptor dependent, complexed IgG mediated activation of DCs. DCs were activated with IFN-γ and low dose of FSL-1 (0.1 ng/mL) to resemble activated DCs in inflamed tissue. Experiments were performed with the hCD47-HAC fusion protein to exclude inhibitory activity resulting from the Fc region of hCD47-hFc. Plate-bound hIgG plus FSL-1 induced a strong TNF-α response in human DCs (FIG. 26A). The TNF-α production induced by immobilized hIgG and FSL-1 (4200 pg/mL) was 14-fold greater when compared to the TNF-α secretion by DC stimulated with plate-bound human transferrin and FSL-1 (300 pg/mL). Transferrin served as a control that does not engage Fc-receptors. These results show that hCD47-HAC significantly inhibited the complexed IgG-mediated activation of the DC in a dose-dependent manner ($IC_{50}$ 21 ng/mL, p<0.0001, two way ANOVA). Conversely, it had no effect on the FSL-1 induced TNF-a production by DCs on the transferrin-coated control plates. Furthermore, the control HAC fusion protein did not affect the TNF-α production of DC in response to FSL-1 or hIgG (FIG. 26B). The inhibitory activity of CD47-HAC required adsorption to the tissue culture plate, since blocking the plate with culture medium inhibited the CD47-HAC activity. The inhibitory activity of hCD47-HAC on Fc-receptor mediated activation of DCs was further validated by determining the effect of hCD47-HAC on a panel of human DC generated from 21 healthy study subjects (FIG. 26C). At the 800 ng/mL dose hCD47-HAC significantly inhibited the immobilized IgG plus FSL-1 induced TNF-α production (p<0.0001, two-tailed paired t-tests) by reducing the TNF-α secretion of DC from 3000±430 pg/mL to 630±170 pg/mL (mean±SEM) when compared to the control-HAC group. In conclusion, the data with human DC demonstrate for the first time, to our knowledge, that a human CD47-fusion protein inhibits Fc-receptor mediated activation of human DC.

Inhibition of IgG Mediated Activation of DC is Dependent on CD47 SIRPα Interactions To confirm that CD47-SIRPα interactions are required for the inhibitory effects of the CD47-fusion protein, experiments with two anti-CD47 antibodies were performed. Pre-incubation of hCD47-HAC with the anti-human CD47 mAb B6H12 prior to the addition of cells blocked the binding of hCD47-HAC to SIRPα transfected 293 cells as determined by flow cytometry (FIG. 27A). In contrast, the anti-human CD47 mAb 2D3 did not affect the binding of hCD47-HAC to SIRPα-293 cells. Given the results of the cytometry experiments we tested whether the blockade of CD47/SIRPα interaction interferes with the inhibitory activity of the CD47-fusion protein. Preincubation of hCD47-HAC with isotype control or 2D3 did not interfere with the CD47-HAC mediated inhibition of complexed-hIgG induced TNF-α production in human (FIG. 27B). In contrast, coincubation with mAb B6H12 blocked the inhibitory activity of hCD47-HAC (p<0.001, Tukey's multiple comparison test) when compared to 2D3 and isotype control suggesting that ligation of SIRPα inhibits the Fc receptor induced TNF-α production. Treatment of the control-HAC protein with the anti-CD47 mAbs did not affect the IgG-induced TNF-α production in human DC. These data indicate that SIRPα-CD47-HAC interactions are required to inhibit Fc-receptor induced cytokine production in human DCs.

mCD47-mFc Inhibits Fc-Mediated Cytokine Production in Bone Marrow Derived DC

To bridge the human in vitro data with murine in vivo studies, experiments were performed to test whether CD47-fusion proteins interfere with IgG complex/Fc-receptor induced activation of murine DCs. In contrast to results in human DCs with hCD47-hFc, mCD47-mFc did not reduce SAC induced cytokine production in murine DC (data not shown). This may be due to the limited responsiveness of murine DCs to SAC. Since protein A binds murine IgG2a (mIgG2a) immune-complex mediated inflammation in the murine system was mimicked by stimulating bone-marrow derived DC with SAC saturated with mIgG2a (SAC-mIgG2a). As shown in FIG. 28a, SAC-mIgG2a is a potent stimulator of TNF-α in DCs from BALB/c mice. mCD47-mFc significantly inhibited SAC-mIgG2a-induced cytokine production in a dose dependent manner when compared to the IgG2a control (p<0.0001 two way ANOVA). To verify that mCD47-mFc blocks IgG/Fc-receptor mediated activation of DCs and to exclude the involvement of the inhibitory FcRIIb receptor experiments were performed with DCs from BALB/c FcRγ$^{-/-}$ and BALB/c FcγRIIb$^{-/-}$ mice. The BALB/c FcRγ$^{-/-}$ mice do not express the common γ chain of activating Fc receptors and consequently cannot produce inflammatory cytokines in response to complexed IgG. DCs from wildtype mice secreted approximately 8 times more TNF-α in response to SAC-mIgG2a when compared to FcRγ$^{-/-}$ DCs (FIGS. 28A, B) indicating that the majority of cytokine production is FcRγ dependent. mCD47-mFc did not affect TNF-α secretion in DC from FcRγ$^{-/-}$ mice (FIG. 28B), confirming that the CD47-fusion protein inhibited Fc-receptor mediated activation of murine DC. Furthermore, the inhibitory activity of mCD47-mFc was not affected in DC generated from FcγRIIb$^{-/-}$ mice (FIG. 28C) indicating that the CD47-Fc induced inhibition does not require signaling mediated by the FcγRIIb receptor. Thus ligation of SIRPα by CD47-Fc inhibits immune complex mediated activation of DCs. This inhibition is not dependent on activation of the inhibitory Fc-receptor pathway.

mCD47-mFc Treatment is Efficacious in the Collagen Antibody-Induced Arthritis Model To determine if systemic mCD47-mFc treatment is efficacious in an FcγR-dependent disease model, we evaluated the effect of mCD47-mFc treatment in the collagen-antibody-induced arthritis model (CAIA). In CAIA induction of disease is dependent on activating FcγR demonstrated by the observation that mice lacking the common FcRγ chain do not develop disease [24]. Arthritis is induced by passive transfer of a cocktail of arthritogenic anti-type II collagen antibodies (anti-CII Ab) on day 0 followed by an LPS challenge on day 3 [25]. To evaluate the therapeutic effect of mCd47-mFc mice (n=7 per group) were treated with mCD47-mFc (500 µg) or mIgG2a (500 µg) days 0, 3, 5, 8 and 10. As shown in FIG. 29A the onset of clinical arthritis in mIgG2a treated mice occurred on day 5. Disease severity increased from days 5 to 8 and maximum clinical disease was observed from days 8 to 16. Mice treated with mCD47-mFc had a significantly reduced average clinical disease score when compared to the mIgG2a isotype control group (p<0.001, repeated measure two-way ANOVA). The reduction of clinical score in mCD47-mFc-treated mice was highly reproducible in the CAIA model in seven independent experiments. Furthermore, in selected experiments, paws were collected on day 11 post anti-CII Ab challenge and joints were histologically examined for inflammation (infiltration of cells), pannus formation, cartilage damage and bone resorption. mCD47mFc treatment significantly reduced the histological signs of disease for each of the four parameters evaluated when compared to the IgG2a control group (FIG. 29B; p<0.01 inflammation, pannus; and bone resorption; p<0.05 cartilage). Representative micrographs of histological findings are shown in FIG. 29C. The fore paw of a mouse treated with mIgG2a showed severe inflammation and marked cartilage damage with moderate pannus formation and bone resorption. In contrast, no signs of arthritis were found in the fore paw of a mouse treated with mCD47-mFc.

In summary, mCD47-mFc ameliorated clinical and histological signs of disease in an Fc-receptor dependent inflammatory disease model, suggesting that the ligation of SIRPα by a CD47 therapeutic may be beneficial in immune complex-mediated autoimmune diseases.

Discussion

SIRPα was first described as a potential regulator of Fc-receptor function by demonstrating that co-aggregation of FcγR with a chimeric molecule containing the cytoplasmic domain of SIRPα and the extracellular domain of FcRIIb inhibited IgE-induced cytokine secretion in mast cells [26]. Activation of the FcR was required for the phosphorylation of SIRPα and the subsequent inhibition of FcγR signaling. Shortly thereafter, CD47 was identified as a self signal that prevented FcγR mediated phagocytosis of opsonized red blood cells by engaging SIRPα on macrophages [11; 27]. Described herein is additional examination of the immunoregulatory role of SIRPα in FcγR signaling by identifying a novel inhibitory pathway in which ligation of SIRPα by CD47 fusion proteins inhibits IgG mediated Fc receptor dependent secretion of TNF-α in human DCs and macrophages.

By demonstrating that hCD47-hFc inhibited SAC-induced IL-23 we extend the list of inflammatory cytokines regulated by CD47/SIRPα interactions. Since IL-23 plays an important role in Th17 mediated organ-specific autoimmune diseases [18] regulation of IL-23 production by SIRPα ligation might be an intriguing therapeutic concept for these diseases.

Initial experiments using anti-Fc antibodies suggested that immobilized IgG induces the secretion of TNF-γ in human DCs. Immobilized human IgG has been previously described as an in vitro model for mimicking immune complex mediated maturation of human DCs by the activating FcRIIa receptor [21; 22]. Interestingly this response can be inhibited by immobilized hCD47-hFc. Using this system we first confirmed that immobilized human IgG induces the secretion of TNF-γ in human DCs and secondly demonstrated that plate-adsorbed CD47-HAC blocks the immune complex mediated TNF-α production in DCs. Experiments using an anti-CD47 antibody which blocks the binding of CD47-HAC to SIRPα indicated that the ligation of SIRPα by CD47-fusion proteins is required to block the Fc-receptor mediated activation of DCs.

The TLR2 ligand FSL-1 enhanced the TNF-α response of DCs to immobilized human IgG. The CD47-fusion proteins, however, also inhibited the hIgG induced TNF-α in the absence of FSL-1 (data not shown) suggesting that the SIRPα mediated inhibition was not dependent on activation of DCs by TLR2 ligands. To further demonstrate that SIRPα ligation does not interfere with the TLR pathway we performed initial experiments in a system in which Fc receptor signaling interferes with TLR signaling. Immune complex-mediated Fc receptor activation inhibits LPS and CD40L induced IL-12 production by human and murine macrophages [28; 29]. In preliminary experiments we showed that hCD47-HAC inhibits the Fc-receptor mediated effects and restores the LPS and CD40L induced IL-12 production in human macrophages and dendritic cells, respectively (data not shown). These data suggest that ligation of SIRPα by CD47-Fc or CD47-HAC does not interfere with CD40L and LPS-mediated activation of macrophages and DCs. Notably, the previously reported inhibition of CD40L and LPS induced TNF-α production of DCs by CD47-Fc SIRPα interaction required the immunoadsorption of CD47-Fc by an anti-Fc antibody [13]. Thus, consistent with our results an alternative interpretation of these data suggests that CD47-Fc inhibited the Fc-receptor mediated activation of DCs instead of blocking the LPS and CD40L signaling pathway in the previous study.

Based on the human in vitro data we developed the therapeutic hypothesis that CD47-Fc may be used for treatment of Fc-receptor mediated inflammatory diseases. To test this concept in a murine model we first confirmed that mCd47-MFc inhibits the FcγR mediated activation of murine DCs. We then performed proof of principle experiments in the CAIA model and demonstrated that mCD47-mFc significantly ameliorates clinical and histological signs of disease. We believe that this is the first demonstration that systemic CD47-Fc treatment has a beneficial effect in an inflammatory disease model. The CAIA model provides the opportunity to study the inflammatory phase of arthritis [30]. In addition, it can also be used as a surrogate model for common pathological processes in many antibody mediated diseases. Development of disease in CAIA is dependent on multiple factors including ligation of FcγR, complement, recruitment of neutrophils and the inflammatory cytokines TNF-α and IL-1β [24; 31; 32]. The human and murine in vitro data in the present report suggest that ligation of SIRPα by mCD47-mFc interferes in general with FcγR-induced inflammatory processes and in particular with the FcγR induced TNF-γ production. As mentioned above, neutrophils play an essential role in the pathogenesis of CAIA. Moreover, transendothelial migration of neutrophils involves CD47 and neutrophils in CD47–/– mice have impaired functions [15; 33]. Thus, it is possible that CD47-Fc blocks the migration and Fc-receptor mediated activation of neutrophils. We tested this hypothesis in the human system. Our initial results suggest that CD47-Fc does not interfere with the transmigration of human neutrophils through TNF-α activated endothelial cells (data not shown).

Depositions of immune complexes are potent inducers of inflammatory responses in a wide range of autoimmune diseases including rheumatoid arthritis (RA) and lupus nephritis [34; 35]. In the present study we demonstrate that ligation of SIRPα by CD47-fusion proteins blocks the immune complex induced secretion of TNF-α an inflammatory cytokine critical for the pathogenesis in RA. The presence of fully matured and activated DCs has been shown in the synovial tissue of rheumatoid arthritis patients [36; 37]. Immune complexes induce the maturation of DCs which is critical for the maintenance of auto reactive T and B cells in inflamed tissues [38]. SIRPα ligation may be involved in controlling the maturation of DCs. Interestingly, it has been shown recently that the inhibition of TNF-α during DC maturation leads to the development of semi-mature tolerogenic DCs [39]. Furthermore, SIRPα ligation by a CD47-Fc SAC complex reverses the maturation of DCs [16]. Thus, SIRPα ligation may also block the immune complex mediated maturation of DCs and induce tolerogenic DCs dampening the inflammatory response. Recent studies in animal models using gene targeted and transgenic mice demonstrated that the imbalance between activating FcγR and the inhibitory FcγRIIb is crucial for the development of antibody mediated autoimmune disease [38; 40]. This impairment may be due to genetic predisposition and environmental factors favoring inflammatory conditions which induce activating Fc receptors and down regulate the inhibitory FcγRIIb. The ligation of SIRPα may provide a potential new strategy for the treatment of immune complex mediated autoimmune diseases under conditions in which the FcγRIIb inhibitory pathway is impaired.

In conclusion, we have identified a novel pathway in which the ligation of SIRPα by CD47-Fc controls the immune complex-mediated activation of DCs and ameliorates clinical and histological signs of disease in an antibody mediated arthritis model. Our data suggest that ligation of SIRPα by CD47-Fc may be a beneficial therapy for immune complex mediated inflammatory diseases.

Material and Methods
Reagents

X Vivo 15 medium was purchased from Lonza (Walkersville, Mass.). RPMI and PBS were purchased from Invitrogen (Carlsbad, Calif.). Recombinant human and murine cytokines, hGM-CSF (Berlex, Richmond, Calif.), hIL-4, human and murine IFN-γ (Peptrotech, Rocky Hill, N.J.) and murine IL-4 and GMCSF (R&D Sciences, Minneapolis, Minn.) were used as purified proteins. The hIgG was obtained from Equitech (Kerrville, Tex.) and mIgG2a (clone C1.18) from BioXcell, West Lebanon, N.H.). Donkey anti-human Fc-fragment specific was purchased from Jackson ImmunoResearch Laboratories (West Grove, Pa.). FSL-1 was purchased from Invivogen (San Diego, Calif.). Fixed Staphylococcus aureus Cowan (Pansorbin, SAC) was from Calbiochem-EMD (Gibbstown, N.J.). Mouse anti-human CD47 (CloneB6H12), and murine IgG1 were purchased from Becton Dickinson (San Jose, Calif.). The anti-human CD47 (Clone 2D3) antibody was purchased from eBioScience (San Diego, Calif.)

Construction of Fusion Proteins

Control-Fc was generated by fusing human Fc, amino acids 245-470 of human IgG1 (Genebank accession #AAH62336), to the human growth hormone leader [MATGSRTSLLLAFGLLCLPWLQEGSA] by PCR sewing. hCD47-hFc was generated by fusing amino acids 1-142 of human CD47 (Genebank accession #NP_001768), to amino acids 245-470 of human IgG1 (Genebank accession #AAH62336 by DNA synthesis (Geneart, Regensburg Germany). mCD47-mFC was generated by fusing amino acids 1-140 of murine CD47 (Genebank accession #Q61735) to amino acids 241 to 469 of murine IgG2a (Genebank accession #S37483 PCR) sowing. CD47- and control-HAC were generated by fusing CD47 amino acids 1-142 or Gluc (New England Biolabs) with the HAC tag. The HAC affinity tag consists of an HA epitope tag, a C-epitope tag and 2 copies of a streptavidin binding tag peptide series; [YPYDVPDYAEDQVDPRLIDGK(MDEKTTGWRGGH-VVEGLAGELEQLRARLEHHPQGQRE P)$_2$]. All fusion constructs were cloned in pEE14.4 (Lonza, Basel Switzerland) using the unique HindIII and EcoRI restriction sites Fusion Protein Generation and Purification Stable cell lines expressing hCD47-hFc, control-Fc, CD47-HAC, mCD47-mFc and the control HAC protein were generated using the pEE14.4 vector and CHO-K1SV cells licensed from Lonza Biologics. Clonal cell lines were cultured in CD CHO medium (Invitrogen, Carlsbad Calif.). HAC-tagged proteins were affinity-purified using high capacity streptavidin sepharose (ThermoFisher Scientific, Waltham, Mass.). The HAC-tag affinity eluate was purified by size exclusion chromatography (SEC) in the presence of PBS. mCD47-mFc, control-Fc and hCD47-hFc were purified using MabSelect SuRE chromatography columns (GE Healthcare, Piscataway, N.J.). mCD47-mFc and control-Fc affinity eluate were then processed by SEC. hCD47-hFc affinity eluate was purified by ion exchange and hydrophobic interaction chromatography, then dialyzed into PBS. CD47-Fc expressed almost entirely as a dimer, while CD47-HAC expressed as a mixture of monomer and dimer. Size exclusion chromatography was utilized to isolate the dimeric form for all the CD47-fusion proteins utilized in this study, as confirmed by SEC with multi-angle light scattering measurements (data not shown).

Mice

DBA/1, BALB/c and FcRγ–/– and FcγRIIb–/– mice on the BALB/c background were obtained from Taconic (Hudson, N.Y.)

Cell Preparations

Human PBMC from healthy study subjects were either isolated from heparinized blood or from leukapheresis product by Ficoll-Hystopaque-1077 (Sigma Chemical) gradient centrifugation prior to aliquoting and freezing. Monocyte derived dendritic cells were prepared as described [41] and cultures in dendritic cell differentiation medium (X Vivo 15, 10 ng/mL GM-CSF, 10 ng/mL IL-4). Phenotypic analysis of the cells revealed that more than 95% of the cells were positive for DC-SIGN, CD4, CD40, CD54, CD86 and major histocompatibility complex class I and class II. DCs populations were negative for CD3, CD19 and CD56. Expression levels for CD14 differed between experiments with cells having either no or low-level expression of CD14.

Murine bone marrow derived DCs were generated as described [42] from the femur and tibias of 8-10 week old mice. Cells were grown in X Vivo 15 with 10% ultra low IgG FCS, 1 mM sodium pyruvate, 2 mM glutamine, 0.1 mM MEM non-essential amino acids, 50 µM 2-ME, 50 µg/mL gentamicin, 20 ng/mL mGMCSF and 10 ng/ml mIL-4.

Dendritic Cell Assays

Human DCs differentiated for 8 days were plated in 96 well flat bottom plates (Costar) at $2 \times 10^4$ cells per well in X Vivo medium in the presence IFN-γ (1000 U/mL). Supernatants were taken 18 h after DCs were treated with the respective stimuli and fusion proteins as indicated in the figure legends. Supernatants were stored immediately at −20° C. until cytokine quantification by ELISA. In immune complex assays plates were coated with either human IgG or donkey anti-human Fc in sodium bicarbonate buffer pH 9.6. After overnight coating human IgG plates were washed twice with PBS and hCD47-HAC or control-HAC was added to the plates for 2 h before DCs were seeded. Plates coated overnight with anti-human Fc were washed twice before titrations of hCD47-hFc or control-Fc were added. After 2 h plates were flicked and DCs were added. Murine DCs differentiated for 9-days were culture overnight in X-Vivo 15, 10% FBS 1000 U/ml IFN-γ 50 µM 2-METhen DCs were harvested and cultured at $2 \times 10^4$ cells per well in 96 well flat bottom plates and treated with indicated concentrations of CD47-mFc. After 2 h DCs were stimulated with SAC-mIgG2a. Supernatants were taken after 18 h, stored immediately at −20° C. until cytokine quantification by ELISA. SAC-mIgG2a was prepared by incubating SAC with saturating amounts of mIgG2a for 2 h. Particles were then washed twice and used in the assays.

Cytokine Assays

Quantification of human IL-23 (Biosource) and human and murine TNF-α (DuoSet, R&D Systems) was done by cytokine specific ELISA according to the manufacturers' protocols. Cytokines were detectable only after stimulation.

Flow Cytometry

Cell surface marker expression analysis was performed by flow cytometry following standard procedures with a FACS-Calibur apparatus (Becton Dickinson). HAC fusion protein binding to cells was determine using a monoclonal anti-HA Alexa Fluor 488 conjugated antibody (Invitrogen).

Collagen Antibody-Induced Arthritis Model (CAIA)

On day 0, DBA/1 mice (Taconic, Hudson, N.Y.) were injected i.v. with a cocktail of anti-type II collagen antibodies, (2 mg/mouse; Arthrogen-CIA® type II collagen specific antibody cocktail, Chondrex, Redmond, Wash.). Mice were then dosed by i.v. injection with PBS (200 µl), mIgG2a (500 µg; clone C1.18, BioXcell, West Lebanon, N.H.), or mCD47-mFc (500 µg). On day 3, mice were dosed with test and control articles as on day 1 and 6 h later injected i.p. with LPS (50 µg; Chondrex, Redmond, Wash.). Dosing with test and control articles continued as described on days 5, 7 and 10 and disease scores were assessed until day 24. The scoring scale was as follows: (0) Normal; (1) Mild inflammation of a single area (midfoot, ankle, or toes); (2) Moderately severe arthritis involving 2 areas of paw (toes and ankle or midfoot); (3) Severe arthritis involving an entire paw including ankle, midfoot and toes.

Histology

Histology was performed by Bolder BioPath (Boulder, Colo.) in selected CAIA experiments. Paws were collected in neutral buffered formalin. Histology was performed). For each animal, the inflammation, pannus, cartilage damage and bone damage scores were determined for each of the joints submitted. After decalcification in 5% formic acid for approximately 5 days, tissues were trimmed, processed for paraffin embedding, sectioned at 8 µm and stained with toluidine blue. Inflammation, pannus, cartilage damage and bone resorption was scored by a scale from 0 to 5. Detailed description of the scoring for each parameter can be found in supporting information Statistic Analysis Statistical analysis was performed using the statistical data package of GraphPad Prism version 5.00 for Windows, GraphPad Software (San Diego Calif.).

Example 9

Formulations for Human CD47-Fc Polypeptide of SEQ ID NO 39

In this Example, "(hCD47-Fc)" refers to hCD47-Fc of SEQ ID NO:39. This example summarizes formulation studies in connection with hCD47-Fc.

Several experiments have been performed to develop the formulation for CD47-Fc. Excipients and buffering agents were chosen to be consistent with those used in other approved products. The intent behind evaluating these different formulations was to stabilize the protein against denaturation, aggregation, degradation, and any other possible modifications that could occur during long term storage that may have an impact on hCD47-Fc's strength or potency.

Initial work focused on looking at the protein stability at a variety of pH values from pH 3 to 9, when stored at room temperature. The results of this first experiment suggested that hCD47-Fc was stable at a wide range of pH values (Data not shown). Subsequently, other formulations were examined, focusing on citrate, histidine and PBS as possible buffering agents. The pKa of hCD47-Fc covers a range from ~4.5 to 6.5. It is generally understood that the stability of proteins is decreased when stored at their pI values. In addition, storage of proteins at pH values>7.0 results in increased risk of deamidation of glutamine and asparagine side-chains. This necessarily focused our efforts on formulations with pH values of ~6.3 to 7.2.

Other excipients were added to the formulation help stabilize the protein. It is generally accepted that the addition of detergents such as Tween-80, and other additives like arginine, sucrose and mannitol can have stabilizing effects on protein structure. In some cases, these excipients can have the opposite effect, and as a result formulations tend to be quite specific for the protein they were developed for. Formulation development of hCD47-Fc attempted to determine which excipients would improve the long term stability of the protein, and to identify the concentration to use additives that appeared to be of benefit. As protein concentration also plays a role in stability, concentrations of 5, 10, and 20 mg/mL were examined. The list of buffers that were examined in various experiments are summarized in Table 2.

Figure 23:
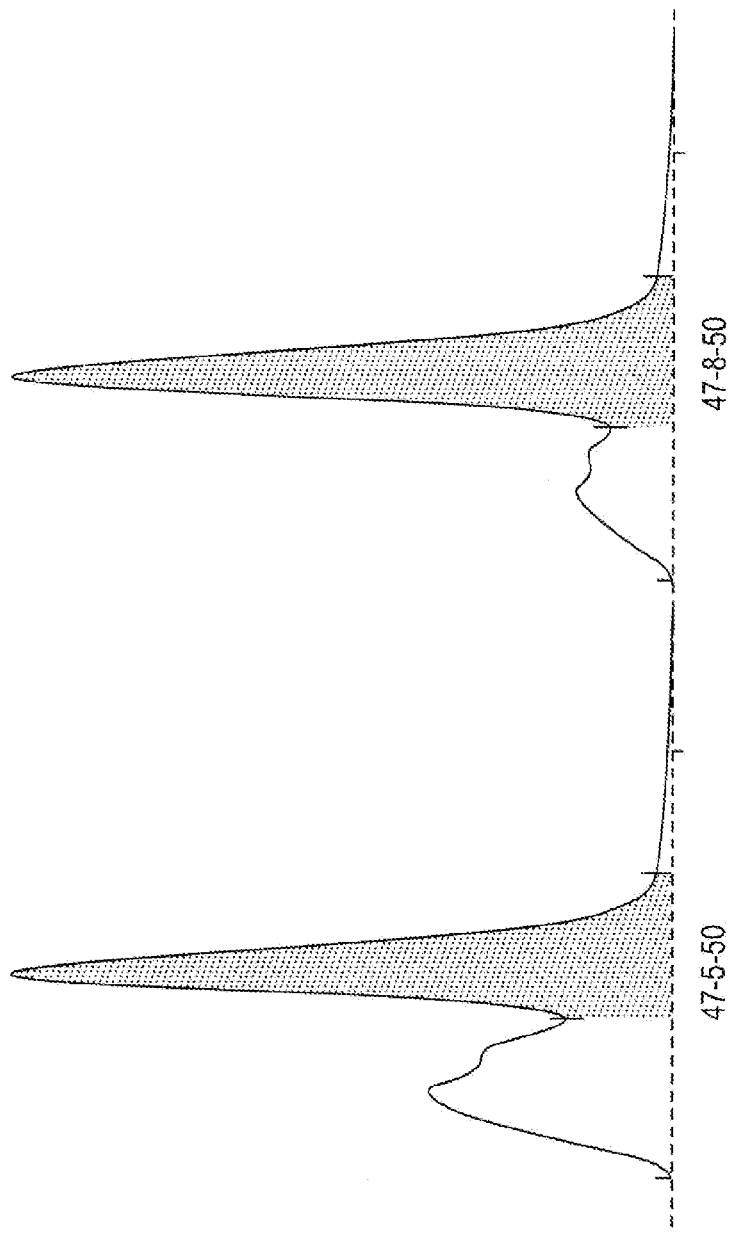

A freeze-thaw experiment was performed to examine formulations 47-FT-1, 47-FT-2 and PBS (Table 2). 20 cycles of −80° C. to room temperature and back were performed, and samples were analyzed via SDS-PAGE, Western blot, and size-exclusion chromatography with light scattering. These three formulations for the most part appeared to be equivalent, showing no obvious differences on the Western blots and SDS-PAGE gels. The light-scattering data implied that histi dine based formulation (47-FT-2 has slightly less aggregated material than PBS (Data not shown). As a result, histidine was used as the primary buffering agent in subsequent experiments. Histidine has sufficient buffering capacity in the pH range that we were interested in (pH 6.3-7.2).

accelerated stability experiment. As suspected, analysis of samples via analytical SEC after 47 days of storage at an elevated temperature showed that 47-8-50, with increased concentration of mannitol and no arginine, had less aggregated material than 47-5-50 (FIG. 23).

TABLE 2

Buffer formulations examined with hCD47-Fc

| Form. I.D. | CD47-Fc mg/mL | Buffer Agent (5 mM) | pH | NaCl (mM) | Arginine (mM) | Sucrose (% W/V) | Mannitol (% W/V) | Tween-80 |
|---|---|---|---|---|---|---|---|---|
| 47-FT-1 | 5 | Citrate | 6.3 | 145 | 0 | 5 mM | 5 mM | 0.01% |
| 47-FT-2 | 5 | Histidine | 6.3 | 145 | 0 | 5 mM | 5 mM | 0.01% |
| 47-1-50 | 10 | Histidine | 6.9 | 154 | 0 | 0 | 0 | 0.01% |
| 47-2-50 | 20 | Histidine | 6.9 | 154 | 0 | 0 | 0 | 0.01% |
| 47-3-50 | 10 | Histidine | 6.9 | 130 | 5 | 1% w/v | 0 | 0.01% |
| 47-4-50 | 20 | Histidine | 6.9 | 130 | 5 | 1% w/v | 0 | 0.01% |
| 47-5-50 | 10 | Histidine | 6.9 | 130 | 5 | 0 | 1% w/v | 0.01% |
| 47-6-50 | 20 | Histidine | 6.9 | 130 | 5 | 0 | 1% w/v | 0.01% |
| 47-7-50 | 20 | PBS | 7.4 | 154 | 0 | 0 | 1% w/v | 0.01% |
| 47-8-50 | 10 | Histidine | 6.9 | 130 | 0 | 0 | 3% w/v | 0.01% |

The conclusive experiments used to finalize the formulation of hCD47-Fc focused on Formulations 47-1-50 through 47-8-50. An accelerated stability experiment at 50° C. was performed to examine these formulations. In addition, another Freeze/Thaw experiment focusing on 47-8-50, the final formulation used with hCD47-Fc, in two different storage containers.

Figure 19:
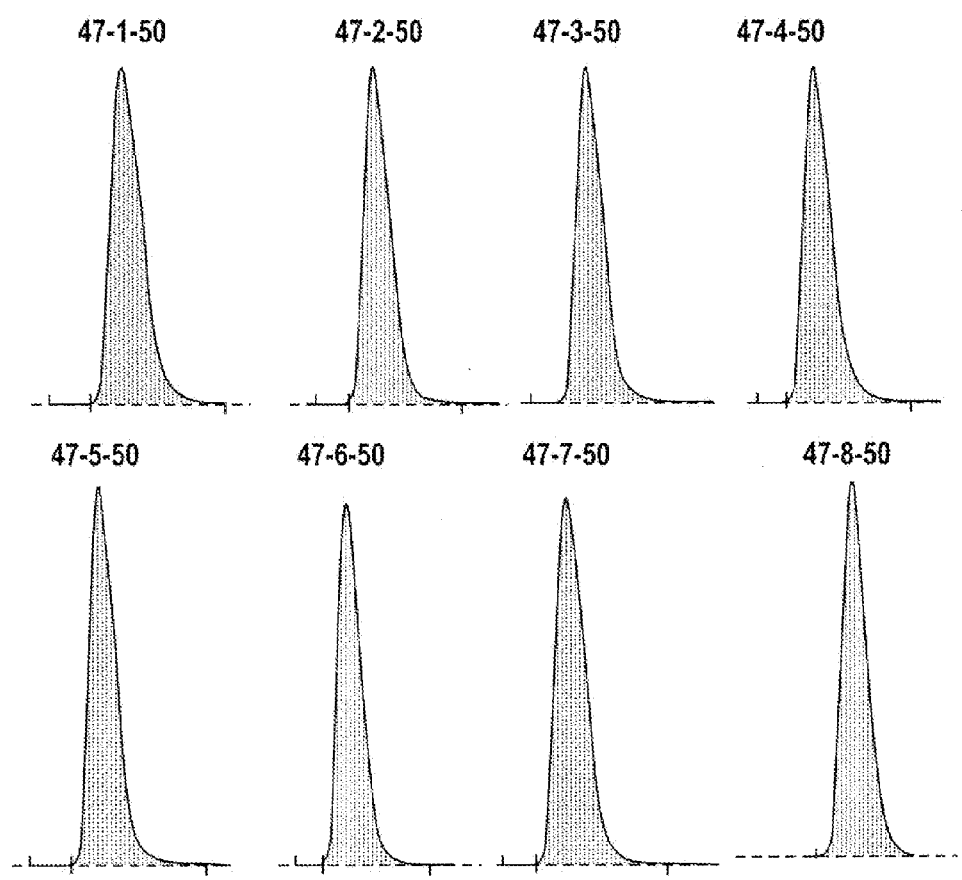
FIGS. 19-23 illustrate formulation analyses for hCD47-Fc of SEQ ID NO:39.
Figure 20:
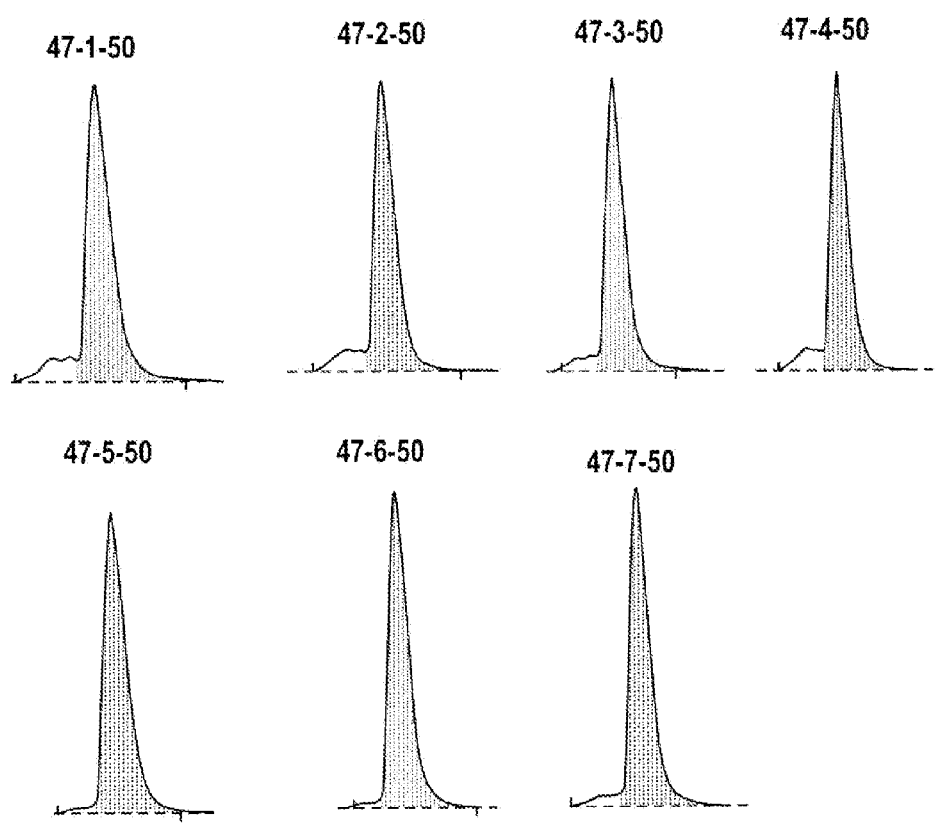
Figure 21:
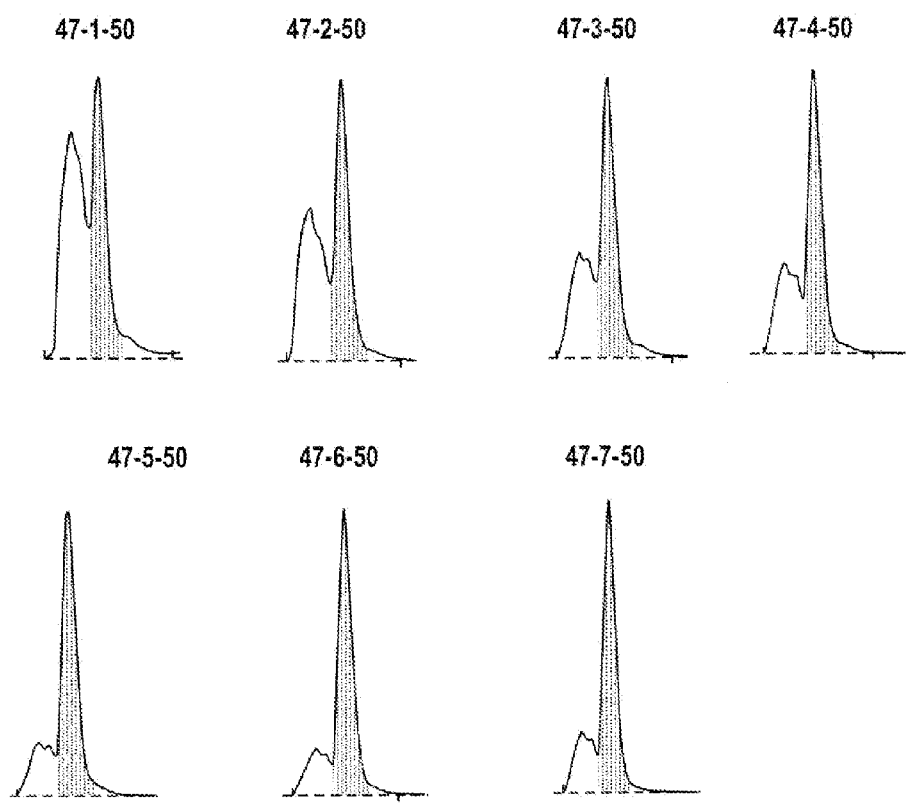
Figure 22:
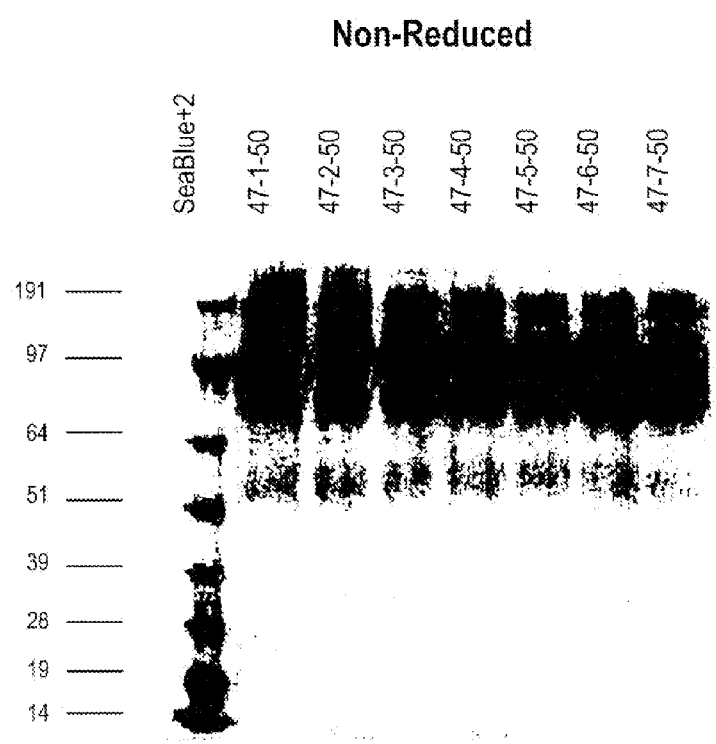

Analytical SEC and SDS-PAGE were the primary tools used to assess the stability of the protein in these formulations. For the accelerated stability study, SEC traces at T=0 showed that the protein eluted from the column as a homogeneous peak (FIG. 19). This peak represents the active form of the protein, the hCD47-Fc dimer. All of the formulations appear to be equivalent at the beginning of the experiment. Non-reduced and reduced SDS-PAGE gels of the Samples of the protein formulated in 47-1-50 through 47-7-50 were stored in an incubator calibrated to 50° C. Samples were removed at various time points and analyzed via analytical SEC and SDS-PAGE. After 8 days of storage, the analytical SEC showed significant differences between the formulations (FIG. 20). All of the formulations containing mannitol (47-5-50, 47-6-50 and 47-7-50) had less aggregated protein, based on the size of the peak eluting immediately before the main hCD47-Fc peak. This suggested that mannitol provides a stabilizing environment for the protein, despite the high heat conditions that the protein was stored in. In subsequent time points this relative trend continued. After 71 days of storage the mannitol-containing formulations, while not completely aggregate free, had less aggregated material than the other formulations that were examined (FIG. 21). The SDS-PAGE gel of these formulations after 71 days also showed that the mannitol formulations seemed to missing a high-order aggregate band that was visible in the other lanes of the gel (FIG. 22). This suggested that the stability of hCD47-Fc drug product during long-term storage at 4° C. would likely be improved by the inclusion of mannitol in the formulation.

A follow-up experiment was performed to examine a higher concentration of mannitol. Arginine was suspected to have minimal impact on improving the stability of the protein, so it was removed. The formulation that incorporated these changes was 47-8-50, which was ultimately chosen as the final formulation for hCD47-Fc. The 47-8-50 was benchmarked against 47-5-50, which had been examined in the first From the foregoing, although specific embodiments of the invention have been described herein for purposes of illustration, various modifications may be made without deviating from the spirit and scope of the invention. Those skilled in the art will recognize, or be able to ascertain, using no more than routine experimentation, many equivalents to the specific embodiments of the invention described herein. Such equivalents are intended to be encompassed by the following claims.

REFERENCES

1. Pulendran, B., Palucka, K., and Banchereau, J., Sensing pathogens and tuning immune responses. Science. 2001. 293: 253-256.
2. Ueno, H., Klechevsky, E., Morita, R., Aspord, C., Cao, T., Matsui, T., Di, P. T., Connolly, J., Fay, J. W., Pascual, V., Palucka, A. K., and Banchereau, J., Dendritic cell subsets in health and disease. Immunol. Rev. 2007. 219:118-42: 118-142.
3. Steinman, R. M. and Banchereau, J., Taking dendritic cells into medicine. Nature. 2007. 449: 419-426.
4. Wenink, M. H., Han, W., Toes, R. E., and Radstake, T. R., Dendritic cells and their potential implication in pathology and treatment of rheumatoid arthritis. Handb. Exp. Pharmacol. 2009. 81-98.
5. Mahnke, K., Bedke, T., and Enk, A. H., Regulatory conversation between antigen presenting cells and regulatory T cells enhance immune suppression. Cell Immunol. 2007. 250: 1-13.
6. Barclay, A. N., Wright, G. J., Brooke, G., and Brown, M. H., CD200 and membrane protein interactions in the control of myeloid cells. Trends Immunol. 2002. 23: 285-290.
7. Barclay, A. N. and Brown, M. H., The SIRP family of receptors and immune regulation. Nat. Rev. Immunol. 2006. 6: 457-464.
8. Matozaki, T., Murata, Y., Okazawa, H., and Ohnishi, H., Functions and molecular mechanisms of the CD47-SIRPalpha signalling pathway. Trends Cell Biol. 2009. 19: 72-80.
9. Kusakari, S., Ohnishi, H., Jin, F. J., Kaneko, Y., Murata, T., Murata, Y., Okazawa, H., and Matozaki, T., Trans-endocytosis of CD47 and SHPS-1 and its role in regulation of the CD47-SHPS-1 system. J. Cell Sci. 2008. 121: 1213-1223.

10. Janssen, W. J., McPhillips, K. A., Dickinson, M. G., Linderman, D. J., Morimoto, K., Xiao, Y. Q., Oldham, K. M., Vandivier, R. W., Henson, P. M., and Gardai, S. J., Surfactant proteins A and D suppress alveolar macrophage phagocytosis via interaction with SIRP alpha. *Am. J. Respir. Crit Care Med.* 2008. 178: 158-167.

11. Oldenborg, P. A., Gresham, H. D., and Lindberg, F. P., CD47-signal regulatory protein alpha (SIRPalpha) regulates Fcgamma and complement receptor-mediated phagocytosis. *J. Exp. Med.* 2001. 193: 855-862.

12. Gardai, S. J., Xiao, Y. Q., Dickinson, M., Nick, J. A., Voelker, D. R., Greene, K. E., and Henson, P. M., By binding SIRPalpha or calreticulin/CD91, lung collectins act as dual function surveillance molecules to suppress or enhance inflammation. *Cell.* 2003. 115: 13-23.

13. Latour, S., Tanaka, H., Demeure, C., Mateo, V., Rubio, M., Brown, E. J., Maliszewski, C., Lindberg, F. P., Oldenborg, A., Ullrich, A., Delespesse, G., and Sarfati, M., Bidirectional negative regulation of human T and dendritic cells by CD47 and its cognate receptor signal-regulator protein-alpha: down-regulation of IL-12 responsiveness and inhibition of dendritic cell activation. *J. Immunol.* 2001. 167: 2547-2554.

14. Brown, E. J. and Frazier, W. A., Integrin-associated protein (CD47) and its ligands. *Trends Cell Biol.* 2001. 11: 130-135.

15. Lindberg, F. P., Bullard, D. C., Caver, T. E., Gresham, H. D., Beaudet, A. L., and Brown, E. J., Decreased resistance to bacterial infection and granulocyte defects in IAP-deficient mice. *Science.* 1996. 274: 795-798.

16. Braun, D., Galibert, L., Nakajima, T., Saito, H., Quang, V. V., Rubio, M., and Sarfati, M., Semimature stage: a checkpoint in a dendritic cell maturation program that allows for functional reversion after signal-regulatory protein-alpha ligation and maturation signals. *J. Immunol.* 2006. 177: 8550-8559.

17. Cameron, C. M., Barrett, J. W., Mann, M., Lucas, A., and McFadden, G., Myxoma virus M128L is expressed as a cell surface CD47-like virulence factor that contributes to the downregulation of macrophage activation in vivo. *Virology* 2005. 337: 55-67.

18. Diveu, C., McGeachy, M. J., and Cua, D. J., Cytokines that regulate autoimmunity. *Curr. Opin. Immunol.* 2008. 20: 663-668.

19. Hashimoto, M., Tawaratsumida, K., Kariya, H., Aoyama, K., Tamura, T., and Suda, Y., Lipoprotein is a predominant Toll-like receptor 2 ligand in *Staphylococcus aureus* cell wall components. *Int. Immunol.* 2006. 18: 355-362.

20. Takai, T., Fc receptors and their role in immune regulation and autoimmunity. *J. Clin. Immunol.* 2005. 25: 1-18.

21. Boruchov, A. M., Heller, G., Veri, M. C., Bonvini, E., Ravetch, J. V., and Young, J. W., Activating and inhibitory IgG Fc receptors on human DCs mediate opposing functions. *J. Clin. Invest.* 2005. 115: 2914-2923.

22. Banki, Z., Kacani, L., Mullauer, B., Wilflingseder, D., Obermoser, G., Niederegger, H., Schennach, H., Sprinzl, G. M., Sepp, N., Erdei, A., Dierich, M. P., and Stoiber, H., Cross-linking of CD32 induces maturation of human monocyte-derived dendritic cells via NF-kappa B signaling pathway. *J. Immunol.* 2003. 170: 3963-3970.

23. Seiffert, M., Cant, C., Chen, Z., Rappold, I., Brugger, W., Kanz, L., Brown, E. J., Ullrich, A., and Buhring, H. J., Human signal-regulatory protein is expressed on normal, but not on subsets of leukemic myeloid cells and mediates cellular adhesion involving its counterreceptor CD47. *Blood.* 1999. 94: 3633-3643.

24. Kagari, T., Tanaka, D., Doi, H., and Shimozato, T., Essential role of Fc gamma receptors in anti-type II collagen antibody-induced arthritis. *J. Immunol.* 2003. 170: 4318-4324.

25. Nandakumar, K. S. and Holmdahl, R., Efficient promotion of collagen antibody induced arthritis (CAIA) using four monoclonal antibodies specific for the major epitopes recognized in both collagen induced arthritis and rheumatoid arthritis. *J. Immunol. Methods.* 2005. 304: 126-136.

26. Lienard, H., Bruhns, P., Malbec, O., Fridman, W. H., and Daeron, M., Signal regulatory proteins negatively regulate immunoreceptor-dependent cell activation. *J. Biol. Chem.* 1999. 274: 32493-32499.

27. Okazawa, H., Motegi, S., Ohyama, N., Ohnishi, H., Tomizawa, T., Kaneko, Y., Oldenborg, P. A., Ishikawa, O., and Matozaki, T., Negative regulation of phagocytosis in macrophages by the CD47-SHPS-1 system. *J. Immunol.* 2005. 174: 2004-2011.

28. Berger, S., Chandra, R., Ballo, H., Hildenbrand, R., and Stutte, H. J., Immune complexes are potent inhibitors of interleukin-12 secretion by human monocytes. *Eur. J. Immunol.* 1997. 27: 2994-3000.

29. Sutterwala, F. S., Noel, G. J., Salgame, P., and Mosser, D. M., Reversal of proinflammatory responses by ligating the macrophage Fcgamma receptor type I. *J. Exp. Med.* 1998. 188: 217-222.

30. Nandakumar, K. S. and Holmdahl, R., Collagen antibody induced arthritis. *Methods Mol. Med.* 2007. 136:215-23: 215-223.

31. Nandakumar, K. S. and Holmdahl, R., Antibody-induced arthritis: disease mechanisms and genes involved at the effector phase of arthritis. *Arthritis Res. Ther.* 2006. 8: 223.

32. Kagari, T., Doi, H., and Shimozato, T., The importance of IL-1 beta and TNF-alpha, and the noninvolvement of IL-6, in the development of monoclonal antibody-induced arthritis. *J. Immunol.* 2002. 169: 1459-1466.

33. Cooper, D., Lindberg, F. P., Gamble, J. R., Brown, E. J., and Vadas, M. A., Transendothelial migration of neutrophils involves integrin-associated protein (CD47). *Proc. Natl. Acad. Sci. U.S.A.* 1995. 92: 3978-3982.

34. Takai, T., Roles of Fc receptors in autoimmunity. *Nat. Rev. Immunol.* 2002. 2: 580-592.

35. Kleinau, S., The impact of Fc receptors on the development of autoimmune diseases. *Curr. Pharm. Des.* 2003. 9: 1861-1870.

36. Radstake, T. R., van Lieshout, A. W., van Riel, P. L., van den Berg, W. B., and Adema, G. J., Dendritic cells, Fc{gamma} receptors, and Toll-like receptors: potential allies in the battle against rheumatoid arthritis. *Ann. Rheum. Dis.* 2005. 64: 1532-1538.

37. Thomas, R., MacDonald, K. P., Pettit, A. R., Cavanagh, L. L., Padmanabha, J., and Zehntner, S., Dendritic cells and the pathogenesis of rheumatoid arthritis. *J. Leukoc. Biol.* 1999. 66: 286-292.

38. Nimmerjahn, F. and Ravetch, J. V., Fc-receptors as regulators of immunity. *Adv. Immunol.* 2007. 96:179-204: 179-204.

39. van Lieshout, A. W., Barrera, P., Smeets, R. L., Pesman, G. J., van Riel, P. L., van den Berg, W. B., and Radstake, T. R., Inhibition of TNF alpha during maturation of dendritic cells results in the development of semi-mature cells: a potential mechanism for the beneficial effects of TNF alpha blockade in rheumatoid arthritis. *Ann. Rheum. Dis.* 2005. 64: 408-414.
40. van, d., V, Mottram, P. L., and Hogarth, P. M., FcgammaRII and multi-system autoimmune disease. *Springer Semin. Immunopathol.* 2006. 28: 329-338.
41. Gervassi, A., Alderson, M. R., Suchland, R., Maisonneuve, J. F., Grabstein, K. H., and Probst, P., Differential regulation of inflammatory cytokine secretion by human dendritic cells upon Chlamydia trachomatis infection. *Infect. Immun.* 2004. 72: 7231-7239.
42. Inaba, K., Inaba, M., Romani, N., Aya, H., Deguchi, M., Ikehara, S., Muramatsu, S., and Steinman, R. M., Generation of large numbers of dendritic cells from mouse bone marrow cultures supplemented with granulocyte/macrophage colony-stimulating factor. *J. Exp. Med.* 1992. 176: 1693-1702.

SEQUENCE LISTING

```
<160> NUMBER OF SEQ ID NOS: 39

<210> SEQ ID NO 1
<211> LENGTH: 124
<212> TYPE: PRT
<213> ORGANISM: Homo sapiens

<400> SEQUENCE: 1

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn
        115                 120

<210> SEQ ID NO 2
<211> LENGTH: 369
<212> TYPE: PRT
<213> ORGANISM: Artificial Sequence
<220> FEATURE:
<223> OTHER INFORMATION: Description of Artificial Sequence: Synthetic
      fusion polypeptide-Human CD47/FC mutein

<400> SEQUENCE: 2

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110
```

```
Thr Cys Glu Val Thr Glu Leu Thr Arg Glu Gly Thr Ile Ile Glu
        115                 120                 125
Leu Lys Tyr Arg Val Val Ser Trp Phe Ser Pro Asn Glu Asn Ser Lys
        130                 135                 140
Thr His Thr Cys Pro Pro Cys Pro Ala Pro Glu Leu Leu Gly Gly Pro
145                 150                 155                 160
Ser Val Phe Leu Phe Pro Pro Lys Pro Lys Asp Thr Leu Met Ile Ser
                165                 170                 175
Arg Thr Pro Glu Val Thr Cys Val Val Val Asp Val Ser His Glu Asp
                180                 185                 190
Pro Glu Val Lys Phe Asn Trp Tyr Val Asp Gly Val Glu Val His Asn
                195                 200                 205
Ala Lys Thr Lys Pro Arg Glu Glu Gln Tyr Asn Ser Thr Tyr Arg Val
        210                 215                 220
Val Ser Val Leu Thr Val Leu His Gln Asp Trp Leu Asn Gly Lys Glu
225                 230                 235                 240
Tyr Lys Cys Lys Val Ser Asn Lys Ala Leu Pro Ala Pro Ile Glu Lys
                245                 250                 255
Thr Ile Ser Lys Ala Lys Gly Gln Pro Arg Glu Pro Gln Val Tyr Thr
                260                 265                 270
Leu Pro Pro Ser Arg Asp Glu Leu Thr Lys Asn Gln Val Ser Leu Thr
                275                 280                 285
Cys Leu Val Lys Gly Phe Tyr Pro Ser Asp Ile Ala Val Glu Trp Glu
        290                 295                 300
Ser Asn Gly Gln Pro Glu Asn Asn Tyr Lys Thr Thr Pro Pro Val Leu
305                 310                 315                 320
Asp Ser Asp Gly Ser Phe Phe Leu Tyr Ser Lys Leu Thr Val Asp Lys
                325                 330                 335
Ser Arg Trp Gln Gln Gly Asn Val Phe Ser Cys Ser Val Met His Glu
                340                 345                 350
Ala Leu His Asn His Tyr Thr Gln Lys Ser Leu Ser Leu Ser Pro Gly
        355                 360                 365
Lys

<210> SEQ ID NO 3
<211> LENGTH: 277
<212> TYPE: PRT
<213> ORGANISM: Variola minor virus

<400> SEQUENCE: 3

Met Leu Arg Val Arg Ile Leu Leu Ile Tyr Leu Cys Thr Phe Val Val
1               5                   10                  15
Ile Thr Ser Thr Lys Thr Ile Glu Tyr Thr Ala Cys Asn Asp Thr Ile
                20                  25                  30
Ile Ile Pro Cys Thr Ile Asp Asn Pro Thr Lys Tyr Ile Arg Trp Lys
                35                  40                  45
Leu Asp Asn His Asn Ile Leu Thr Tyr Asn Lys Thr Ser Lys Thr Ile
        50                  55                  60
Ile Leu Ser Lys Trp His Thr Ser Ala Lys Leu His Ser Leu Ser Asp
65                  70                  75                  80
Asn Asp Val Ser Leu Ile Ile Lys Tyr Lys Asp Ile Leu Pro Gly Thr
                85                  90                  95
Tyr Thr Cys Glu Asp Asn Thr Gly Ile Lys Ser Thr Val Lys Leu Val
                100                 105                 110
Gln Arg His Thr Asn Trp Phe Asn Asp His His Thr Met Leu Met Phe
```

```
            115                 120                 125
Ile Phe Thr Gly Ile Thr Leu Phe Leu Leu Phe Leu Glu Ile Ala Tyr
            130                 135                 140

Thr Ser Ile Ser Val Val Phe Ser Thr Asn Leu Gly Ile Leu Gln Val
145                 150                 155                 160

Phe Gly Cys Ile Ile Ala Met Ile Glu Leu Cys Gly Ala Phe Leu Phe
            165                 170                 175

Tyr Pro Ser Met Phe Thr Leu Arg His Ile Ile Gly Leu Leu Met Met
            180                 185                 190

Thr Leu Pro Ser Ile Phe Leu Ile Ile Thr Lys Val Phe Ser Phe Trp
            195                 200                 205

Leu Leu Cys Lys Leu Ser Cys Ala Val His Leu Ile Ile Tyr Tyr Gln
            210                 215                 220

Leu Ala Gly Tyr Ile Leu Thr Val Leu Gly Leu Gly Leu Ser Leu Lys
225                 230                 235                 240

Glu Cys Val Asp Gly Thr Leu Leu Leu Ser Gly Leu Gly Thr Ile Met
            245                 250                 255

Val Ser Glu His Phe Ser Leu Leu Phe Leu Val Cys Phe Pro Ser Thr
            260                 265                 270

Gln Arg Asp Tyr Tyr
            275

<210> SEQ ID NO 4
<211> LENGTH: 105
<212> TYPE: PRT
<213> ORGANISM: Variola minor virus

<400> SEQUENCE: 4

Lys Thr Ile Glu Tyr Thr Ala Cys Asn Asp Thr Ile Ile Ile Pro Cys
1               5                   10                  15

Thr Ile Asp Asn Pro Thr Lys Tyr Ile Arg Trp Lys Leu Asp Asn His
            20                  25                  30

Asn Ile Leu Thr Tyr Asn Lys Thr Ser Lys Thr Ile Ile Leu Ser Lys
        35                  40                  45

Trp His Thr Ser Ala Lys Leu His Ser Leu Ser Asp Asn Asp Val Ser
    50                  55                  60

Leu Ile Ile Lys Tyr Lys Asp Ile Leu Pro Gly Thr Tyr Thr Cys Glu
65                  70                  75                  80

Asp Asn Thr Gly Ile Lys Ser Thr Val Lys Leu Val Gln Arg His Thr
                85                  90                  95

Asn Trp Phe Asn Asp His His Thr Met
            100                 105

<210> SEQ ID NO 5
<211> LENGTH: 351
<212> TYPE: PRT
<213> ORGANISM: Artificial Sequence
<220> FEATURE:
<223> OTHER INFORMATION: Description of Artificial Sequence: Synthetic
      Human CD47/FC mutein fusion polypeptide

<400> SEQUENCE: 5

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45
```

```
Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ser Lys Thr His
            115                 120                 125

Thr Cys Pro Pro Cys Pro Ala Pro Glu Ala Glu Gly Ala Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Arg Asp Glu Leu Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly Lys
            340                 345                 350

<210> SEQ ID NO 6
<211> LENGTH: 228
<212> TYPE: PRT
<213> ORGANISM: Homo sapiens

<400> SEQUENCE: 6

Cys Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80
```

```
Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
210                 215                 220

Ser Pro Gly Lys
225

<210> SEQ ID NO 7
<211> LENGTH: 226
<212> TYPE: PRT
<213> ORGANISM: Artificial Sequence
<220> FEATURE:
<223> OTHER INFORMATION: Description of Artificial Sequence: Synthetic
      mutated human sequence

<400> SEQUENCE: 7

Lys Thr His Thr Cys Pro Pro Cys Pro Ala Pro Glu Ala Glu Gly Ala
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205
```

Glu Ala Leu His Asn His Tyr Thr Gln Lys Ser Leu Ser Leu Ser Pro
            210                 215                 220

Gly Lys
225

<210> SEQ ID NO 8
<211> LENGTH: 228
<212> TYPE: PRT
<213> ORGANISM: Artificial Sequence
<220> FEATURE:
<223> OTHER INFORMATION: Description of Artificial Sequence: Synthetic
      mutated human sequence

<400> SEQUENCE: 8

Cys Asp Lys Thr His Thr Cys Pro Pro Cys Pro Ala Pro Glu Ala Glu
1               5                   10                  15

Gly Ala Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
210                 215                 220

Ser Pro Gly Lys
225

<210> SEQ ID NO 9
<211> LENGTH: 323
<212> TYPE: PRT
<213> ORGANISM: Homo sapiens

<400> SEQUENCE: 9

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

```
Gln Asn Thr Thr Glu Val Tyr Val Lys Trp Lys Phe Lys Gly Arg Asp
         50                  55                  60

Ile Tyr Thr Phe Asp Gly Ala Leu Asn Lys Ser Thr Val Pro Thr Asp
 65                  70                  75                  80

Phe Ser Ser Ala Lys Ile Glu Val Ser Gln Leu Leu Lys Gly Asp Ala
                 85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
290                 295                 300

Ala Val Glu Glu Pro Leu Asn Ala Phe Lys Glu Ser Lys Gly Met Met
305                 310                 315                 320

Asn Asp Glu

<210> SEQ ID NO 10
<211> LENGTH: 305
<212> TYPE: PRT
<213> ORGANISM: Homo sapiens

<400> SEQUENCE: 10

Gln Leu Leu Phe Asn Lys Thr Lys Ser Val Glu Phe Thr Phe Cys Asn
 1               5                  10                  15

Asp Thr Val Val Ile Pro Cys Phe Val Thr Asn Met Glu Ala Gln Asn
             20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
 65                  70                  75                  80

Lys Met Asp Lys Ser Asp Ala Val Ser His Thr Gly Asn Tyr Thr Cys
                 85                  90                  95

Glu Val Thr Glu Leu Thr Arg Glu Gly Glu Thr Ile Ile Glu Leu Lys
```

-continued

```
                    100                 105                 110
Tyr Arg Val Val Ser Trp Phe Ser Pro Asn Glu Asn Ile Leu Ile Val
            115                 120                 125
Ile Phe Pro Ile Phe Ala Ile Leu Leu Phe Trp Gly Gln Phe Gly Ile
        130                 135                 140
Lys Thr Leu Lys Tyr Arg Ser Gly Gly Met Asp Glu Lys Thr Ile Ala
145                 150                 155                 160
Leu Leu Val Ala Gly Leu Val Ile Thr Val Ile Val Gly Ala
                165                 170                 175
Ile Leu Phe Val Pro Gly Glu Tyr Ser Leu Lys Asn Ala Thr Gly Leu
            180                 185                 190
Gly Leu Ile Val Thr Ser Thr Gly Ile Leu Ile Leu Leu His Tyr Tyr
        195                 200                 205
Val Phe Ser Thr Ala Ile Gly Leu Thr Ser Phe Val Ile Ala Ile Leu
    210                 215                 220
Val Ile Gln Val Ile Ala Tyr Ile Leu Ala Val Val Gly Leu Ser Leu
225                 230                 235                 240
Cys Ile Ala Ala Cys Ile Pro Met His Gly Pro Leu Leu Ile Ser Gly
                245                 250                 255
Leu Ser Ile Leu Ala Leu Ala Gln Leu Leu Gly Leu Val Tyr Met Lys
            260                 265                 270
Phe Val Ala Ser Asn Gln Lys Thr Ile Gln Pro Arg Lys Ala Val
        275                 280                 285
Glu Glu Pro Leu Asn Ala Phe Lys Ser Lys Gly Met Met Asn Asp
    290                 295                 300
Glu
305

<210> SEQ ID NO 11
<211> LENGTH: 142
<212> TYPE: PRT
<213> ORGANISM: Homo sapiens

<400> SEQUENCE: 11

Met Trp Pro Leu Val Ala Ala Leu Leu Leu Gly Ser Ala Cys Cys Gly
1               5                   10                  15
Ser Ala Gln Leu Leu Phe Asn Lys Thr Lys Ser Val Glu Phe Thr Phe
            20                  25                  30
Cys Asn Asp Thr Val Val Ile Pro Cys Phe Val Thr Asn Met Glu Ala
        35                  40                  45
Gln Asn Thr Thr Glu Val Tyr Val Lys Trp Lys Phe Lys Gly Arg Asp
    50                  55                  60
Ile Tyr Thr Phe Asp Gly Ala Leu Asn Lys Ser Thr Val Pro Thr Asp
65                  70                  75                  80
Phe Ser Ser Ala Lys Ile Glu Val Ser Gln Leu Leu Lys Gly Asp Ala
                85                  90                  95
Ser Leu Lys Met Asp Lys Ser Asp Ala Val Ser His Thr Gly Asn Tyr
            100                 105                 110
Thr Cys Glu Val Thr Glu Leu Thr Arg Glu Gly Glu Thr Ile Ile Glu
        115                 120                 125
Leu Lys Tyr Arg Val Val Ser Trp Phe Ser Pro Asn Glu Asn
    130                 135                 140

<210> SEQ ID NO 12
<211> LENGTH: 124
<212> TYPE: PRT
```

-continued

<210> ORGANISM: Artificial Sequence
<220> FEATURE:
<223> OTHER INFORMATION: Description of Artificial Sequence: Synthetic mutated human sequence

<400> SEQUENCE: 12

```
Gln Leu Leu Phe Asn Lys Thr Lys Ser Val Glu Phe Thr Phe Ser Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn
        115                 120
```

<210> SEQ ID NO 13
<211> LENGTH: 5313
<212> TYPE: DNA
<213> ORGANISM: Homo sapiens

<400> SEQUENCE: 13

```
ggggagcagg cggggagcg ggcgggaagc agtgggagcg cgcgtgcgcg cggccgtgca      60
gcctgggcag tgggtcctgc ctgtgacgcg cggcggcggt cggtcctgcc tgtaacggcg    120
gcggcggctg ctgctccaga cacctgcggg ggcggcggcg accccgcggc gggcgcggag    180
atgtggcccc tggtagcggc gctgttgctg ggctcggcgt gctgcggatc agctcagcta    240
ctatttaata aacaaaatc tgtagaattc acgttttgta atgacactgt cgtcattcca     300
tgctttgtta ctaatatgga ggcacaaaac actactgaag tatacgtaaa gtggaaattt    360
aaaggaagag atatttacac ctttgatgga gctctaaaca gtccactgt ccccactgac     420
tttagtagtg caaaaattga gtctcacaa ttactaaaag gagatgcctc tttgaagatg     480
gataagagtg atgctgtctc acacacagga aactacactt gtgaagtaac agaattaacc    540
agagaaggtg aaacgatcat cgagctaaaa tatcgtgttg tttcatggtt ttctccaaat    600
gaaaatattc ttattgttat tttcccaatt tttgctatac tcctgttctg gggacagttt    660
ggtattaaaa cacttaaaata tagatccggt ggtatggatg agaaaacaat tgctttactt    720
gttgctggac tagtgatcac tgtcattgtc attgttggag ccattctttt cgtcccaggt    780
gaatattcat taagaatgc tactggcctt ggtttaattg tgacttctac agggatatta    840
atattacttc actactatgt gtttagtaca gcgattggat taacctcctt cgtcattgcc    900
atattggtta ttcaggtgat agcctatatc ctcgctgtgg ttggactgag tctctgtatt    960
gcggcgtgta taccaatgca tggccctctt ctgatttcag gtttgagtat cttagctcta   1020
gcacaattac ttggactagt ttatatgaaa tttgtggctt ccaatcagaa gactataaca   1080
cctcctagga agctgtagaa ggaaccccct aatgaataac tgaagtgaag tgatggactc   1140
cgatttggag agtagtaaga cgtgaaagga atacacttgt gtttaagcac catggccttg   1200
atgattcact gttggggaga agaaacaaga aaagtaactg gttgtcacct atgagaccct   1260
```

```
tacgtgattg ttagttaagt ttttattcaa agcagctgta atttagttaa taaaataatt    1320
atgatctatg ttgtttgccc aattgagatc cagttttttg ttgttatttt taatcaatta    1380
ggggcaatag tagaatggac aatttccaag aatgatgcct ttcaggtcct agggcctctg    1440
gcctctaggt aaccagttta aattggttca gggtgataac tacttagcac tgccctggtg    1500
attacccaga gatatctatg aaaccagtg gcttccatca aacctttgcc aactcaggtt     1560
cacagcagct ttgggcagtt atggcagtat ggcattagct gagaggtgtc tgccacttct    1620
gggtcaatgg aataataaat taagtacagg caggaatttg gttgggagca tcttgtatga    1680
tctccgtatg atgtgatatt gatggagata gtggtcctca ttcttggggg ttgccattcc    1740
cacattcccc cttcaacaaa cagtgtaaca ggtccttccc agatttaggg tacttttatt    1800
gatggatatg ttttccttt attcacataa ccccttgaaa ccctgtcttg tcctcctgtt     1860
acttgcttct gctgtacaag atgtagcacc ttttctcctc tttgaacatg gtctagtgac    1920
acggtagcac cagttgcagg aaggagccag acttgttctc agagcactgt gttcacactt    1980
ttcagcaaaa atagctatgg ttgtaacata tgtattccct tcctctgatt tgaaggcaaa    2040
aatctacagt gtttcttcac ttcttttctg atctggggca tgaaaaagc aagattgaaa     2100
tttgaactat gagtctcctg catggcaaca aaatgtgtgt caccatcagg ccaacaggcc    2160
agcccttgaa tgggattta ttactgttgt atctatgttg catgataaac attcatcacc     2220
ttcctcctgt agtcctgcct cgtactcccc ttcccctatg attgaaaagt aaacaaaacc    2280
cacatttcct atcctggtta gaagaaaatt aatgttctga cagttgtgat cgcctggagt    2340
acttttagac ttttagcatt cgttttttac ctgtttgtgg atgtgtgttt gtatgtgcat    2400
acgtatgaga taggcacatg catcttctgt atggacaaag gtggggtacc tacaggagag    2460
caaaggttaa ttttgtgctt ttagtaaaaa catttaaata caaagttctt tattgggtgg    2520
aattatattt gatgcaaata tttgatcact taaaacttt aaaacttcta ggtaatttgc     2580
cacgcttttt gactgctcac caatacccgt aaaaatacg taattcttcc tgtttgtgta    2640
ataagatatt catatttgta gttgcattaa taatagttat ttcttagtcc atcagatgtt    2700
cccgtgtgcc tcttttatgc caaattgatt gtcatatttc atgttgggac caagtagttt    2760
gcccatggca aacctaaatt tatgacctgc tgaggcctct cagaaaactg agcatactag    2820
caagacagct cttcttgaaa aaaaaatat gtatacacaa atatatacgt atatctatat     2880
atacgtatgt atatacacac atgtatattc ttccttgatt gtgtagctgt ccaaaataat    2940
aacatatata gagggagctg tattcccttta tacaaatctg atggctcctg cagcactttt   3000
tccttctgaa aatatttaca ttttgctaac ctagttgtt actttaaaaa tcagttttga     3060
tgaaaggagg gaaaagcaga tggacttgaa aaagatccaa gctcctatta gaaaaggtat    3120
gaaaatcttt atagtaaaat tttttataaa ctaaagttgt accttttaat atgtagtaaa    3180
ctctcattta tttggggttc gctcttggat ctcatccatc cattgtgttc tctttaatgc    3240
tgcctgcctt ttgaggcatt cactgcccta gacaatgcca ccagagatag tgggggaaat    3300
gccagatgaa accaactctt gctctcacta gttgtcagct tctctggata agtgaccaca    3360
gaagcaggag tcctcctgct tgggcatcat tgggccagtt ccttctcttt aaatcagatt    3420
tgtaatggct cccaaattcc atcacatcac atttaaattg cagacagtgt tttgcacatc    3480
atgtatctgt tttgtcccat aatatgcttt ttactccctg atcccagttt ctgctgttga    3540
ctcttccatt cagtttttatt tattgtgtgt tctcacagtg acaccatttg tccttttctg    3600
caacaacctt tccagctact tttgccaaat tctatttgtc ttctccttca aaacattctc    3660
```

| | |
|---|---|
| ctttgcagtt cctcttcatc tgtgtagctg ctcttttgtc tcttaactta ccattcctat | 3720 |
| agtactttat gcatctctgc ttagttctat tagttttttg gccttgctct tctccttgat | 3780 |
| tttaaaattc cttctatagc tagagctttt cttctttca ttctctcttc ctgcagtgtt | 3840 |
| ttgcatacat cagaagctag gtacataagt taaatgattg agagttggct gtatttagat | 3900 |
| ttatcacttt ttaatagggt gagcttgaga gttttcttc tttctgtttt ttttttttgt | 3960 |
| tttttttttt tttttttttt tttttttttt tgactaattt cacatgctct aaaaaccttc | 4020 |
| aaaggtgatt attttctcc tggaaactcc aggtccattc tgtttaaatc cctaagaatg | 4080 |
| tcagaattaa aataacaggg ctatcccgta attggaaata tttcttttt caggatgcta | 4140 |
| tagtcaattt agtaagtgac caccaaattg ttatttgcac taacaaagct caaaacacga | 4200 |
| taagtttact cctccatctc agtaataaaa attaagctgt aatcaacctt ctaggtttct | 4260 |
| cttgtcttaa aatgggtatt caaaaatggg gatctgtggt gtatgtatgg aaacacatac | 4320 |
| tccttaattt acctgttgtt ggaaactgga gaaatgattg tcgggcaacc gtttattttt | 4380 |
| tattgtattt tatttggttg agggatttt ttataaacag ttttacttgt gtcatatttt | 4440 |
| aaaattacta actgccatca cctgctgggg tcctttgtta ggtcattttc agtgactaat | 4500 |
| agggataatc caggtaactt tgaagagatg agcagtgagt gaccaggcag ttttctgcc | 4560 |
| tttagctttg acagttctta attaagatca ttgaagacca gctttctcat aaatttctct | 4620 |
| ttttgaaaaa aagaaagcat tgtactaag ctcctctgta agacaacatc ttaaatctta | 4680 |
| aaagtgttgt tatcatgact ggtgagagaa gaaaacattt tgttttatt aaatggagca | 4740 |
| ttatttacaa aaagccattg ttgagaatta gatcccacat cgtataaata tctattaacc | 4800 |
| attctaaata aagagaactc cagtgttgct atgtgcaaga tcctctcttg gagctttttt | 4860 |
| gcatagcaat taaggtgtg ctatttgtca gtagccattt ttttgcagtg atttgaagac | 4920 |
| caaagttgtt ttacagctgt gttaccgtta aaggttttt tttttatatg tattaaatca | 4980 |
| atttatcact gttaaagct ttgaatatct gcaatctttg ccaaggtact ttttattta | 5040 |
| aaaaaaaca taactttgta aatattaccc tgtaatatta tatatactta ataaaacatt | 5100 |
| ttaagctatt ttgttgggct atttctattg ctgctacagc agaccacaag cacatttctg | 5160 |
| aaaaatttaa tttattaatg tatttttaag ttgcttatat tctaggtaac aatgtaaaga | 5220 |
| atgatttaaa atattaatta tgaatttttt gagtataata cccaataagc ttttaattag | 5280 |
| agcagagttt taattaaaag ttttaaatca gtc | 5313 |

```
<210> SEQ ID NO 14
<211> LENGTH: 5346
<212> TYPE: DNA
<213> ORGANISM: Homo sapiens

<400> SEQUENCE: 14
```

| | |
|---|---|
| ggggagcagg cgggggagcg ggcgggaagc agtgggagcg cgcgtgcgcg cggccgtgca | 60 |
| gcctgggcag tgggtcctgc ctgtgacgcg cggcggcggt cggtcctgcc tgtaacggcg | 120 |
| gcggcggctg ctgctccaga cacctgcggc ggcggcggcg accccgcggc gggcgcggag | 180 |
| atgtggcccc tggtagcggc gctgttgctg ggctcggcgt gctgcggatc agctcagcta | 240 |
| ctatttaata aaacaaaatc tgtagaattc acgttttgta atgacactgt cgtcattcca | 300 |
| tgctttgtta ctaatatgga ggcacaaaac actactgaag tatacgtaaa gtggaaattt | 360 |
| aaaggaagag atatttacac ctttgatgga gctctaaaca gtccactgt ccccactgac | 420 |
| tttagtagtg caaaaattga agtctcacaa ttactaaaag gagatgcctc tttgaagatg | 480 |

```
gataagagtg atgctgtctc acacacagga aactacactt gtgaagtaac agaattaacc    540
agagaaggtg aaacgatcat cgagctaaaa tatcgtgttg tttcatggtt ttctccaaat    600
gaaaatattc ttattgttat tttcccaatt tttgctatac tcctgttctg gggacagttt    660
ggtattaaaa cacttaaata tagatccggt ggtatggatg agaaaacaat tgctttactt    720
gttgctggac tagtgatcac tgtcattgtc attgttggag ccattctttt cgtcccaggt    780
gaatattcat taaagaatgc tactggcctt ggtttaattg tgacttctac agggatatta    840
atattacttc actactatgt gtttagtaca gcgattggat taacctcctt cgtcattgcc    900
atattggtta ttcaggtgat agcctatatc ctcgctgtgg ttggactgag tctctgtatt    960
gcggcgtgta taccaatgca tggccctctt ctgatttcag gtttgagtat cttagctcta    1020
gcacaattac ttggactagt ttatatgaaa tttgtggctt ccaatcagaa gactatacaa    1080
cctcctagga aagctgtaga ggaaccccett aatgcattca aagaatcaaa aggaatgatg    1140
aatgatgaat aactgaagtg aagtgatgga ctccgatttg gagagtagta agacgtgaaa    1200
ggaatacact tgtgtttaag caccatggcc ttgatgattc actgttgggg agaagaaaca    1260
agaaaagtaa ctggttgtca cctatgagac ccttacgtga ttgttagtta agttttttatt    1320 caaagcagct gtaatttagt taataaaata attatgatct atgttgtttg cccaattgag    1380
atccagtttt ttgttgttat ttttaatcaa ttaggggcaa tagtagaatg gacaatttcc    1440
aagaatgatg cctttcaggt cctagggcct ctggcctcta ggtaaccagt ttaaattggt    1500
tcagggtgat aactacttag cactgccctg gtgattaccc agagatatct atgaaaacca    1560
gtggcttcca tcaaaccttt gccaactcag gttcacagca gctttgggca gttatggcag    1620
tatggcatta gctgagaggt gtctgccact tctgggtcaa tggaataata aattaagtac    1680
aggcaggaat ttggttggga gcatcttgta tgatctccgt atgatgtgat attgatggag    1740
atagtggtcc tcattcttgg gggttgccat tcccacattc cccctcaac aaacagtgta    1800 acaggtcctt cccagattta gggtactttt attgatggat atgttttcct tttattcaca    1860
taaccccttg aaaccctgtc ttgtcctcct gttacttgct tctgctgtac aagatgtagc    1920
accttttctc ctctttgaac atggtctagt gacacggtag caccagttgc aggaaggagc    1980
cagacttgtt ctcagagcac tgtgttcaca cttttcagca aaaatagcta tggttgtaac    2040
atatgtattc ccttcctctg atttgaaggc aaaaatctac agtgtttctt cacttctttt    2100
ctgatctggg gcatgaaaaa agcaagattg aaatttgaac tatgagtctc tgcatggca    2160 acaaaatgtg tgtcaccatc aggccaacag gccagcccett gaatggggat ttattactgt    2220
tgtatctatg ttgcatgata acattcatc accttcctcc tgtagtcctg cctcgtactc    2280
cccttcccct atgattgaaa agtaaacaaa acccacattt cctatcctgg ttagaagaaa    2340
attaatgttc tgacagttgt gatcgcctgg agtactttta gacttttagc attcgttttt    2400
tacctgtttg tggatgtgtg tttgtatgtg catacgtatg agataggcac atgcatcttc    2460
tgtatggaca aaggtggggt acctacagga gagcaaaggt taattttgtg cttttagtaa    2520
aaacatttaa atacaaagtt ctttattggg tggaattata tttgatgcaa atatttgatc    2580
acttaaaact tttaaaactt ctaggtaatt tgccacgctt tttgactgct caccaatacc    2640
ctgtaaaaat acgtaattct tcctgtttgt gtaataagat attcatattt gtagttcat    2700 taataatagt tatttcttag tccatcagat gttcccgtgt gcctcttta tgccaaattg    2760 attgtcatat ttcatgttgg gaccaagtag tttgcccatg gcaaacctaa atttatgacc    2820
tgctgaggcc tctcagaaaa ctgagcatac tagcaagaca gctcttcttg aaaaaaaaaa    2880
```

-continued

```
tatgtataca caaatatata cgtatatcta tatatacgta tgtatataca cacatgtata    2940
ttcttccttg attgtgtagc tgtccaaaat aataacatat atagagggag ctgtattcct    3000
ttatacaaat ctgatggctc ctgcagcact ttttccttct gaaaatattt acattttgct    3060
aacctagttt gttactttaa aaatcagttt tgatgaaagg agggaaaagc agatggactt    3120 gaaaagatc caagctccta ttagaaaagg tatgaaaatc tttatagtaa aatttttat      3180 aaactaaagt tgtacctttt aatatgtagt aaactctcat ttatttgggg ttcgctcttg    3240
gatctcatcc atccattgtg ttctctttaa tgctgcctgc cttttgaggc attcactgcc    3300
ctagacaatg ccaccagaga tagtgggga aatgccagat gaaaccaact cttgctctca     3360
ctagttgtca gcttctctgg ataagtgacc acagaagcag gagtcctcct gcttgggcat    3420
cattgggcca gttccttctc tttaaatcag atttgtaatg ctcccaaat tccatcacat     3480 cacatttaaa ttgcagacag tgttttgcac atcatgtatc tgttttgtcc cataatatgc    3540
tttttactcc ctgatcccag tttctgctgt tgactcttcc attcagtttt atttattgtg    3600
tgttctcaca gtgacaccat ttgtcctttt ctgcaacaac cttccagct acttttgcca     3660 aattctattt gtcttctcct tcaaaacatt ctcctttgca gttcctcttc atctgtgtag    3720
ctgctctttt gtctcttaac ttaccattcc tatagtactt tatgcatctc tgcttagttc    3780
tattagtttt ttggccttgc tcttctcctt gattttaaaa ttccttctat agctagagct    3840
tttctttctt tcattctctc ttcctgcagt gttttgcata catcagaagc taggtacata    3900
agttaaatga ttgagagttg gctgtattta gatttatcac ttttaatag ggtgagcttg     3960 agagttttct ttctttctgt ttttttttt tgtttttttt tttttttttt tttttttttt     4020
ttttgactaa tttcacatgc tctaaaaacc ttcaaaggtg attattttc tcctggaaac     4080 tccaggtcca ttctgtttaa atccctaaga atgtcagaat taaaataaca gggctatccc    4140
gtaattggaa atatttcttt tttcaggatg ctatagtcaa tttagtaagt gaccaccaaa    4200
ttgttatttg cactaacaaa gctcaaaaca cgataagttt actcctccat ctcagtaata    4260
aaaattaagc tgtaatcaac cttctaggtt tctcttgtct taaaatgggg attcaaaaat    4320
ggggatctgt ggtgtatgta tggaaacaca tactccttaa tttacctgtt gttggaaact    4380
ggagaaatga ttgtcgggca accgttattt ttttattgta ttttatttgg ttgagggatt    4440 ttttttataaa cagtttact tgtgtcatat tttaaaatta ctaactgcca tcacctgctg    4500 gggtccttg ttaggtcatt ttcagtgact aataggata atccaggtaa ctttgaagag     4560
atgagcagtg agtgaccagg cagttttct gcctttagct ttgacagttc ttaattaaga    4620
tcattgaaga ccagctttct cataaatttc tctttttgaa aaaagaaag catttgtact    4680 aagctcctct gtaagacaac atcttaaatc ttaaaagtgt tgttatcatg actggtgaga   4740
gaagaaaaca ttttgttttt attaaatgga gcattattta caaaaagcca ttgttgagaa    4800
ttagatccca catcgtataa atatctatta accattctaa ataagagaa ctccagtgtt     4860 gctatgtgca agatcctctc ttggagcttt tttgcatagc aattaaaggt gtgctatttg    4920
tcagtagcca ttttttttgca gtgatttgaa gaccaaagtt gttttacagc tgtgttaccg    4980
ttaaaggttt tttttttttat atgtattaaa tcaatttatc actgttaaa gctttgaata   5040 tctgcaatct ttgccaaggt actttttat ttaaaaaaaa acataacttt gtaaatatta    5100
ccctgtaata ttatatatac ttaataaaac attttaagct attttgttgg gctatttcta    5160
ttgctgctac agcagaccac aagcacattt ctgaaaaatt taatttatta atgtattttt    5220
aagttgctta tattctaggt aacaatgtaa agaatgattt aaaatattaa ttatgaattt    5280
```

```
tttgagtata ataccaata agcttttaat tagagcagag ttttaattaa aagttttaaa    5340
tcagtc                                                              5346
```

<210> SEQ ID NO 15
<211> LENGTH: 305
<212> TYPE: PRT
<213> ORGANISM: Homo sapiens

<400> SEQUENCE: 15

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Asn
    290                 295                 300

Asn
305
```

<210> SEQ ID NO 16
<211> LENGTH: 5288
<212> TYPE: DNA
<213> ORGANISM: Homo sapiens

<400> SEQUENCE: 16

```
ggggagcagg cggggagcg ggcgggaagc agtgggagcg cgcgtgcgcg cggccgtgca      60
gcctgggcag tgggtcctgc ctgtgacgcg cggcggcggt cggtcctgcc tgtaacggcg    120
gcggcggctg ctgctccaga cacctgcggg ggcggcggcg accccgcggc gggcgcggag    180
atgtggcccc tggtagcggc gctgttgctg ggctcggcgt gctgcggatc agctcagcta    240
ctatttaata aaacaaaatc tgtagaattc acgttttgta atgacactgt cgtcattcca    300
tgctttgtta ctaatatgga ggcacaaaac actactgaag tatacgtaaa gtggaaattt    360
aaaggaagag atatttacac ctttgatgga gctctaaaca agtccactgt ccccactgac    420
tttagtagtg caaaaattga agtctcacaa ttactaaaag gagatgcctc tttgaagatg    480
gataagagtg atgctgtctc acacacagga aactacactt gtgaagtaac agaattaacc    540
agagaaggtg aaacgatcat cgagctaaaa tatcgtgttg tttcatggtt ttctccaaat    600
gaaaatattc ttattgttat tttcccaatt tttgctatac tcctgttctg gggacagttt    660
ggtattaaaa acttaaaata tagatccggt ggtatggatg agaaaacaat tgctttactt    720
gttgctggac tagtgatcac tgtcattgtc attgttggag ccattctttt cgtcccaggt    780
gaatattcat aaagaatgc tactggcctt ggtttaattg tgacttctac agggatatta    840
atattacttc actactatgt gtttagtaca gcgattggat taacctcctt cgtcattgcc    900
atattggtta ttcaggtgat agcctatatc ctcgctgtgg ttggactgag tctctgtatt    960
gcggcgtgta taccaatgca tggccctctt ctgatttcag gtttgagtat cttagctcta   1020
gcacaattac ttggactagt ttatatgaaa tttgtggctt ccaatcagaa gactatacaa   1080
cctcctagga ataactgaag tgaagtgatg gactccgatt tggagagtag taagacgtga   1140
aaggaataca cttgtgttta agcaccatgg ccttgatgat tcactgttgg ggagaagaaa   1200
caagaaaagt aactggttgt cacctatgag acccttacgt gattgttagt aagttttta    1260
ttcaaagcag ctgtaattta gttaataaaa taattatgat ctatgttgtt tgcccaattg   1320
agatccagtt ttttgttgtt attttttaatc aattagggc aatagtagaa tggacaattt   1380
ccaagaatga tgcctttcag gtcctagggc ctctggcctc taggtaacca gtttaaattg   1440
gttcagggtg ataactactt agcactgccc tggtgattac ccagagatat ctatgaaaac   1500
cagtggcttc catcaaacct tgccaactc aggttcacag cagctttggg cagttatggc    1560
agtatggcat tagctgagag gtgtctgcca cttctgggtc aatggaataa taaattaagt   1620
acaggcagga atttggttgg gagcatcttg tatgatctcc gtatgatgtg atattgatgg   1680
agatagtggt cctcattctt gggggttgcc attcccacat tccccttca acaaacagtg    1740
taacaggtcc ttcccagatt tagggtactt ttattgatgg atatgttttc ctttattca    1800
cataacccct tgaaaccctg tcttgtcctc ctgttacttg cttctgctgt acaagatgta   1860
gcaccttttc tcctctttga acatggtcta gtgacacggt agcaccagtt gcaggaagga   1920
gccagacttg ttctcagagc actgtgttca cacttttcag caaaaatagc tatggttgta   1980
acatatgtat tcccttcctc tgatttgaag gcaaaaatct acagtgtttc ttcacttctt   2040
ttctgatctg gggcatgaaa aaagcaagat tgaaatttga actatgagtc tcctgcatgg   2100
caacaaaatg tgtgtcacca tcaggccaac aggccagccc ttgaatgggg atttattact   2160
gttgtatcta tgttgcatga taaacattca tcaccttcct cctgtagtcc tgcctcgtac   2220
tccccttccc ctatgattga aaagtaaaca aaacccacat ttcctatcct ggttagaaga   2280
aaattaatgt tctgacagtt gtgatcgcct ggagtacttt tagactttta gcattcgttt   2340
tttacctgtt tgtggatgtg tgtttgtatg tgcatacgta tgagataggc acatgcatct   2400
```

```
tctgtatgga caaaggtggg gtacctacag gagagcaaag gttaattttg tgcttttagt    2460
aaaaacattt aaatacaaag ttctttattg ggtggaatta tatttgatgc aaatatttga    2520
tcacttaaaa cttttaaaac ttctaggtaa tttgccacgc tttttgactg ctcaccaata    2580
ccctgtaaaa atacgtaatt cttcctgttt gtgtaataag atattcatat ttgtagttgc    2640
attaataata gttatttctt agtccatcag atgttcccgt gtgcctcttt tatgccaaat    2700
tgattgtcat atttcatgtt gggaccaagt agtttgccca tggcaaacct aaatttatga    2760
cctgctgagg cctctcagaa aactgagcat actagcaaga cagctcttct tgaaaaaaaa    2820
aatatgtata cacaaatata tacgtatatc tatatatacg tatgtatata cacacatgta    2880
tattcttcct tgattgtgta gctgtccaaa ataataacat atatagaggg agctgtattc    2940
ctttatacaa atctgatggc tcctgcagca cttttttcctt ctgaaaatat ttacattttg    3000
ctaacctagt ttgttacttt aaaaatcagt tttgatgaaa ggagggaaaa gcagatggac    3060
ttgaaaaaga tccaagctcc tattagaaaa ggtatgaaaa tctttatagt aaaattttt    3120 ataaactaaa gttgtacctt ttaatatgta gtaaactctc atttatttgg ggttcgctct    3180
tggatctcat ccatccattg tgttctcttt aatgctgcct gccttttgag gcattcactg    3240
ccctagacaa tgccaccaga gatagtgggg gaaatgccag atgaaaccaa ctcttgctct    3300
cactagttgt cagcttctct ggataagtga ccacagaagc aggagtcctc ctgcttgggc    3360
atcattgggc cagttccttc tctttaaatc agatttgtaa tggctcccaa attccatcac    3420
atcacattta aattgcagac agtgttttgc acatcatgta tctgttttgt cccataatat    3480 gcttttact ccctgatccc agtttctgct gttgactctt ccattcagtt ttatttattg    3540
tgtgttctca cagtgacacc atttgtcctt ttctgcaaca acctttccag ctacttttgc    3600
caaattctat ttgtcttctc cttcaaaaca ttctcctttg cagttcctct tcatctgtgt    3660
agctgctctt ttgtctctta acttaccatt cctatagtac tttatgcatc tctgcttagt    3720
tctattagtt ttttggcctt gctcttctcc ttgattttaa aattccttct atagctagag    3780
cttttctttc tttcattctc tcttcctgca gtgtttgca tacatcagaa gctaggtaca    3840
taagttaaat gattgagagt tggctgtatt tagatttatc actttttaat agggtgagct    3900
tgagagtttt ctttctttct gtttttttttt ttgttttttt tttttttttt tttttttttt    3960
ttttttgact aatttcacat gctctaaaaa ccttcaaagg tgattatttt tctcctggaa    4020
actccaggtc cattctgttt aaatccctaa gaatgtcaga attaaaataa cagggctatc    4080
ccgtaattgg aaatatttct ttttttcagga tgctatagtc aatttagtaa gtgaccacca    4140
aattgttatt tgcactaaca aagctcaaaa cacgataagt ttactcctcc atctcagtaa    4200
taaaaattaa gctgtaatca accttctagg tttctcttgt cttaaaatgg gtattcaaaa    4260
atggggatct gtggtgtatg tatggaaaca catactcctt aatttacctg ttgttggaaa    4320
ctggagaaat gattgtcggg caaccgttta ttttttattg tatttatttt ggttgaggga    4380
tttttttata aacagtttta cttgtgtcat atttttaaaat tactaactgc catcacctgc    4440
tggggtcctt tgttaggtca ttttcagtga ctaatagggga taatccaggt aactttgaag    4500
agatgagcag tgagtgacca ggcagttttt ctgcctttag ctttgacagt tcttaattaa    4560
gatcattgaa gaccagcttt ctcataaatt tctcttttg aaaaaagaa agcatttgta    4620 ctaagctcct ctgtaagaca acatcttaaa tcttaaaagt gttgttatca tgactggtga    4680
gagaagaaaa cattttgttt ttattaaatg gagcattatt tacaaaaagc cattgttgag    4740
aattagatcc cacatcgtat aaatatctat taaccattct aaataaagag aactccagtg    4800
```

-continued

```
ttgctatgtg caagatcctc tcttggagct tttttgcata gcaattaaag gtgtgctatt    4860
tgtcagtagc catttttttg cagtgatttg aagaccaaag ttgttttaca gctgtgttac    4920
cgttaaaggt tttttttttt atatgtatta aatcaattta tcactgttta aagctttgaa    4980
tatctgcaat ctttgccaag gtactttttt atttaaaaaa aaacataact ttgtaaatat    5040
taccctgtaa tattatatat acttaataaa acattttaag ctattttgtt gggctatttc    5100
tattgctgct acagcagacc acaagcacat ttctgaaaaa tttaatttat taatgtattt    5160
ttaagttgct tatattctag gtaacaatgt aaagaatgat ttaaaatatt aattatgaat    5220
tttttgagta taatacccaa taagctttta attagagcag agttttaatt aaaagttttt    5280
aatcagtc                                                              5288
```

```
<210> SEQ ID NO 17
<211> LENGTH: 312
<212> TYPE: PRT
<213> ORGANISM: Homo sapiens

<400> SEQUENCE: 17

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285
```

```
Met Lys Phe Val Ala Ser Asn Gln Lys Thr Ile Gln Pro Pro Arg Lys
    290                 295                 300
Ala Val Glu Glu Pro Leu Asn Glu
305                 310
```

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      signal peptide of human CD47

<400> SEQUENCE: 18

```
Met Trp Pro Leu Val Ala Ala Leu Leu Leu Gly Ser Ala Cys Cys Gly
1               5                   10                  15
Ser Ala
```

<210> SEQ ID NO 19
<211> LENGTH: 5346
<212> TYPE: DNA
<213> ORGANISM: Homo sapiens

<400> SEQUENCE: 19

| | | | | | |
|---|---|---|---|---|---|
| ggggagcagg | cggggagcg | ggcgggaagc | agtgggagcg | cgcgtgcgcg | cggccgtgca | 60 |
| gcctgggcag | tgggtcctgc | ctgtgacgcg | cggcggcggt | cggtcctgcc | tgtaacggcg | 120 |
| gcggcggctg | ctgctccaga | cacctgcggc | ggcggcggcg | accccgcggc | gggcgcggag | 180 |
| atgtggcccc | tggtagcggc | gctgttgctg | ggctcggcgt | gctgcggatc | agctcagcta | 240 |
| ctatttaata | aaacaaaatc | tgtagaattc | acgttttgta | atgacactgt | cgtcattcca | 300 |
| tgctttgtta | ctaatatgga | ggcacaaaac | actactgaag | tatacgtaaa | gtggaaattt | 360 |
| aaaggaagag | atatttacac | ctttgatgga | gctctaaaca | agtccactgt | ccccactgac | 420 |
| tttagtagtg | caaaaattga | agtctcacaa | ttactaaaag | gagatgcctc | tttgaagatg | 480 |
| gataagagtg | atgctgtctc | acacacagga | aactacactt | gtgaagtaac | agaattaacc | 540 |
| agagaaggtg | aaacgatcat | cgagctaaaa | tatcgtgttg | tttcatggtt | ttctccaaat | 600 |
| gaaaatattc | ttattgttat | tttcccaatt | tttgctatac | tcctgttctg | ggacagtttt | 660 |
| ggtattaaaa | cacttaaata | tagatccggt | ggtatggatg | agaaaacaat | tgctttactt | 720 |
| gttgctggac | tagtgatcac | tgtcattgtc | attgttggag | ccattctttt | cgtcccaggt | 780 |
| gaatattcat | taagaatgc | tactggcctt | ggtttaattg | tgacttctac | agggatatta | 840 |
| atattacttc | actactatgt | gtttagtaca | gcgattggat | taacctcctt | cgtcattgcc | 900 |
| atattggtta | ttcaggtgat | agcctatatc | ctcgctgtgg | ttggactgag | tctctgtatt | 960 |
| gcggcgtgta | taccaatgca | tggccctctt | ctgatttcag | gtttgagtat | cttagctcta | 1020 |
| gcacaattac | ttgactagt | ttatatgaaa | tttgtggctt | ccaatcagaa | gactatacaa | 1080 |
| cctcctagga | aagctgtaga | ggaacccctt | aatgcattca | agaatcaaa | aggaatgatg | 1140 |
| aatgatgaat | aactgaagtg | aagtgatgga | ctccgatttg | gagagtagta | agacgtgaaa | 1200 |
| ggaatacact | tgtgtttaag | caccatggcc | ttgatgattc | actgttgggg | agaagaaaca | 1260 |
| agaaaagtaa | ctggttgtca | cctatgagac | ccttacgtga | ttgttagtta | agtttttatt | 1320 |
| caaagcagct | gtaatttagt | taataaaata | attatgatct | atgttgtttg | cccaattgag | 1380 |
| atccagttt | ttgttgttat | ttttaatcaa | ttaggggcaa | tagtagaatg | gacaatttcc | 1440 |
| aagaatgatg | cctttcaggt | cctagggcct | ctggcctcta | ggtaaccagt | ttaaattggt | 1500 |

```
tcagggtgat aactacttag cactgccctg gtgattaccc agagatatct atgaaaacca     1560
gtggcttcca tcaaacctt  gccaactcag gttcacagca gctttgggca gttatggcag     1620
tatggcatta gctgagaggt gtctgccact tctgggtcaa tggaataata aattaagtac     1680
aggcaggaat ttggttggga gcatcttgta tgatctccgt atgatgtgat attgatggag     1740
atagtggtcc tcattcttgg gggttgccat tcccacattc ccccttcaac aaacagtgta     1800
acaggtcctt cccagattta gggtactttt attgatggat atgttttcct tttattcaca     1860
taaccccttg aaaccctgtc ttgtcctcct gttacttgct tctgctgtac aagatgtagc     1920 acctttctc  ctctttgaac atggtctagt gacacggtag caccagttgc aggaaggagc     1980
cagacttgtt ctcagagcac tgtgttcaca cttttcagca aaatagcta  tggttgtaac     2040 atatgtattc ccttcctctg atttgaaggc aaaaatctac agtgtttctt cacttctttt     2100
ctgatctggg gcatgaaaaa agcaagattg aaatttgaac tatgagtctc ctgcatggca     2160
acaaaatgtg tgtcaccatc aggccaacag gccagccctt gaatgggat  ttattactgt     2220 tgtatctatg ttgcatgata acattcatc  accttcctcc tgtagtcctg cctcgtactc     2280 cccttccccct atgattgaaa agtaaacaaa acccacattt cctatcctgg ttagaagaaa     2340
attaatgttc tgacagttgt gatcgcctgg agtacttta  gacttttagc attcgttttt     2400
tacctgtttg tggatgtgtg tttgtatgtg catacgtatg agataggcac atgcatcttc     2460
tgtatggaca aggtggggt  acctacagga gagcaaaggt taattttgtg cttttagtaa     2520
aaacatttaa atacaaagtt ctttattggg tggaattata tttgatgcaa atatttgatc     2580
acttaaaact tttaaaactt ctaggtaatt tgccacgctt tttgactgct caccaatacc     2640
ctgtaaaaat acgtaattct tcctgttgt  gtaataagat attcatattt gtagttgcat     2700
taataatagt tatttcttag tccatcagat gttcccgtgt gcctcttta  tgccaaattg     2760 attgtcatat ttcatgttgg gaccaagtag tttgcccatg gcaaacctaa atttatgacc     2820
tgctgaggcc tctcagaaaa ctgagcatac tagcaagaca gctcttcttg aaaaaaaaaa     2880
tatgtataca caaatatata cgtatatcta tatatacgta tgtatataca cacatgtata     2940
ttcttccttg attgtgtagc tgtccaaaat aataacatat atagagggag ctgtattcct     3000
ttatacaaat ctgatggctc ctgcagcact ttttccttct gaaaatattt acattttgct     3060
aacctagttt gttactttaa aaatcagttt tgatgaaagg agggaaaagc agatggactt     3120 gaaaagatc  caagctccta ttagaaaagg tatgaaaatc tttatagtaa aattttttat     3180
aaactaaagt tgtacctttt aatatgtagt aaactctcat ttatttgggg ttcgctcttg     3240
gatctcatcc atccattgtg ttctctttaa tgctgcctgc cttttgaggc attcactgcc     3300
ctagacaatg ccaccagaga tagtgggga  aatgccagat gaaaccaact cttgctctca     3360
ctagttgtca gcttctctgg ataagtgacc acagaagcag gagtcctcct gcttgggcat     3420
cattgggcca gttccttctc tttaaatcag atttgtaatg gctcccaaat tccatcacat     3480
cacatttaaa ttgcagacag tgttttgcac atcatgtatc tgttttgtcc cataatatgc     3540
tttttactcc ctgatcccag tttctgctgt tgactcttcc attcagtttt atttattgtg     3600
tgttctcaca gtgacaccat ttgtcctttt ctgcaacaac cttccagct  acttttgcca     3660 aattctattt gtcttctcct tcaaaacatt tcccttttgca gttcctcttc atctgtgtag    3720
ctgctctttt gtctcttaac ttaccattcc tatagtactt tatgcatctc tgcttagttc     3780
tattagtttt ttggccttgc tcttctcctt gattttaaaa ttccttctat agctagagct     3840 tttcttttctt tcattctctc ttcctgcagt gttttgcata catcagaagc taggtacata    3900
```

```
agttaaatga ttgagagttg gctgtatttta gatttatcac ttttttaatag ggtgagcttg    3960 agagttttct ttctttctgt tttttttttt tgtttttttt tttttttttt tttttttttt    4020
ttttgactaa tttcacatgc tctaaaaacc ttcaaaggtg attattttttc tcctggaaac    4080 tccaggtcca ttctgtttaa atccctaaga atgtcagaat taaaataaca gggctatccc    4140
gtaattggaa atatttcttt tttcaggatg ctatagtcaa tttagtaagt gaccaccaaa    4200 tgttatttg cactaacaaa gctcaaaaca cgataagttt actcctccat ctcagtaata    4260
aaaattaagc tgtaatcaac cttctaggtt tctcttgtct taaaatgggg attcaaaaat    4320
ggggatctgt ggtgtatgta tggaaacaca tactccttaa tttacctgtt gttggaaact    4380
ggagaaatga ttgtcgggca accgttatt ttttattgta ttttatttgg ttgagggatt    4440
tttttataaa cagtttttact tgtgtcatat tttaaaatta ctaactgcca tcacctgctg    4500
gggtcctttg ttaggtcatt ttcagtgact aatagggata atccaggtaa ctttgaagag    4560
atgagcagtg agtgaccagg cagttttttct gcctttagct ttgacagttc ttaattaaga    4620
tcattgaaga ccagctttct cataaatttc tcttttttgaa aaaagaaaag catttgtact    4680
aagctcctct gtaagacaac atcttaaatc ttaaaagtgt tgttatcatg actggtgaga    4740
gaagaaaaca tttttgtttttt attaaatgga gcattattta caaaaagcca ttgttgagaa    4800
ttagatccca catcgtataa atatctatta accattctaa ataaagagaa ctccagtgtt    4860
gctatgtgca agatcctctc ttggagcttt tttgcatagc aattaaaggt gtgctatttg    4920
tcagtagcca tttttttgca gtgatttgaa gaccaaagtt gttttacagc tgtgttaccg    4980
ttaaaggttt tttttttttat atgtattaaa tcaatttatc actgtttaaa gctttgaata    5040
tctgcaatct ttgccaaggt actttttttat ttaaaaaaaa ataacttt gtaaatatta    5100 ccctgtaata ttatatatac ttaataaaac attttaagct attttgttgg gctatttcta    5160
ttgctgctac agcagaccac aagcacattt ctgaaaaatt taatttatta atgtattttt    5220
aagttgctta tattctaggt aacaatgtaa agaatgattt aaaatattaa ttatgaattt    5280
tttgagtata atacccaata agcttttaat tagagcagag ttttaattaa aagttttaaa    5340
tcagtc                                                                5346
```

<210> SEQ ID NO 20
<211> LENGTH: 1273
<212> TYPE: DNA
<213> ORGANISM: Homo sapiens

<400> SEQUENCE: 20

```
tgcctgtgac gcgcggcggc ggtcggtcct gcctgtaacg gcggcggcgg ctgctgctcc      60
agacacctgc ggcggcggcg gcgaccccgc ggcgggcgcg gagatgtggc ccctggtagc     120
ggcgctgttg ctgggctcgg cgtgctgcgg atcagctcag ctactattta ataaaacaaa     180
atctgtagaa ttcacgtttt gtaatgacac tgtcgtcatt ccatgctttg ttactaatat     240
ggaggcacaa aacactactg aagtatacgt aaagtggaaa tttaaaggaa gagatattta     300
cacctttgat ggagctctaa acaagtccac tgtccccact gactttagta gtgcaaaaat     360
tgaagtctca caattactaa aaggagatgc ctctttgaag atggataaga gtgatgctgt     420
ctcacacaca ggaaactaca cttgtgaagt aacagaatta accagagaag gtgaaacgat     480
catcgagcta aaatatcgtg ttgtttcatg gttttctcca aatgaaaata ttcttattgt     540 tatttttccca atttttgcta tactcctgtt ctggggacag tttggtatta aaacacttaa     600
atatagatcc ggtggtatgg atgagaaaac aattgctttta cttgttgctg gactagtgat     660
```

```
cactgtcatt gtcattgttg gagccattct tttcgtccca ggtgaatatt cattaaagaa    720
tgctactggc cttggtttaa ttgtgacttc tacagggata ttaatattac ttcactacta    780
tgtgtttagt acagcgattg gattaacctc cttcgtcatt gccatattgg ttattcaggt    840
gatagcctat atcctcgctg tggttggact gagtctctgt attgcggcgt gtataccaat    900
gcatggccct cttctgattt caggtttgag tatcttagct ctagcacaat tacttggact    960
agtttatatg aaatttgtgg cttccaatca gaagactata caacctccta ggaataactg   1020
aagtgaagtg atggactccg atttggagag tagtaagacg tgaaaggaat acacttgtgt   1080
ttaagcacca tggccttgat gattcactgt tggggagaag aaacaagaaa agtaactggt   1140
tgtcacctat gagacccta cgtgattgtt agttaagttt ttattcaaag cagctgtaat   1200
ttagttaata aaataattat gatctatgtt gtttgcccaa aaaaaaaaaa aaaaaaaaaa   1260
aaaaaaaaaa aaa                                                      1273
```

```
<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      residues in the amino terminal portion of the CH2 domain that
      contribute to IgG Fc receptor binding

<400> SEQUENCE: 21

Leu Leu Gly Gly Pro Ser
1               5

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      amino acid sequence at amino terminal end of an exemplary mutein
      Fc polypeptide

<400> SEQUENCE: 22

Lys Thr His Thr Cys Pro Pro Cys Pro Ala Pro Glu Ala Glu Gly Ala
1               5                   10                  15

Pro Ser

<210> SEQ ID NO 23
<211> LENGTH: 227
<212> TYPE: PRT
<213> ORGANISM: Artificial Sequence
<220> FEATURE:
<223> OTHER INFORMATION: Description of Artificial Sequence: Synthetic
      mutated human mutein FC

<400> SEQUENCE: 23

Ser Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      FLAG epitope tag

<400> SEQUENCE: 24

Asp Tyr Lys Asp Asp Asp Asp Lys
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      XPRESS epitope tag

<400> SEQUENCE: 25

Asp Leu Tyr Asp Asp Asp Asp Lys
1               5

<210> SEQ ID NO 26
<211> LENGTH: 20
<212> TYPE: PRT
<213> ORGANISM: Variola minor virus

<400> SEQUENCE: 26

Met Leu Arg Val Arg Ile Leu Leu Ile Tyr Leu Cys Thr Phe Val Val
1               5                   10                  15
Ile Thr Ser Thr
            20

<210> SEQ ID NO 27
<211> LENGTH: 305
<212> TYPE: PRT
<213> ORGANISM: Homo sapiens

<400> SEQUENCE: 27
```

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
50                      55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
                195                 200                 205

Gly Leu Gly Leu Ile Val Thr Ser Thr Gly Ile Leu Ile Leu Leu His
            210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
                275                 280                 285

Met Lys Phe Val Ala Ser Asn Gln Lys Thr Ile Gln Pro Pro Arg Asn
                290                 295                 300

Asn
305

<210> SEQ ID NO 28
<211> LENGTH: 608
<212> TYPE: PRT
<213> ORGANISM: Artificial Sequence
<220> FEATURE:
<223> OTHER INFORMATION: Description of Artificial Sequence: Synthetic
      human fusion polypeptide
<220> FEATURE:
<221> NAME/KEY: MOD_RES
<222> LOCATION: (458)..(458)
<223> OTHER INFORMATION: Any amino acid except Asn

<400> SEQUENCE: 28

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
```

```
                    20                  25                  30
Cys Asn Asp Thr Val Val Ile Pro Cys Phe Val Thr Asn Met Glu Ala
            35                  40                  45
Gln Asn Thr Thr Glu Val Tyr Val Lys Trp Lys Phe Lys Gly Arg Asp
            50                  55                  60
Ile Tyr Thr Phe Asp Gly Ala Leu Asn Lys Ser Thr Val Pro Thr Asp
65                  70                  75                  80
Phe Ser Ser Ala Lys Ile Glu Val Ser Gln Leu Leu Lys Gly Asp Ala
            85                  90                  95
Ser Leu Lys Met Asp Lys Ser Asp Ala Val Ser His Thr Gly Asn Tyr
            100                 105                 110
Thr Cys Glu Val Thr Glu Leu Thr Arg Glu Gly Glu Thr Ile Ile Glu
            115                 120                 125
Leu Lys Tyr Arg Val Val Ser Trp Phe Ser Pro Asn Glu Asn Lys Thr
            130                 135                 140
His Thr Cys Pro Pro Cys Pro Ala Pro Glu Leu Leu Gly Gly Pro Ser
145                 150                 155                 160
Val Phe Leu Phe Pro Pro Lys Pro Lys Asp Thr Leu Met Ile Ser Arg
                165                 170                 175
Thr Pro Glu Val Thr Cys Val Val Asp Val Ser His Glu Asp Pro
            180                 185                 190
Glu Val Lys Phe Asn Trp Tyr Val Asp Gly Val Glu Val His Asn Ala
            195                 200                 205
Lys Thr Lys Pro Arg Glu Glu Gln Tyr Ser Thr Tyr Arg Val Val Ser
            210                 215                 220
Val Leu Thr Val Leu His Gln Asp Trp Leu Asn Gly Lys Glu Tyr Lys
225                 230                 235                 240
Met Trp Pro Leu Val Ala Ala Leu Leu Leu Gly Ser Ala Cys Cys Gly
                245                 250                 255
Ser Ala Gln Leu Leu Phe Asn Lys Thr Lys Ser Val Glu Phe Thr Phe
            260                 265                 270
Cys Asn Asp Thr Val Val Ile Pro Cys Phe Val Thr Asn Met Glu Ala
            275                 280                 285
Gln Asn Thr Thr Glu Val Tyr Val Lys Trp Lys Phe Lys Gly Arg Asp
            290                 295                 300
Ile Tyr Thr Phe Asp Gly Ala Leu Asn Lys Ser Thr Val Pro Thr Asp
305                 310                 315                 320
Phe Ser Ser Ala Lys Ile Glu Val Ser Gln Leu Leu Lys Gly Asp Ala
                325                 330                 335
Ser Leu Lys Met Asp Lys Ser Asp Ala Val Ser His Thr Gly Asn Tyr
                340                 345                 350
Thr Cys Glu Val Thr Glu Leu Thr Arg Glu Gly Glu Thr Ile Ile Glu
            355                 360                 365
Leu Lys Tyr Arg Val Val Ser Trp Phe Ser Pro Asn Glu Asn Lys Thr
            370                 375                 380
His Thr Cys Pro Pro Cys Pro Ala Pro Glu Leu Leu Gly Gly Pro Ser
385                 390                 395                 400
Val Phe Leu Phe Pro Pro Lys Pro Lys Asp Thr Leu Met Ile Ser Arg
                405                 410                 415
Thr Pro Glu Val Thr Cys Val Val Asp Val Ser His Glu Asp Pro
            420                 425                 430
Glu Val Lys Phe Asn Trp Tyr Val Asp Gly Val Glu Val His Asn Ala
            435                 440                 445
```

```
Lys Thr Lys Pro Arg Glu Glu Gln Tyr Xaa Ser Thr Tyr Arg Val Val
        450                 455                 460

Ser Val Leu Thr Val Leu His Gln Asp Trp Leu Asn Gly Lys Glu Tyr
465                 470                 475                 480

Lys Cys Lys Val Ser Asn Lys Ala Leu Pro Ala Pro Ile Glu Lys Thr
                485                 490                 495

Ile Ser Lys Ala Lys Gly Gln Pro Arg Glu Pro Gln Val Tyr Thr Leu
            500                 505                 510

Pro Pro Ser Arg Asp Glu Leu Thr Lys Asn Gln Val Ser Leu Thr Cys
        515                 520                 525

Leu Val Lys Gly Phe Tyr Pro Ser Asp Ile Ala Val Glu Trp Glu Ser
    530                 535                 540

Asn Gly Gln Pro Glu Asn Asn Tyr Lys Thr Thr Pro Pro Val Leu Asp
545                 550                 555                 560

Ser Asp Gly Ser Phe Phe Leu Tyr Ser Lys Leu Thr Val Asp Lys Ser
                565                 570                 575

Arg Trp Gln Gln Gly Asn Val Phe Ser Cys Ser Val Met His Glu Ala
            580                 585                 590

Leu His Asn His Tyr Thr Gln Lys Ser Leu Ser Leu Ser Pro Gly Lys
        595                 600                 605

<210> SEQ ID NO 29
<211> LENGTH: 367
<212> TYPE: PRT
<213> ORGANISM: Artificial Sequence
<220> FEATURE:
<223> OTHER INFORMATION: Description of Artificial Sequence: Synthetic
      human fusion polypeptide

<400> SEQUENCE: 29

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Thr His
    130                 135                 140

Thr Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205
```

```
Thr Lys Pro Arg Glu Glu Gln Tyr Asn Ser Thr Tyr Arg Val Val Ser
    210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Ser Arg Asp Glu Leu Thr Lys Asn Gln Val Ser Leu Thr Cys Leu
        275                 280                 285

Val Lys Gly Phe Tyr Pro Ser Asp Ile Ala Val Glu Trp Glu Ser Asn
    290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
        355                 360                 365

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      Gly-Ser linker sequence

<400> SEQUENCE: 30

Gly Gly Gly Gly Ser
1               5

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      Gly-Ser linker sequence

<400> SEQUENCE: 31

Gly Gly Gly Gly Ser Gly Gly Gly Gly Ser
1               5                   10

<210> SEQ ID NO 32
<211> LENGTH: 372
<212> TYPE: PRT
<213> ORGANISM: Artificial Sequence
<220> FEATURE:
<223> OTHER INFORMATION: Description of Artificial Sequence: Synthetic
      human fusion polypeptide

<400> SEQUENCE: 32

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60
```

```
Ile Tyr Thr Phe Asp Gly Ala Leu Asn Lys Ser Thr Val Pro Thr Asp
 65                  70                  75                  80

Phe Ser Ser Ala Lys Ile Glu Val Ser Gln Leu Leu Lys Gly Asp Ala
                 85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Gly Gly
130                 135                 140

Gly Gly Ser Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Asp Glu Leu Thr Lys Asn Gln Val
        275                 280                 285

Ser Leu Thr Cys Leu Val Lys Gly Phe Tyr Pro Ser Asp Ile Ala Val
290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
        370

<210> SEQ ID NO 33
<211> LENGTH: 377
<212> TYPE: PRT
<213> ORGANISM: Artificial Sequence
<220> FEATURE:
<223> OTHER INFORMATION: Description of Artificial Sequence: Synthetic
      human fusion polypeptide

<400> SEQUENCE: 33

Met Trp Pro Leu Val Ala Ala Leu Leu Leu Gly Ser Ala Cys Cys Gly
 1               5                  10                  15

Ser Ala Gln Leu Leu Phe Asn Lys Thr Lys Ser Val Glu Phe Thr Phe
                 20                  25                  30

Cys Asn Asp Thr Val Val Ile Pro Cys Phe Val Thr Asn Met Glu Ala
             35                  40                  45
```

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Gly Gly
    130                 135                 140

Gly Gly Ser Gly Gly Gly Gly Ser Thr His Thr Cys Pro Pro Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Asp Glu Leu
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
        355                 360                 365

Lys Ser Leu Ser Leu Ser Pro Gly Lys
    370                 375

<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic
      peptide sequence of combined affinity tags

<400> SEQUENCE: 34

Ala Gly Gly Pro Gly Gly Tyr Pro Tyr Asp Val Pro Asp Tyr Ala Glu
1               5                   10                  15

Asp Gln Val Asp Pro Arg Leu Ile Asp Gly Lys Met Asp Glu Lys Thr
            20                  25                  30

Thr Gly Trp Arg Gly Gly His Val Val Glu Gly Leu Ala Gly Glu Leu
        35                  40                  45

Glu Gln Leu Arg Ala Arg Leu Glu His His Pro Gln Gly Gln Arg Glu
 50                  55                  60

Pro Gly Ser Gly Met Asp Glu Lys Thr Thr Gly Trp Arg Gly Gly His
65                  70                  75                  80

Val Val Glu Gly Leu Ala Gly Glu Leu Glu Gln Leu Arg Ala Arg Leu
                85                  90                  95

Glu His His Pro Gln Gly Gln Arg Glu Pro
            100                 105

<210> SEQ ID NO 35
<211> LENGTH: 327
<212> TYPE: DNA
<213> ORGANISM: Artificial Sequence
<220> FEATURE:
<223> OTHER INFORMATION: Description of Artificial Sequence: Synthetic
      nucleotide sequence of combined affinity tags

<400> SEQUENCE: 35
gcggccgctg gcggcccggg cggctacccc tacgacgtgc ccgactacgc cgaggaccag      60
gtggaccccc ggctgatcga cggcaagatg gacgagaaga ccaccggctg gcggggcggc     120
cacgtggtgg agggcctggc cggcgagctg gagcagctgc gggcccggct ggagcaccac     180
ccccagggcc agcgggagcc cggaagcggt atggatgaaa aaactactgg ttggagaggg     240
ggacatgtag tcgaaggtct ggccggcgag ttagaacaat taagagctag attggaacat     300
catccacaag gtcaaagaga accttag                                         327

<210> SEQ ID NO 36
<211> LENGTH: 1928
<212> TYPE: DNA
<213> ORGANISM: Mus musculus

<400> SEQUENCE: 36
cccgggcagc ctgggcggcc gctcctgcct gtcactgctg cggcgctgct ggtcggtcgt      60
ttcccttgaa ggcagcagcg gaggcggcgg ctgctccaga cacctgcggc ggcgaccccc     120
cggcggcgcg gagatgtggc ccttggcggc ggcgctgttg ctgggctcct gctgctgcgg     180
ttcagctcaa ctactgttta gtaacgtcaa ctccatagag ttcacttcat gcaatgaaac     240
tgtggtcatc ccttgcatcg tccgtaatgt ggaggcgcaa agcaccgaag aaatgtttgt     300
gaagtggaag ttgaacaaat cgtatatttt catctatgat ggaaataaaa atagcactac     360
tacagatcaa aactttacca gtgcaaaaat ctcagtctca gacttaatca atggcattgc     420
ctctttgaaa atggataagc gcgatgccat ggtgggaaac tacacttgcg aagtgacaga     480
gttatccaga gaaggcaaaa cagttataga gctgaaaaac cgcacggcct tcaacactga     540
ccaaggatca gcctgttctt acgaggagga gaaaggaggt tgcaaattag tttcgtggtt     600
ttctccaaat gaaagatccc tcattgttat tttcccaatt ttggctatac tcctgttctg     660
gggaaagttt ggtattttaa cactcaaata taatccagc catacgaata agagaatcat     720
tctgctgctc gttgccgggc tggtgctcac agtcatcgtg gttgttggag ccatccttct     780
catcccagga gaaaagcccg tgaagaatgc ttctggactt ggcctcattg taatctctac     840
ggggatatta atactacttc agtacaatgt gttatgaca gcttttggaa tgacctcttt     900
caccattgcc atattgatca ctcaagtgct gggctacgtc cttgctttgg tcgggctgtg     960
tctctgcatc atggcatgtg agccagtgca cggcccccctt ttgatttcag gtttggggat    1020

```
catagctcta gcagaactac ttggattagt ttatatgaag tttgtcgctt ccaaccagag    1080
gactatccaa cctcctagga ataggtgaag ggaagtgacg gactgtaact tggaagtcag    1140
aaatggaaga atacagttgt ctaagcacca ggtcttcacg actcacagct ggaaggaaca    1200
gacaacagta actgacttcc atccaggaaa acatgtcaca taaatgatta ctaagtttat    1260
attcaaagca gctgtacttt acataataaa aaaaatatga tgtgctgtgt aaccaattgg    1320
aatcccattt ttctattgtt tctactcaac taggggcaaa cgtttcaggg gcaacttcca    1380
agaatgatgc ttgttagatc ctagagtctc tgaacactga gtttaaattg attccgagtg    1440
agactcgcca agcactaacc tgagggttag ttacccagag atacctatga aaaacagtgg    1500
tatccagcaa gccttagtaa actcaggttg ccagcagctt tgccacttcc gctgctagct    1560
gaataacaag actgccactt ctgggtcata gtgatagaga ctgaagtaga aaaacgaatg    1620
tggttgggca aatcccgtgt ggcccctctg tgtgctatga tattgatggc actggtgtct    1680
tcattcttgg gggttgccat cattcacaca cacccctttg acatacagtg caccccagtt    1740
ttgaatacat tttttttgca ccctgtcccg ttctgctact ttgatttgcg ttatgatata    1800
tatatatata tataatacct tttctcctct taaacatgg tcctgtgaca caatagtcag    1860
ttgcagaaag gagccagact tattcgcaaa gcactgtgct caaactcttc agaaaaaaaa    1920
aaaaaaaa                                                            1928
```

<210> SEQ ID NO 37
<211> LENGTH: 324
<212> TYPE: PRT
<213> ORGANISM: Mus musculus

<400> SEQUENCE: 37

```
Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Asp Gln Asn
65                  70                  75                  80

Phe Thr Ser Ala Lys Ile Ser Val Ser Asp Leu Ile Asn Gly Ile Ala
            85                  90                  95

Ser Leu Lys Met Asp Lys Arg Asp Ala Met Val Gly Asn Tyr Thr Cys
        100                 105                 110

Glu Val Thr Glu Leu Ser Arg Glu Gly Lys Thr Val Ile Glu Leu Lys
    115                 120                 125

Asn Arg Thr Ala Phe Asn Thr Asp Gln Gly Ser Ala Cys Ser Tyr Glu
130                 135                 140

Glu Glu Lys Gly Gly Cys Lys Leu Val Ser Trp Phe Ser Pro Asn Glu
145                 150                 155                 160

Lys Ile Leu Ile Val Ile Phe Pro Ile Leu Ala Ile Leu Leu Phe Trp
            165                 170                 175

Gly Lys Phe Gly Ile Leu Thr Leu Lys Tyr Lys Ser Ser His Thr Asn
        180                 185                 190

Lys Arg Ile Ile Leu Leu Val Ala Gly Leu Val Leu Thr Val Ile
    195                 200                 205
```

```
Val Val Val Gly Ala Ile Leu Leu Ile Pro Gly Glu Lys Pro Val Lys
    210                 215                 220

Asn Ala Ser Gly Leu Gly Leu Ile Val Ile Ser Thr Gly Ile Leu Ile
225                 230                 235                 240

Leu Leu Gln Tyr Asn Val Phe Met Thr Ala Phe Gly Met Thr Ser Phe
                245                 250                 255

Thr Ile Ala Ile Leu Ile Thr Gln Val Leu Gly Tyr Val Leu Ala Leu
                260                 265                 270

Val Gly Leu Cys Leu Cys Ile Met Ala Cys Glu Pro Val His Gly Pro
                275                 280                 285

Leu Leu Ile Ser Gly Leu Gly Ile Ile Ala Leu Ala Glu Leu Leu Gly
                290                 295                 300

Leu Val Tyr Met Lys Phe Val Ala Ser Asn Gln Arg Thr Ile Gln Pro
305                 310                 315                 320

Pro Arg Asn Arg

<210> SEQ ID NO 38
<211> LENGTH: 303
<212> TYPE: PRT
<213> ORGANISM: Mus musculus

<400> SEQUENCE: 38

Met Trp Pro Leu Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
                20                  25                  30

Cys Asn Glu Thr Val Val Ile Pro Cys Ile Val Arg Asn Val Glu Ala
                35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
                100                 105                 110

Glu Val Thr Glu Leu Ser Arg Glu Gly Lys Thr Val Ile Glu Leu Lys
                115                 120                 125

Asn Arg Thr Val Ser Trp Phe Ser Pro Asn Glu Lys Ile Leu Ile Val
130                 135                 140

Ile Phe Pro Ile Leu Ala Ile Leu Leu Phe Trp Gly Lys Phe Gly Ile
145                 150                 155                 160

Leu Thr Leu Lys Tyr Lys Ser Ser His Thr Asn Lys Arg Ile Ile Leu
                165                 170                 175

Leu Leu Val Ala Gly Leu Val Leu Thr Val Ile Val Val Gly Ala
                180                 185                 190

Ile Leu Leu Ile Pro Gly Glu Lys Pro Val Lys Asn Ala Ser Gly Leu
                195                 200                 205

Gly Leu Ile Val Ile Ser Thr Gly Ile Leu Ile Leu Leu Gln Tyr Asn
    210                 215                 220

Val Phe Met Thr Ala Phe Gly Met Thr Ser Phe Thr Ile Ala Ile Leu
225                 230                 235                 240

Ile Thr Gln Val Leu Gly Tyr Val Leu Ala Leu Val Gly Leu Cys Leu
                245                 250                 255

Cys Ile Met Ala Cys Glu Pro Val His Gly Pro Leu Leu Ile Ser Gly
```

```
                260                 265                 270
Leu Gly Ile Ile Ala Leu Ala Glu Leu Leu Gly Leu Val Tyr Met Lys
        275                 280                 285

Phe Val Ala Ser Asn Gln Arg Thr Ile Gln Pro Pro Arg Asn Arg
        290                 295                 300

<210> SEQ ID NO 39
<211> LENGTH: 350
<212> TYPE: PRT
<213> ORGANISM: Artificial Sequence
<220> FEATURE:
<223> OTHER INFORMATION: Description of Artificial Sequence: Synthetic
      hCD47-hFc polypeptide

<400> SEQUENCE: 39

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320
```

-continued

```
Gln Gln Gly Asn Val Phe Ser Cys Ser Val Met His Glu Ala Leu His
            325                 330                 335

Asn His Tyr Thr Gln Lys Ser Leu Ser Leu Ser Pro Gly Lys
            340                 345                 350
```

We claim the following:

1. A formulation comprising a fusion polypeptide having the amino acid sequence set forth in SEQ ID NO:39 and a pharmaceutically suitable carrier in which mannitol is present in an amount of at least 1% w/v.

2. The formulation of claim 1 further comprising a buffering agent, wherein the buffering agent is histidine.

3. The formulation of claim 2 wherein mannitol is present in an amount of about 3% w/v.

4. The formulation of claim 1, wherein the fusion polypeptide forms a dimer of two fusion polypeptide monomers, and wherein the dimer comprises a disulfide bond between each of the extracellular CD47 domain moieties of each of the two fusion polypeptide monomers.

5. The formulation according to claim 4 wherein the disulfide bond between each of the extracellular domain moieties is formed between a cysteine residue of each extracellular CD47 domain moiety, which cysteine residue of each extracellular CD47 domain moiety is most proximal to the amino terminus.

6. The formulation according to claim 5 wherein the fusion polypeptide retains the capability to bind at least one CD47 ligand selected from SIRP-α, SIRPbeta-2, thrombospondin-1, $α_v β_3$ integrin, and $α_2 β_1$ integrin.

* * * * *